US011553924B2

(12) United States Patent
Mantri et al.

(10) Patent No.: US 11,553,924 B2
(45) Date of Patent: Jan. 17, 2023

(54) MINIMALLY INVASIVE SYSTEMS WITH EXPANDABLE SUPPORTS FOR HEMOSTASIS IN A BLEEDING CLOSED TISSUE VOLUME

(71) Applicant: PROCEPT BioRobotics Corporation, Redwood City, CA (US)

(72) Inventors: Surag Mantri, Sunnyvale, CA (US); Nikolai Aljuri, Hillsborough, CA (US); Kevin Patrick Staid, Lowell, MA (US); James Luis Badia, Redwood City, CA (US); Peter Bentley, Newark, CA (US); Nishey Wanchoo, Foster City, CA (US)

(73) Assignee: PROCEPT BioRobotics Corporation, Redwood City, CA (US)

( * ) Notice: Subject to any disclaimer, the term of this patent is extended or adjusted under 35 U.S.C. 154(b) by 0 days.

(21) Appl. No.: 16/376,645

(22) Filed: Apr. 5, 2019

(65) Prior Publication Data
US 2019/0231359 A1 Aug. 1, 2019

Related U.S. Application Data

(63) Continuation of application No. 15/976,650, filed on May 10, 2018, now Pat. No. 10,315,023, which is a
(Continued)

(51) Int. Cl.
*A61B 17/00* (2006.01)
*A61B 17/12* (2006.01)
(Continued)

(52) U.S. Cl.
CPC .... *A61B 17/12136* (2013.01); *A61B 17/0057* (2013.01); *A61B 17/00234* (2013.01);
(Continued)

(58) Field of Classification Search
CPC .. A61M 31/00; A61M 39/06; A61M 25/1011; A61M 2025/1013;
(Continued)

(56) References Cited

U.S. PATENT DOCUMENTS

| 1,032,611 A | 7/1912 | Keyes |
| 4,133,303 A | 1/1979 | Patel |

(Continued)

FOREIGN PATENT DOCUMENTS

| CN | 2493163 Y | 5/2002 |
| CN | 104352252 | 2/2015 |

(Continued)

OTHER PUBLICATIONS

A to Z List of Cancer Drugs—National Cancer Institute. Aug. 18, 2016. 25 pages.
(Continued)

*Primary Examiner* — Nathan R Price
*Assistant Examiner* — William R Frehe
(74) *Attorney, Agent, or Firm* — FisherBroyles LLP; John Shimmick

(57) ABSTRACT

Disclosed herein are improved methods and apparatuses for providing hemostasis within a cavity defined by an internal surface of a bleeding tissue space. A catheter comprising a proximal end and a distal end may be advanced into the cavity through a proximal opening of the tissue space into the cavity. A distal balloon coupled to the catheter may be positioned adjacent a distal opening of the tissue space, and expanded to seal the distal opening. A hemostatic agent may be applied from the catheter to the internal surface of the tissue space to inhibit bleeding of the tissue space. The hemostatic agent may be applied without occluding the proximal opening, the distal opening, and a path extending therebetween with the hemostatic agent.

26 Claims, 84 Drawing Sheets

Related U.S. Application Data continuation of application No. PCT/US2017/023062, filed on Mar. 17, 2017.

(60) Provisional application No. 62/380,321, filed on Aug. 26, 2016, provisional application No. 62/324,831, filed on Apr. 19, 2016, provisional application No. 62/310,614, filed on Mar. 18, 2016.

(51) Int. Cl.

| | | |
|---|---|---|
| *A61B 90/00* | (2016.01) | |
| *A61M 25/10* | (2013.01) | |
| *A61M 39/06* | (2006.01) | |
| *A61N 5/10* | (2006.01) | |
| *A61N 5/00* | (2006.01) | |
| *A61B 18/00* | (2006.01) | |
| *A61M 25/01* | (2006.01) | |
| *A61F 13/00* | (2006.01) | |
| *A61F 13/02* | (2006.01) | |
| *A61B 18/14* | (2006.01) | |

(52) U.S. Cl.
CPC .... *A61B 17/00491* (2013.01); *A61B 17/1204* (2013.01); *A61B 17/12045* (2013.01); *A61B 17/12186* (2013.01); *A61B 18/00* (2013.01); *A61B 90/39* (2016.02); *A61M 25/1011* (2013.01); *A61M 25/10184* (2013.11); *A61M 39/06* (2013.01); *A61N 5/00* (2013.01); *A61N 5/1007* (2013.01); *A61N 5/1015* (2013.01); *A61B 17/12177* (2013.01); *A61B 18/1492* (2013.01); *A61B 2017/00274* (2013.01); *A61B 2017/00676* (2013.01); *A61B 2017/12004* (2013.01); *A61B 2090/065* (2016.02); *A61B 2090/3966* (2016.02); *A61F 13/00008* (2013.01); *A61F 13/00063* (2013.01); *A61F 13/00068* (2013.01); *A61F 13/0216* (2013.01); *A61M 25/0108* (2013.01); *A61M 25/1002* (2013.01); *A61M 2025/105* (2013.01); *A61M 2025/1052* (2013.01); *A61M 2025/1081* (2013.01); *A61M 2210/16* (2013.01); *A61M 2210/166* (2013.01); *A61N 2005/1021* (2013.01); *A61N 2005/1024* (2013.01)

(58) Field of Classification Search
CPC .. A61M 2025/1015; A61M 2025/1059; A61M 2025/1068; A61M 2025/1072; A61M 25/0017; A61M 2210/1078; A61M 2210/16; A61M 2210/166; A61M 31/002; A61M 2025/105; A61M 2025/1093; A61K 9/02; A61K 9/0031; A61K 9/0034
USPC ........................................................ 604/544
See application file for complete search history.

(56) References Cited

U.S. PATENT DOCUMENTS

| | | | |
|---|---|---|---|
| 4,219,026 A | | 8/1980 | Layton |
| 4,349,029 A | | 9/1982 | Mott |
| 5,007,898 A | | 4/1991 | Rosenbluth |
| 5,207,651 A | | 5/1993 | Snyder |
| 5,314,443 A | | 5/1994 | Rudnick |
| 5,443,480 A | | 8/1995 | Jacobs |
| 5,443,481 A | | 8/1995 | Lee |
| 5,836,951 A | * | 11/1998 | Rosenbluth ........ A61M 25/1011 |
| | | | 600/116 |
| 5,902,275 A | | 5/1999 | Dobkin |
| 6,007,521 A | | 12/1999 | Bidwell |
| 6,102,929 A | | 8/2000 | Conway |
| 6,602,243 B2 | | 8/2003 | Noda |
| 6,706,051 B2 | | 3/2004 | Hudson |
| 7,018,392 B2 | | 3/2006 | Hudson |
| 7,837,670 B2 | | 11/2010 | Barath |
| 8,353,895 B2 | | 1/2013 | Russo |
| 10,315,023 B2 | | 6/2019 | Mantri |
| 11,278,293 B2 | | 3/2022 | Mantri et al. |
| 2002/0013548 A1 | | 1/2002 | Hinchliffe |
| 2002/0032486 A1 | * | 3/2002 | Lazarovitz ......... A61M 25/1011 |
| | | | 606/108 |
| 2002/0062119 A1 | | 5/2002 | Zadno-Azizi |
| 2002/0173815 A1 | * | 11/2002 | Hogendijk ............. A61B 17/22 |
| | | | 606/200 |
| 2004/0002647 A1 | | 1/2004 | Desai |
| 2004/0230316 A1 | * | 11/2004 | Cioanta .............. A61M 25/1011 |
| | | | 623/1.21 |
| 2005/0149173 A1 | | 7/2005 | Hunter |
| 2006/0217680 A1 | | 9/2006 | Barath |
| 2006/0281968 A1 | | 12/2006 | Duran |
| 2007/0185478 A1 | | 8/2007 | Cosentino |
| 2007/0208252 A1 | * | 9/2007 | Makower ................ A61B 6/032 |
| | | | 606/198 |
| 2007/0239110 A1 | | 10/2007 | Shah |
| 2008/0114286 A1 | * | 5/2008 | Hamel .................. A61M 25/04 |
| | | | 604/21 |
| 2008/0243081 A1 | | 10/2008 | Nance |
| 2008/0311086 A1 | | 12/2008 | Popowski |
| 2009/0018533 A1 | | 1/2009 | Perkins |
| 2009/0240234 A1 | * | 9/2009 | Doerr ................. A61M 25/0017 |
| | | | 604/517 |
| 2009/0270787 A1 | | 10/2009 | Oepen |
| 2010/0082012 A1 | * | 4/2010 | Hattangadi ........ A61M 25/1011 |
| | | | 604/509 |
| 2011/0152683 A1 | * | 6/2011 | Gerrans ............ A61M 25/0108 |
| | | | 600/435 |
| 2011/0184391 A1 | | 7/2011 | Aljuri |
| 2011/0238144 A1 | | 9/2011 | Hoey |
| 2012/0165680 A1 | | 6/2012 | Akifumi |
| 2012/0296313 A1 | | 11/2012 | Andreacchi |
| 2012/0302827 A1 | | 11/2012 | Copa |
| 2013/0131626 A1 | | 5/2013 | Thompson |
| 2013/0238038 A1 | | 9/2013 | Auyoung |
| 2013/0253574 A1 | * | 9/2013 | Catanese, III ..... A61B 17/0401 |
| | | | 606/201 |
| 2013/0253622 A1 | | 9/2013 | Hooven |
| 2014/0005674 A1 | | 1/2014 | Angel |
| 2014/0012234 A1 | * | 1/2014 | Pinchuk .......... A61M 25/10186 |
| | | | 604/544 |
| 2014/0031631 A1 | | 1/2014 | Hall |
| 2014/0052105 A1 | | 2/2014 | Hattangadi |
| 2015/0094696 A1 | * | 4/2015 | Adams, Jr. .............. A61M 1/84 |
| | | | 604/544 |
| 2015/0250988 A1 | | 9/2015 | Dib |
| 2015/0335321 A1 | | 11/2015 | Edelman |
| 2016/0324571 A1 | * | 11/2016 | Beeckler .......... A61B 17/12136 |
| 2017/0000981 A1 | | 1/2017 | Gerrans |
| 2017/0043138 A1 | * | 2/2017 | Dib .................... A61M 25/1034 |
| 2017/0232273 A1 | * | 8/2017 | Aljuri .................. A61B 5/0071 |
| | | | 600/4 |
| 2018/0015264 A1 | * | 1/2018 | Wang ..................... A61M 5/172 |
| 2019/0240505 A1 | | 8/2019 | Aljuri |

FOREIGN PATENT DOCUMENTS

| | | |
|---|---|---|
| DE | 10302241 | 8/2004 |
| JP | 2015112265 | 6/2015 |
| RU | 2143848 | 1/2000 |
| WO | 9325265 A1 | 12/1993 |
| WO | 9518646 | 7/1995 |
| WO | 9736632 | 10/1997 |
| WO | 0119445 | 3/2001 |
| WO | 0170325 | 9/2001 |
| WO | 03099171 | 12/2003 |
| WO | 2007059959 | 5/2007 |
| WO | 2008083407 A1 | 7/2008 |
| WO | 2009038612 | 3/2009 |
| WO | 2009111736 A1 | 9/2009 |
| WO | 2011097505 A1 | 8/2011 |
| WO | 2013010600 A1 | 1/2013 |

(56) References Cited

FOREIGN PATENT DOCUMENTS

| WO | 2013130895 | A1 | 9/2013 |
|----|------------|----|--------|
| WO | 2013133182 |    | 9/2013 |
| WO | 2014127242 | A2 | 8/2014 |
| WO | 2014131742 | A1 | 9/2014 |
| WO | 2014165703 | A1 | 10/2014 |
| WO | 2015035249 | A2 | 3/2015 |
| WO | 2015168522 | A1 | 11/2015 |
| WO | 2015200538 | A1 | 12/2015 |
| WO | 2016004071 | A1 | 1/2016 |
| WO | 2016037132 | A1 | 3/2016 |
| WO | 2016037137 | A1 | 3/2016 |
| WO | 2017161331 | A1 | 9/2017 |
| WO | 2017174950 | A1 | 10/2017 |

OTHER PUBLICATIONS

Brachytherapy—Wikipedia the free encyclopedia. Aug. 1, 2016. 14 pages.
International search report with written opinion dated Aug. 2, 2017 for Application No. PCT/US2017/023062.
List of antibodies—Wikipedia the free encyclopedia. Aug. 10, 2016. 12 pages.
List of Pain Relief Medications—eMed Expert. Jan. 12, 2016. 5 pages.
List of Radiopharmaceuticals nuclearpharmacy. Jul. 20, 2015. 3 pages.
Radiopharmaceutical List and Package Inserts. University of Arkansas for Medical Sciences. Jan. 12, 2016. 4 pages.
Foley Catheter, Wikipedia, dated Jan. 30, 2013.
Final Office Action for U.S. Appl. No. 16/376,738, dated Jun. 12, 2020.
Final Office Action for U.S. Appl. No. 16/376,806, dated Jun. 18, 2020.
Feri, C.D.R, et al., "A Randomized-Controlled Trial Comparing an Abdominally-Anchored Catheter versus a Thigh-Anchored Urethral Catheter in Controlling Bleeding and Pain After Transurethral Resection of the Prostate," Philippine Journal of Urology, 29(1):55-59 (Jun. 2019).
Moradi, M., et al., "Intraprostatis fossa foley balloon tamponade: a novel technique for controlling of life-threatening bleeding during simle prostatectomy," Urol Nephrol Open Access J. 3(5):167-169 (2016).
Welliver, C., et al., "Technique considerations and complication management in transurethral resection of the prostate and photoselective vaporization of the prostate," Transl Androl Urol 6(4):695-703 (2017).

\* cited by examiner

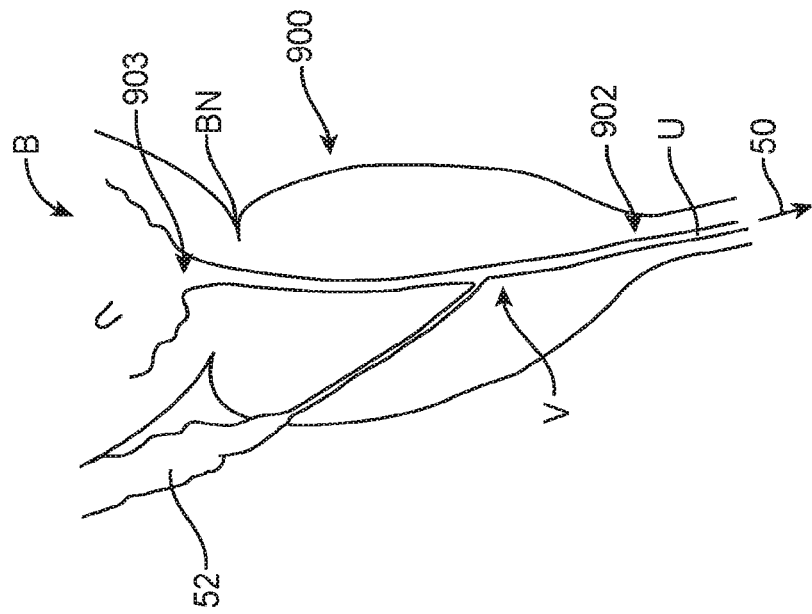
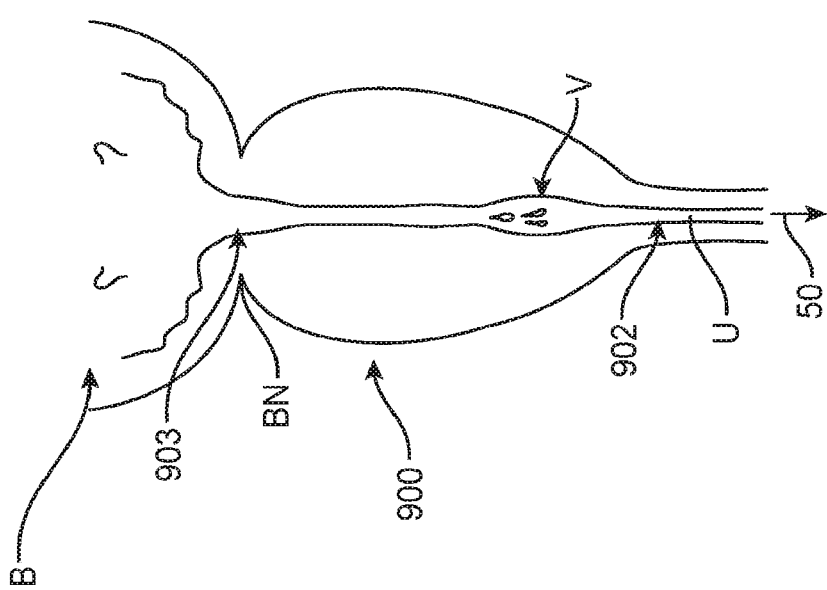
FIG. 21A
FIG. 21B

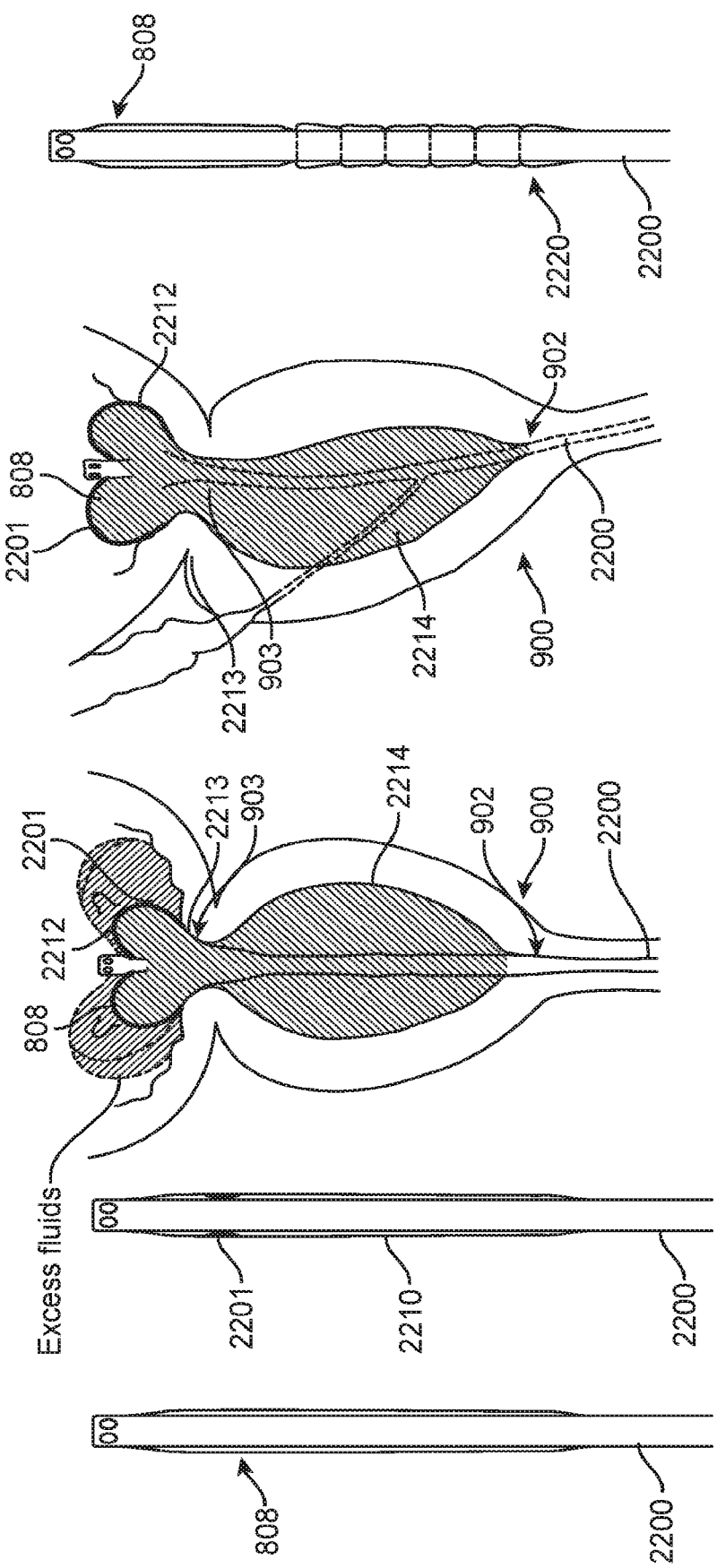

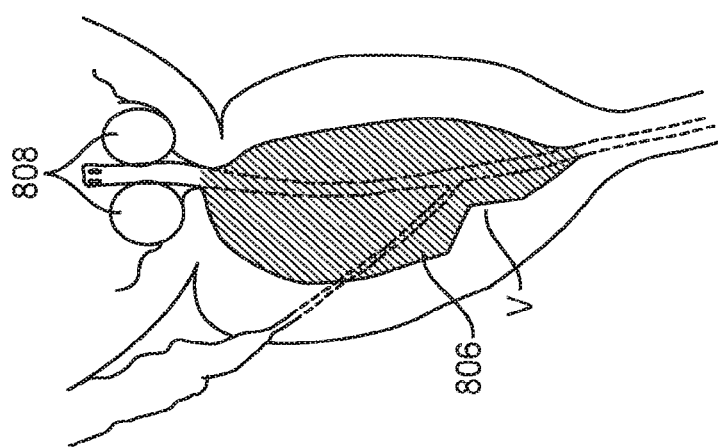
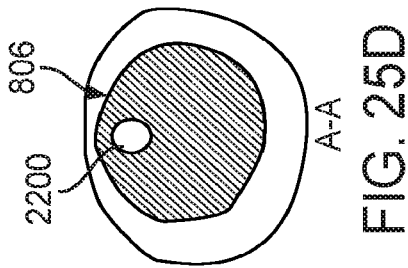
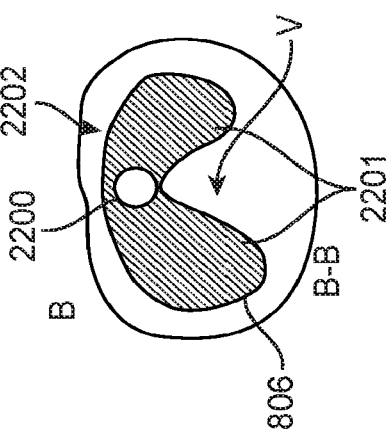
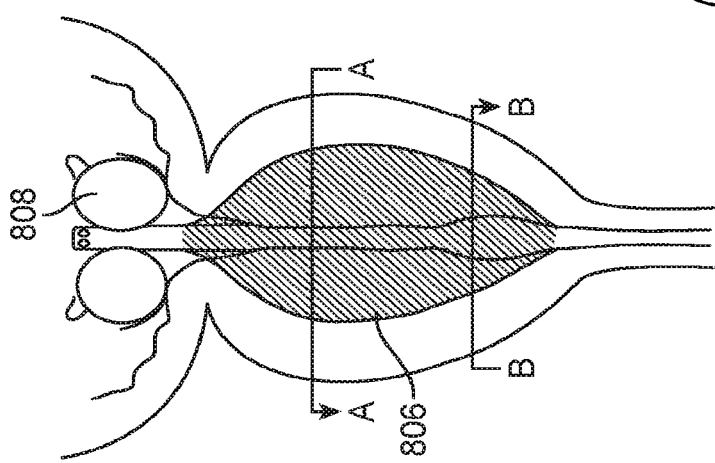
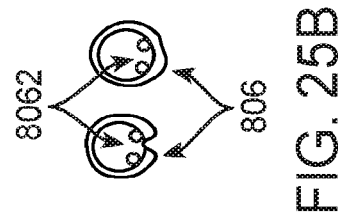
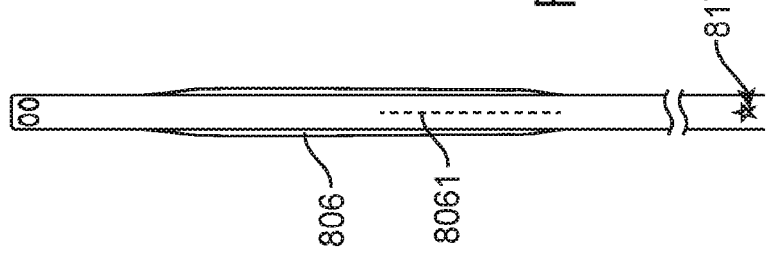

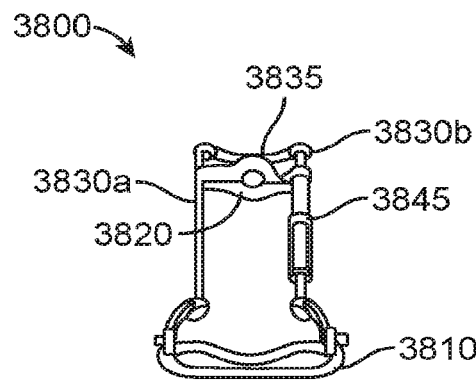
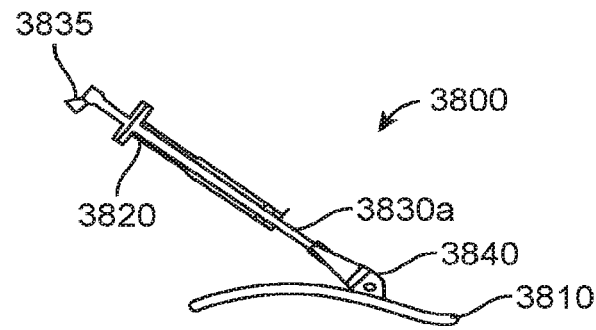
FIG. 38A
FIG. 38B
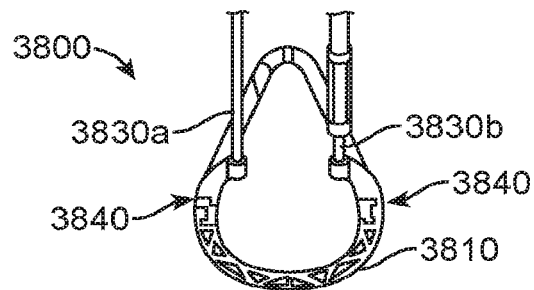
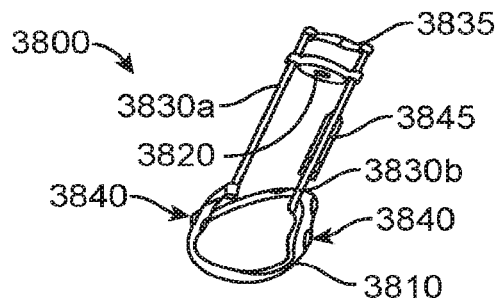
FIG. 38C
FIG. 38D
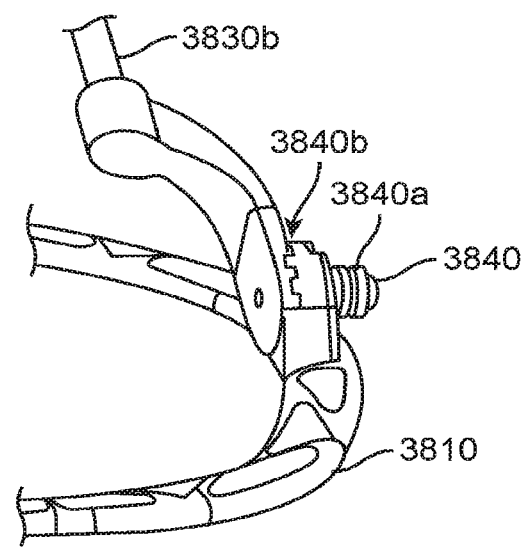
FIG. 38E

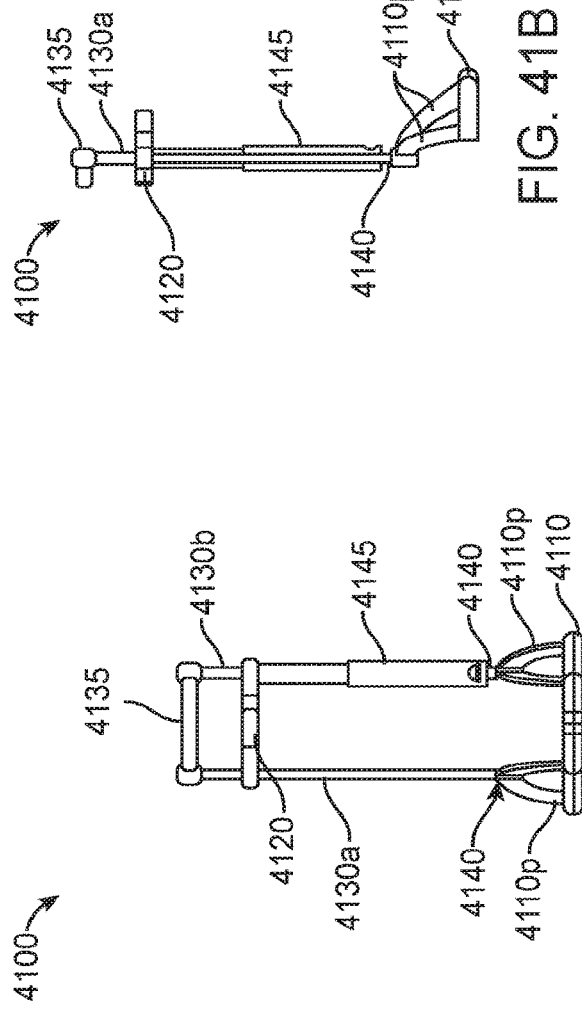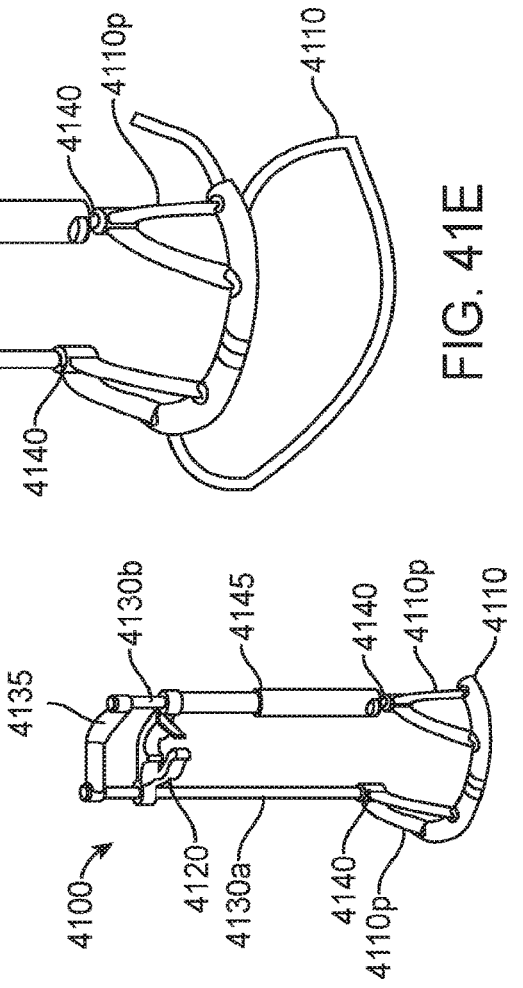

MINIMALLY INVASIVE SYSTEMS WITH EXPANDABLE SUPPORTS FOR HEMOSTASIS IN A BLEEDING CLOSED TISSUE VOLUME

CROSS-REFERENCE

The present application is a continuation of U.S. application Ser. No. 15/976,650, filed May 10, 2018, which is a continuation of International Application No. PCT/US17/23062, filed Mar. 17, 2017, which claims the benefit of U.S. Provisional Application No. 62/380,321, filed Aug. 26, 2016, U.S. Provisional Application No. 62/324,831, filed Apr. 19, 2016, and U.S. Provisional Application No. 62/310,614, filed Mar. 18, 2016, the entire disclosures of which are incorporated herein by reference.

BACKGROUND OF THE INVENTION

Prior methods and systems for achieving hemostasis following a minimally invasive tissue removal procedure can be less than ideal in at least some respects. Prior methods and systems frequently use thermal means to stop the bleeding, such as cauterization of one or more sites within the tissue. For example, following resection of the prostate in the treatment of prostate cancer or benign prostate hyperplasia, prophylactic cauterization may be applied around the neck of the bladder to reduce bleeding. Thermal means of hemostasis can damage the surrounding parenchymal tissue when used to reduce bleeding. Therefore a safer means of hemostasis is desired following tissue resection.

Prior methods and systems frequently employ a Foley or indwelling catheter following a tissue removal procedure. The Foley catheter can allow for irrigation of the tissue volume to prevent clot buildup, and the color of the fluid outflow from the tissue volume can be monitored to determine the extent of bleeding and/or identify whether the bleeding has stopped. Such a procedure often requires a patient to stay at the hospital for an extended period of time for monitoring until hemostasis is achieved, frequently necessitating an overnight stay following the tissue removal procedure, and thus resulting in additional expenses as well as inconvenience for the patient.

In light of the above, it would be desirable to provide improved systems and methods for achieving hemostasis in a tissue volume following a minimally invasive tissue removal procedure. In particular, it would be desirable to provide improved systems and methods that can achieve hemostasis in a safe and effective manner while shortening the amount of time required to achieve hemostasis, such that the entire the tissue removal procedure can be performed as an outpatient procedure.

SUMMARY OF THE INVENTION

The present disclosure describes minimally invasive systems, apparatus, and methods for providing hemostasis within a tissue cavity defined by an internal surface of a bleeding tissue volume. The disclosed systems, apparatus, and methods are suitable for providing a hemostatic agent to a tissue volume having a proximal opening and a distal opening, without occluding the proximal opening, the distal opening, and a path extending between the proximal and distal openings with the hemostatic agent. The embodiments disclosed herein are particularly advantageous in achieving hemostasis within a closed tissue volume, such as a volume of an organ disposed between two or more organs, wherein maintaining fluid communication between the organs is helpful for the proper functioning of the organs. For example, the tissue volume may comprise a prostatic capsule of a prostate, the prostate having a proximal opening to the urethra and a distal opening to the bladder, wherein it is helpful to maintain a clear pathway from the bladder through the prostate to the urethra.

In one aspect, a method of providing treatment to a tissue enclosing a space, such as providing hemostasis, comprises advancing a catheter into the space enclosed within the tissue, and applying a treatment agent, for example a hemostatic agent or a sealant, from the catheter to the space enclosed with the tissue to inhibit bleeding from the tissue into the space. The treatment agent may be applied from a delivery port positioned proximally of a distal end of the advanced catheter. The method may further comprise positioning a distal expandable support, such as a distal balloon, coupled to the catheter adjacent a distal opening of the tissue to the space and expanding the distal expandable support to seal the distal opening. The method may further comprise positioning a proximal expandable support, such as a proximal balloon, coupled to the catheter at least partially within the space. The method may further comprise expanding the proximal expandable support to compress the sealant against the internal surface of the tissue. The method may further comprise positioning the proximal expandable support adjacent a proximal opening of the tissue to the space and expanding the proximal expandable support to seal the proximal opening. The method may further comprise moving the expanded proximal expandable support along a longitudinal axis of the catheter between the proximal opening and the distal opening to spread the sealant over the internal surface of the tissue space. The method may further comprise removing excess treatment agent from the space through an overflow port of the catheter. The method may further comprise aspirating resected tissue and fluids from the space through an aspiration port of the catheter and insufflating the space to the predetermined profile.

The hemostatic agent may be applied to an internal surface of the tissue without occluding a proximal opening of the tissue to the space, the distal opening of the tissue, and a path extending therebetween with the treatment agent.

The distal expandable support may comprise a plurality of pores such that applying the treatment agent comprises expanding the distal expandable support with the treatment agent and delivering the treatment agent from the distal expandable support through the plurality of pores into the space between the expanded distal expandable support and an internal surface of the tissue.

Applying the treatment agent from the catheter may comprise delivering the treatment agent from the catheter into the space. Delivering the treatment agent may comprise delivering the treatment agent into the space between the internal surface of the tissue and the proximal balloon in an unexpanded configuration, and expanding the proximal expandable support to compress the treatment agent against the internal surface of the tissue. The proximal expandable support may comprise a plurality of pores such that delivering the treatment agent comprises expanding the proximal expandable support with the treatment agent and delivering the treatment agent from the proximal expandable support through the plurality of pores into the space between the expanded proximal expandable support and the internal surface of the tissue space. Delivering the treatment agent may comprise delivering the treatment agent into the space between the sealed distal opening and the sealed proximal opening.

Applying the treatment agent may comprise providing a scaffold within the space, and compressing the scaffold against an internal surface of the tissue. The scaffold may be disposed over at least a portion of an external surface of the proximal expandable support such that compressing the scaffold comprises expanding the proximal expandable support to expand the scaffold, thereby compressing the scaffold against the internal surface of the tissue. The scaffold may be further disposed over at least a portion of an external surface of the distal expandable support such that expanding the distal expandable support expands the scaffold to compress the scaffold against the internal surface of the tissue near the distal opening.

Alternatively or in combination, applying the treatment agent may comprise expanding the proximal expandable support within the space in a manner so as to cause a sheath covering the treatment agent to retract or detach from the treatment agent, exposing the treatment agent to the tissue.

The proximal expandable support and the distal expandable support may be continuous with one another and may together comprise a single expandable support assembly having an expandable proximal portion and an expandable distal portion. One or more of the proximal or distal expandable support may be expanded to one or more of a spherical, toroidal, cylindrical, conical, dual cone, irregular, or dumbbell shape. One or more of the proximal or the distal expandable support may comprise a proximal or distal inflatable balloon, respectively, and the one or more of the proximal or distal expandable support may be expanded by inflating the one or more of the proximal or distal inflatable balloon, such as to a fully expanded configuration.

The catheter may comprise a delivery probe configured to deliver energy to a predetermined profile of the tissue space. Applying the treatment agent may comprise delivering a treatment agent from the delivery probe to the predetermined profile of the tissue space. Energy may be delivered from the delivery probe to the tissue at a first flow rate to resect the tissue and thereby create the tissue space having the predetermined profile, wherein delivering the treatment agent comprises delivering the treatment agent at a second flow rate lower than the first flow rate. Resected tissue and fluids may be aspirated from the space through an aspiration port of the catheter, and the space may be insufflated to the predetermined profile.

The tissue may comprise a prostatic capsule of a prostate, wherein the proximal opening comprises an opening to a urethra and the distal opening comprises a bladder neck between the prostate and a bladder. Positioning the distal expandable support may comprise positioning the distal expandable support within the bladder adjacent the bladder neck. Expanding the distal expandable support may comprise sealing the bladder neck.

One or more of the proximal or distal expandable members may be expanded to apply a pressure against the tissue. The pressure applied may be greater than a blood pressure of the subject so as to promote hemostasis. The blood pressure of the subject may be measured and the pressure to which the one or more of the proximal or distal members are expanded to may be based on the measured pressure.

A location of the catheter may be determined in response to a visual or tactile inspection of one or more indicia positioned on an outer surface of a proximal portion of the catheter advanced into the space.

One or more of the distal or the proximal expandable supports may be visualized such as with ultrasound. One or more radiopaque markers coupled to the one or more of the proximal or distal expandable supports may be visualized.

The tissue may comprise a prostatic capsule of a prostate, and the proximal expandable support may be expanded within the space in a manner to reduce contact between the expanded proximal expandable support in a fully expanded configuration and a verumontanum of the prostate. The expanded proximal expandable support in the fully expanded configuration may comprise a concavity in a region near the verumontanum of the prostate, and one or more of the catheter or the proximal expandable support may comprise a user-perceptible indicia for the concavity.

In another aspect, an apparatus for providing treatment to a tissue enclosing a space, such as providing hemostasis, comprises a catheter having a distal end and a proximal end and configured to be advanced into the space enclosed with the tissue through an opening into the enclosed space. The catheter comprises a treatment agent infusion port near the proximal end, and a treatment agent delivery port of the catheter coupled to the treatment agent infusion port. The treatment agent delivery port is configured to deliver a treatment agent introduced into the catheter through the treatment agent infusion port to the space such as to inhibit bleeding of the tissue.

The apparatus may further comprise a distal expandable support adjacent the distal end of the catheter, the distal expandable support may comprise a distal inflatable balloon fluidly coupled to the distal inflation port. The apparatus may be configured to prevent the treatment agent from occluding the opening into the space. The distal expandable support may comprise a plurality of pores, wherein the treatment agent infusion port and the distal inflation port are the same port, and wherein the expandable support introduced into the catheter is delivered to the distal expandable support to expand the distal expandable support and to subsequently enter the space through the plurality of pores of the distal expandable support. The distal expandable support may be configured to have one or more of a spherical, toroidal, cylindrical, conical, dual cone, irregular, or dumbbell shape when expanded.

The catheter may further comprise a proximal inflation port at the proximal end, and the apparatus may further comprise a proximal expandable support which may comprise a proximal inflatable balloon positioned proximally with respect to the distal expandable support. The proximal expandable support may be configured to be expanded within the space to compress the treatment agent delivered to the space against an internal surface of the tissue. The proximal expandable support may comprise a plurality of pores, wherein the treatment agent infusion port and the proximal inflation port are the same port. The treatment agent introduced into the catheter may be delivered to the proximal expandable support to expand the proximal expandable support and to subsequently enter the space through the plurality of pores of the proximal expandable support. The proximal expandable support may be configured to be expanded near a proximal opening of the tissue to seal the proximal opening, and the sealant delivery port may be positioned distally with respect to the proximal expandable support to deliver the sealant in the space between the sealed distal opening and the sealed proximal opening. The apparatus may further comprise an actuation mechanism coupled to the proximal expandable support, the actuation mechanism configured to move the proximal expandable support, in an expanded configuration, along a longitudinal axis of the catheter between the proximal opening and the distal opening to spread the sealant over the internal surface of the tissue. The proximal expandable support may be configured to have one or more of a spherical, toroidal, cylindrical, conical, dual cone, irregular, or dumbbell shape when expanded.

The catheter may further comprise a sealant overflow port distally adjacent the sealant delivery port, the sealant overflow port configured to remove excess sealant from the space.

The tissue may comprise a prostatic capsule of a prostate, and wherein the proximal expandable support has a fully expanded shape configured to reduce contact with a verumontanum of the prostate. The proximal expandable support may further comprise a user-perceptible indicia for the concavity. The proximal expandable support may have a non-uniform thickness, which may be configured to provide the proximal balloon with a predetermined shape.

The tissue may comprise a prostatic capsule of a prostate, the proximal opening may comprise an opening to a urethra, and the distal opening may comprise a bladder neck between the prostate and a bladder. The distal balloon may be sized and shaped to be advanced into the bladder and engage the bladder neck when expanded.

At least a portion of an outer surface of the distal expandable support may be textured. The distal expandable support may comprise one or more of an ultrasound hyperechoic material or a radiopaque marker to aid visualization. The distal expandable support may have a non-uniform thickness. The non-uniform thickness of the distal expandable support may be configured to provide the distal expandable support with a predetermined shape. The distal expandable support may comprise one or more of a compliant material or a non-compliant material. At least a portion of the distal expandable support may be coated with a hemostatic agent.

The proximal expandable support may comprise one or more of a compliant material or a non-compliant material. At least a portion of the proximal expandable support may be coated with a treatment agent.

The catheter may further comprise a treatment agent overflow port distally adjacent the treatment agent delivery port, the treatment agent overflow port configured to remove excess treatment agent from the space.

The apparatus may further comprise a sheath positioned over a region of the catheter adjacent the treatment agent port and coupled to the distal balloon, wherein expansion of the distal expandable support may cause the sheath to retract or detach from the region to expose the treatment agent port.

The catheter may comprise one or more indicia disposed on an outer surface of a proximal portion thereof, the one or more indicia may be configured to be visually or tactilely inspected to determine a location of the catheter relative to the tissue. The one or more indicia may comprise a plurality of bands positioned on the outer surface of the proximal portion of the catheter.

In another aspect, an apparatus for providing hemostasis to a tissue enclosing a space comprises a catheter having a distal end and a proximal end, the catheter comprising a distal balloon inflation port and a proximal balloon inflation port at the proximal end. The apparatus further comprises a distal balloon adjacent the distal end of the catheter, the distal balloon fluidly coupled to the distal balloon inflation port. The apparatus further comprises a proximal balloon proximally adjacent the distal balloon, the proximal balloon fluidly coupled to the proximal balloon inflation port. The apparatus further comprises a sealant scaffold disposed over at least a portion of an external surface of the proximal balloon. The catheter is configured to be advanced into the space through a proximal opening of the tissue, the distal balloon is configured to be expanded near a distal opening of the tissue to seal the distal opening, and the proximal balloon is configured to be expanded with the space thereby expanding and compressing the sealant scaffold against an internal surface of the tissue.

The sealant scaffold may be further disposed over at least a portion of an external surface of the distal balloon, and wherein expanding the distal balloon may expand the sealant scaffold to compress the sealant scaffold against the internal surface of the tissue space near the distal opening.

In another aspect, an apparatus for providing hemostasis to a tissue enclosing a space comprises a delivery probe having a proximal end and a distal end, the delivery probe configured to be advanced into the space through a proximal opening of the tissue. The delivery probe comprises an opening near the distal end to deliver a sealant through the proximal opening. The apparatus further comprises a processor operably coupled to the delivery probe and configured to control delivery of the sealant from the delivery probe to deliver the sealant to a predetermined profile of the tissue space. The apparatus may be configured to prevent the sealant from occluding the proximal opening.

The apparatus may further comprise a distal balloon adjacent the distal end of the delivery probe and a distal balloon inflation port at the proximal end of the delivery probe, wherein the distal balloon may be configured to be expanded near a distal opening of the tissue to seal the distal opening. The delivery probe may further comprise an aspiration port near the distal end, the aspiration port configured to remove resected tissue and fluids from the cavity. The delivery probe may further comprise an insufflation port near the distal end, the insufflation port configured to insufflate the cavity to the predetermined profile.

In another aspect, a method of providing hemostasis to a tissue enclosing a space comprises advancing a catheter into the space through a proximal opening of the tissue, wherein the tissue has the proximal opening and a distal opening to the space. The method further comprises applying a hemostatic agent from the catheter to an internal surface of the tissue to inhibit bleeding of the tissue, without occluding the proximal opening, the distal opening, and a path extending therebetween with the hemostatic agent.

In another aspect, a method of providing hemostasis within a prostatic capsule of a prostate is provided. A catheter may be advanced into the prostatic capsule through a proximal opening of the prostatic capsule. An expandable support coupled to the catheter may be positioned adjacent a distal opening of the prostatic capsule. The expandable support may be expanded to seal the distal opening. A hemostatic agent may be applied from the catheter to the internal surface of the prostatic capsule to inhibit bleeding. The hemostatic agent may be applied to the internal surface of the prostatic capsule without occluding the proximal opening, the distal opening, and a path extending therebetween with the hemostatic agent.

To apply the hemostatic agent, a sealant may be delivered from the catheter into the prostatic capsule. The sealant may be delivered through a delivery port disposed near the expandable support. The sealant may be delivered into the prostatic capsule between the internal surface of the prostatic capsule and the expandable support in an unexpanded configuration. The expandable support may be expanded to compress the sealant against the internal surface of the prostatic capsule. Excess sealant may be removed from the cavity through a sealant overflow port of the catheter.

The expandable support may comprise a plurality of pores. To deliver the sealant, the expandable support with the sealant may be expanded and the sealant may be delivered from the expandable support through the plurality of pores into the prostatic capsule between the expanded expandable support and the internal surface of the prostatic capsule.

To apply the hemostatic agent, a sealant scaffold may be provided within the prostatic capsule, and the sealant scaffold may be compressed against the internal surface of the prostatic capsule. The sealant scaffold may be disposed over at least a portion of an external surface of the expandable support. To compress the sealant scaffold, the expandable support may be expanded to expand the sealant scaffold, thereby compressing the sealant scaffold against the internal surface of the prostatic capsule.

The catheter may comprise a delivery probe configured to deliver energy to a predetermined profile of the tissue space, and to apply the hemostatic agent, a sealant may be delivered from the delivery probe to the predetermined profile of the tissue space. Energy may be delivered from the delivery probe to the tissue space at a first flow rate to resect the tissue space and thereby create the cavity having the predetermined profile. The sealant may be delivered at a second flow rate lower than the first flow rate. Resected tissue and fluids may be aspirated from the cavity through an aspiration port of the catheter, and the cavity may be insufflated to the predetermined profile.

The proximal opening may comprise an opening to a urethra and the distal opening comprises a bladder neck between the prostate and a bladder. The distal balloon may be positioned within the bladder adjacent the bladder neck, and the distal balloon may be expanded to seal the bladder neck.

The expandable support may be expanded to a pressure greater than a blood pressure of a subject. The target pressure may be determined in response to a blood pressure of a patient, which may be determined or measured.

The expandable support may be visualized, such as with ultrasound. One or more radiopaque markers coupled to the expandable support may be visualized to visualize the expandable support.

The expandable support may be expanded to one or more of a spherical, toroidal, cylindrical, conical, dual cone, irregular, or dumbbell shape.

The expandable support may be expanded in a manner to reduce contact between the expanded expandable support in a fully expanded configuration and a verumontanum of the prostate. The expanded expandable support in the fully expanded configuration may comprise a concavity in a region near the verumontanum of the prostate. One or more of the catheter or the expandable support may comprise a user-perceptible indicia for the concavity.

The hemostatic agent may be covered by a sheath, and expanding the expandable support may cause the sheath to retract or detach from the hemostatic agent, exposing the hemostatic agent.

The expandable support may comprise an inflatable balloon and the expandable support may be expanded by inflating the inflatable balloon.

The expandable support may comprise a distal expandable support, and a proximal expandable support coupled to the catheter may be positioned at least partially within the prostatic cavity. The hemostatic agent may be delivered into the prostatic capsule between the internal surface of the prostatic capsule and the proximal expandable support in an unexpanded configuration. The proximal expandable support may be expanded to compress the sealant against the internal surface of the prostatic capsule. The proximal expandable support may be positioned adjacent the proximal opening and the proximal expandable support may be expanded to seal the proximal opening. The sealant may be delivered into the cavity between the sealed distal opening and the sealed proximal opening. The proximal expandable support may be expanded and moved along a longitudinal axis of the catheter between the proximal opening and the distal opening to spread the sealant over the internal surface of the prostatic capsule. The proximal expandable support may comprise a proximal inflatable balloon, and the proximal expandable support may be expanded by inflating the proximal inflatable balloon. The expandable support may comprise the proximal expandable support and the distal expandable support, the distal expandable support may comprise a distal balloon in fluid communication with the proximal balloon, inflating the proximal inflatable balloon may also inflate the distal inflatable balloon.

A location of the catheter may be determined in response to a visual or tactile inspection of one or more indicia positioned on an outer surface of a proximal portion of the catheter advanced into the space. The one or more indicia may comprise a plurality of bands positioned on the outer surface of the proximal portion of the catheter.

In another aspect, an apparatus for providing hemostasis within a cavity defined by an internal surface of a bleeding tissue space is provided. The apparatus may comprise a catheter having a distal end and a proximal end, a balloon adjacent the distal end of the catheter, and a sealant delivery port of the catheter proximally adjacent to the balloon. The catheter may comprise a distal balloon inflation port near the distal end and a sealant infusion port at the proximal end. The balloon may be fluidly coupled to the distal balloon inflation port. The sealant delivery port may be fluidly coupled to the sealant infusion port. The catheter may be configured to be advanced into the cavity through a proximal opening of the tissue space. The balloon may be configured to be expanded near a distal opening of the tissue space to reversibly seal the distal opening. The sealant delivery port may be configured to deliver a sealant introduced into the catheter through the sealant infusion port to the cavity to inhibit bleeding of the tissue space.

The apparatus may be configured to prevent the sealant from occluding the distal opening, the proximal opening, and a path extending therebetween.

The balloon may comprise a distal balloon. The catheter may further comprise a proximal balloon inflation port at the proximal end. The apparatus may further comprise a proximal balloon positioned proximally with respect to the distal balloon. The proximal balloon may be configured to be expanded within the cavity to compress the sealant delivered to the cavity against the internal surface of the tissue space. The proximal balloon may comprise a plurality of pores, the sealant infusion port and the proximal balloon inflation port may be the same port, and the sealant introduced into the catheter may be delivered to the proximal balloon to expand the proximal balloon and to subsequently enter the cavity through the plurality of pores of the proximal balloon. The proximal balloon may be configured to be expanded near a proximal opening of the tissue space to seal the proximal opening, and the sealant delivery port may be positioned distally with respect to the proximal balloon to deliver the sealant in the cavity between the sealed distal opening and the sealed proximal opening.

The apparatus may further comprise an actuation mechanism coupled to the proximal balloon. The actuation mechanism may be configured to move the proximal balloon, in an expanded configuration, along a longitudinal axis of the catheter between the proximal opening and the distal opening to spread the sealant over the internal surface of the tissue space.

The catheter may further comprise a sealant overflow port distally adjacent the sealant delivery port. The sealant overflow port may be configured to remove excess sealant from the cavity.

The tissue space may comprise a prostatic capsule of a prostate. The proximal opening may comprise an opening to a urethra, the distal opening may comprise a bladder neck between the prostate and a bladder, and the distal balloon may be sized and shaped to be advanced into the bladder and engage the bladder neck when expanded.

In another aspect, an apparatus for providing hemostasis within a cavity defined by an internal surface of a bleeding tissue space is provided. The apparatus may comprise a catheter having a distal end and a proximal end, a distal balloon adjacent the distal end of the catheter, a proximal balloon proximally adjacent the distal balloon, and a sealant scaffold disposed over at least a portion of an external surface of the proximal balloon. The catheter may comprise a distal balloon inflation port near the distal end and a proximal balloon inflation port near the proximal end. The distal balloon may be fluidly coupled to the distal balloon inflation port. The proximal balloon may be fluidly coupled to the proximal balloon inflation port. The catheter may be configured to be advanced into the cavity through a proximal opening of the tissue space. The distal balloon may be configured to be expanded near a distal opening of the tissue space to seal the distal opening. The proximal balloon may be configured to be expanded with the cavity thereby expanding and compressing the sealant scaffold against the internal surface of the tissue space. The sealant scaffold may be further disposed over at least a portion of an external surface of the distal balloon. Expanding the distal balloon may expand the sealant scaffold to compress the sealant scaffold against the internal surface of the tissue space near the distal opening.

In another aspect, an apparatus for providing hemostasis non-invasively within a cavity defined by an internal surface of a bleeding tissue space is provided. The apparatus may comprise a delivery probe having a proximal end and a distal end. The delivery probe may be configured to be advanced into the cavity through a proximal opening of the tissue space, and may comprise an opening near the distal end to deliver a sealant through the opening into the cavity. The apparatus may further comprise a processor operably coupled to the delivery probe and configured to control delivery of the sealant from the delivery probe to deliver the sealant to a predetermined profile of the tissue space.

The apparatus may be configured to prevent the sealant from occluding the distal opening, the proximal opening, and a path extending therebetween.

The apparatus may further comprise a distal balloon adjacent the distal end of the delivery probe and a distal balloon inflation port at the proximal end of the delivery probe. The distal balloon may be configured to be expanded near a distal opening of the tissue space to seal the distal opening.

The delivery probe may further comprise an aspiration port near the distal end. The aspiration port may be configured to remove resected tissue and fluids from the cavity. The delivery probe may further comprise an insufflation port near the distal end, the insufflation port configured to insufflate the cavity to the predetermined profile.

In another aspect, a method of providing hemostasis to a tissue enclosing a space is provided. The tissue may have a proximal opening and a distal opening to the space. A catheter may be advanced into the space through the proximal opening of the tissue. A hemostatic agent may be applied from the catheter to an internal surface of the tissue to inhibit bleeding of the tissue, without occluding the proximal opening, the distal opening, and a path extending therebetween with the hemostatic agent.

In another aspect, an apparatus for providing hemostasis to a tissue enclosing a space is provided. The apparatus may comprise a catheter having a distal end and a proximal end, a catheter balloon inflation port near the proximal end, a balloon fluidly coupled to the balloon inflation port, and a sealant and a therapeutic agent supported with the balloon. The catheter may be configured to be advanced into the space through a proximal opening of the tissue. The balloon may be configured to be expanded within the space thereby expanding and urging the sealant against an internal surface of the tissue.

In another aspect, an apparatus for providing hemostasis to a tissue enclosing a space is provided. The apparatus may comprise a catheter having a distal end and a proximal end, a catheter balloon inflation port near the proximal end, an expandable member coupled to the distal end of the catheter, and a sealant and a therapeutic agent supported with the expandable member. The catheter may be configured to be advanced into the space through a proximal opening of the tissue. The expandable member may be configured to be expanded within the space thereby expanding and urging the sealant against an internal surface of the tissue. The expandable member may comprise one or more of a self-expanding nitinol stent, a polymer-based stent, a dissolvable stent, one or more staples, one or more sutures, one or more barbs, or any combination thereof.

In another aspect, a method of providing hemostasis to a tissue enclosing a space of a subject is provided. A catheter may be applied into the space enclosed within the tissue. An expandable support coupled to the catheter may be positioned adjacent a distal opening of the tissue to the space. The expandable support may be expanded to a balloon pressure greater than a blood pressure of the subject, thereby applying compression to the tissue with the expandable support. The balloon pressure may be determined in response to a blood pressure of the subject, which may be determined or measured.

The expandable support may be visualized, such as with ultrasound. One or more radiopaque markers coupled to the expandable support may be visualized to visualize the expandable support.

The expandable support may be expanded to one or more of a spherical, toroidal, cylindrical, conical, dual cone, irregular, or dumbbell shape.

The expandable support may comprise an inflatable balloon, and the expandable support may be expanded by inflating the inflatable balloon.

The tissue may comprise a prostatic capsule of a prostate, and wherein the expandable support may be expanded in a way to reduce contact between the expanded expandable support in a fully expanded configuration and a verumontanum of the prostate. The expanded expandable support in the fully expanded configuration may comprise a concavity in a region near the verumontanum of the prostate. One or more of the catheter or the expandable support may comprise a user-perceptible indicia for the concavity.

When the expandable support is expanded to seal the opening, the expanded expandable support may conform to a shape of the space.

A size of the expandable support may be selected in response to a volume of the space prior to applying the catheter and positioning the expandable support.

The tissue may comprise a prostatic capsule of a prostate, the proximal opening may comprise an opening to a urethra, and the distal opening may comprise a bladder neck between the prostate and a bladder. The expandable support may be positioned within the bladder adjacent the bladder neck, and the expandable support may be expanded to seal the bladder neck. The expandable support may be expanded to an expanded configuration at least partially filling the prostatic capsule and extruding into the bladder. The expandable support may comprise a rigid bladder portion for extruding into the bladder.

The expandable support may comprise a distal expandable support. A proximal expandable support coupled to the catheter may be positioned adjacent the distal opening of the tissue to the space. The proximal expandable support may be expanded to apply compression to the tissue in the space. The proximal expandable support may be made of one or more of a compliant material or a non-compliant material.

The expandable support may be expanded by pressing a mesh disposed over the expandable support against the tissue. The expandable support may further be collapsed, retracting the collapsed expandable support and the catheter from the space, and leaving the mesh in the space. The mesh may be at least partially bioabsorbable or resorbable. The mesh may be coated with a clot promoting agent. The clot promoting agent may comprise one or more of fibrin or thrombin.

When the expandable support is expanded, a scaffold disposed over the expandable support may be pressed against the tissue. The scaffold may comprise a silicone shaped stent. The expandable support may further be collapsed, retracting the collapsed expandable support and the catheter from the space, and leaving the scaffold in the space. The scaffold may be removed from the space after a time delay such as between about 1 to 3 days.

The balloon may be coated with a hemostatic agent.

The expandable support may comprise a plurality of pores, and a therapeutic agent may be delivered from the balloon through the plurality of pores into the space between the expanded expandable support and an internal surface of the tissue.

A location of the catheter may be determined in response to a visual or tactile inspection of one or more indicia positioned on an outer surface of a proximal portion of the catheter advanced into the space. The one or more indicia may comprise a plurality of bands positioned on the outer surface of the proximal portion of the catheter.

In another aspect, a method of providing hemostasis to a tissue enclosing a space within a subject is provided. A blood pressure of the subject may be received. A catheter having an expandable support may be advanced into the space enclosed within the tissue. A first internal pressure of the expandable support may be measured. The expandable support may be expanded to a second internal pressure greater than the blood pressure of the subject in response to the received blood pressure in order to apply compression to the tissue. The expandable support may comprise an inflatable balloon, and the expandable support may be expanded by inflating the inflatable balloon.

In another aspect, an apparatus for providing hemostasis non-invasively within a cavity defined by an internal surface of a bleeding tissue space of a subject may be provided. The apparatus may comprise an expandable member configured to be advanced into the cavity through an opening of the tissue space and to apply compression to the internal surface of the bleeding tissue space. The apparatus may further comprise a processor operably coupled to the expandable support and configured to (i) receive a blood pressure of the subject and (ii) control expansion of the expandable member in response to the received blood pressure. The processor may be further configured to control expansion of the expandable member so that the expandable member is expanded to an internal pressure greater than the received blood pressure of the subject in order to apply compression to the tissue. The processor may be configured to measure a first internal pressure of the expandable support and cause the expandable member to expand to a second internal pressure greater than the blood pressure of the subject in response to the received blood pressure. The expandable support may comprise an inflatable balloon, and the controller is configured to control inflation of the inflatable balloon.

In another aspect, an apparatus for providing hemostasis to a prostatic capsule of a prostate may be provided. The prostatic capsule may enclose a space. The apparatus may comprise a catheter having a distal end and a proximal end and an expandable support assembly adjacent the distal end of the catheter. The catheter may be configured to be advanced into the space enclosed with the prostatic capsule through an opening into the enclosed space. The expandable support assembly may have an expanded configuration configured to anchor along a bladder neck adjacent the distal opening to the prostatic capsule and at least partially fill the space enclosed by the prostatic capsule.

The expandable support assembly may comprise an inflatable balloon assembly.

The expanded configuration of the expandable support assembly may comprise an hourglass shape having a distal bladder region, a proximal prostatic region, and a neck region therebetween. The neck region may have a greater wall thickness than one or more of the distal bladder region and the proximal prostatic region. The distal bladder region may comprise a rigid balloon.

The expandable support assembly may comprise a proximal expandable support and a distal expandable support. The distal expandable support or the proximal expandable support may be configured to have one or more of a spherical, toroidal, cylindrical, conical, dual cone, irregular, or dumbbell shape when expanded.

The expandable support assembly may have an expanded shape configured to reduce contact with a verumontanum of the prostate.

At least a portion of an outer surface of the expandable support assembly may be textured.

The expandable support assembly may comprise one or more of an ultrasound hyperechoic material or a radiopaque marker to aid visualization.

The expandable support assembly may have a non-uniform thickness. The non-uniform thickness of the expandable support assembly may be configured to provide the expandable support assembly with a predetermined shape. The non-uniform thickness expandable support assembly may be configured to be expanded in a stepwise manner.

The expandable support assembly may comprise one or more of a compliant material or a non-compliant material.

At least a portion of the expandable support assembly may be coated with a hemostatic agent.

The catheter may comprise one or more indicia disposed on an outer surface of a proximal portion thereof. The one or more indicia may be configured to be visually or tactilely inspected to determine a location of the catheter relative to the tissue. The one or more indicia may comprise a plurality of bands positioned on the outer surface of the proximal portion of the catheter.

The apparatus may further comprise a bulb positioned on the catheter proximal of the expandable support assembly. The bulb may be configured to be positioned in the ureter when the expandable support assembly is positioned in the prostatic capsule so as to minimize migration of the catheter. The bulb may be expandable or inflatable.

In many embodiments, the apparatus may further comprise a scope to visualize the enclosed space such as when the tissue sealant is delivered to the tissue.

In many embodiments, the apparatus may further comprise a scope to visualize tissue of the enclosed space and a sheath with a balloon. The scope may comprise a shaft to view the tissue space. The shaft may comprise a length, and the sheath with the balloon may comprise a length from a proximal end to a distal end sized smaller than the length of the balloon.

In many embodiments, the treatment agent may comprise a therapeutic agent.

In many embodiments, the treatment agent may comprise a mixture of a gel and a therapeutic agent.

In many embodiments, the treatment agent may comprise a chemotherapeutic agent.

In many embodiments, the expandable support may be expanded by successively expanding the expandable support to a plurality of predetermined sizes.

In many embodiments, the expandable support has a non-uniform thickness to provide stepwise expansion.

In many embodiments, tension may be applied to the catheter with the expandable support expanded within the space or prostatic capsule such as by coupling a proximal portion of the catheter to a preselected weight. The preselected weight may be coupled to one or more of a stirrup or bed frame. The preselected weight may comprise a fluid container. The tension applied to the catheter by the preselected weight may be measured such as with a tension measurement element or scale coupled to the catheter. The preselected weight may be selected in response to a measured blood pressure.

In another aspect, an apparatus for maintaining a position of a catheter advanced into a bodily member may be provided. The apparatus may comprise an enclosure adapted to enclose the bodily member and the catheter positioned at least partially within the bodily member. The enclosure may be shaped to conform and apply pressure to the bodily member to resist repositioning of the enclosure when enclosing the bodily member. A distal tip of the enclosure may be configured to couple to a segment of the catheter extending out of the bodily member. The bodily member may comprise a penis and the catheter may be extending out of a urethral os. The flexible enclosure may be configured to be concentric with a urethra of the penis when enclosing the penis.

The enclosure may comprise a flexible enclosure. The enclosure may be configured to be coupled to the segment of the catheter extending out of the bodily member through a retainer element coupled to the segment. The retainer element may comprise a soft, compliant material to minimize irritation against tissue of the bodily member. The enclosure may be at least partially cylindrical in shape.

The catheter may comprise one or more expandable supports configured to be expanded within one or more of a urethra, a prostatic capsule of a prostate, or a bladder to be lodged therein.

The enclosure may be configured to be coupled to a pelvic or groin mount. The bodily member may comprise a penis, and the pelvic or groin mount may be configured to pull on the enclosure and the penis to align a urethra of the penis with a urethral sphincter.

The apparatus may further comprise a tension element configured to couple to one or more of the catheter or the flexible enclosure to align the urethra with the urethral sphincter. The tension measurement element or scale may be configured to couple to the tension element.

In another aspect, a method for maintaining a position of a catheter advanced into a bodily member may be provided. The bodily member may be enclosed at least partially within an enclosure so that a proximal segment of the catheter extends from a distal tip of the flexible enclosure. A distal tip of the enclosure may be coupled to the proximal segment of the catheter extending out of the bodily member. The enclosure may be shaped to conform and apply pressure to the bodily member to resist repositioning of the enclosure when enclosing the bodily member. The bodily member may comprise a penis and the catheter is extending out of a urethral os. To enclose the bodily member at least partially within the enclosure, the flexible enclosure may be positioned to be concentric with a urethra of the penis.

The enclosure may comprise a flexible enclosure. The enclosure may be coupled to the segment of the catheter extending out of the bodily member through a retainer element coupled to the segment. The retainer element may comprise a soft, compliant material to minimize irritation against tissue of the bodily member. The enclosure may be at least partially cylindrical in shape.

One or more expandable supports of the catheter may be expanded within one or more of a urethra, a prostatic capsule of a prostate, or a bladder to be lodged therein.

The enclosure may be coupled to a pelvic or groin mount. The bodily member may comprise a penis, and the enclosure and the penis may be pulled with the pelvic or groin mount to align a urethra of the penis with a urethral sphincter.

A tension element may be coupled to one or more of the catheter or the flexible enclosure to align the urethra with the urethral sphincter. Tension applied by the tension element may be measured using a tension measurement element or scale coupled thereto.

In another aspect, an apparatus for maintaining a position of a catheter advanced into a bodily member may be provided. The apparatus may comprise a base configured to be placed over a pelvis or groin, at least one extension struts coupled to and extending from the base, and a retainer element coupled to at least one extension strut and configured to releasably couple to the catheter. The base and the at least one extension strut may together define an accommodation space for one or more of a penis or scrotum to pass therethrough.

The base may comprise a pelvic or groin mount contoured to match a shape of the pelvis or groin. The base may have an opening to allow the catheter to pass from an exterior of the base to within a perimeter of the base and within the accommodation space. The base may be U-shaped. The base may comprise a malleable wire with a soft covering.

The at least one extension strut may be coupled to the base with a hinge, which may be adjustable. Alternatively or in combination, the at least one extension strut may be coupled to the pelvic or groin mount with a rigid coupling.

The retainer element may comprise a clamp for clamping one or more of the catheter or a medical tape flag coupled to the catheter.

The apparatus may further comprise an adjustable tensioning mechanism coupled to one or more of the extension struts. The apparatus may further comprise a tension measurement element or scale coupled to the at least one extension strut. The adjustable tensioning mechanism may comprise a constant force spring configured to apply a substantially constant tension to the catheter over a stroke length of the catheter. The constant force spring may apply a substantially constant tension to the catheter over a range greater than the stroke length, such as within about 25% or even within about 50% more than the stroke length. The stroke length may be at least 0.5 mm. The stroke length may be in a range of about 0.5 cm to about 8 cm, a range of about 1 cm to about 8 cm, a range of about 1 cm to about 5 cm, or a range of about 2 cm to about 3 cm. A position of the retainer member relative to the base may be adjustable to adjust a tension applied to the catheter.

One or more of the extension struts may be rounded such as to maximize the accommodation space.

The apparatus may further comprise a belt or strap coupled to the base. The belt or strap may be configured to be wrapped around and strapped to at least a portion of a patient to maintain a position of the base over the pelvis or groin.

The at least one extension strut may comprise a plurality of extension struts, the base and the plurality of extension struts together defining the accommodation space. The apparatus may further comprise a cross-member coupling two or more of the extension struts to one another. The retainer element may be positioned between the cross-member and the base.

The apparatus may be collapsible into a flat package.

In another aspect, a method for maintaining a position of a catheter advanced into a bodily member may be provided. One or more of a penis or scrotum may be passed through a base, enclosing the one or more of the penis or scrotum within an accommodation space defined by the base and at least one extension strut coupled to and extending from the base. The catheter may be coupled to a retaining element coupled to the at least one extension strut. The base may comprise a pelvic or groin mount contoured to match a shape of the pelvis or groin.

A catheter may be passed from an exterior of the base through an opening of the base to within a perimeter of the base and within the accommodation space.

An angle of the at least one extension strut relative to the base may be adjusted with a hinge coupling the one or more of the extension struts to the base.

A medical tape may be coupled to the catheter to form a flag and one or more of the catheter or the medical tape flag may be clamped with a clamp of the retainer element.

A tension applied to the retainer element and the catheter coupled thereto may be adjusted with an adjustable tensioning mechanism coupled to one or more of the extension struts.

A tension applied to the retainer element and the catheter coupled thereto may be measured with a tension measurement element or scale coupled to the at least one extension strut. The adjustable tensioning mechanism may comprise a constant force spring configured to apply a substantially constant tension to the catheter over a stroke length of the catheter. The constant force spring may apply a substantially constant tension to the catheter over a range greater than the stroke length, such as within about 25% or even within about 50% more than the stroke length. The stroke length may be at least 0.5 mm. The stroke length may be in a range of about 0.5 cm to about 8 cm, a range of about 1 cm to about 8 cm, a range of about 1 cm to about 5 cm, or a range of about 2 cm to about 3 cm. The tension may be adjusted by adjusting a distance between the retainer element coupling the catheter and the base over the pelvis or groin.

A belt or strap coupled to the base around may be wrapped around at least a portion of the patient to maintain a position of the base over the pelvis or groin.

The at least one extension strut may comprise a plurality of extension struts, the base and the plurality of extension struts defining the accommodation space.

The base, the at least one extension strut, and the retainer element may be collapsed into a flat package.

In another aspect, a method for providing treatment to a tissue enclosing a space is provided. A catheter may be advanced into the space enclosed within the tissue such that at least a portion of the catheter is extending outside of a body of a patient. An expandable member of the catheter may be expanded within the space enclosed within the tissue. Tension may be applied to the catheter with a constant force spring.

The constant force spring may be coupled to at least the portion of the catheter extending outside of the body of a patient. The tissue may comprise a prostatic capsule, and the catheter may extend outside of the body of the patient from a penis of the patient. The constant force spring may be coupled to a leg of the patient to apply tension to the catheter toward feet of the patient. Alternatively, the constant force spring may be coupled to one or more of an abdomen, a chest, an arm, a neck, or a head of the patient to apply tension to the catheter toward the head of the patient.

A substantially constant tension may be applied to the catheter over at least a stroke length of the catheter. The substantially constant tension may be applied within about 25% or about 50% over the stroke length of the catheter. The substantially constant tension may be applied within about 50% over the stroke length of the catheter. The stroke length may be in a range of about 0.5 cm to about 8 cm, a range of about 1 cm to about 8 cm, a range of about 1 cm to about 5 cm, or a range of about 2 cm to about 3 cm.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 21A shows a front section view of a prostate, urethra, and bladder, in accordance with embodiments;

FIG. 21B shows a side section view of a prostate, urethra, and bladder, in accordance with embodiments;

FIGS. 22A-22E show various sectional schematic views of a catheter with inflatable balloon assembly comprising a single compliant balloon to provide compression hemostasis, in accordance with embodiments;

FIGS. 25A-25F show various sectional schematic views of a catheter with inflatable balloon assembly shaped to provide compression hemostasis and reduce compression of the verumontanum, in accordance with embodiments;

FIGS. 38A, 38B, 38C, 38D, and 38E show front, side, top, perspective, and magnified views, respectively, of another saddle traction device configured to resist repositioning of an anatomical member and catheter enclosed therewithin, in accordance with embodiments;

FIGS. 41A, 41B, 41C, 41D, and 41E show front, side, top, perspective, and perspective views, respectively, of another saddle traction device configured to resist repositioning of an anatomical member and catheter enclosed therewithin, in accordance with embodiments.

DETAILED DESCRIPTION OF THE INVENTION

Figure 1A:
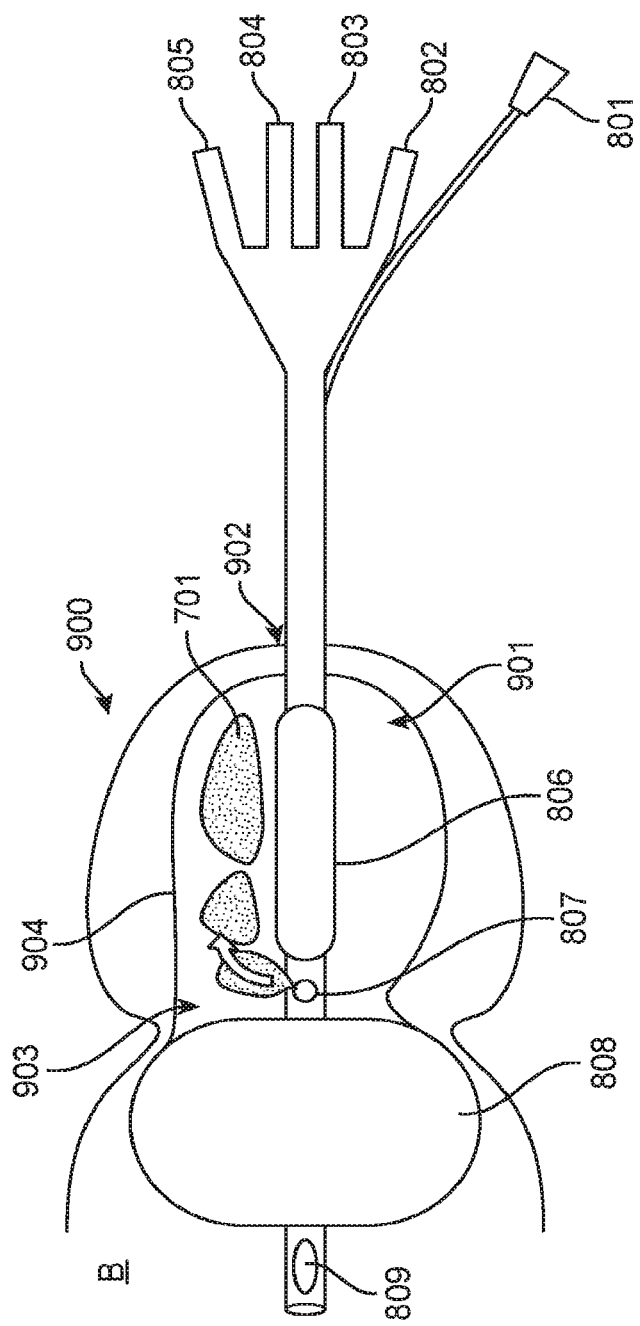
FIGS. 1A-1C show sectional schematic views of a sealant delivery device comprising a catheter, in accordance with embodiments.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The methods and apparatus of the present disclosure is well suited for combination with the following patents and applications: U.S. Pat. No. 7,882,841, issued Feb. 8, 2011, entitled "MINIMALLY INVASIVE METHODS AND DEVICES FOR THE TREATMENT OF PROSTATE DISEASES"; U.S. Pat. No. 8,814,921, issued Aug. 26, 2014, entitled "TISSUE ABLATION AND CAUTERY WITH OPTICAL ENERGY CARRIED IN FLUID STREAM"; U.S. Pat. No. 9,232,959, entitled "MULTI FLUID TISSUE RESECTION METHODS AND DEVICES"; International Application No. PCT/US2013/028441, filed on Feb. 28, 2013, entitled "AUTOMATED IMAGE-GUIDED TISSUE RESECTION AND TREATMENT"; International Application No. PCT/US2014/054412, filed on Sep. 5, 2014, entitled "AUTOMATD IMAGE-GUIDED TISSUE RESECTION AND TREATMENT"; International Application No. PCT/US2015/037521, filed Jun. 24, 2015, entitled "TISSUE SAMPLING AND CANCER TREATMENT METHODS AND APPARATUS"; International Application No. PCT/US2015/038605, filed on Jun. 30, 2015, entitled "FLUID JET TISSUE RESECTION AND COLD COAGULATION (AQUABLATION) METHODS AND APPARATUS"; and International Application No. PCT/US2015/048695, filed on Sep. 4, 2015, entitled "PHYSICIAN CONTROLLED TISSUE RESECTION INTEGRATED WITH TREATMENT MAPPING OF TARGET ORGAN IMAGES", the entire disclosures of which are incorporated herein by reference, and suitable for combination in accordance with embodiments disclosed herein.

As used herein, the terms proximal and distal in the context of the apparatus refer to proximal and distal as referenced from the apparatus outside the patient, such that proximal may refer to components outside the patient or nearer the operator and distal may refer to components inside the patient or further from the operator.

As used herein, the terms proximal and distal in the context of anatomical locations are with respect to the operator of the apparatus, such that proximal may refer to anatomical locations nearer the operator and distal may refer to anatomical locations further from the operator.

As used herein, the terms "cavity", "closed tissue volume" and "space" are used interchangeably to refer to a space enclosed within a tissue.

Although specific reference is made to treatment of the prostate, the methods and systems disclosed herein can be used with many tissues. For example, the embodiments disclosed herein may be used to treat any tissue cavity defined by an internal surface of a bleeding tissue volume. The embodiments described herein may provide hemostasis to a tissue enclosing a space to inhibit bleeding from the tissue into the space. Embodiments as disclosed herein may be used to treat any tissue cavity comprising a proximal opening and a distal opening, the proximal and distal openings allowing the tissue volume to fluidly communicate with other organs or parts of the body adjacent the tissue volume. For example, although specific reference is made to the advancement of the hemostasis device through the urethra into the prostate, and through the bladder neck into the bladder, a hemostasis device as described herein may be advanced through any proximal opening of a tissue cavity into the cavity, and through any distal opening of the tissue cavity into another organ or body part adjacent the tissue volume.

The methods and systems disclosed herein relate to the administration of a hemostatic material or sealant to fill in whole, or in part, any bleeding closed tissue volume. Such tissue volumes may comprise tissue spaces or voids occurring naturally, for example an aneurysm, fissure, or postpartum hemorrhage of the uterus. Such tissue volumes may for example be formed as a result of tissue removal of unnecessary or undesirable growths, fluids, cells, or tissues. The methods and systems disclosed herein are well-suited for treating closed tissue volumes remaining after tumor resection, endometrial ablation, polyp removal, cyst removal, and the like.

The methods and systems disclosed herein are well-suited for treating many types of closed tissue volumes such as within the nose, stomach, eye, spine, brain, rectum, prostate, uterus, cervix, liver, kidney, bowel, pancreas, lung, breast, muscle, and the like.

As used herein, the term "sealant" may refer to a hemostatic agent, a gel, a flowable material containing particles, a tissue sealant, or adhesive. Further, the sealants used herein may be combined with therapeutic agents such as anesthetics, radiopharmaceuticals, antibiotics, chemotherapeutics, and the like.

The methods and systems disclosed herein may for example employ one or more of the following sealants commonly used in urologic surgery practices: BioGlue® Surgical Adhesive (CryoLife), Surgicel® (Ethicon), Floseal® Hemostatic Matrix (Baxter Healthcare), TISSEL® (Baxter Healthcare), COSEAL Surgical Sealant (Baxter Healthcare), TachoSil® (Baxter Healthcare), SPONGOSTAN™ Absorbable Haemostatic Gelatin Sponge (Ethicon), Glubran 2™ (MediVogue), Hemaseel APR™ (Haemacure Corporation), or the like. Other sealants which may be used include Dermabond™, Gelfoam®, Surgifoam™, Avitene®, Helistat®, Superstat®, Instat®, Surgiflo™, Thrombinar®, rFVIIa, and the like. Possible sealant classes which may be used may include fibrin sealants, PEG polymers, biologic surgical GRF glues, thrombins, polymeric hydrogels, topical hemostats, anti-fibrinolytics, matrix hemostats, and other hemostatic agents. Sealants may be liquid, gel, or dry. Other agents that may be applied may include Afrin® (oxymetazoline), epinephrine, or platelet-rich plasma (PRP).

The methods and systems disclosed herein may be configured to apply a sealant to the internal surface of a tissue space without occluding a proximal opening of the tissue space, a distal opening of the tissue space, or a path extending therebetween with the hemostatic sealant.

As used herein, the terms closed tissue volume, tissue cavity, tissue space, and tissue void may be used interchangeably.

Figure 1B:
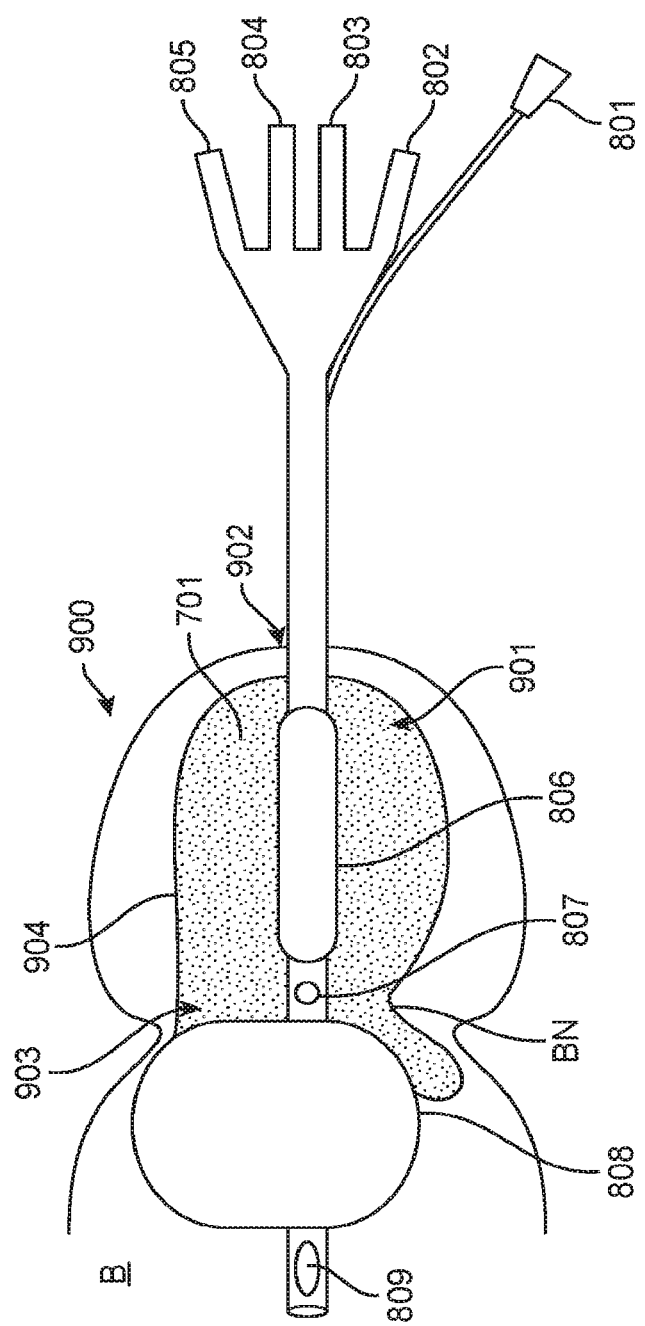
Figure 1C:
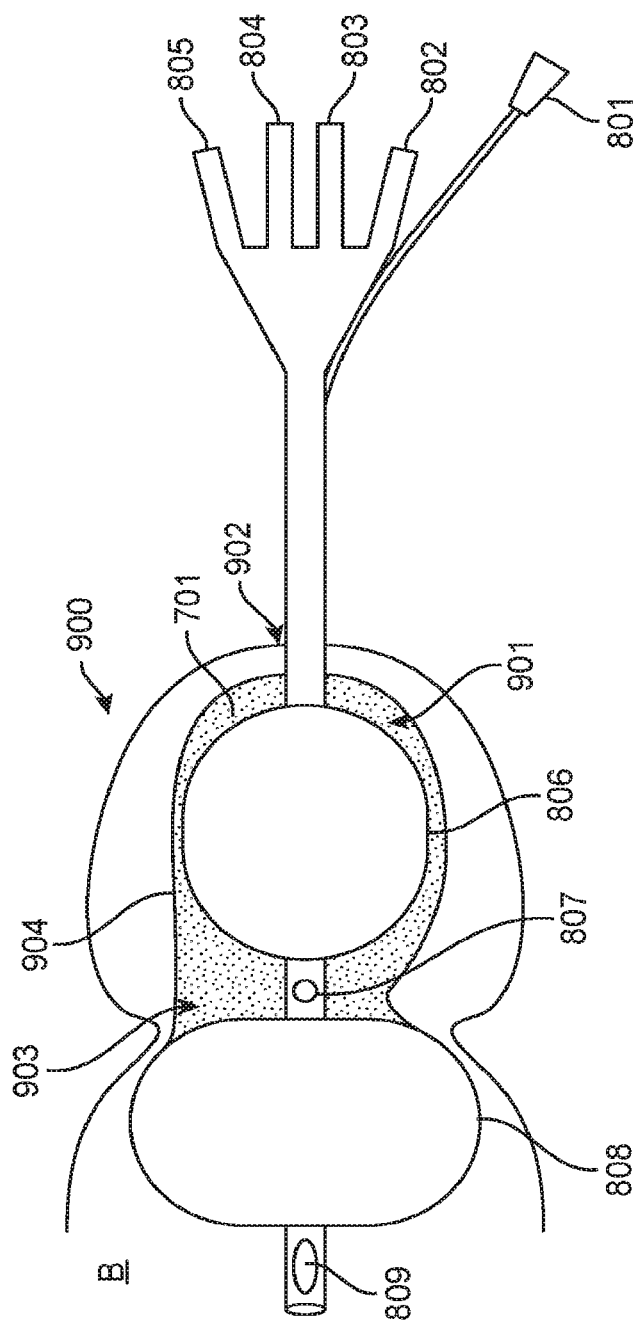

FIGS. 1A-1C show an embodiment of a minimally invasive sealant delivery device. The sealant delivery device may be a modified Foley catheter for example. A conventional three-way Foley irrigation catheter is a large indwelling urinary catheter comprising three lumens. The first lumen may be used to inflate a distal balloon used to retain the catheter in the bladder. The second lumen may be used for irrigation. The third lumen may be used for drainage of urine. The catheter simultaneously allows fluid to run into and drain out of the bladder. Foley catheters are typically large enough (e.g. 16-24ch) to accommodate the passage of clots from the bladder.

The sealant delivery device may for example be used to deliver a hemostatic agent or sealant into a cavity created by tissue resection in the prostatic capsule. The cavity may be defined by an internal surface of the tissue volume, such as the resected surface of the prostatic capsule. The sealant delivery device may comprise a catheter comprising a distal balloon and a proximal balloon and may be delivered through the urethra such that distal balloon and proximal balloon are fully inserted into the bladder and prostatic capsule, respectively. The catheter may be sized and shaped to the closely fit within the proximal opening of the prostatic capsule to the urethra, such that when the catheter is advanced into the prostatic capsule, the catheter body substantially seals off the proximal opening. The distal balloon may be positioned adjacent to a distal opening of the tissue space so as to seal the bladder upon inflation and close off the tissue resection cavity. The proximal balloon may be positioned so as to reside within the resection cavity of the prostatic capsule.

The catheter may further comprise one or more of an irrigation port, a drainage port, an inflation port for the distal bladder balloon, an inflation port for the proximal prostatic balloon, or a sealant infusion port. The inflation ports may be fluidly coupled to the balloons and used to inflate the distal and proximal balloons, respectively. The irrigation and drainage ports may be used to introduce fluids, such as saline and medications, into the bladder and remove fluids, such as urine, from the bladder, respectively, via one or more ports at the distal end of the catheter. The prostatic capsule may be sealed off from the bladder while still allowing for the passage of fluids to and from the bladder when the distal balloon is inflated using the inflation port for the distal balloon. The sealant infusion port may be coupled to a sealant delivery port and used to deliver sealant to the resection cavity prior to, during, or after inflation of the distal balloon.

FIG. 1A shows delivery of a sealant 701 into the resection cavity 901 of the prostatic capsule 900. The catheter may be advanced into the prostatic capsule 900 through the proximal opening 902 of the prostatic capsule 900. The sealant 701 may be introduced or infused into the catheter through a sealant infusion port 801 located near the proximal end of the catheter. The sealant 701 may be delivered to the resection cavity 901 via a sealant delivery port 807 in fluid communication with the sealant infusion port 801 and located near the distal end of the catheter residing inside the prostatic capsule 900. The sealant delivery port 807 may, for example, be located between the distal balloon 808 and the proximal balloon 806.

FIG. 1B shows the resection cavity 901 filled with the sealant 701 after delivery with the proximal balloon 806 in an unexpanded configuration. The distal balloon 808 may be inflated so as to completely seal off the bladder B from the prostatic capsule 900 at the distal opening 903 of the prostatic capsule 900 comprising the bladder neck, such that only the resection cavity 901 receives the sealant 701. Alternatively, the distal balloon 808 may be inflated so as to partially, or nearly completely, seal off the bladder B from the prostatic capsule 900. For example, the distal balloon 808 may be inflated so as to leave a small space between the bladder neck and the distal balloon 808. This may allow a small amount of sealant 701 to reach the bladder neck itself, as shown in FIG. 1B. This may be advantageous in situations where the bladder neck area is the source of bleeding, as the bladder neck common location of bleeding following tissue resection in the prostatic capsule 900. The catheter body may seal off the proximal opening 902 while the catheter is positioned with the cavity, such that the sealant does not enter the urethra.

FIG. 1C shows the inflation of the proximal balloon 806 after delivery of the sealant 701 to an expanded configuration. The proximal balloon 806 may be inflated prior to or during delivery of the sealant 701 in order to reduce the amount of sealant 701 need to coat the edge of the cavity. The proximal balloon 806 may be inflated in order to compress the sealant against an internal surface of the cavity, for example, the cavity edge 904 at the periphery of the resection cavity 901, thus ensuring delivery to the entire tissue area of the cavity edge 904. The catheter may be left in the patient with the proximal balloon 806 inflated for an amount of time to ensure hemostasis has occurred. The amount of time for hemostasis may depend on the sealant used and may range from minutes to hours to overnight.

While the sealant delivery port 807 may be disposed proximally of the distal end of the catheter of shown, it will be understood by one of ordinary skill in the art that the sealant delivery port in this or any embodiment may be disposed anywhere along the catheter to deliver the sealant 701 to the cavity as desired. For example, the sealant delivery port may be disposed near the proximal opening 902 of the tissue or the distal opening 903 of the tissue. The sealant delivery port may for example be disposed between the proximal and distal balloons near the distal tissue opening as shown or proximal to the proximal balloon 806 near the proximal tissue opening. Alternatively, the catheter may comprise a single balloon, for example the proximal balloon 806 disposed in the cavity. The sealant delivery port may be disposed proximally or distally to the proximal balloon 806. Infusion of sealant and expansion of the proximal balloon 806 may deliver sealant 701 to the cavity edge 904 and may optionally urge sealant 701 towards the bladder neck to reduce bleeding in locations which are not in contact with the proximal balloon 806.

Figure 2A:
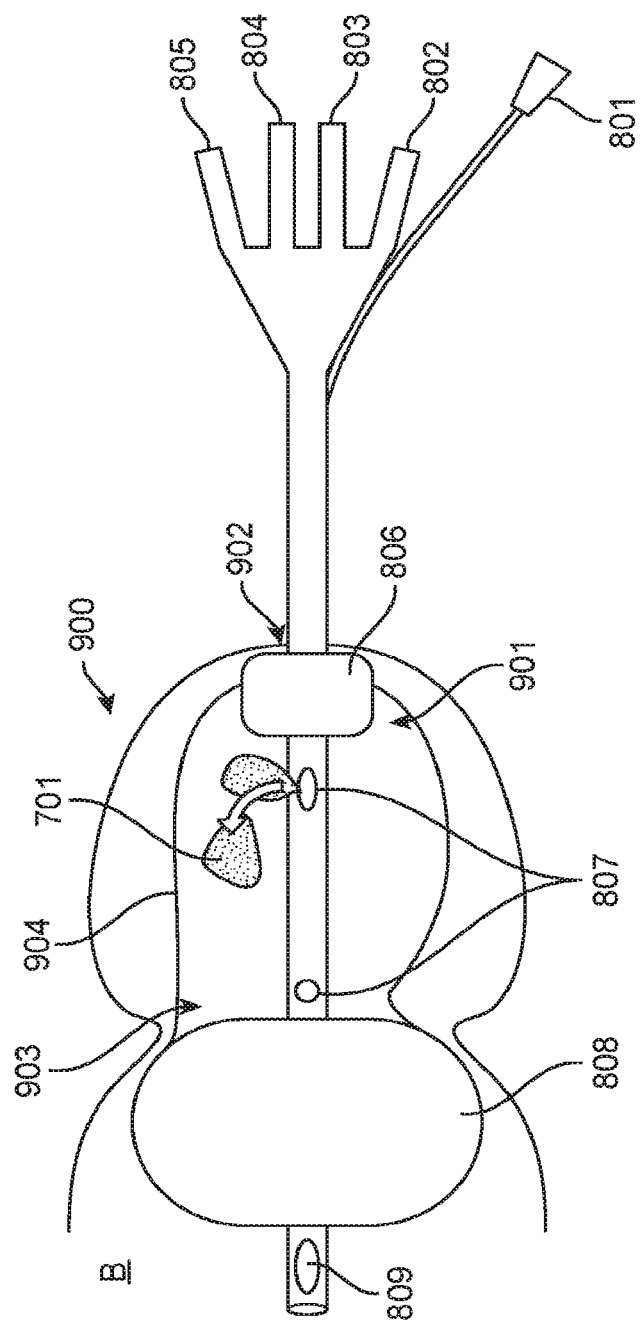
FIGS. 2A-2B show sectional schematic views of a sealant delivery device comprising a catheter, in accordance with embodiments.
Figure 2B:
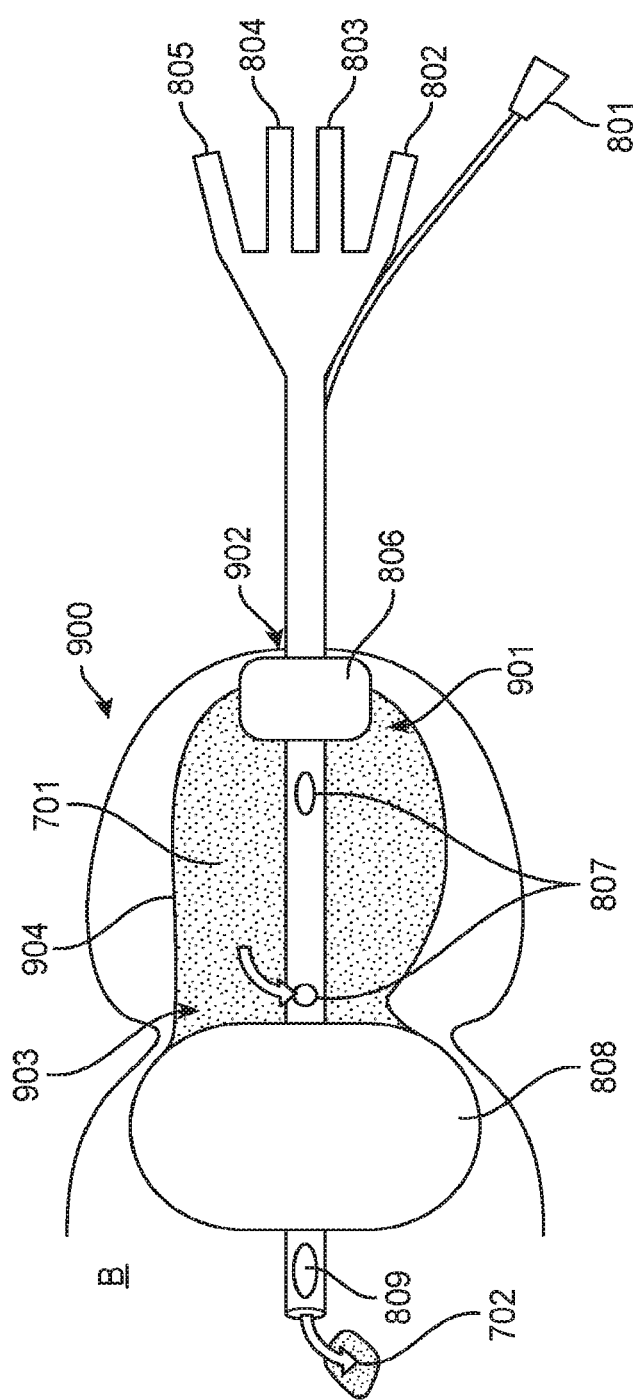

FIGS. 2A-2B show another embodiment of a minimally invasive sealant delivery device. The sealant delivery device may, for example, be used to deliver a hemostatic agent or sealant into a cavity created by tissue resection in the prostatic capsule. The sealant delivery device may comprise a catheter comprising a distal balloon and a proximal and may be delivered through the urethra such that distal balloon and proximal balloon are fully inserted into the bladder and prostatic capsule, respectively. The distal balloon may be positioned adjacent to a distal opening of the tissue space so as to seal the bladder upon inflation and close off the tissue resection cavity. The proximal balloon may be positioned adjacent the proximal opening of the resection cavity so as to reside within the resection cavity of the prostatic capsule and seal the cavity at the urethra upon expansion. Positioning the proximal balloon at the urethra may allow for homogeneous fill of sealant within the resection cavity.

The catheter may further comprise one or more of an irrigation port 805, a drainage port 802, an inflation port 804 for the distal bladder balloon, an inflation port 803 for the proximal prostatic balloon, or a sealant infusion port 801 as previously described herein. The inflation ports may be fluidly coupled to the balloons and used to inflate the distal and proximal balloons, respectively. The sealant infusion port may be used to deliver sealant to the resection cavity prior to, during, or after inflation of the distal balloon.

FIG. 2A shows delivery of a sealant 701 into the resection cavity 901 of the prostatic capsule 900. The catheter may be advanced through the urethra into the cavity via the proximal opening 902. The sealant 701 may be infused into the catheter through a sealant infusion port 801 located near the proximal end of the catheter and positioned distally with respect to the proximal balloon 806. The sealant 701 may be delivered to the resection cavity 901 via a sealant delivery port 807 located on the catheter residing inside the prostatic capsule 900. The sealant delivery port 807 may, for example, be located between the distal balloon 808 and the proximal balloon 806. The proximal balloon 806 may be inflated prior to delivery of the sealant. The distal balloon 808 may be inflated so as to at least partially or completely seal off the bladder B from the prostatic capsule 900 at the bladder neck BN as previously described herein.

FIG. 2B shows the resection cavity 901 filled with the sealant 701 after delivery. The catheter may comprise a sealant overflow port 807 adjacent the sealant delivery port 807 so as to remove excess sealant 702 from the resection cavity 901 after the cavity has been completely filled. The excess sealant 702 may be removed to the bladder B, where it can then be taken up by the catheter for removal from the body through the drainage port 802. The sealant overflow port 807 may further help to remove fluid from the resection cavity 901 as the sealant infuses into the cavity in order to promote a homogenous mixture within the cavity. Removal of excess sealant 702 may be controlled such that inflow of sealant through the sealant delivery port 807 results in a positive pressure within the resection cavity 901. The positive pressure may ensure even distribution of the sealant to the cavity edge 904 without the use of a balloon as in the embodiments of FIGS. 1A-1C. The positive pressure may also be useful in opening a cavity which has collapsed following tissue resection. The size of the sealant overflow port 807 can vary outflow resistance and may be used to modulate the amount of pressure that accumulates within the resection cavity 901. Alternatively or in combination, the pressure of the sealant inside the catheter may cause the sealant overflow port 807 to distend, thereby encouraging outflow of the sealant and maintenance of the positive pressure within the resection cavity 901. The catheter may be left in the patient with said positive pressure for an amount of time to ensure hemostasis has occurred. The amount of time for hemostasis may depend on the sealant used and may range from minutes to hours to overnight.

Figure 3A:
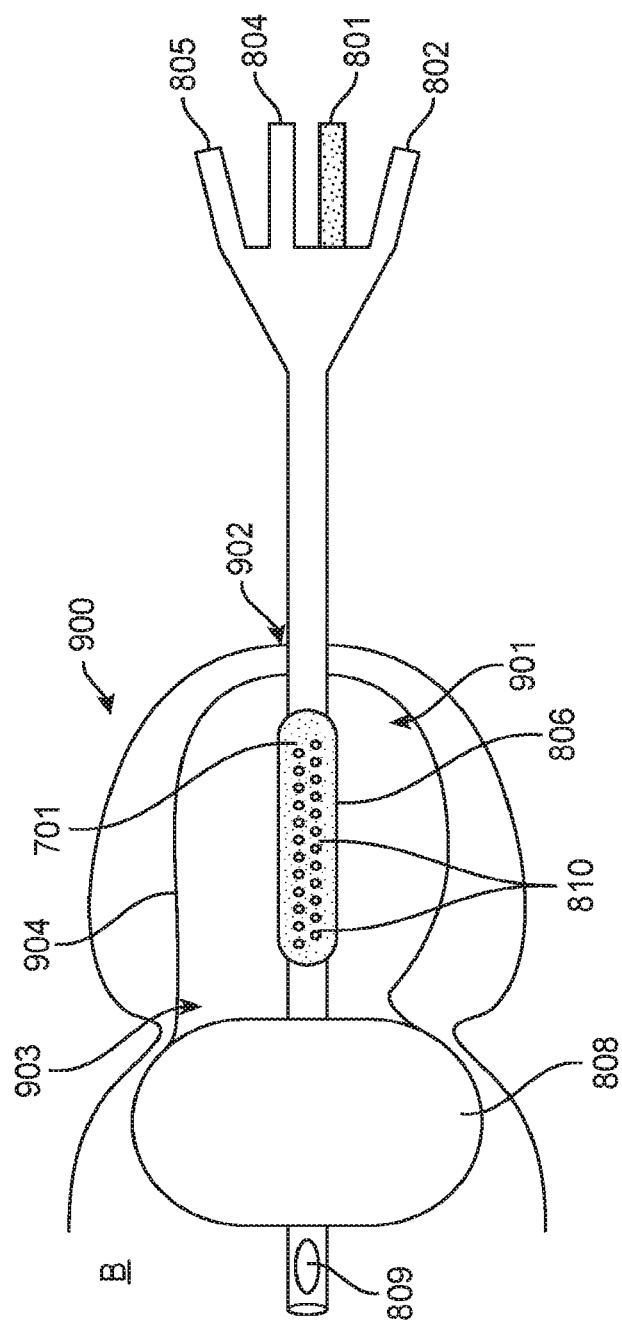
FIGS. 3A-3B show sectional schematic views of another sealant delivery device comprising a catheter, in accordance with embodiments.
Figure 3B:
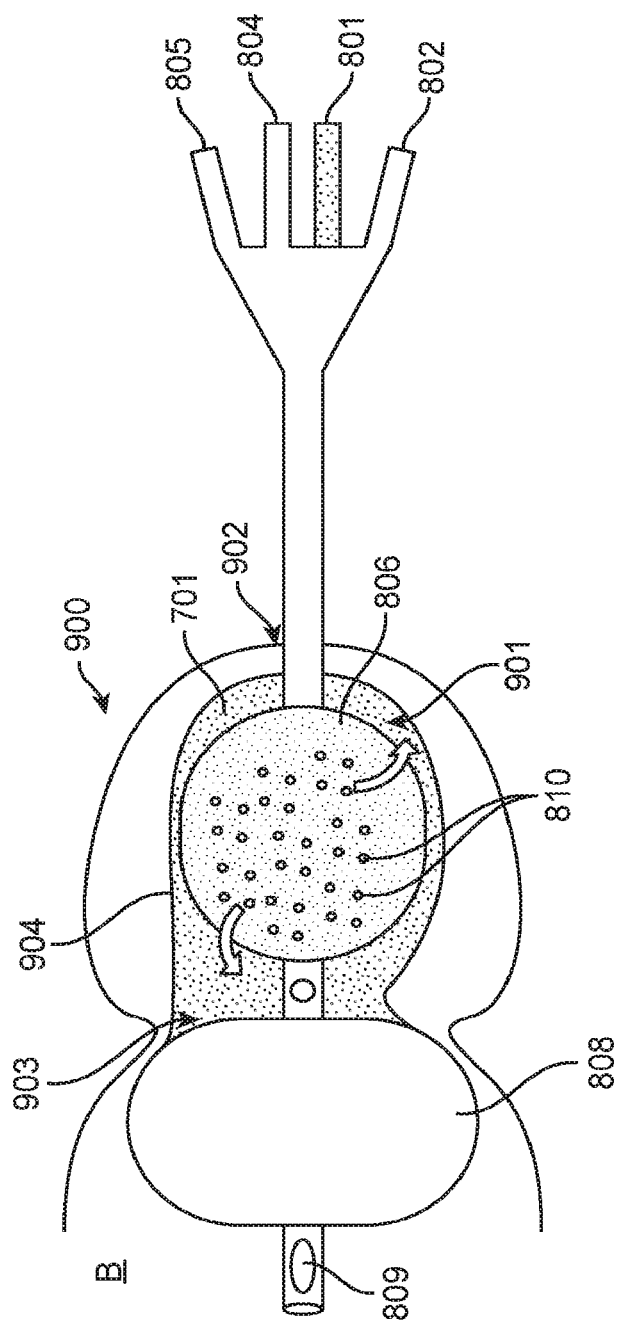

FIGS. 3A-3B show another embodiment of a minimally invasive sealant delivery device. The sealant delivery device may, for example, be used to deliver a hemostatic agent or sealant into a cavity created by tissue resection in the prostatic capsule 900. The sealant delivery device may comprise a catheter comprising a distal balloon 808 and a proximal balloon 806 and may be delivered through the urethra such that distal balloon 808 and proximal balloon 806 are fully inserted into the bladder B and prostatic capsule 900, respectively. The distal balloon 808 may be positioned adjacent to a distal opening 903 of the tissue space so as to seal the bladder B upon inflation and close off the tissue resection cavity 901. The proximal balloon 806 may be positioned so as to reside within the resection cavity 901 of the prostatic capsule 900.

The catheter may further comprise one or more of an irrigation port 805, a drainage port 802, an inflation port 804 for the distal bladder balloon, or an inflation port 803 for the proximal prostatic balloon. The inflation ports may be fluidly coupled to the balloons and used to inflate the distal and proximal balloons, respectively. The irrigation and drainage ports may be used as previously described herein. The inflation port 803 for the proximal balloon may, for example, comprise a sealant infusion port, for example, a sealant balloon infusion port 801. The sealant balloon infusion port 801 may be used to deliver sealant 701 to the resection cavity 901 prior to, during, or after inflation of the distal balloon 808.

FIG. 3A shows delivery of a sealant 701 into the resection cavity 901 of the prostatic capsule 900. The sealant may be infused into the proximal balloon 806 through a sealant balloon infusion port 801 located near the proximal end of the catheter. The proximal balloon 806 may, for example, be porous and may comprise one or more sealant delivery pores 810. Infusion of the sealant 701 into the proximal balloon 806 may cause the balloon to distend and thereby allow the sealant to ooze or seep into the resection cavity 901. The distal balloon 808 may be inflated so as to completely seal off the bladder B from the prostatic capsule 900 at the bladder neck BN such that only the resection cavity 901 receives the sealant 701. Alternatively, the distal balloon 808 may be inflated so as to partially, or nearly completely, seal off the bladder B from the prostatic capsule 900 as previously described herein.

FIG. 3B shows the resection cavity 901 filled with the sealant 701 after delivery. The proximal balloon 806 has been inflated, allowing for the release of the sealant into the resection cavity 901. Pressure generated in the proximal balloon 806 by the infusion of sealant 701 as it inflates may lead to stretching of the sealant delivery pores 810. As the balloon inflates, the pores 810 stretch and sealant is allowed to flow out of the proximal balloon 806 into the resection cavity 901. The proximal balloon 806 may be configured such that the rates of sealant delivery and balloon inflation are controllable, for example, by controlling the strength of the material of the proximal balloon 806 or the size of the pores 810. The proximal balloon 806 may be inflated in order to compress the sealant into the cavity edge 904 at the periphery of the resection cavity 901, thus ensuring delivery to the entire tissue area of the cavity edge 904. The catheter may be left in the patient with the proximal balloon 806 inflated for an amount of time to ensure hemostasis has occurred. The amount of time for hemostasis may depend on the sealant used and may range from minutes to hours to overnight.

It will be understood by one of ordinary skill in the art that any of the embodiments described herein may comprise any number of balloons or expandable supports as desired. For example, the device shown in FIGS. 3A-3B may comprise a single balloon, for example the proximal balloon. A catheter comprising the proximal balloon with a plurality of pores may be used to deliver sealant into the resection cavity of the prostatic capsule as described herein.

Figure 4A:
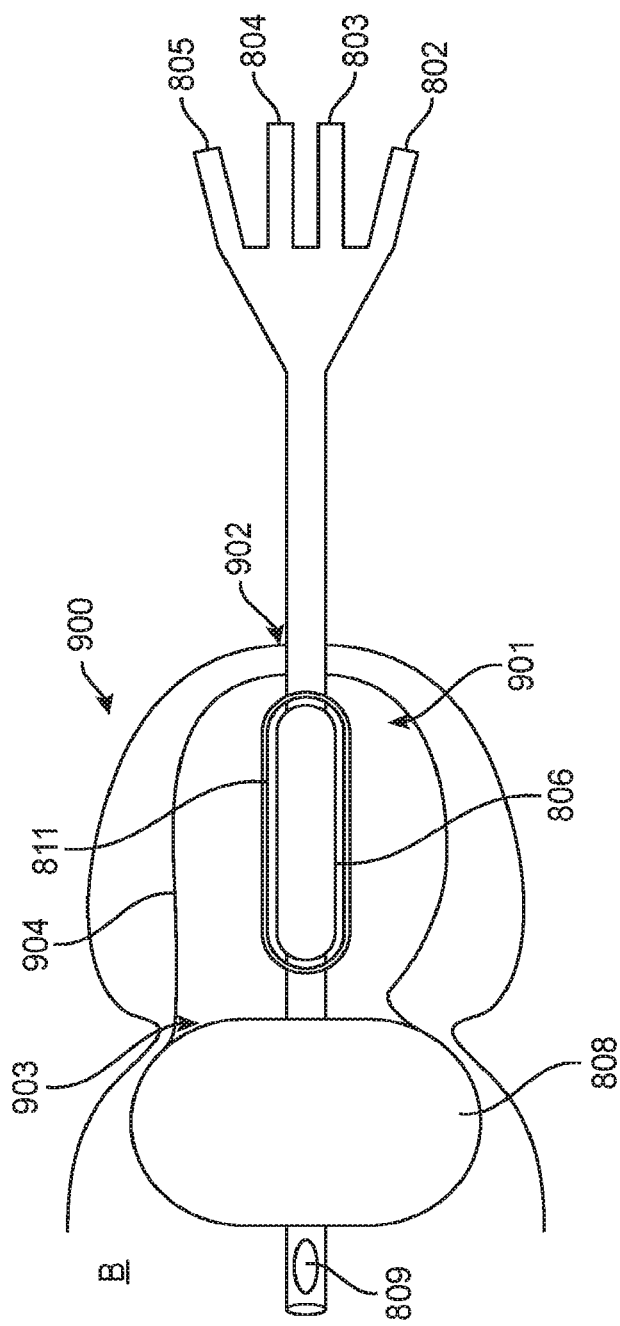
FIGS. 4A-4B show sectional schematic views of another sealant delivery device comprising a catheter, in accordance with embodiments.
Figure 4B:
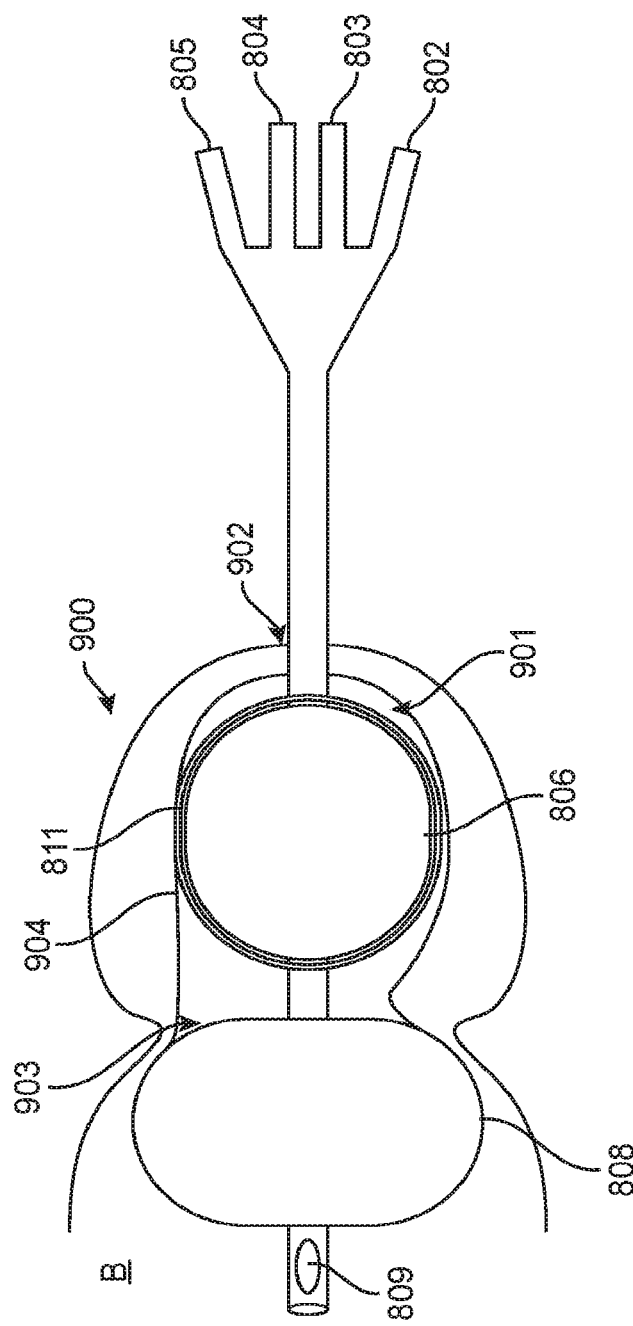

FIGS. 4A-4B show another embodiment of a minimally invasive sealant delivery device. The sealant delivery device may, for example, be used to deliver a hemostatic agent or sealant into a cavity created by tissue resection in the prostatic capsule. The sealant delivery device may comprise a catheter comprising a distal balloon and a proximal balloon and may be delivered through the urethra such that distal balloon and proximal balloon are fully inserted into the bladder and prostatic capsule respectively. The distal balloon may be positioned adjacent to a distal opening of the tissue space so as to seal the bladder upon inflation and close off the tissue resection cavity. The proximal balloon may be positioned so as to reside within the resection cavity of the prostatic capsule.

The catheter may further comprise one or more of an irrigation port 805, a drainage port 802, an inflation port 804 for the distal bladder balloon, or an inflation port 803 for the proximal prostatic balloon. The inflation ports may be fluidly coupled to the balloons and used to inflate the distal and proximal balloons, respectively. The irrigation and drainage ports may be used as previously described herein. The proximal balloon may comprise a scaffold member disposed over at least a portion of an external surface of the proximal balloon.

FIG. 4A shows a sealant delivery device comprising a sealant scaffold member 811 in the resection cavity 901 of the prostatic capsule 900. The sealant scaffold 811 may, for example, be a mesh, a composite mesh, a collagen membrane, a patch, an adhesive, or the like. Inflation of the proximal balloon 806 may expand the scaffold member 811 to the cavity edge 904 for hemostasis. The scaffold member 811 may be biodegradable. The scaffold member 811 may be embedded with a hemostatic agent or gel to enhance hemostasis. The scaffold member 811 may not be embedded with a hemostatic agent or gel to enhance hemostasis and may instead promote hemostasis by acting as a mechanical seal. The scaffold member 811 may be delivered to the cavity edge 904 so as to apply pressure to promote hemostasis until the scaffold member 811 dissolves or is removed. The distal balloon 808 may be inflated so as to completely seal off the bladder B from the prostatic capsule 900 at the bladder neck BN such that only the resection cavity 901 receives the sealant scaffold 811.

FIG. 4B shows the inflation of the proximal balloon 806 and delivery of the sealant scaffold 811 to the cavity edge 904. The proximal balloon 806 may be inflated in order to compress the sealant scaffold into the cavity edge 904 at the periphery of the resection cavity 901, thus ensuring delivery to the entire tissue area of the cavity edge 904. The catheter may be left in the patient with the proximal balloon 806 inflated for an amount of time to ensure hemostasis has occurred. The balloon and scaffold may be collapsed together for removal. Alternatively, the sealant scaffold may be configured so as to remain expanded after the proximal balloon 806 has collapsed. The sealant scaffold may, for example, be biodegradable and may thus be left in the resection cavity 901 to absorb or dissolve over time after removal of the catheter. The amount of time for hemostasis to occur may depend on the sealant used and may range from minutes to hours to overnight.

Figure 5A:
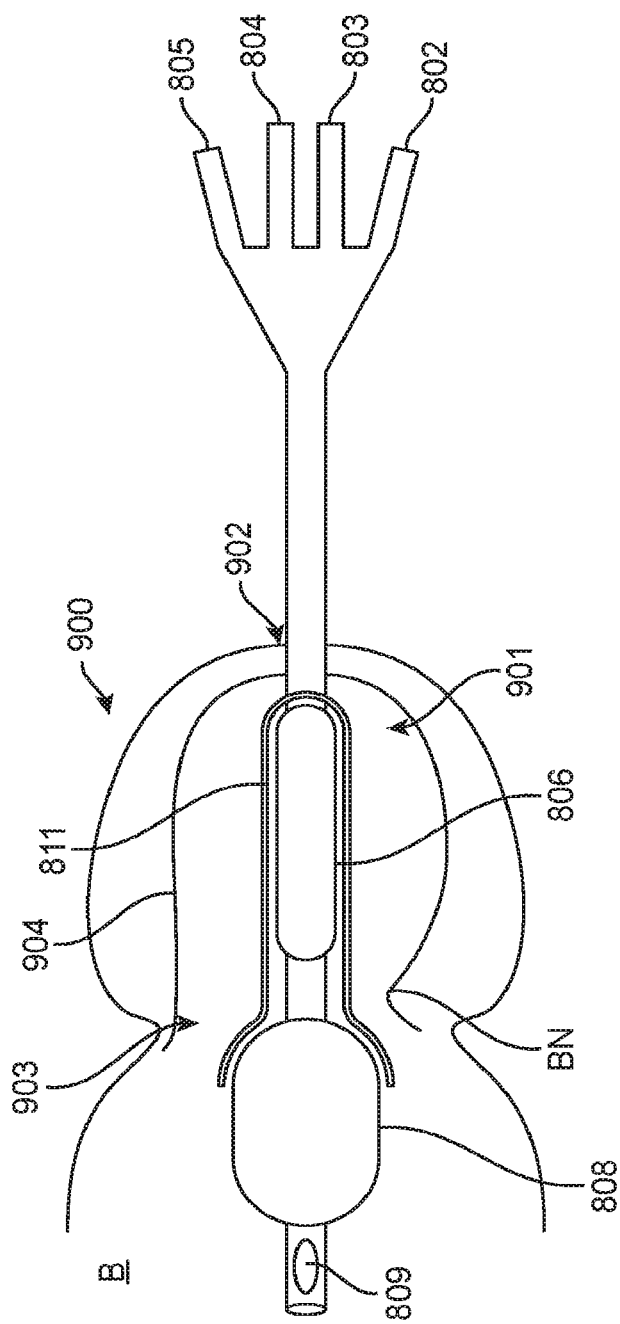
FIGS. 5A-5B show sectional schematic views of yet another sealant delivery device comprising a catheter, in accordance with embodiments.
Figure 5B:
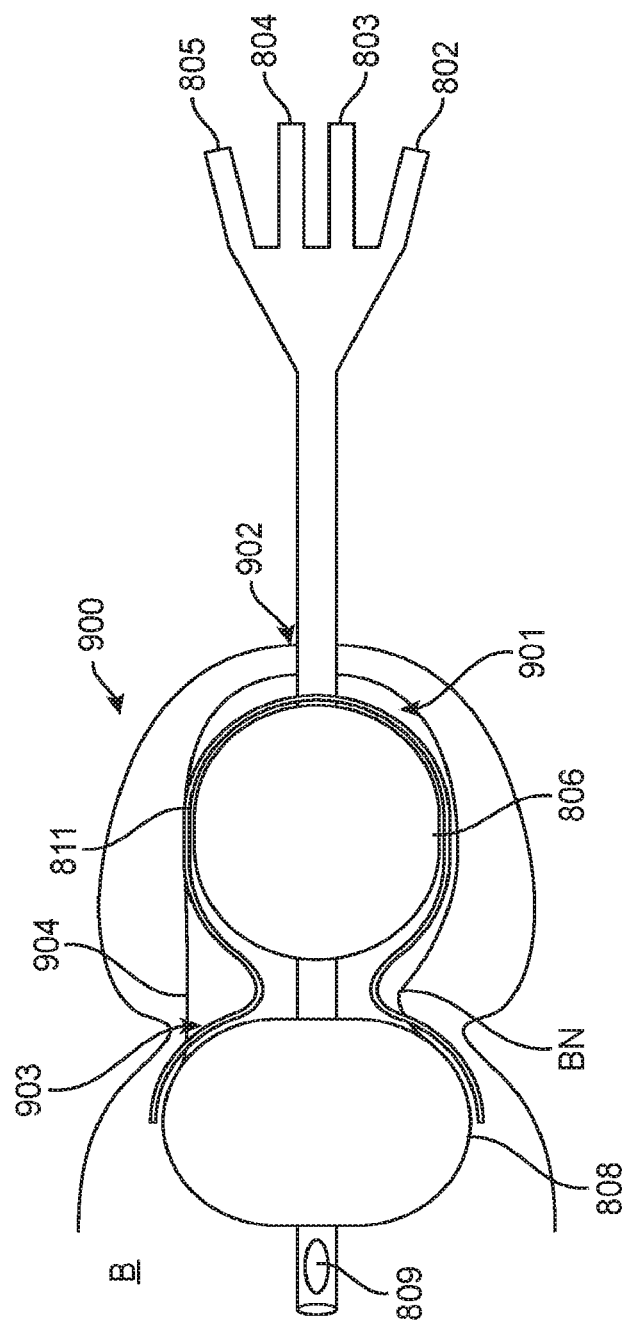

FIGS. 5A-5B show another embodiment of a minimally invasive sealant delivery device. The sealant delivery device may be substantially similar to the embodiment of FIGS. 4A-4B. The sealant delivery device may for example be used to deliver a hemostatic agent or sealant into a cavity created by tissue resection in the prostatic capsule 900. The sealant delivery device may comprise a catheter comprising a distal balloon 808 and a proximal and may be delivered through the urethra such that distal balloon 808 and proximal balloon 806 are fully inserted into the bladder B and prostatic capsule 900, respectively. The distal balloon 808 may be positioned adjacent to a distal opening of the tissue space so as to seal the bladder B upon inflation and close off the tissue resection cavity 901. The proximal balloon 806 may be positioned so as to reside within the resection cavity 901 of the prostatic capsule 900.

The catheter may further comprise one or more of an irrigation port 805, a drainage port 802, an inflation port 804 for the distal bladder balloon, or an inflation port 803 for the proximal prostatic balloon. The inflation ports may be fluidly coupled to the balloons and used to inflate the distal and proximal balloons, respectively. In some embodiments, the same port may be used to inflate both the distal and proximal balloons simultaneously. The irrigation and drainage ports may be used as previously described herein. The proximal balloon 806 may comprise a scaffold member 811 disposed over at least a portion of an external surface of the proximal balloon 806. The distal balloon 808 may comprise at least a portion of the scaffold member 811 disposed over at least a portion of an external surface of the distal balloon 808 such that the scaffold member 811 extends distally through the bladder neck BN when the catheter is positioned in the urethra as previously described herein.

FIG. 5A shows a sealant delivery device comprising a sealant scaffold member 811 in the resection cavity 901 of the prostatic capsule 900. The sealant scaffold 811 may for example be a mesh, a composite mesh, a collagen membrane, a patch, an adhesive, or the like. Inflation of the proximal balloon 806 may expand the scaffold member 811 to the cavity edge 904 for hemostasis. The scaffold member 811 may be biodegradable. The scaffold member 811 may be embedded with a hemostatic agent or gel to enhance hemostasis. A portion of the scaffold member 811 may extend to the distal balloon 808 such that inflation of the distal balloon 808 expands the scaffold member 811 to the bladder neck BN. The distal balloon 808 may be inflated so as to completely seal off the bladder B from the prostatic capsule 900 at the bladder neck BN such that only the resection cavity 901 and the tissue space near or in the bladder neck BN receive the sealant scaffold 811.

FIG. 5B shows the inflation of the proximal balloon 806 and distal balloon 808 for delivery of the sealant scaffold 811 to the cavity edge 904 and bladder neck BN. The proximal balloon 806 may be inflated in order to compress the sealant scaffold 811 into the cavity edge 904 at the periphery of the resection cavity 901, thus ensuring delivery to the entire tissue area of the cavity edge 904. The distal balloon 808 may be inflated in order to compress the sealant scaffold 811 into the cavity edge 904 at the bladder neck BN. This may allow a small amount of sealant to reach the bladder neck itself, which may be advantageous in situations where the bladder neck area is the source of bleeding as previously described herein. The catheter may be left in the patient with one or more of the proximal balloon 806 or distal balloon 808 inflated for an amount of time to ensure hemostasis has occurred. The proximal balloon 806, distal balloon 808, and scaffold 811 may be collapsed together for removal. Alternatively, the sealant scaffold 811 may be configured so as to remain expanded after the proximal balloon 806 and distal balloon 808 have collapsed. The sealant scaffold 811 may, for example, be biodegradable and may thus be left in the resection cavity 901 to absorb or dissolve over time after removal of the catheter. The amount of time for hemostasis to occur may depend on the sealant used and may range from minutes to hours to overnight.

Figure 6A:
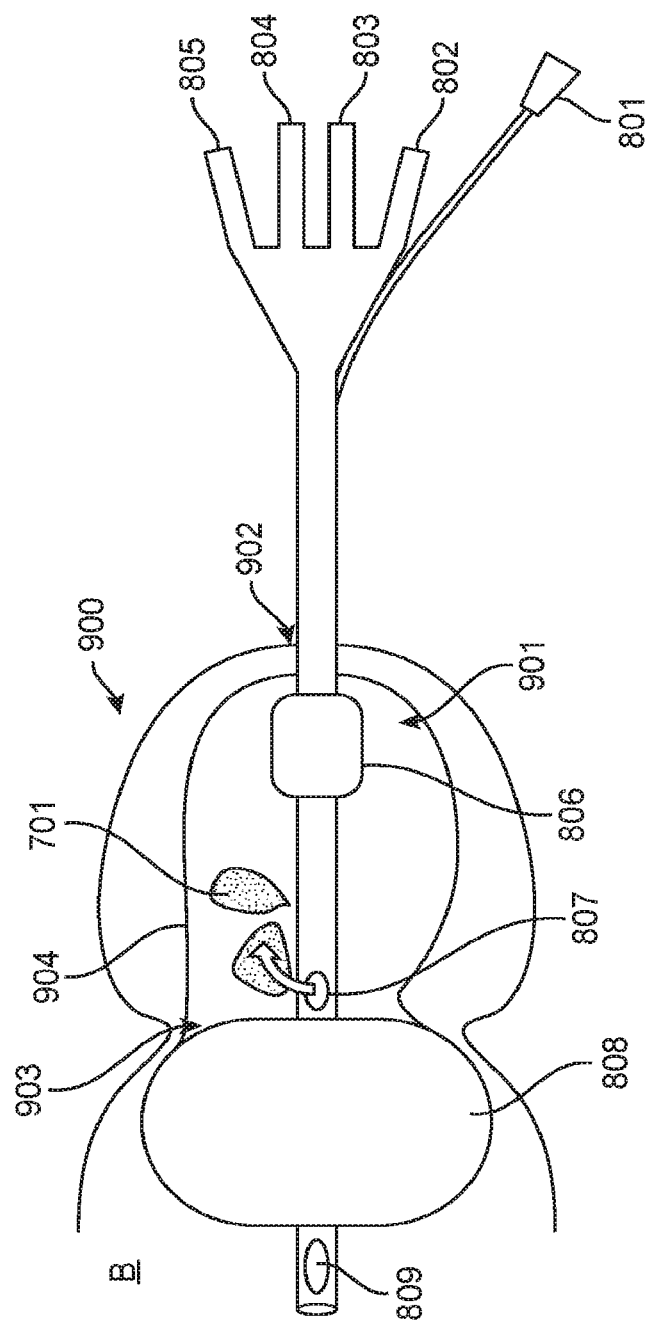
FIGS. 6A-6C show sectional schematic views of still another sealant delivery device comprising a catheter, in accordance with embodiments.
Figure 6B:
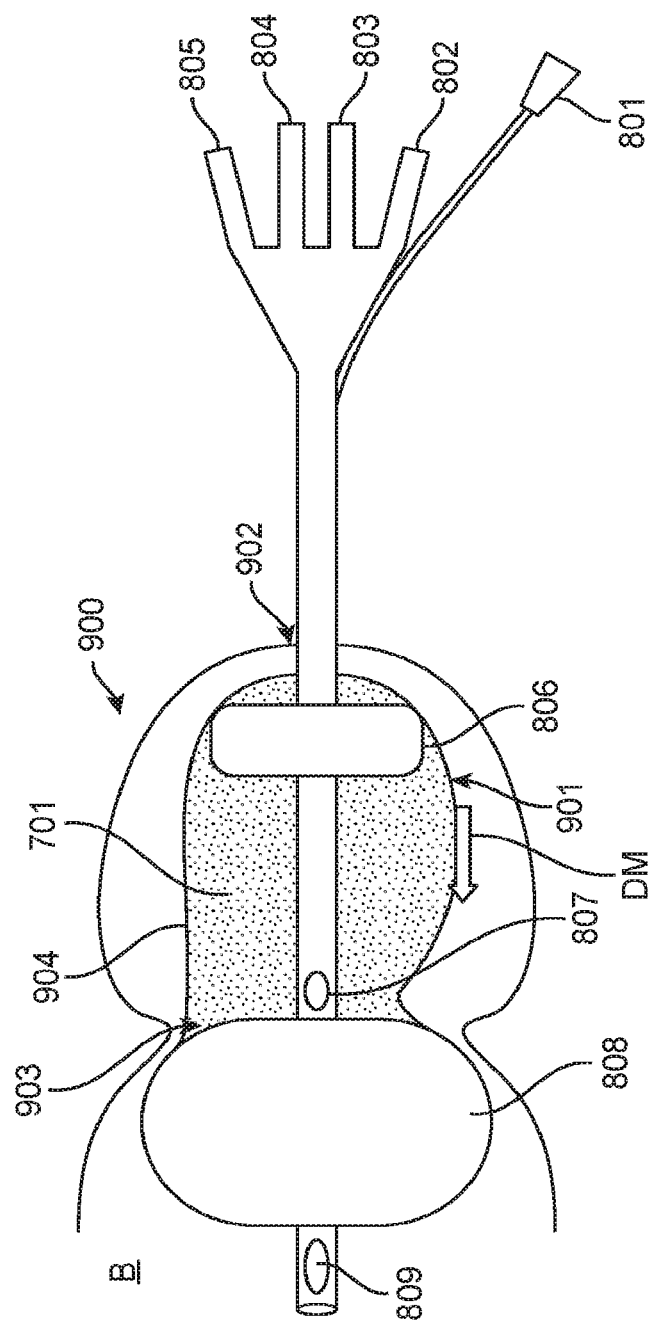
Figure 6C:
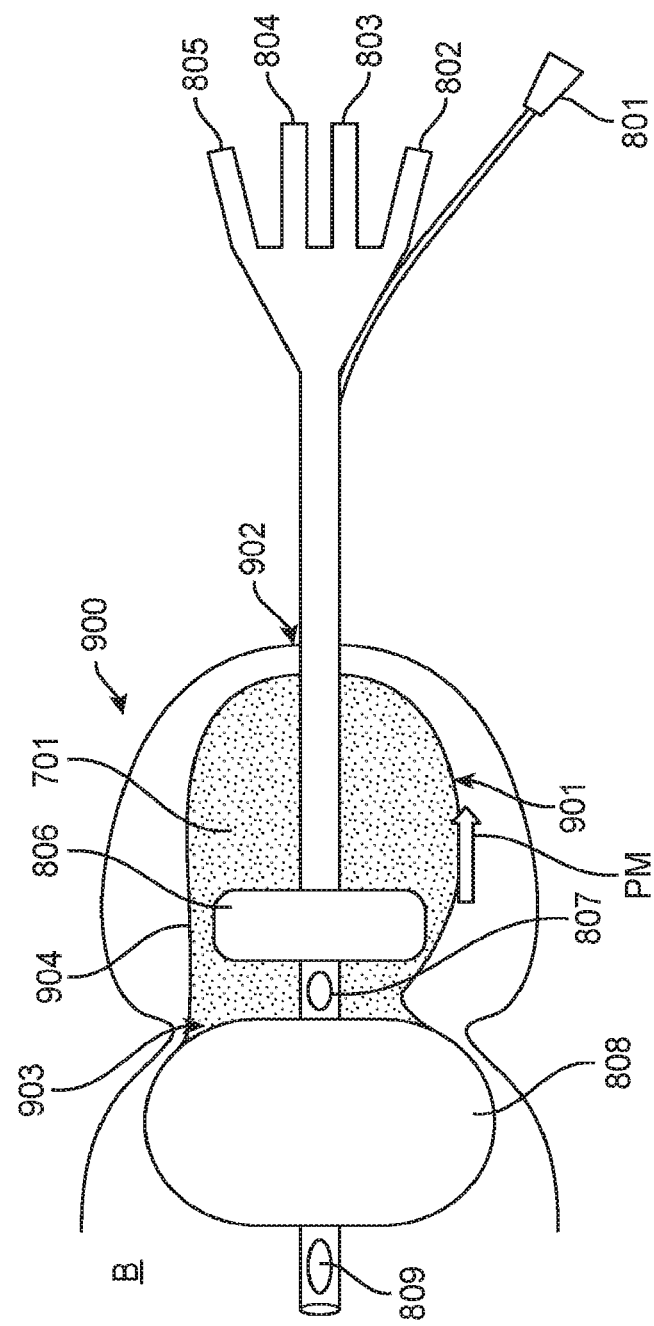

FIGS. 6A-6C show yet another embodiment of a minimally invasive sealant delivery device. The sealant delivery device may, for example, be used to deliver a hemostatic agent or sealant into a cavity created by tissue resection in the prostatic capsule 900. The sealant delivery device may comprise a catheter comprising a distal balloon 808 and a proximal balloon 806 and may be delivered through the urethra such that distal balloon 808 and proximal balloon 806 are fully inserted into the bladder B and prostatic capsule 900, respectively. The distal balloon 808 may be positioned adjacent to a distal opening of the tissue space so as to seal the bladder B upon inflation and close off the tissue resection cavity 901. The proximal balloon 806 may be positioned so as to reside within the resection cavity 901 of the prostatic capsule 900. The proximal balloon 806 may be an actuatable balloon.

The catheter may further comprise one or more of an irrigation port 805, a drainage port 802, an inflation port 804 for the distal bladder balloon, an inflation port 803 for the proximal prostatic balloon, or a sealant infusion port 801. The inflation ports may be fluidly coupled to the balloons and used to inflate the distal and proximal balloons, respectively. The irrigation and drainage ports may be used as previously described herein. The sealant infusion port 801 may be used to deliver sealant to the resection cavity 901 prior to, during, or after inflation of the distal balloon 808.

FIG. 6A shows delivery of a sealant 701 into the resection cavity 901 of the prostatic capsule 900. The sealant may be infused into the catheter through a sealant infusion port 801 located near the proximal end of the catheter. The sealant 701 may be delivered to the resection cavity 901 via a sealant delivery port 807 located on the catheter residing inside the prostatic capsule 900. The sealant delivery port 807 may for example be located between the distal balloon 808 and the proximal balloon 806, for example.

The distal balloon 808 may be inflated so as to completely seal off the bladder B from the prostatic capsule 900 at the bladder neck such that only the resection cavity 901 receives the sealant, as shown in FIG. 6C. Alternatively, the distal balloon 808 may be inflated so as to partially, or nearly completely, seal off the bladder B from the prostatic capsule 900 as previously described herein. This may allow a small amount of sealant to reach the bladder neck itself, as shown in FIG. 6B. This may be advantageous in situations where the bladder neck area is the source of bleeding, as the bladder neck common location of bleeding following tissue resection in the prostatic capsule 900.

The proximal balloon 806 may be inflated after sealant delivery and longitudinally actuated so as to help spread or "paint" the sealant evenly along the cavity edge 904. The proximal balloon 806 may move along a longitudinal axis of the catheter between the proximal opening 902 and the distal opening of the cavity. FIG. 6B shows the inflation of the proximal balloon 806 after delivery of the sealant. Alternatively, the proximal balloon 806 may be inflated prior to or during delivery of the sealant in order to reduce the amount of sealant need to coat the edge of the cavity. The proximal balloon 806 may be inflated in order to compress the sealant into the cavity edge 904 at the periphery of the resection cavity 901. The proximal balloon 806 may be actuated to help spread the sealant through movement in a distal direction. FIG. 6C shows the proximal balloon 806 at the distal end of resection cavity 901 following the distal movement DM. The proximal balloon 806 may further be actuated to move in a proximal direction PM. The balloon may for example be moved back and forth, distally and proximally, to help spread the sealant along the cavity edge 904 as it moves within the resection cavity 901. The proximal balloon 806 may be manually actuated through tension force-stretching or through a mechanical linkage to the proximal balloon 806. Differing material properties along the catheter, for example, an accordion-like section, an elastic section, or built-in springs in the resection cavity 901, may facilitate transmission of manual movement primarily to the proximal balloon 806. The use of such a "painting" technique may result in a reduced amount of sealant used as the proximal balloon 806 scrubs the sealant across the cavity edge 904. The catheter may be left in the patient with the proximal balloon 806 inflated for an amount of time to ensure hemostasis has occurred. The amount of time for hemostasis may depend on the sealant used and may range from minutes to hours to overnight.

Optionally, in any of the embodiments described herein, at least a portion of the sealant may be stored in and delivered from one or more built-in reservoirs within the catheter, alternatively to or in combination with the delivery of sealant from a sealant infusion port at the proximal end of the catheter. The sealant may comprise one or more components which, when mixed, form an active hemostatic agent. For example, the sealant may comprise a first component and a second component. The first component and the second component may be hemostatically inert when unmixed. The first component and the second component may be mixed to form an active sealant. The sealant delivery device of any of the embodiments described herein may comprise one or more built-in reservoirs in which one or more of the first component or the second component may be stored prior to mixing. The sealant delivery device may be adapted to mix the first component with the second component prior to or during delivery into the resection cavity in order to create and deliver the active hemostatic sealant. Mixing may for example occur during balloon inflation. Alternatively or in combination, mixing may occur due to mechanical agitation prior to, during, or after delivery to the resection cavity.

Optionally, any of the embodiments described herein may further comprise a targeted sealant delivery catheter, which may be provided within or separately from a main catheter of the sealant delivery device (e.g., modified Foley catheter). The targeted sealant delivery catheter may comprise a small-lumen catheter capable of being navigated to specific locations within the tissue space. For example, the targeted sealant delivery catheter may be operably coupled with an actuation mechanism (e.g., manual mechanisms such as knobs or sliders, or automated mechanisms such as motors controlled by a computer) that enables movement of the targeted sealant delivery catheter within the tissue space such as the prostatic cavity. The targeted sealant delivery catheter may be visualized within the tissue space using any appropriate visualization method known in the art, in order to track and control the movement of the catheter to desired locations within the tissue space. The targeted delivery of sealant to specific portions of the internal surface of the tissue space, such as the portions that are bleeding, can reduce the amount of sealant needed to achieve hemostasis in the tissue space. Such targeted sealant delivery may be particularly well-suited for use following procedures that cause focal punctures or bleeding sites within the tissue space, such as the application of staples to specific portions of the internal surface, or the focal injection (e.g., through needles) of steam or other sources of energy to specific portions of the internal surface.

Optionally, any of the embodiments described herein may comprise one or more light sources. The light source may promote direct visualization of the tissue space during use of the sealant delivery device. The light source may for example act as a waveguide. The light source may also be configured to cure photo-curable tissue sealants or adhesives. For example, some tissue adhesives such as cyanoacrylate-based sealants can be cured using UV light, and the sealant delivery device may further comprise a UV light source to cure the sealant after delivery of the sealant into the resection cavity.

Optionally, any of the embodiments described herein may be adapted to heat or chill the tissue sealant. For example, some tissue sealants are temperature-activated. The sealant delivery device may for example be adapted to deliver heated or chilled fluid to one or more of the distal or proximal balloons in order to activate or cure the tissue sealant prior to, during, or after delivery into the resection volume.

Figure 7A:
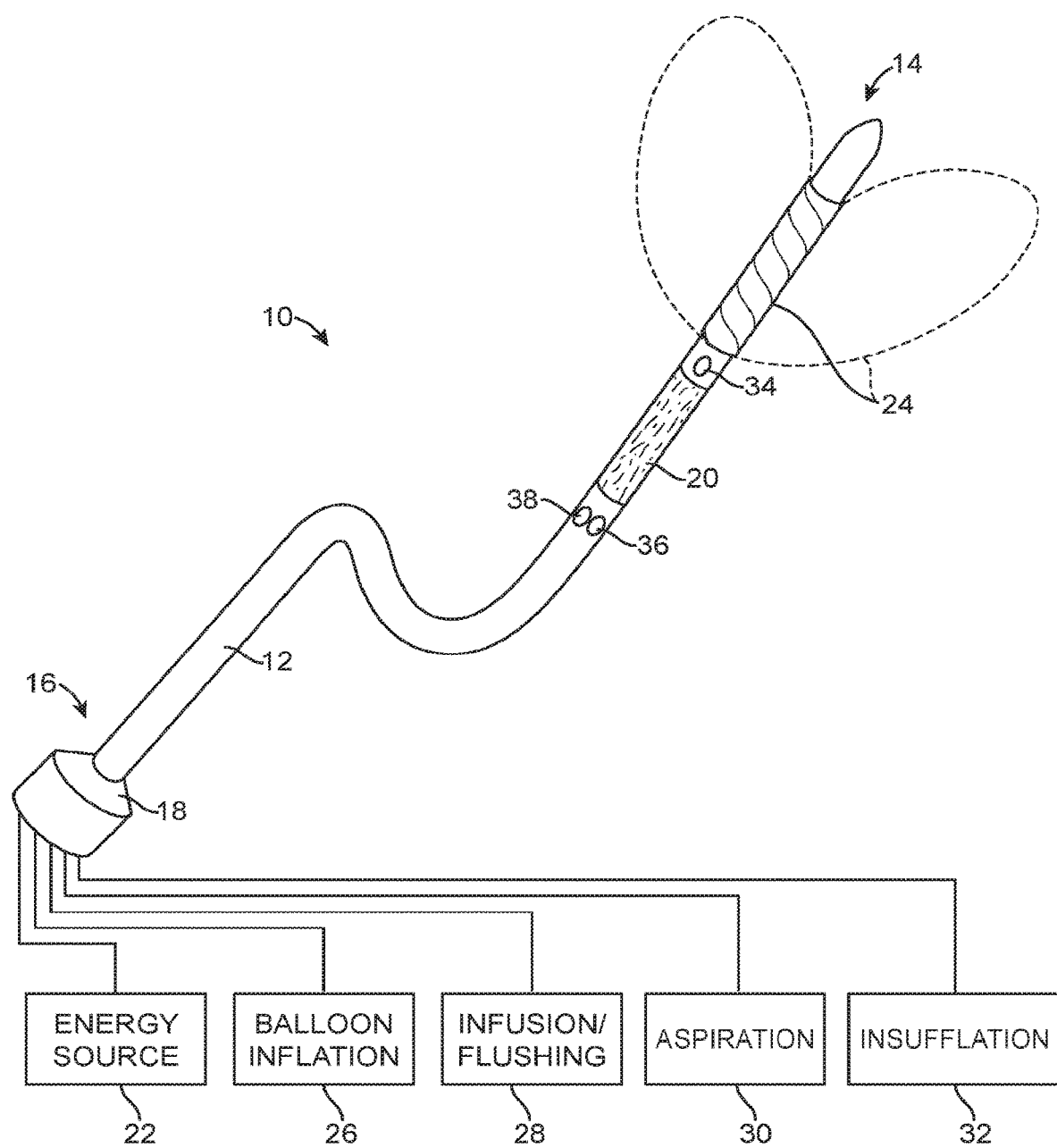
FIG. 7A is a schematic illustration of a device suitable for performing intraurethral prostatic tissue debulking, in accordance with embodiments.
Figure 7B:
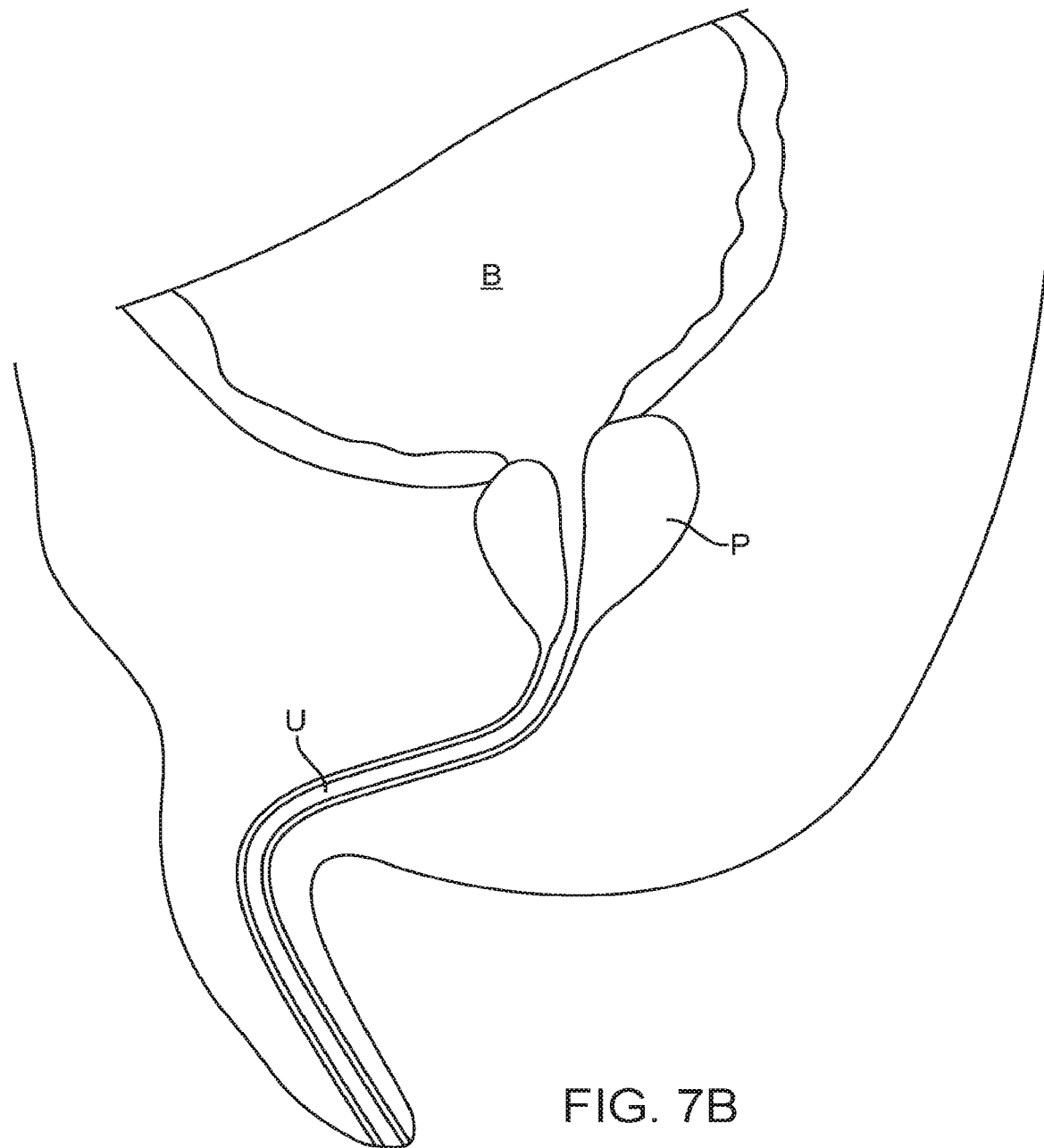
FIGS. 7B-7E show sectional schematic views of the use of the device of FIG. 7A in performing prostatic tissue debulking; in accordance with embodiments.
Figure 7C:
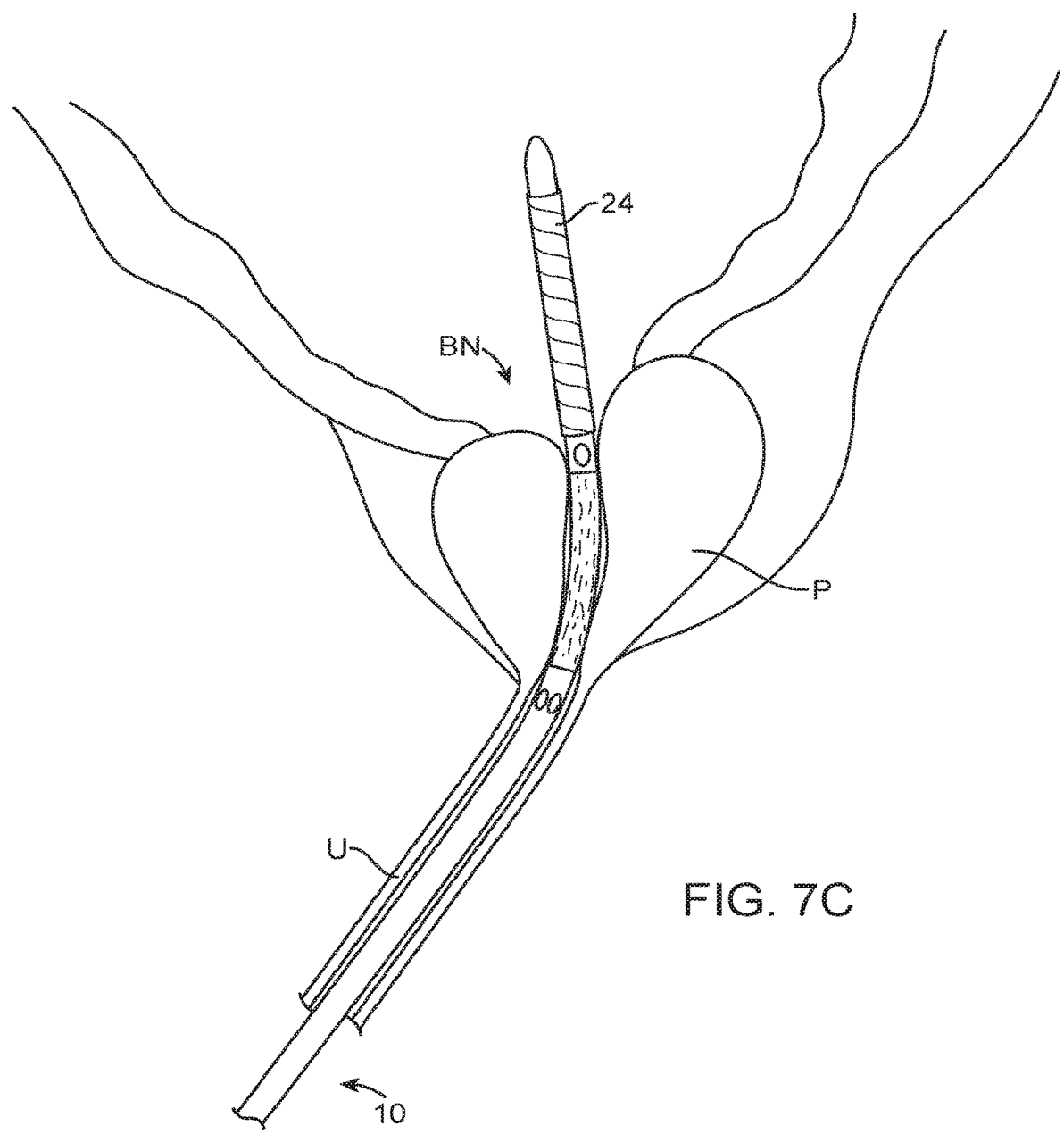
Figure 7D:
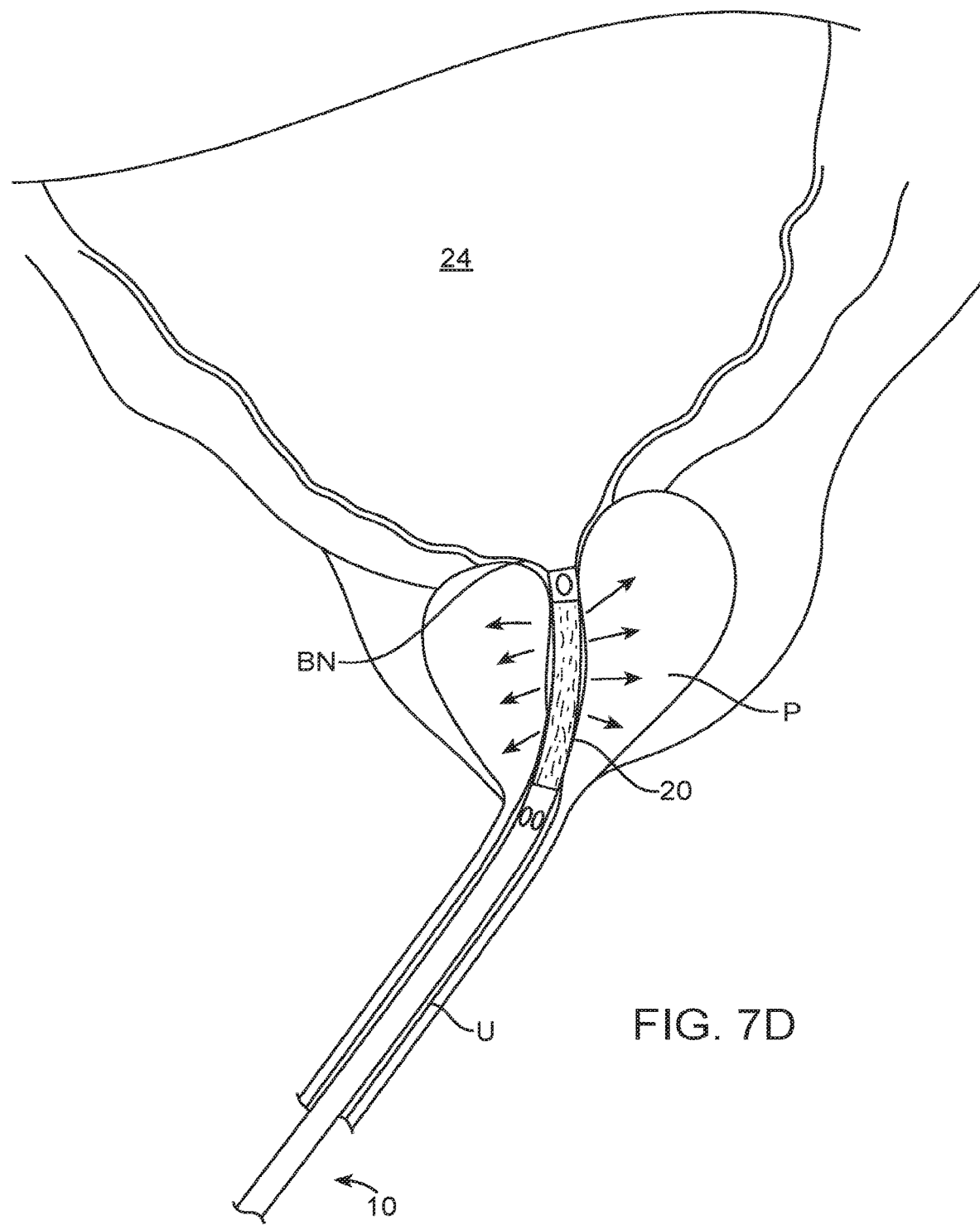
Figure 7E:
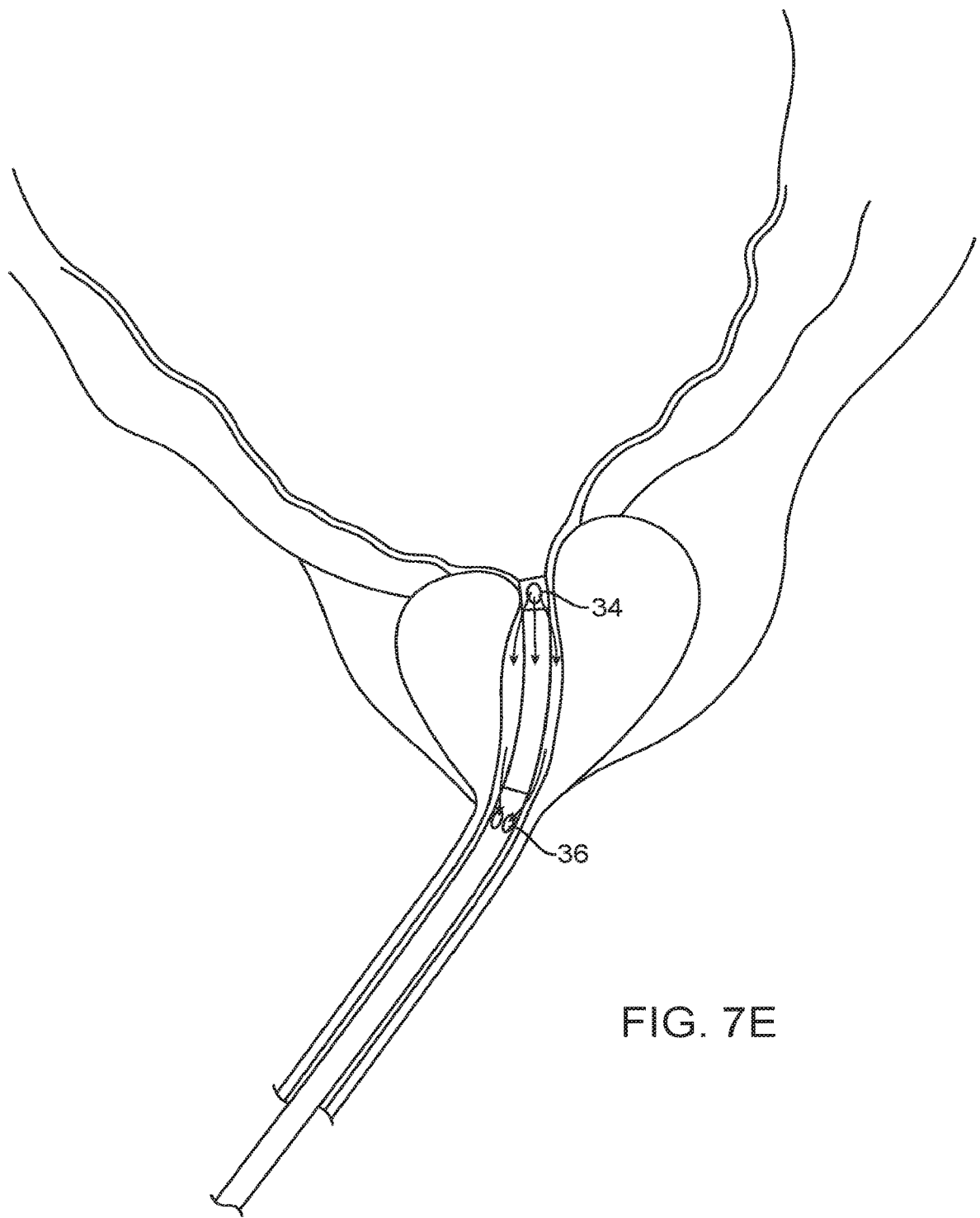
Figure 7F:
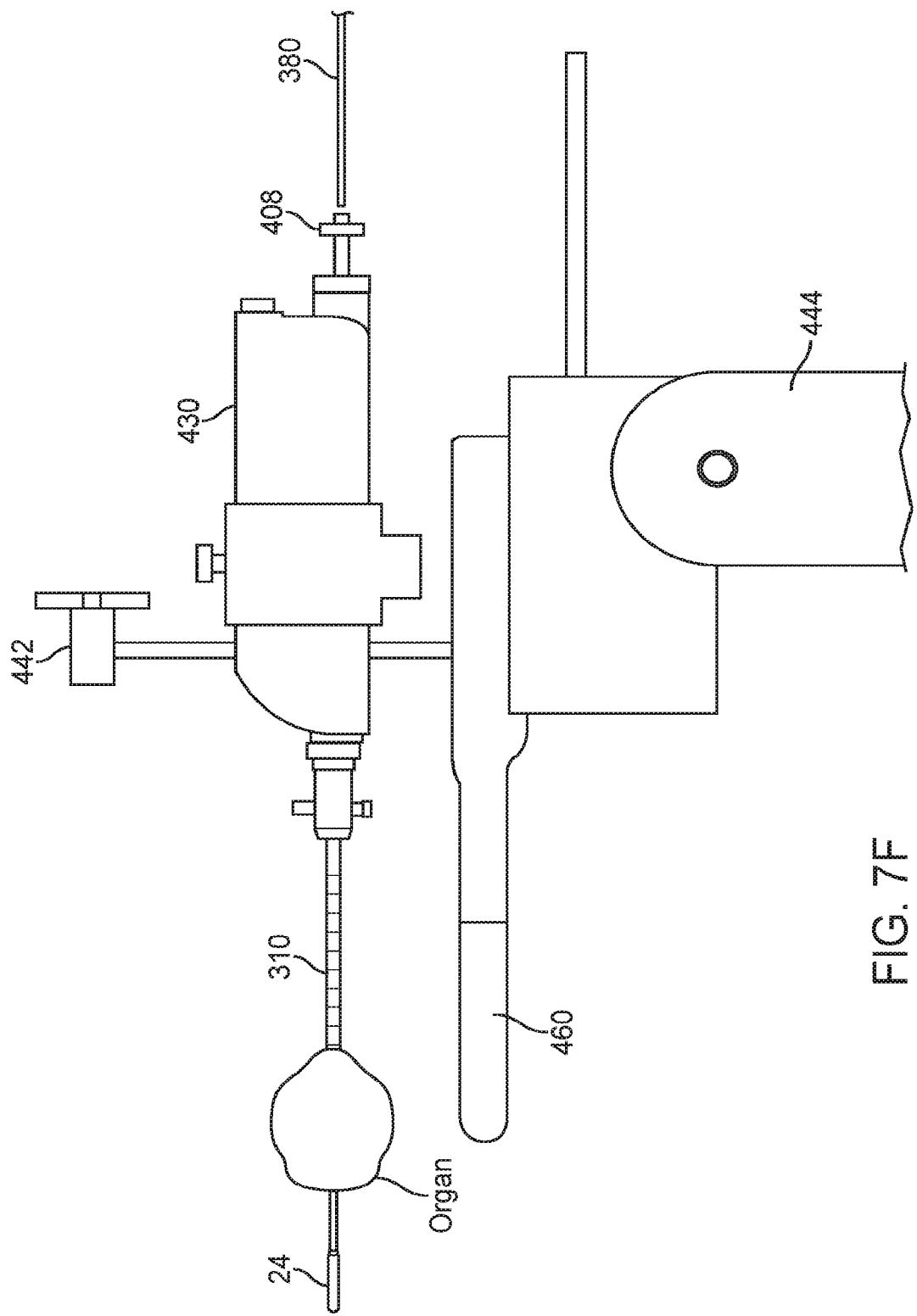
FIG. 7F shows a sectional schematic view of rapid exchange of a carrier when the linkage is coupled to the elongate element anchored to a target location of an organ, in accordance with embodiments.
Figure 7H:
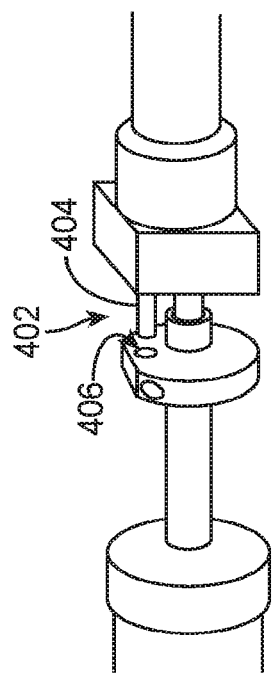
FIG. 7H shows a magnified perspective view of the carrier advanced toward a locking structure on the proximal end of the linkage as in FIG. 7F.
Figure 7G:
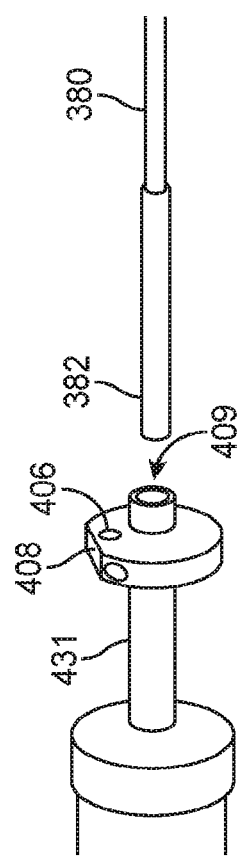
FIG. 7G shows a magnified perspective view of the alignment of the distal tip of the carrier with the proximal end of the linkage to insert the carrier tube as in FIG. 7F.
Figure 7I:
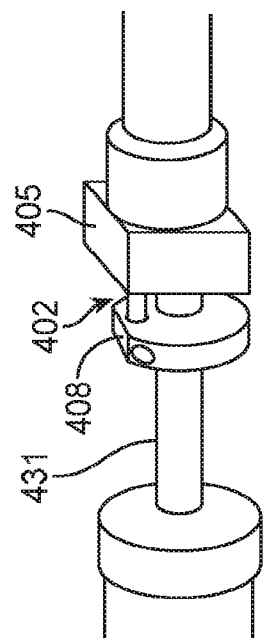
FIG. 7I shows a magnified perspective view of the carrier locked to the linkage as in FIGS. 7F and 7G.
Figure 8A:
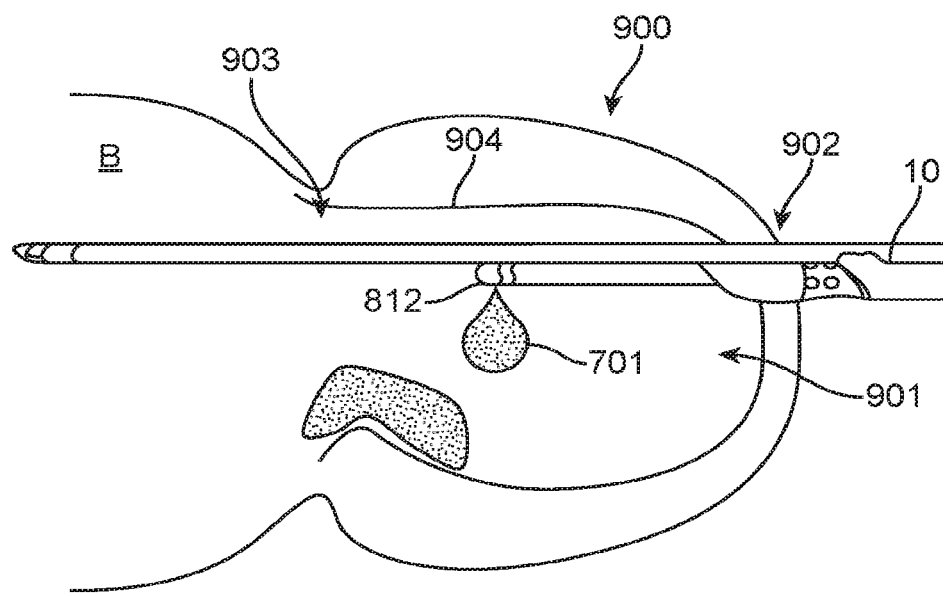
FIGS. 8A-8B show sectional schematic views of sealant delivery devices comprising a tissue resection device and sealant applicator nozzle, in accordance with embodiments.
Figure 8B:
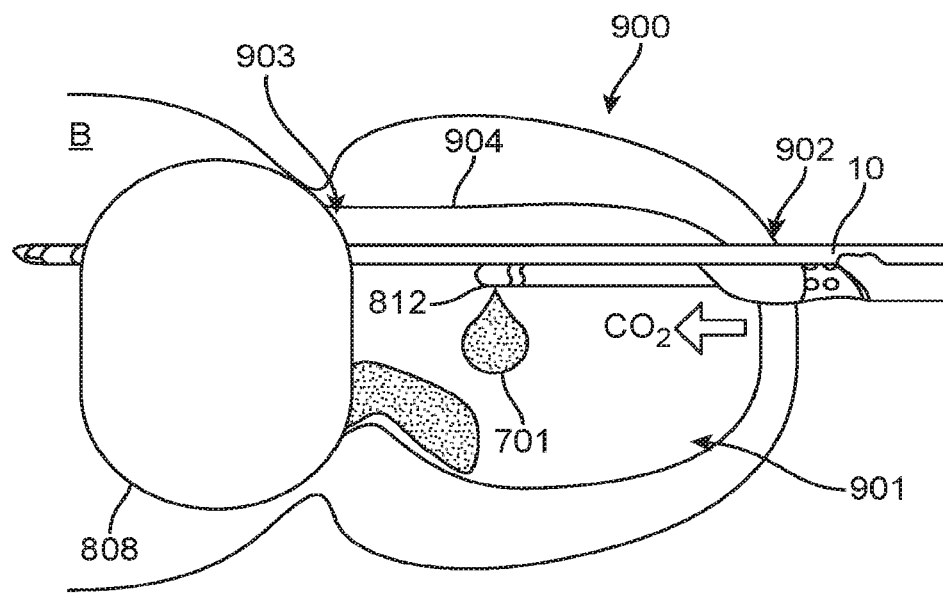

FIGS. 7A-7I show embodiments of a tissue debulking device which may be adapted as described in FIGS. 8A-8B for sealant delivery. FIGS. 7A-7E show the deployment and mechanism of action of a tissue debulking device or delivery probe used to deliver energy for prostatic tissue debulking. FIGS. 7F-7I show another embodiment of a tissue debulking device. A plurality of carrier probes can be provided to allow the user to treat one or more of many tissues in a variety of ways. An elongate structural element having a working channel such as a shaft remains positioned in the patient when a first carrier probe is exchanged with one or more carrier probes. In many embodiments, the carrier probes can be rapidly exchanged while a linkage remains fixedly attached to the elongate element anchored to an internal structure of the patient. Each of the carrier probes inserted into the patient can be identified based on a treatment plan, for example.

Referring to FIG. 7A, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 2 mm to 6 mm. The shaft will have sufficient column strength so that it may be introduced upwardly through the male urethra, as described in more detail below.

The shaft may include an energy source positioned in the energy delivery region 20, where the energy source can be any one of a number of specific components as discussed in more detail below. Distal to the energy delivery region, an inflatable anchoring balloon 24 may be positioned at or very close to the distal end 14 of the shaft. The balloon may be connected through one of the axial lumens to a balloon inflation source 26 connected through the hub 18. In addition to the energy source 22 and the balloon inflation source 26, the hub may optionally further include connections for an infusion/flushing source 28, an aspiration (a vacuum) source 30, and/or an insufflation (pressurized $CO_2$ or other gas) source 32. In the exemplary embodiment, the infusion or flushing source 28 can be connected through an axial lumen (not shown) to one or more delivery ports 34 proximal to the balloon anchor 24 and distal to the energy delivery region 20. The aspiration source 30 can be connected to a second port or opening 36, usually positioned proximally of the energy delivery region 20, while the insufflation source 32 can be connected to an additional port 38, also usually located proximal of the energy delivery region. It will be appreciated that the locations of the ports 34, 36, and 38 are not critical, although certain positions may result in particular advantages described herein, and that the lumens and delivery means could be provided by additional catheters, tubes, and the like, for example including coaxial sleeves, sheathes, and the like which could be positioned over the shaft 12.

While the present embodiments are described with reference to the human prostate, it is understood that they may be used to treat mammal prostates in general. Referring now to FIGS. 7B-7E, the prostatic tissue debulking device 10 may be introduced through the male urethra U to a region within the prostate P which is located immediately distal to the bladder B. The anatomy is shown in FIG. 7B. Once the catheter 10 has been positioned so that the anchoring balloon 24 is located just distal of the bladder neck BN (FIG. 7C) the balloon can be inflated, preferably to occupy substantially the entire interior of the bladder B, as shown in FIG. 7D. Once the anchoring balloon 24 is inflated, the position of the prostatic tissue debulking device 10 may be fixed and stabilized within the urethra U so that the energy delivery region 20 is positioned within the prostate P. It will be appreciated that proper positioning of the energy delivery region 20 may depend only on the inflation of the anchoring balloon 24 within the bladder B. As the prostate is located immediately proximal to the bladder neck BN, by spacing the distal end of the energy delivery region very close to the proximal end of the balloon, typically within the range from 0 mm to 5 mm, preferably from 1 mm to 3 mm, the delivery region can be properly located. After the anchoring balloon 24 has been inflated, energy can be delivered into the prostate for debulking, as shown by the arrows in FIG. 7D. Once the energy has been delivered for a time and over a desired surface region, the energy region can be stopped and the prostate will be debulked to relieve pressure on the urethra, as shown in FIG. 7E. At that time, a flushing fluid may be delivered through port 34 and aspirated into port 36, as shown in FIG. 7E.

FIG. 7F shows rapid exchange of a carrier tube 380 when the linkage 430 is coupled to the elongate element 310 anchored to a target location of an organ. The elongate element 410 can be inserted or removed from the linkage by the user. The elongate element 380 can be advanced into opening 409 near connection structure 405 of the elongate tubular structure 431.

The imaging probe 460 can be mounted on a second linkage and configured to move with the nozzle of carrier 382, so as to image interaction of the energy stream from carrier 382 when tissue is treated. The images of the treatment may comprise axial images and sagittal images from the imaging probe 460. The linkage can be coupled to the controller or processor (or both) as described herein to move the imaging probe 460 synchronously along the axis with the carrier 382 and nozzle of the carrier, for example. The imaging probe 460 may comprise a trans-rectal ultrasound probe and the carrier 482 may comprise a component of the treatment probe 450 as described herein.

FIG. 7G shows alignment of the distal tip of the carrier 382 with the opening 409 of proximal end of the elongate tubular structure 431 to insert the carrier tube 380 as in FIG. 7F.

FIG. 7H shows the carrier advanced toward a locking structure 406 on the proximal end of the linkage as in FIG. 7F. The locking structure 406 may be sized to receive protrusion 404 so as to form a locked joint 402.

FIG. 7I shows the carrier tube 380 locked to the linkage 430 as in FIGS. 7F and 7G. The protrusion 404 has been inserted into an opening of locking structure 406 so as to form the locked joint. The joint can be unlocked by user manipulation.

Additional details regarding tissue resection or debulking devices suitable for incorporation with embodiments are disclosed in U.S. Pat. No. 7,882,841, issued Feb. 8, 2011, entitled "MINIMALLY INVASIVE METHODS AND DEVICES FOR THE TREATMENT OF PROSTATE DISEASES", U.S. Pat. No. 9,232,959, entitled "MULTI FLUID TISSUE RESECTION METHODS AND DEVICES", and International Application No. PCT/US2013/028441, filed on Feb. 28, 2013, entitled "AUTOMATED IMAGE-GUIDED TISSUE RESECTION AND TREATMENT", the full disclosures of which have been previously incorporated herein by reference.

FIGS. 8A-8B show embodiments comprising the tissue debulking device or delivery probe of FIGS. 7A-7I and a sealant applicator nozzle. The sealant delivery device may, for example, be used to deliver a hemostatic agent or sealant into a cavity created by tissue resection by the tissue debulking action of the device in the prostatic capsule. While the tissue debulking device of FIGS. 7A-7I is shown, it will be understood that many other existing tissue resection or tissue debulking devices may be adapted for sealant delivery FIG. 8A shows a tissue debulking device 10 with attached sealant applicator nozzle 812. The tissue debulking device 10 may be a delivery probe configured to deliver energy to a predetermined profile of the prostatic capsule 900. A processor may be operatively coupled to the delivery probe and configured to control delivery of the sealant 701 from the delivery probe to a predetermined profile of the tissue space. The sealant applicator nozzle 812 may be integral to the tissue resection device. The sealant applicator nozzle 812 may be interchangeable with a tissue resection nozzle, for example, by rapid exchange of carrier probes as previously described herein. Alternatively or in combination, the input fluid of the energy delivery probe may be altered so as to provide for sealant delivery through the tissue resection nozzle. For example, the input fluid may be changed from saline to sealant after tissue resection. In some embodiments, the saline used for tissue resection may be infused with a sealant prior to, during, or after tissue resection in order to promote hemostasis. The sealant may be applied through the sealant applicator nozzle 812 following tissue resection such that the sealant lines the cavity edge 904 and promotes hemostasis. The sealant may for example be sprayed by the tissue resection device. In the case of a tissue resection device using water to ablate tissue, as previously described above, the sealant spray may be directed along the cavity edge 904 using the same angle and depth profiles used during the tissue resection surgery. The water, or other energy source, may be delivered to the predetermined profile of the tissue volume at a first flow rate to resect the tissue and create a resection cavity 901. The sealant 701 may be delivered to the resection cavity 901 at a second flow rate lower than the first flow rate. The tissue resection device probe may also help to spread the sealant along the cavity edge 904 after delivery. The tissue resection device may further comprise a distal balloon adjacent the distal end of the delivery probe and a distal balloon inflation port at the proximal end of the delivery probe in fluid communication with the distal balloon. The distal balloon may be positioned adjacent to a distal opening of the tissue space so as to seal the bladder B upon inflation and close off the tissue resection cavity 901, as shown in FIG. 8B. Delivery of the sealant may be confined to the resection cavity 901 by the inflation of the distal balloon. For sealants which are inactivated or do not bind to tissue in liquids, the liquids and resected tissues may first be aspirated from the resection cavity 901 through an aspiration port of the sealant delivery device. The prostatic capsule 900 may then be insufflated by the infusion of a gas or other fluid, for example, carbon dioxide ($CO_2$), through an insufflation port to provide a dry volume in which to apply the sealant. The creation of a dry volume inside the resection cavity 901 may further promote the spraying action of the sealant and may improve the reach of the sealant into the cavity edge 904. Alternatively, a dry sealant may be delivered in any of the embodiments described herein which, upon delivery to the resection cavity 901, mixes with the liquid inside the resection cavity 901 and forms a sealant agent. Alternatively, the prostatic capsule 900 may be insufflated by the introduction of the sealant fluid. Any of the embodiments described herein may be configured to aspirate one or more of tissues or fluids from the cavity, for example through an aspiration port in the catheter or delivery probe. Any of the embodiments described herein may be configured to insufflate the cavity, for example through a gas infusion port in the catheter or delivery probe.

Alternatively or in combination, the sealant delivery device may be configured such that any of the catheter embodiments described herein may replace the sealant applicator nozzle shown. The tissue resection nozzle may for example be rapidly exchanged with a catheter comprising one or more balloons to deliver the sealant to the cavity as described herein. Alternatively or in combination, the sealant applicator nozzle may deliver sealant to the cavity as described then be exchanged with a catheter comprising one or more expandable members, for example a proximal balloon, to compress and/or move the sealant along the cavity walls as described herein.

Figure 9:
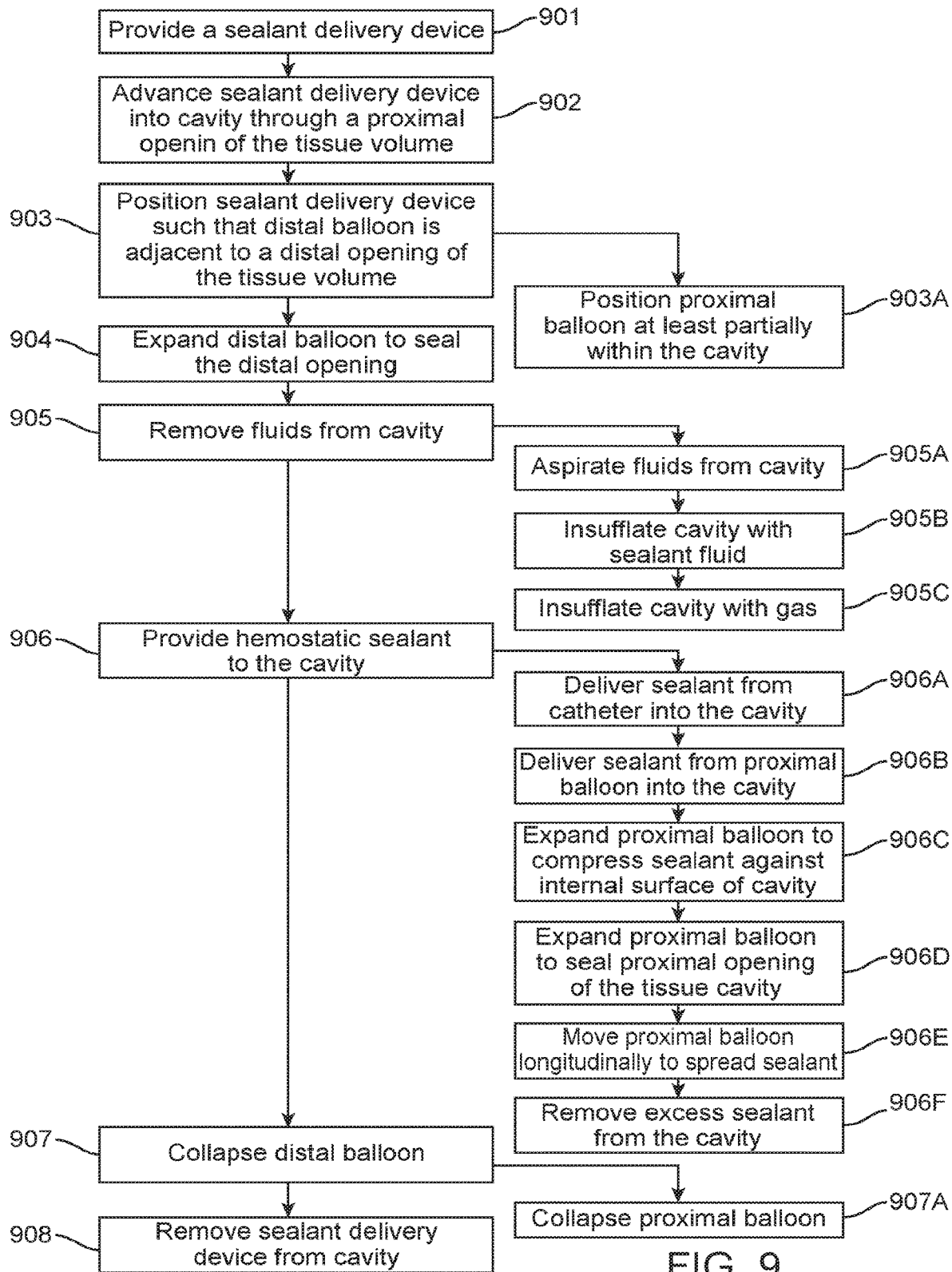
FIG. 9 shows a flowchart of a method of providing hemostasis within a tissue cavity, in accordance with embodiments.

FIG. 9 shows a flowchart of a method of providing hemostasis within a tissue cavity.

At Step 901, a sealant delivery device may be provided. The sealant delivery device may, for example, be any of the embodiments described herein.

At Step 902, the sealant delivery device may be advanced through a proximal opening of the tissue volume into a cavity defined by an internal surface of a bleeding tissue volume.

At Step 903, the sealant delivery device may be positioned such that a distal balloon is adjacent a distal opening of the tissue volume. Step 903 may further comprise a substep, Step 903A, in which a proximal balloon of the sealant delivery device is positioned at least partially within the cavity.

At Step 904, the distal balloon may be expanded to seal the distal opening. Sealing the distal opening may comprise conforming the expanded distal balloon to a shape of the bladder neck and/or cavity space.

At Step 905, the fluids may optionally be removed from the tissue cavity. Fluid removal may comprise one or more substeps. At Step 905A, the fluids may be aspirated from the tissue cavity. At Step 905B, the cavity may be insufflated with the sealant fluid. At Step 905C, the cavity may be insufflated with a gas or other fluid.

At Step 906, a hemostatic sealant is provided to the cavity. Step 906 may comprise one or more substeps. For example, at Step 906A, the sealant may be delivered from a catheter of the sealant delivery device into the cavity. At Step 906B, the sealant may be delivered from, or delivered by in the form of a sealant scaffold for example, the proximal balloon into the tissue cavity. At Step 906C, the proximal balloon may be expanded to compress the sealant against the internal surface of the cavity, for example the cavity edge. At Step 906D, the proximal balloon may be expanded to seal the proximal opening of the tissue cavity. At Step 906E, the proximal balloon may be moved along a longitudinal axis of the sealant delivery catheter to spread the sealant over the internal surface of the tissue volume. At Step 906F, the excess sealant may be removed from the cavity.

At Step 907, the distal balloon may be collapsed. Step 907 may further comprise the substep Step 907A in which the proximal balloon is collapsed.

At Step 908, the sealant delivery device may be removed from the cavity.

Although the steps above show a method of providing hemostasis using sealant delivery device in accordance with embodiments, a person of ordinary skill in the art will recognize many variations based on the teaching described herein. The steps may be completed in a different order. Steps may be added or deleted. Some of the steps may comprise sub-steps. Many of the steps may be repeated to provide hemostasis in a bleeding closed tissue volume.

In an exemplary embodiment of the method described by FIG. 9, the sealant delivery device may comprise the sealant delivery device of FIGS. 1A-1C. The tissue volume may comprise a prostatic capsule of the prostate, wherein the proximal opening comprises an opening to the urethra and the distal opening comprises a bladder neck between the prostate and the bladder. The cavity may comprise a resection cavity left after tissue debulking. The sealant delivery device may be advanced through the urethra into the resection cavity and positioned such that the distal balloon resides within the bladder adjacent the bladder neck. Expansion of the distal balloon may seal the cavity by sealing the bladder neck. The proximal balloon may be inflated prior to, during, or after sealant delivery. The sealant may be delivered into the cavity through the catheter. Expansion of the proximal balloon may compress the sealant into the internal surface of the cavity comprising the cavity edge. The proximal and distal balloons may remain inflated until hemostasis has occurred, at which point the balloons may be collapsed and the sealant delivery device removed from the cavity.

In another exemplary embodiment of the method described by FIG. 9, the sealant delivery device may comprise a tissue debulking device such as the sealant delivery device of FIGS. 8A-8B. The sealant delivery device may comprise an energy delivery probe, for example a tissue debulking device, with a sealant delivery nozzle. The tissue volume may comprise a prostatic capsule of the prostate, wherein the proximal opening comprises an opening to the urethra and the distal opening comprises a bladder neck between the prostate and the bladder. The sealant delivery device may be advanced into the tissue volume through the urethra into the prostatic capsule and positioned such that the distal balloon resides within the bladder adjacent the bladder neck. Energy may be delivered from the energy delivery probe to a predetermined profile of the tissue volume at a first flow rate to debulk the tissue volume and thereby create the resection cavity. The distal balloon may then be expanded to seal the resection cavity and fluids may be aspirated from the cavity. The cavity may then be insufflated with a gas, for example $CO_2$. The sealant delivery device may then deliver the sealant into the closed cavity. The distal balloon may be collapsed once hemostasis has begun for removal of the sealant delivery device.

While specific mention has been made herein to delivery of a sealant by one or more of the proximal balloon, catheter, or delivery probe, the distal balloon may also be adapted to deliver sealant into the tissue space. For example, a proximal portion of the distal balloon, which forms a seal about the tissue space at the distal opening of the space, may be configured to deliver sealant into the tissue cavity. The proximal portion of the distal balloon may for example comprise pores or holes through which sealant may be delivered, as described herein. In any of the embodiments described herein, one or more of the catheter, delivery probe, proximal balloon, or distal balloon may configured to apply a sealant to the space enclosed within the tissue. For example, in some embodiments, the distal balloon and the catheter are configured to deliver sealant. In some embodiments, the distal balloon and the proximal balloon are configured to deliver sealant. In some embodiments, the distal balloon and the delivery probe are configured to deliver sealant. In some embodiments, only the distal balloon is configured to deliver sealant. In some embodiments, only the proximal balloon is configured to deliver the sealant. It will be understood that embodiments of the sealant delivery device may take on many configurations, which may include one or more balloons, one or more catheter, or one or more delivery probe.

While specific mention has been made herein to uniform delivery of a hemostatic sealant to a tissue enclosing a space, for example a resection cavity, delivery of the sealant may also be targeted to specific locations within said tissue space. The embodiments described herein may be configured to deliver sealant to specific locations within the tissue space. In many embodiments, the sealant delivery device may comprise a separate small lumen catheter which may be used to direct sealant to a certain part of the tissue. For example, many tissue resection devices developed for use in the prostate may leave behind focal lesions or injuries, particularly in cases where needles are used to puncture the tissue space, which could be treated by focal delivery of sealant.

The sealant delivery device may be brought under direct visualization to help direct it to the site of bleeding. The punctures may be sealed with focal delivery of sealant applied by the catheter. Targeting the delivery of sealant may minimize the sealant required to establish hemostasis and may prevent or minimize any side effects which may occur due to over-use of the sealant. Visualization of bleeding and targeted delivery of sealant may be used with any of the embodiments described herein to minimize the amount of sealant required and promote hemostasis.

FIGS. 10A-10G show embodiments of a minimally invasive sealant delivery device comprising a scope and related methods. The sealant delivery device may, for example, be used to deliver a hemostatic agent or sealant into a cavity created by tissue resection in the prostatic capsule 900.

The sealant delivery device may comprise one or more of a rigid scope, a flexible scope, or a telescopic scope. The scope may be a cystoscope, a resectoscope, a ureteroscope, or the like. The scope can be configured in many ways and may be used to visualize and/or guide sealant delivery into the cavity. The scope can be positioned in order to view the delivery of the sealant when placed from the delivery device and at other times during the tissue sealing procedure. The outer sheath as disclosed herein can be configured for use with a resectoscope or other device used for surgery as described in the applications incorporated herein by reference. The scope may comprise an outer shaft over which the sheath is placed, and the sheath may have a length sized smaller than the length of the shaft in order to allow visualization when the sheath is placed over scope. In many embodiments, the outer sheath comprises a length within a range from about 15 to 30 mm in order to allow visualization of the treatment size with the scope when the sheath is placed over the scope.

The sealant delivery device may be delivered through the urethra such that the distal end of the scope is in the bladder or tissue resection cavity, for example, near the bladder neck. The sealant delivery device may be stationary in the cavity during at least a portion of the sealing procedure. The sealant delivery device may be moved within the cavity in order to direct sealant delivery to locations of bleeding within the tissue resection cavity, for example near the bladder neck. The sealant delivery device may further comprise an injection port fluidly coupled via a working channel to the distal end of the sealant delivery device. A syringe may be used to inject a sealant at the injection port as shown.

Figure 10A:
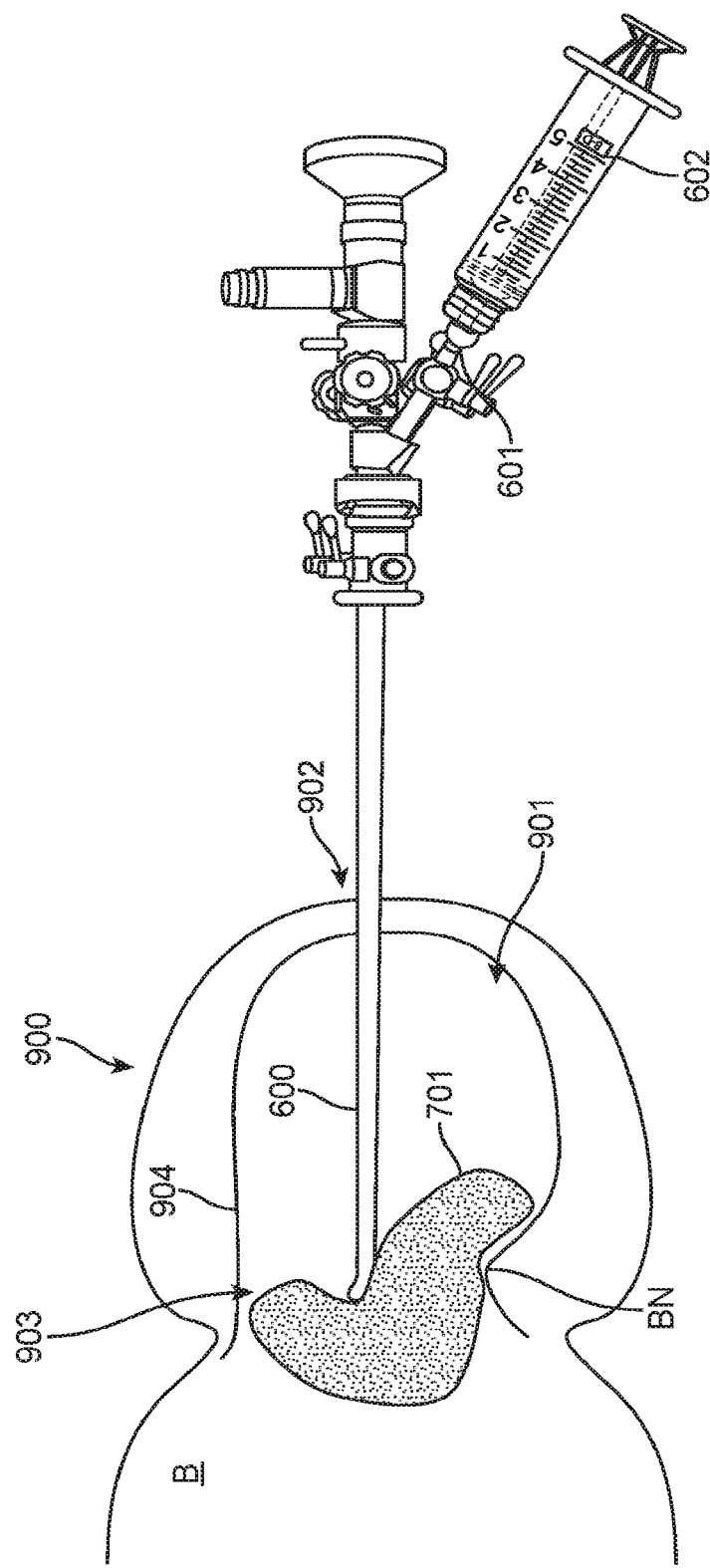
FIGS. 10A-10G show sectional schematic views of sealant delivery devices comprising a scope, in accordance with embodiments.

FIG. 10A shows delivery of a sealant 701 into the resection cavity 901 of the prostatic capsule 900. The scope 600 may be advanced through the urethra into the cavity via the proximal opening 902. The sealant 701 may be infused into the scope 600 through a sealant injection port 601 located near the proximal end of the scope 600. The sealant 701 may be delivered to the resection cavity 901 via a sealant delivery port or the opening of the working channel of the scope 600 (not shown) located near the distal end of the scope 600 residing inside the prostatic capsule 900.

Figure 10B:
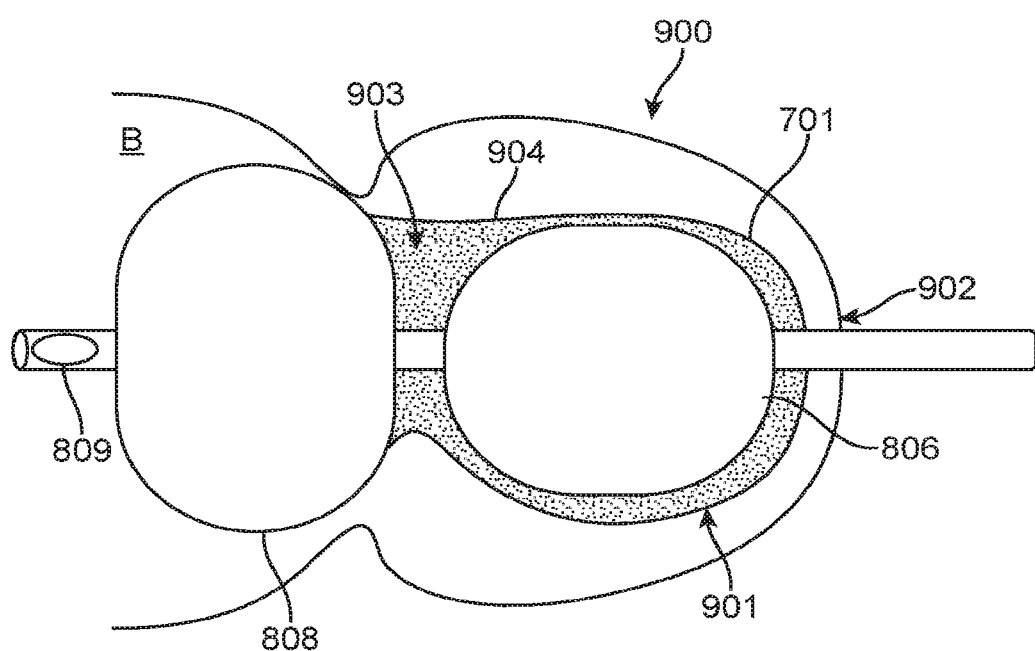

The scope 600 may further comprise an optional catheter sleeve similar to any of the catheter embodiments described herein. The catheter may be a customizable sleeve configured to be deployed inside or outside the scope 600 to enhance sealant delivery. FIG. 10B shows an embodiment of a catheter sleeve comprising a modified Foley catheter. The catheter may comprise a distal balloon and a proximal balloon and may be delivered through the urethra such that distal balloon and proximal balloon are partially or fully inserted into the bladder B and prostatic capsule 900, respectively. The catheter may be sized and shaped to closely fit within the proximal opening 902 of the prostatic capsule 900 to the urethra, such that when the catheter is advanced into the prostatic capsule 900, the catheter body can substantially seal off the proximal opening 902 to inhibit leakage of the sealant into the urethra. The sealant can be applied to the resected tissue near the bladder neck BN in order to inhibit bleeding, and the sealant can be applied without a balloon, for example.

The catheter may further comprise one or more of an irrigation port, a drainage port, an inflation port for the distal bladder balloon, or an inflation port for the proximal prostatic balloon as described herein. The inflation ports may be fluidly coupled to the balloons and used to inflate the distal and proximal balloons, respectively. The irrigation and drainage ports may be used to introduce fluids, such as saline and medications, into the bladder and remove fluids, such as urine, from the bladder, respectively, via one or more ports at the distal end of the catheter. The prostatic capsule 900 may be sealed off from the bladder while still allowing for the passage of fluids to and from the bladder when the distal balloon in inflated using the inflation port for the distal balloon.

FIG. 10B shows the resection cavity 901 filled with the sealant 701 after delivery through the working channel of the scope as described herein. The distal balloon 808 may be inflated prior to, during, or after delivery of the sealant to the cavity. The distal balloon 808 may be inflated so as to completely seal off the bladder B from the prostatic capsule 900 at the distal opening 903 of the prostatic capsule 900 comprising the bladder neck BN, such that only the resection cavity 901 receives the sealant. Alternatively, the distal balloon 808 may be inflated so as to partially, or nearly completely, seal off the bladder B from the prostatic capsule 900. For example, the distal balloon 808 may be inflated so as to leave a small space between the bladder neck BN and the distal balloon 808. This may allow a small amount of sealant to reach the bladder neck itself, as described herein. This may be advantageous in situations where the bladder neck area is the source of bleeding, as the bladder neck common location of bleeding following tissue resection in the prostatic capsule 900. The catheter body may seal off the proximal opening 902 while the catheter is positioned with the cavity, such that the sealant does not enter the urethra.

The balloons can be filled and the sealant applied in any order or repeatedly, for example. The distal balloon 808 may be positioned adjacent to a distal opening 903 of the tissue space so as to seal the bladder upon inflation and isolate the tissue resection cavity 901 in order to apply sealant to the tissue of the resection cavity 901. The proximal balloon 806 may be positioned so as to reside within the resection cavity 901 of the prostatic capsule 900. The proximal balloon 806 can be inflated in order to urge tissue sealant toward the tissue of the resection cavity 901. The distal balloon 808 can be inflated first in order to isolate the tissue resection cavity 901, and the proximal balloon 806 inflated after the distal balloon 808 in order to allow reduced amounts of sealant to be used. The tissue sealant can be delivered before or after (or both) inflation of the proximal balloon 806.

The proximal balloon 806 may be inflated after delivery of the sealant 701 to an expanded configuration. Alternatively, the proximal balloon 806 may be inflated prior to or during delivery of the sealant in order to reduce the amount of sealant need to coat the edge of the cavity. The proximal balloon 806 may be inflated in order to compress the sealant against an internal surface of the cavity, for example the cavity edge 904 at the periphery of the resection cavity 901, thus ensuring delivery to the entire tissue area of the cavity edge 904. The proximal balloon 806 may be an actuatable balloon, similar to the example shown in FIGS. 6A-6C for example, which may be actuated to spread sealant within the cavity. The catheter may be left in the patient with the proximal balloon 806 inflated for an amount of time to ensure hemostasis has occurred. The amount of time for hemostasis may depend on the sealant used and may range from minutes to hours to overnight. The sealant delivery device may be removed from the patient after the sealant has sealed.

Although reference is made to balloons, any expandable member can be used similarly to the balloons as described herein, such as expandable wires, meshes, coverings, and actuators and combinations thereof.

Figure 10C:
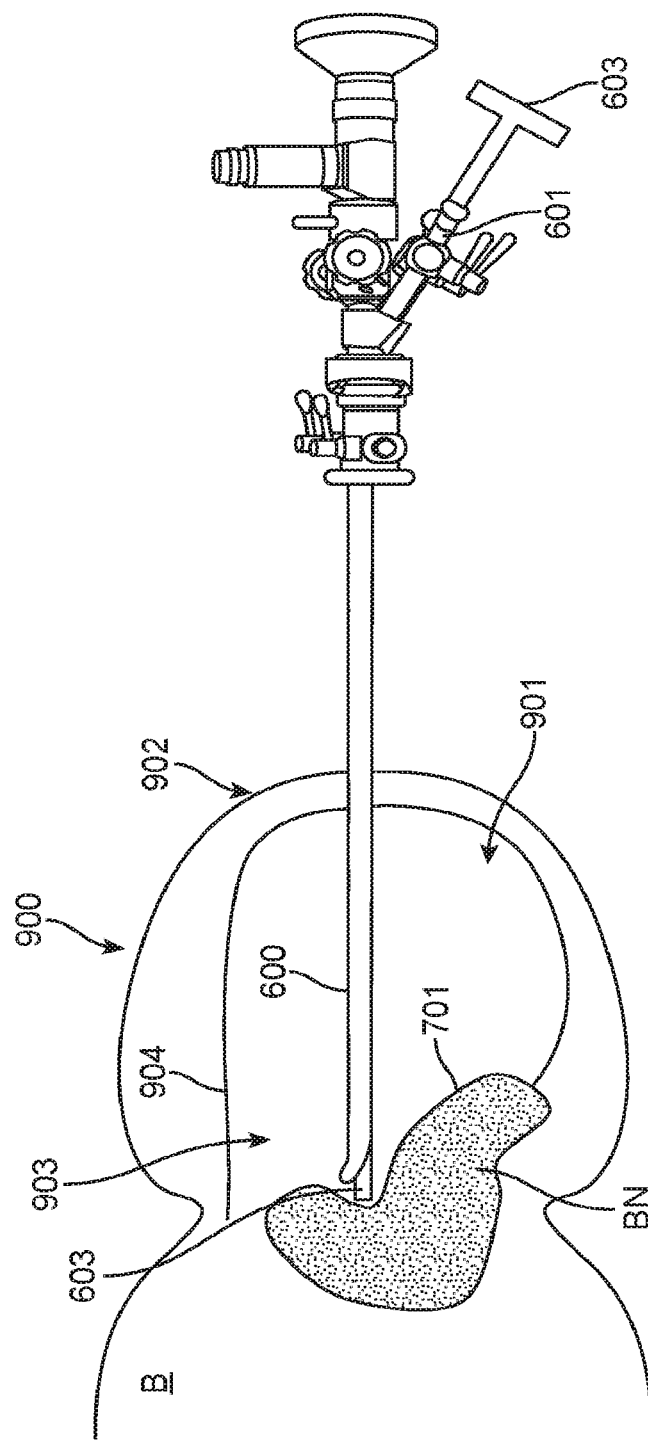

FIG. 10C shows delivery of the sealant 701 into the resection cavity 901 of the prostatic capsule 900 using a stylet 603 or other plunger, for example. In at least some instances, the working channel or sealant injection pathway of the sealant deliver device may comprise a volume larger than the available volume of sealant or the volume of sealant necessary to seal the bleeding tissue. In many cases, sealants may be provided in small packages by manufacturers, for example about 5 ml to about 10 ml per package. Therefore, there may be a benefit to the methods and apparatus described herein that are capable of delivering small volumes without costly wastage of sealant. For example, a stylet may be used after injecting sealant into the working channel via the injection port 601. The stylet 603 may be loaded into the injection port 601 and pushed towards the distal end of the sealant delivery device so as to push at least a portion of the sealant residing in the device out into the resection cavity 901. The stylet 603 may be sized and shaped to fit the working channel such that little or no sealant remains within the device when the stylet 603 is advanced completely through the working channel to the distal end of the device.

Figure 10D:
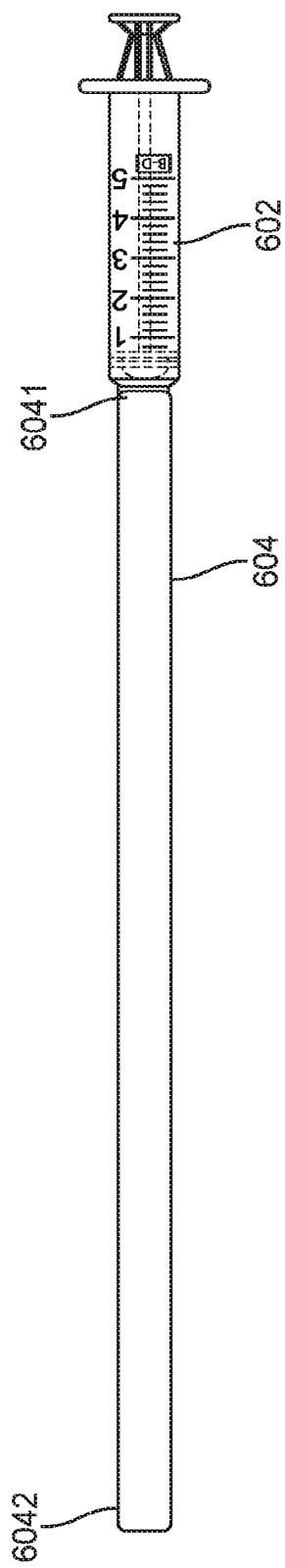
Figure 10E:
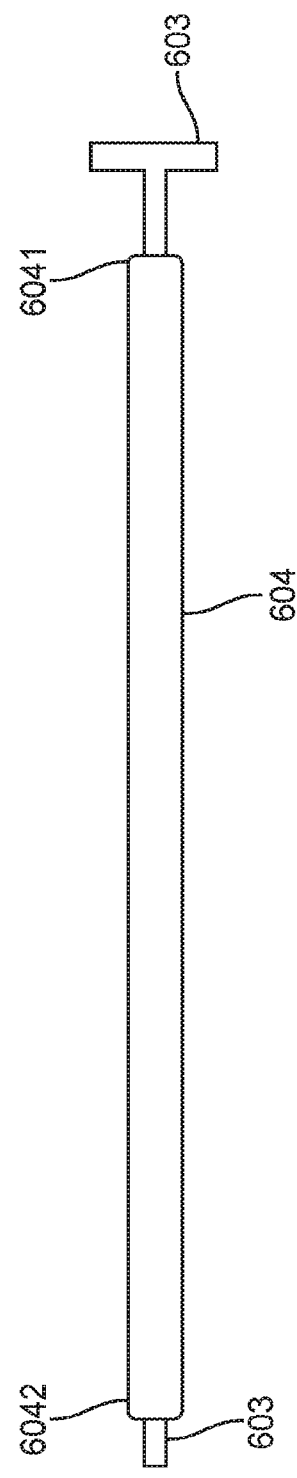
Figure 10F:
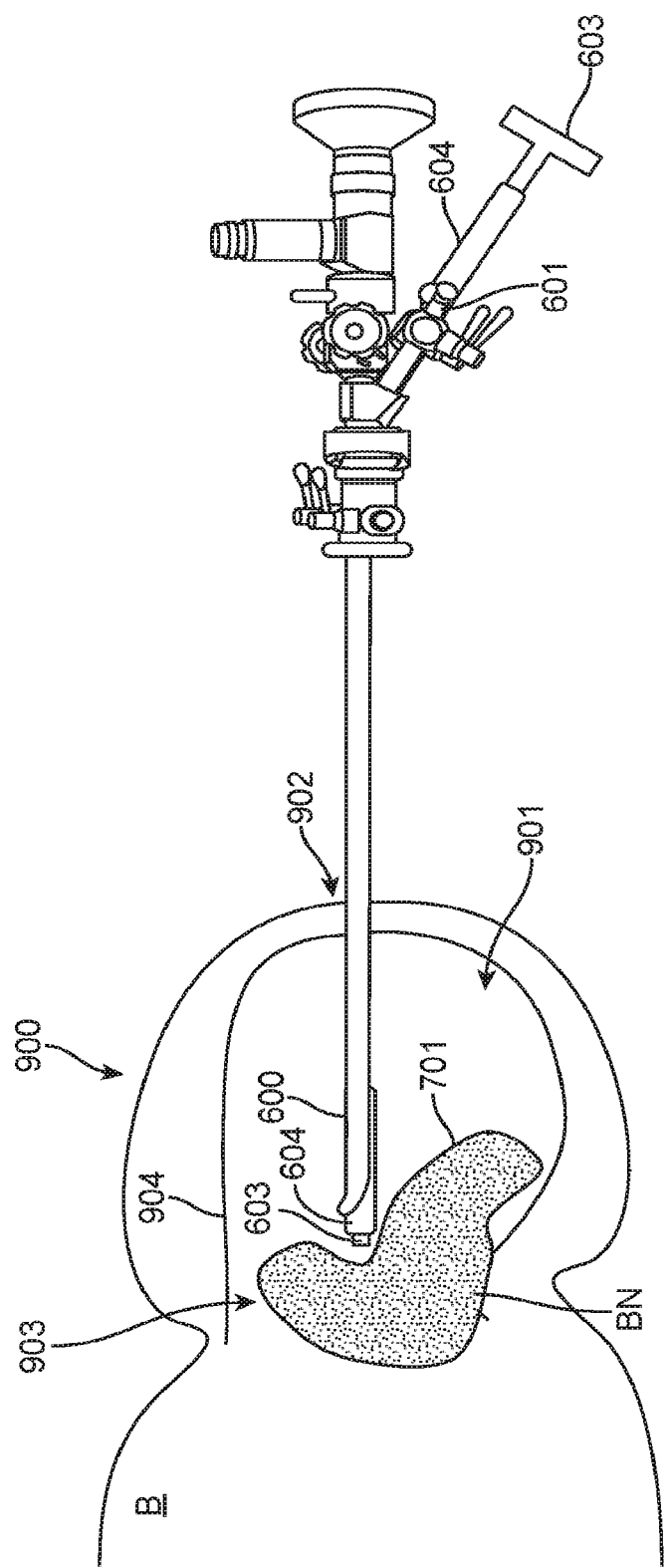

FIGS. 10D-10F show alternative embodiments of a sealant delivery device. The sealant delivery device shown in FIG. 10A may further comprise a cannula or tube 604. In at least some instances, the internal geometry of the working channel may be tortuous or not round which may limit delivery of the sealant into the resection cavity 901. The cannula 604 may be inserted into the working channel of the scope through the injection port so as to provide a smooth, round sealant delivery pathway. The cannula 604 may be sized and shaped to fit within the working channel of the scope. FIG. 10D shows an exemplary cannula 604 which may have proximal and distal ends 6041 and 6042 corresponding to the proximal and distal ends of the working channel of the scope, respectively. Sealant may be injected with a syringe 602 into the proximal end 6041 of the cannula 604 and delivered to the cavity by the distal end 6042 which resides at the distal end of the scope inside the cavity as described herein. An optional stylet may be used after injecting sealant into the cannula 604 to plunge the sealant out of the cannula 604, for example, if there is more dead space than ideal or where amounts of sealant are limited, for example as show in FIG. 10E. FIG. 10F shows the sealant delivery device of FIG. 10A further comprising a cannula and stylet 603 so as to provide more complete delivery of sealant to the resection cavity 901, for example in situations where the volume of the working channel or cannula 604 is larger than the available or cost-effective volume of sealant.

Figure 10G:
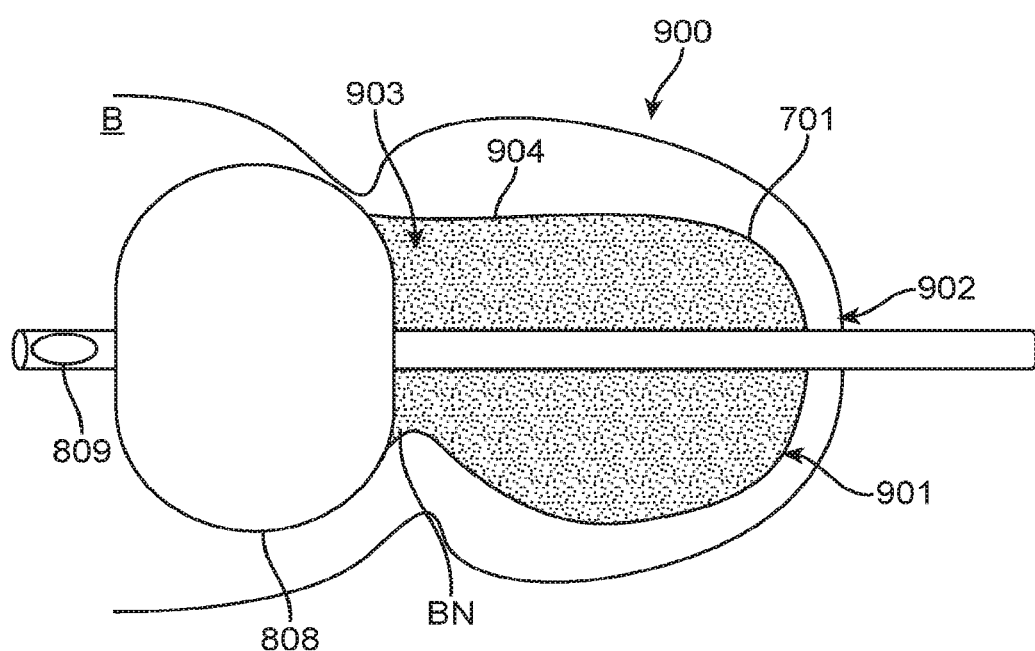

FIG. 10G shows an alternative embodiment of a catheter sleeve. The catheter may comprise a distal balloon 808 and may be delivered through the urethra such that distal balloon 808 is fully inserted into the bladder B. The catheter may be sized and shaped to the closely fit within the proximal opening 902 of the prostatic capsule 900 to the urethra, such that when the catheter is advanced into the prostatic capsule 900, the catheter body substantially seals off the opening. The distal balloon 808 may be positioned adjacent to a distal opening 903 of the tissue space so as to seal the bladder B upon inflation and close off the tissue resection cavity 901 as shown. Alternatively, the distal balloon 808 may be positioned so as to reside within the resection cavity 901 of the prostatic capsule 900 and may compress the sealant toward the resected tissue.

The catheter may further comprise one or more of an irrigation port, a drainage port, or an inflation port for the distal bladder balloon, as described herein (not shown). The inflation port may be fluidly coupled to the distal balloon 808 and used to inflate the balloon. The irrigation and drainage ports may be used as described herein. The prostatic capsule 900 may be sealed off from the bladder B while still allowing for the passage of fluids to and from the bladder B when the distal balloon 808 in inflated using the inflation port for the distal balloon.

The resection cavity 901 may be filled with the sealant after delivery through the working channel of the scope as described herein. The distal balloon 808 may be inflated prior to, during, or after delivery of the sealant to the cavity. The distal balloon 808 may be inflated so as to completely seal off the bladder B from the prostatic capsule 900 at the distal opening 903 of the prostatic capsule 900 comprising the bladder neck BN, such that only the resection cavity 901 receives the sealant. Alternatively, the distal balloon 808 may be inflated so as to partially, or nearly completely, seal off the bladder B from the prostatic capsule 900. For example, the distal balloon 808 may be inflated so as to leave a small space between the bladder neck BN and the distal balloon 808 as described herein. The catheter body may seal off the proximal opening 902 while the catheter is positioned within the cavity, such that the sealant does not enter the urethra.

The catheter may be left in the patient with the proximal balloon inflated for an amount of time to ensure hemostasis has occurred. The amount of time for hemostasis may depend on the sealant used and may range from minutes to hours to overnight. The sealant delivery device may be removed from the patient after the sealant has sealed.

FIGS. 11A-11D show an embodiments of a minimally invasive sealant delivery device and related methods of use. The sealant delivery device may be used to deliver a hemostatic agent or sealant into a cavity created by tissue resection in the prostatic capsule, for example. The sealant delivery device may comprise a catheter comprising a distal balloon and may be delivered through the urethra such that distal balloon is positioned in the urethra near the external sphincter during sealant delivery into the resection cavity. The distal balloon may be fully inserted into the prostatic capsule after sealant delivery so as to reside within the resection cavity. The catheter may be sized and shaped to the closely fit within the proximal opening of the prostatic capsule to the urethra, such that when the catheter is advanced into the prostatic capsule, the catheter body substantially seals off the proximal opening.

In some embodiments, the catheter may comprise a second balloon, for example a proximal balloon located proximal to the distal balloon. In such embodiments, the catheter may be inserted into the prostatic capsule after sealant delivery such that the distal balloon and proximal balloon are fully inserted into the bladder and prostatic capsule, respectively, as described herein. The distal balloon may be positioned adjacent to a distal opening of the tissue space so as to seal the bladder upon inflation and close off the tissue resection cavity. The proximal balloon may be positioned so as to reside within the resection cavity of the prostatic capsule and compress the sealant to the cavity edge upon inflation.

The catheter may further comprise one or more of an irrigation port, a drainage port, an inflation port for the distal balloon, or a cannula. The inflation port may be fluidly coupled to the balloon and used to inflate the distal balloon. The irrigation and drainage ports may be used as previously described herein. The cannula may be inserted into the drainage port of the catheter so as to provide a smooth, round sealant delivery pathway as described herein.

Figure 11A:
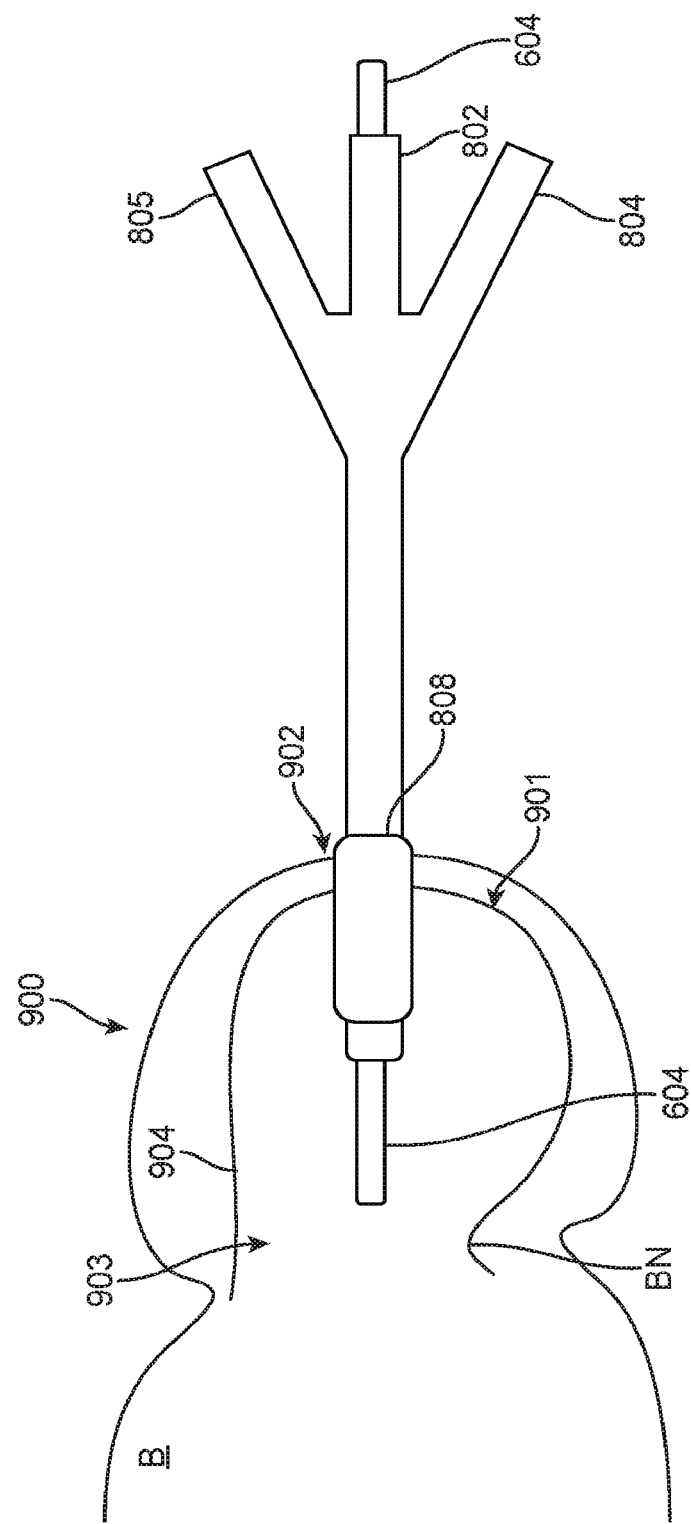
FIGS. 11A-11D show sectional schematic views of a sealant delivery device comprising a catheter, in accordance with embodiments.

FIG. 11A shows initial deployment of the sealant delivery device into the resection cavity 901 of the prostatic capsule 900. The device may be advanced through the urethra into the cavity via the proximal opening 902. The distal balloon may be positioned in the urethra such that the distal end of the catheter is near the proximal opening 902 of the tissue volume. The cannula 604 may be positioned within the catheter such that the distal end of the cannula 604 extends beyond the distal end of the catheter into the cavity for sealant delivery. The cannula 604 may be sized and shaped to fit within the drainage port. The cannula 604 may be sized and shaped to provide a sealant injection pathway comprising a smaller internal volume than the drainage port and lumen of the catheter. For example, in many cases sealants are provided in small packages by manufacturers, for example about 5 ml to about 10 ml per package, while a traditional Foley catheter comprises an internal volume of about 20 ml. By providing an appropriately shaped and sized cannula, the working internal volume of the sealant delivery pathway may reduce the amount of sealant used and prevent waste.

The delivery devices as described herein may comprise an internal volume of no more than about 5 ml along the sealant delivery channel between the proximal and distal ends, for example, an internal volume within a range from about 0.5 ml to about 5 ml.

Figure 11B:
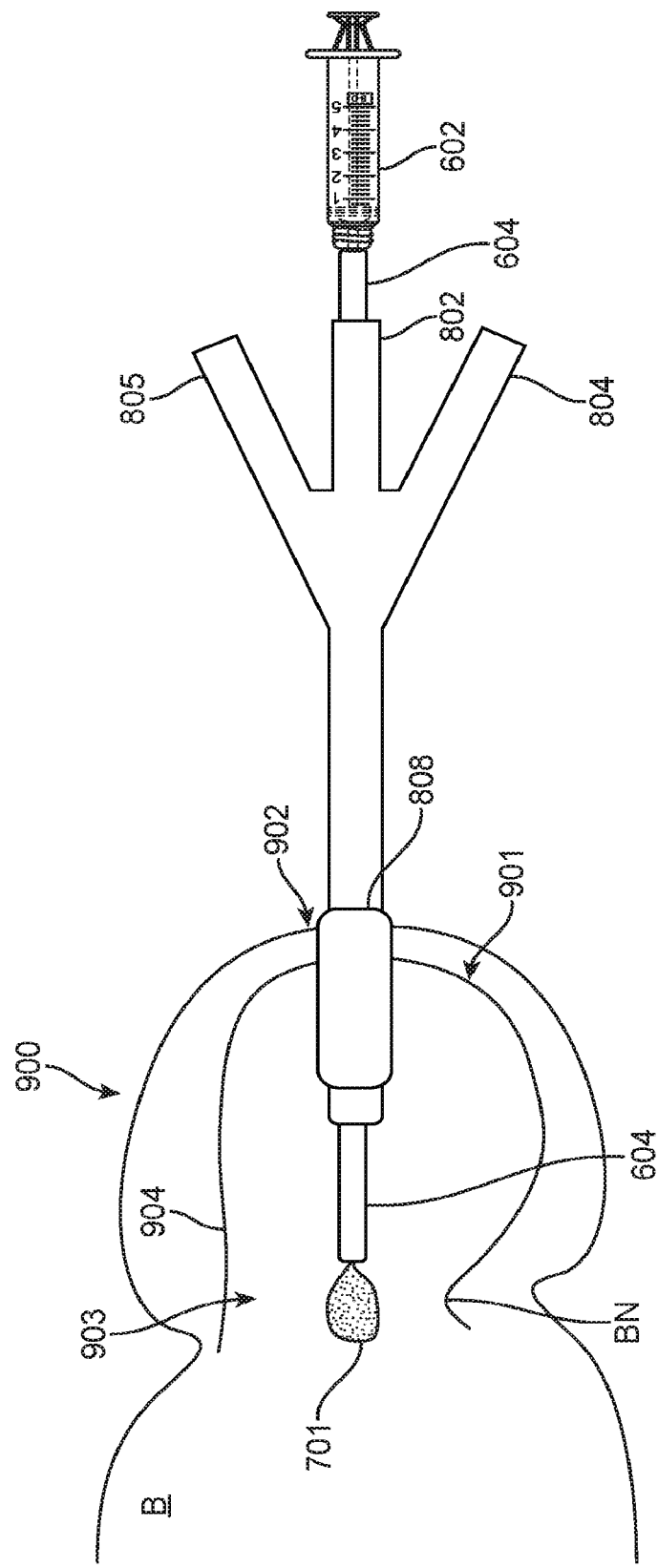
Figure 11C:
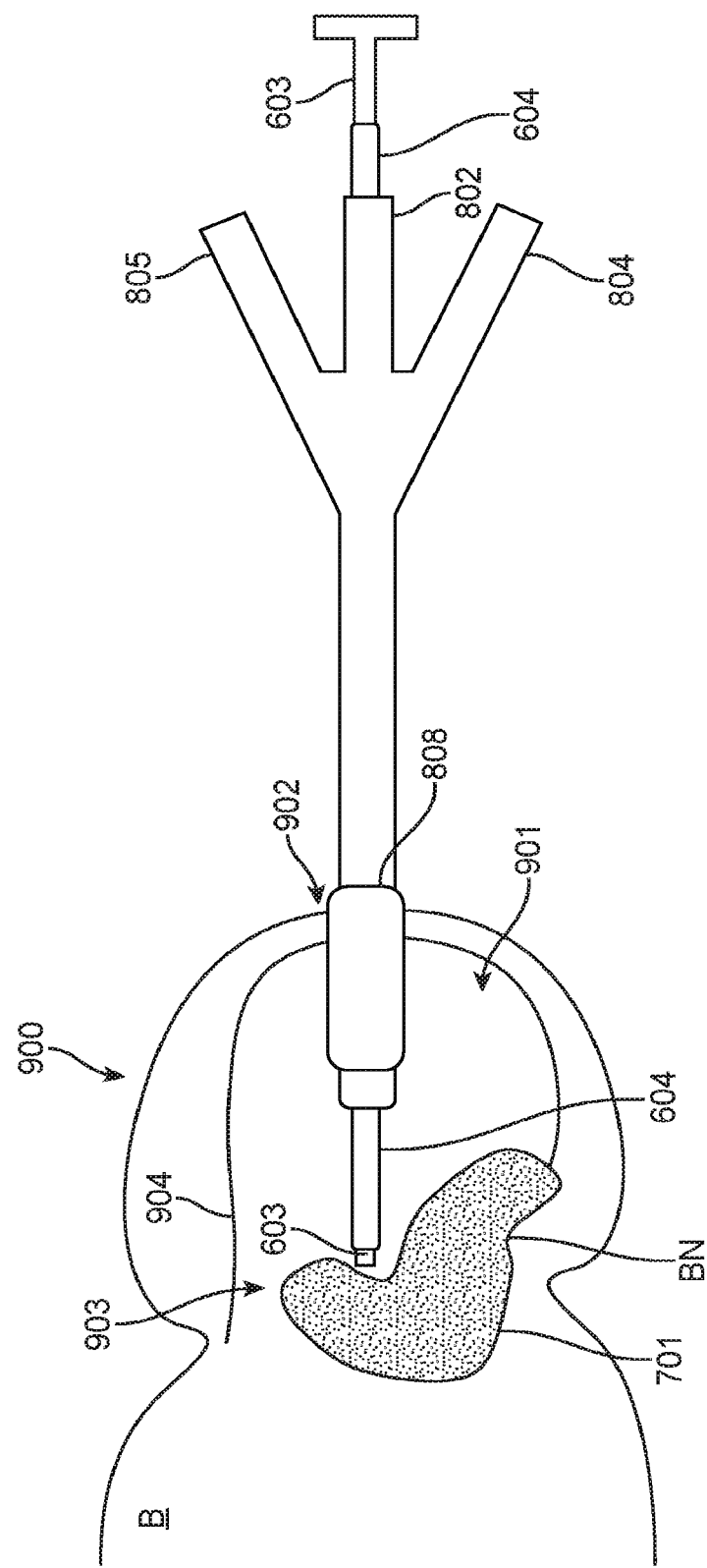

FIG. 11B shows delivery of a sealant 701 into the resection cavity 901 of the prostatic capsule 900. Sealant may be injected with a syringe 602 into the proximal end of the cannula 604 and delivered to the cavity by the distal end of the cannula 604 residing inside the prostatic capsule 900. FIG. 11C shows the use of an optional stylet 603 to plunge the sealant out of the cannula 604 stylet so as to ensure complete delivery of sealant to the resection cavity 901 as described herein. Alternatively, the stylet 603 may be sized and shaped to fit within the drainage port 802 such that the cannula 604 is optional and the stylet 603 may push sealant out of the catheter without the use of a cannula 604 therebetween. A stylet 603 may be applied to any of the embodiments described herein with or without a cannula. The stylet 603 may be loaded into the cannula 604 or drainage port and pushed towards the distal end of the sealant delivery device so as to push at least a portion of the sealant residing in the device out into the resection cavity 901.

Figure 11D:
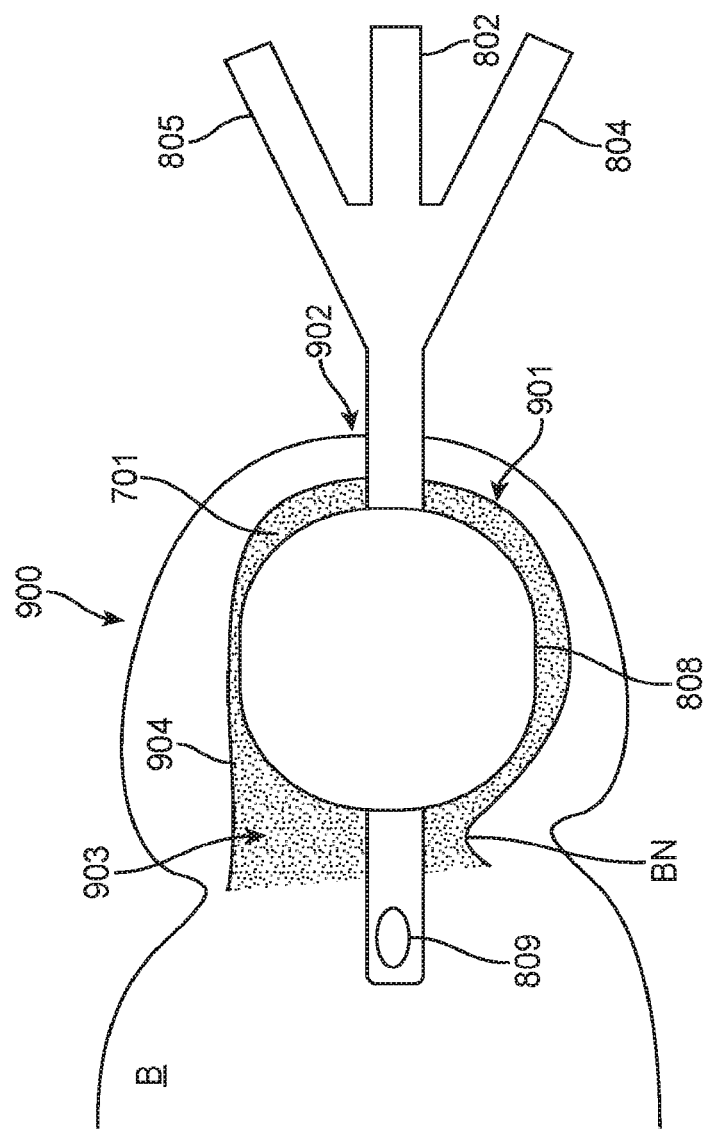

FIG. 11D shows the resection cavity 901 filled with the sealant 701 after delivery through the drainage port or cannula. The drainage channel extending between the drainage port 802 and bladder port 809 can be substantially clear of tissue sealant in order to allow drainage through the catheter, although some residual sealant may remain in the drainage channel when urine is passed through the channel used to tissue sealant. Following delivery of sealant to the cavity, the sealant delivery device may be advanced into the prostatic capsule 900. The distal balloon 808 may reside within the resection cavity 901 and may be inflated in order to compress the sealant against an internal surface of the cavity, for example the cavity edge 904 at the periphery of the resection cavity 901, thus ensuring delivery to the most of tissue area of the cavity edge 904, and in some instances the entire cavity edge 904. The catheter may be left in the patient with the distal balloon 808 inflated for an amount of time to ensure hemostasis has occurred. The amount of time for hemostasis may depend on the sealant used and may range from minutes to hours to overnight or longer. The sealant delivery device may be removed from the patient after the sealant has sealed, and residual sealant may remain in the drainage port 802 subsequent to removal.

Figure 12A:
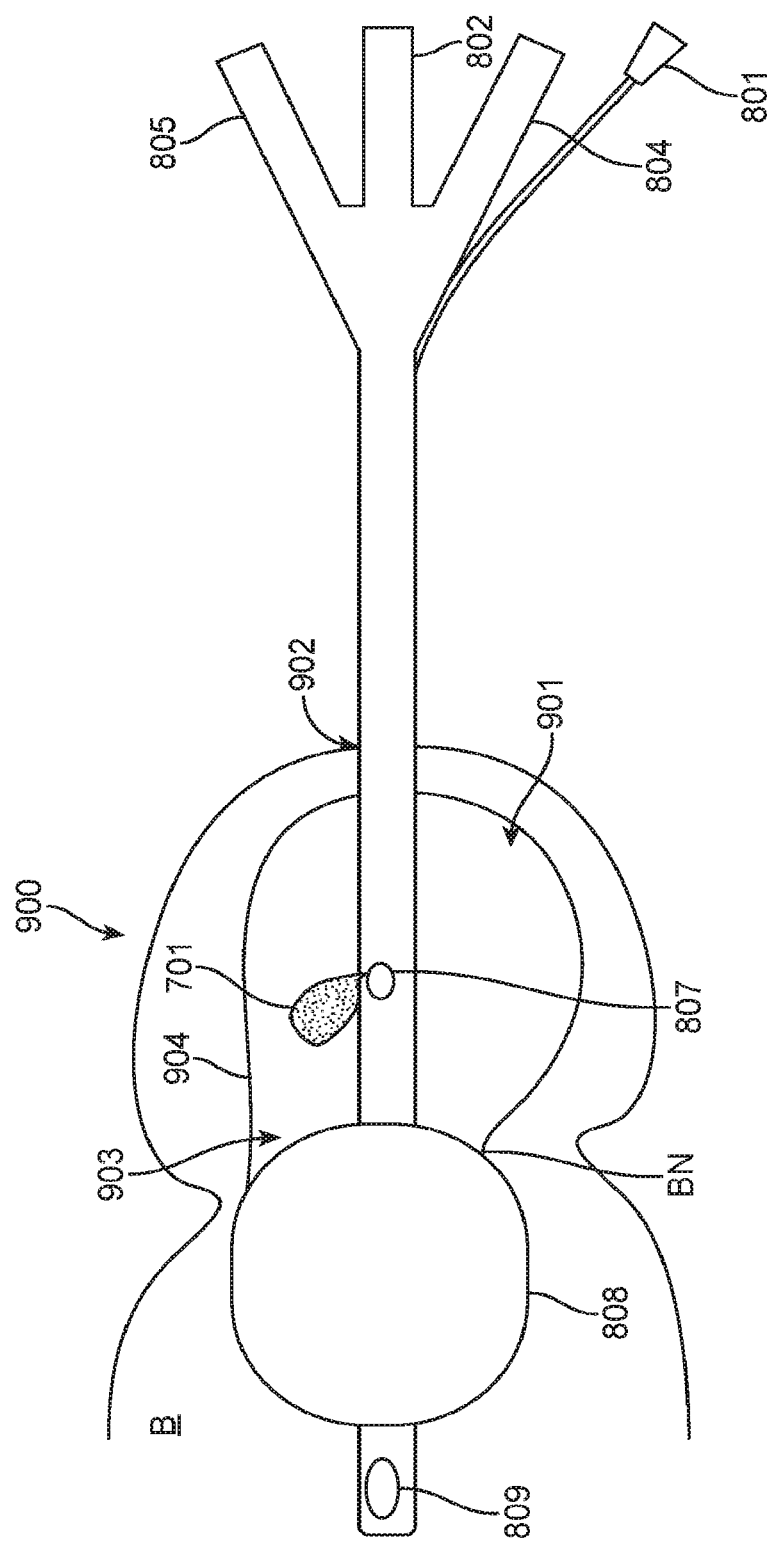
FIGS. 12A-12B show sectional schematic views of another sealant delivery device comprising a catheter, in accordance with embodiments.
Figure 12B:
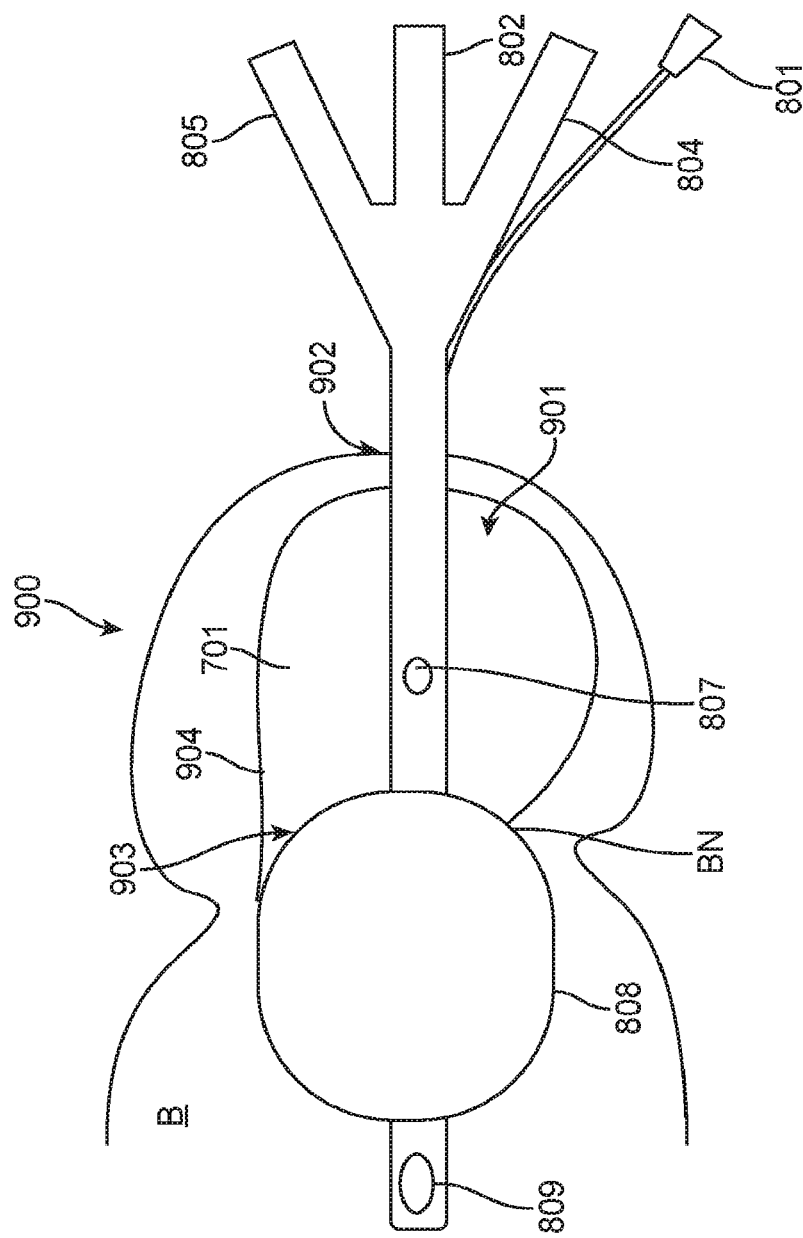

In any of the embodiments described herein, insertion of the sealant delivery device and/or delivery of sealant to the cavity may be guided by transrectal ultrasound (TRUS) or other imaging modalities for visual guidance. TRUS may be used to guide actuation of the catheter during sealant delivery, for example by retracting or advancing the catheter within the cavity by mechanical or manual means. The delivery device may for example deliver sealant to the distal opening 903 of the resection cavity and move proximally as the sealant is injected so as to promote even and homogeneous sealant delivery FIGS. 12A-12B show another an embodiment and related methods of a minimally invasive sealant delivery device. The sealant delivery device may, for example, be used to deliver a hemostatic agent or sealant into a cavity created by tissue resection in the prostatic capsule. The sealant delivery device may comprise a catheter comprising a distal balloon and may be delivered through the urethra such that distal balloon is fully inserted into the bladder. The distal balloon may be positioned adjacent to a distal opening of the tissue space so as to seal the bladder upon inflation and close off the tissue resection cavity.

The catheter may further comprise one or more of an irrigation port, a drainage port, an inflation port for the distal bladder balloon, or a sealant infusion port as previously described herein. The inflation port may be fluidly coupled to the balloon and used to inflate the distal balloon. The sealant infusion port may be used to deliver sealant to the resection cavity prior to, during, or after inflation of the distal balloon.

FIG. 12A shows delivery of a sealant 701 into the resection cavity 901 of the prostatic capsule 900. The catheter may be advanced through the urethra into the cavity via the proximal opening 902. The sealant 701 may be infused into the catheter through a sealant infusion port 801 located near the proximal end of the catheter and positioned distally with respect to the distal balloon 808. The sealant may be delivered to the resection cavity 901 via a sealant delivery port 807 located on the catheter residing inside the prostatic capsule 900. The sealant delivery port 807 may be located near the distal balloon 808. The sealant delivery port may be about 0.1 mm to about 70 mm away from the distal balloon, for example about 0.1 mm to about 60 mm. The sealant delivery port may have a maximum dimension across, for example a diameter, within a range from about 15 to 30 mm. Although only one sealant delivery port is shown, it will be understood that the catheter may comprise a plurality of sealant delivery ports. The distal balloon 808 may be inflated so as to completely seal off the bladder B from the prostatic capsule 900 at the bladder neck BN as previously described herein.

FIG. 12B shows the resection cavity 901 filled with the sealant 701 after delivery. Inflow of sealant through the sealant delivery port 807 may result in a positive pressure within the resection cavity 901. The positive pressure may ensure even distribution of the sealant to the cavity edge 904 without the use of an additional as described herein. The positive pressure may also be useful in opening a cavity which has collapsed following tissue resection. The catheter may be left in the patient with said positive pressure for an amount of time to ensure hemostasis has occurred. The amount of time for hemostasis may depend on the sealant used and may range from minutes to hours to overnight.

FIGS. 13A-13D show yet another embodiment of a minimally invasive sealant delivery device and related methods. The device may be substantially similar to the device of FIGS. 11A-11D. The sealant delivery device may, for example, be used to deliver a hemostatic agent or sealant into a cavity created by tissue resection in the prostatic capsule. The sealant delivery device may comprise a catheter comprising a distal balloon and may be delivered through the urethra such that distal balloon is positioned in the urethra near the external sphincter during sealant delivery into the resection cavity. The distal balloon may be fully inserted into the prostatic capsule after sealant delivery so as to be positioned adjacent to a distal opening of the tissue space so as to seal the bladder upon inflation and close off the tissue resection cavity. The catheter may be sized and shaped to the closely fit within the proximal opening of the prostatic capsule to the urethra, such that when the catheter is advanced into the prostatic capsule, the catheter body substantially seals off the proximal opening.

In some embodiments, the catheter may comprise a second balloon, for example, a proximal balloon located proximal to the distal balloon. In such embodiments, the catheter may be inserted into the prostatic capsule after sealant delivery such that the distal balloon and proximal balloon are fully inserted into the bladder and prostatic capsule, respectively, as described herein. The proximal balloon may be positioned so as to reside within the resection cavity of the prostatic capsule and compress the sealant to the cavity edge upon inflation.

The catheter may further comprise one or more of an irrigation port, a drainage port, an inflation port for the distal balloon, or a cannula. The inflation port may be fluidly coupled to the balloon and used to inflate the distal balloon. The irrigation and drainage ports may be used as previously described herein. The cannula may be inserted into the drainage port of the catheter so as to provide a smooth, round sealant delivery pathway as described herein.

Figure 13A:
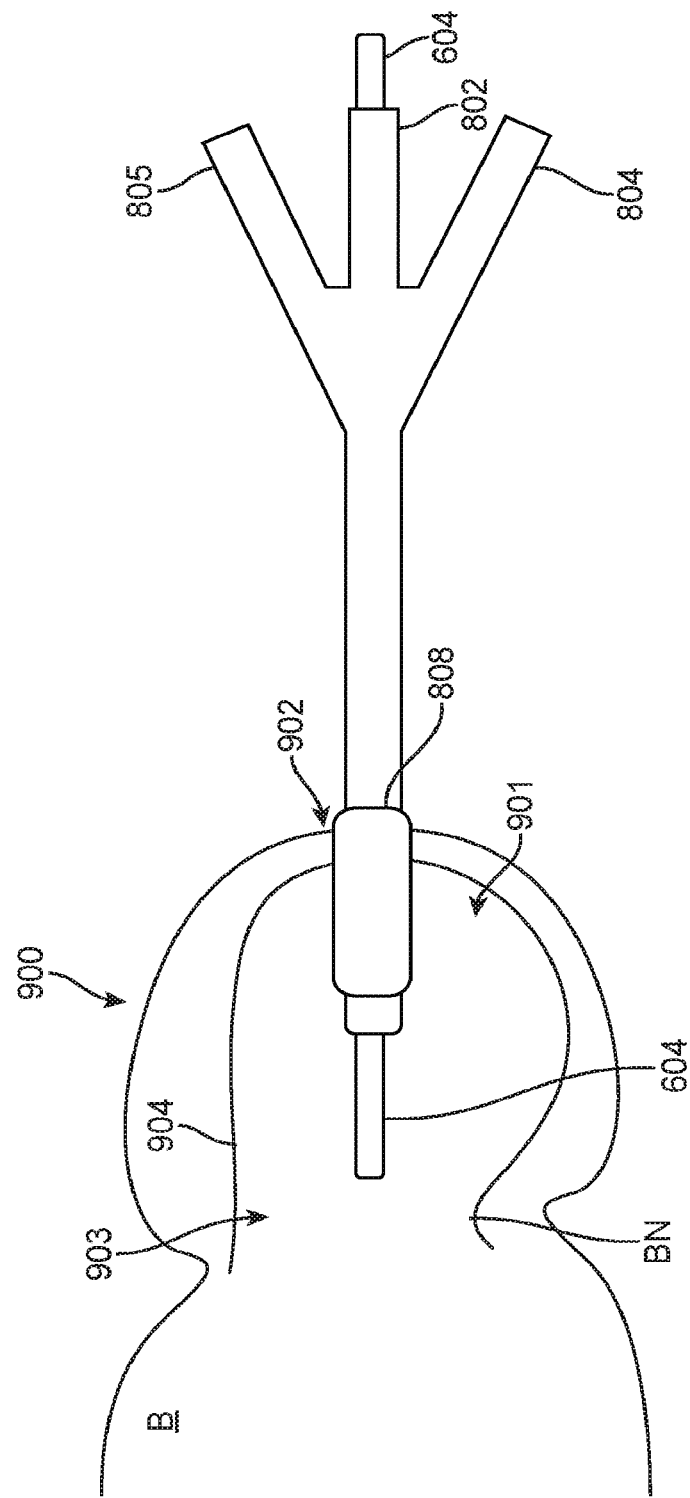
FIGS. 13A-13D show sectional schematic of yet another sealant delivery device comprising a catheter, in accordance with embodiments.

FIG. 13A shows initial deployment of the sealant delivery device into the resection cavity 901 of the prostatic capsule 900. The device may be advanced through the urethra into the cavity via the proximal opening 902. The distal balloon 808 may be positioned in the urethra such that the distal end of the catheter is near the proximal opening 902 of the tissue volume. The cannula 604 may be positioned within the catheter such that the distal end of the cannula 604 extends beyond the distal end of the catheter into the cavity for sealant delivery. The cannula 604 may be sized and shaped to fit within the drainage port 802. The cannula 604 may be sized and shaped to provide a sealant injection pathway comprising a smaller internal volume than the drainage port and lumen of the catheter to prevent waste as described herein.

Figure 13B:
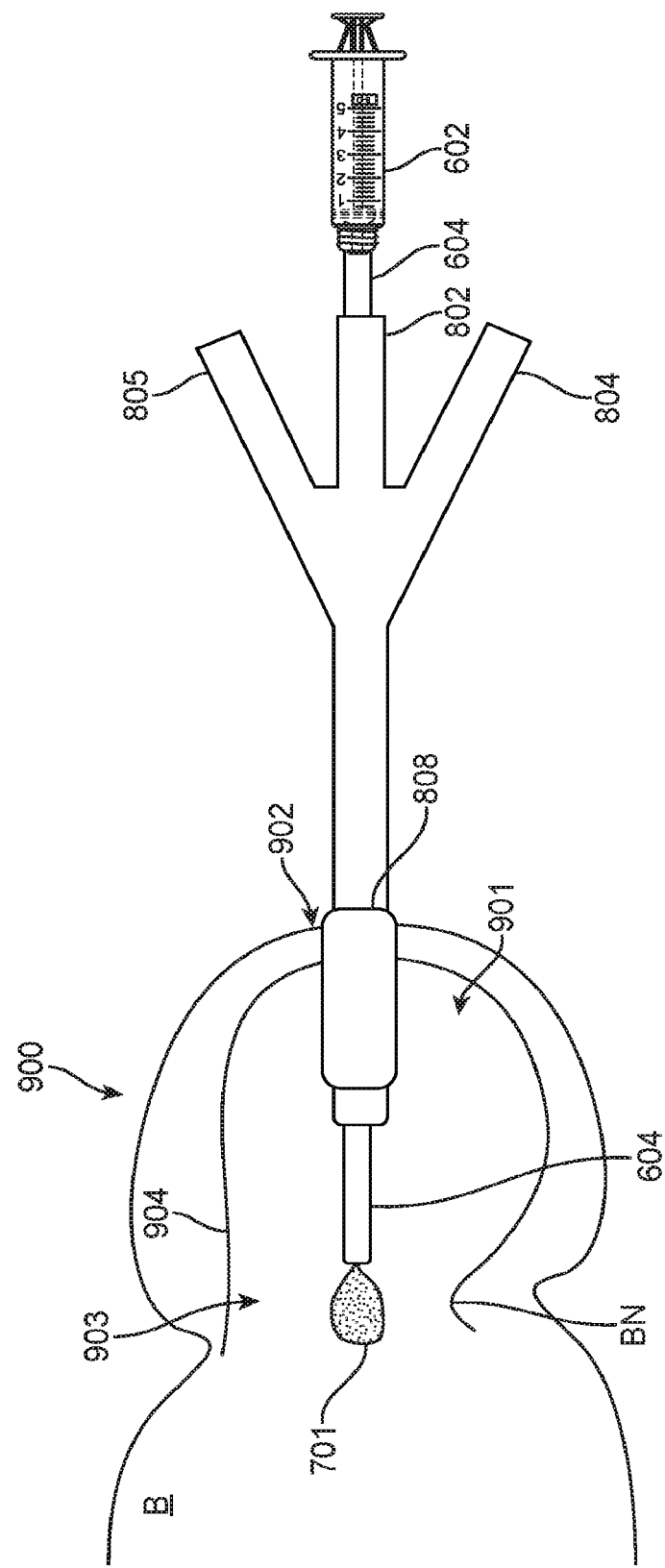
Figure 13C:
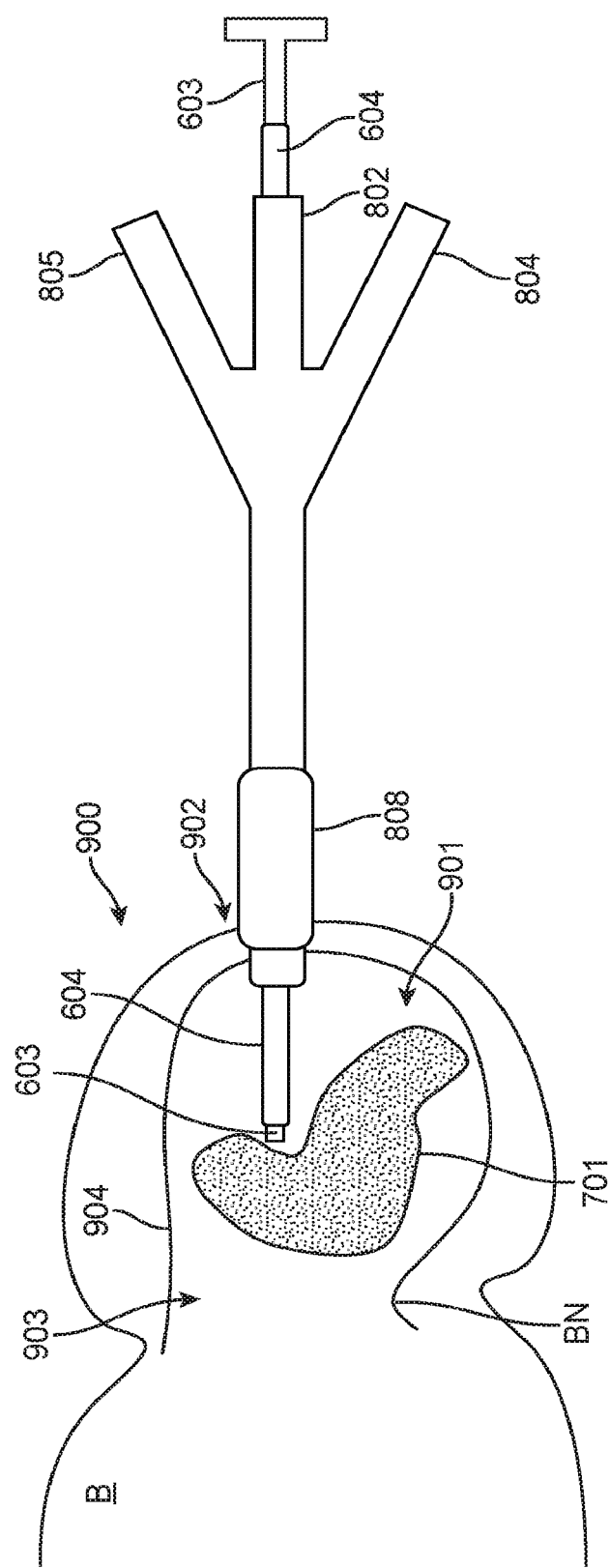

FIG. 13B shows delivery of a sealant 701 into the resection cavity 901 of the prostatic capsule 900. Sealant 701 may be injected with a syringe 602 into the proximal end of the cannula 604 and delivered to the cavity by the distal end of the cannula 604 residing inside the prostatic capsule 900. FIG. 13C shows the use of an optional stylet 603 to plunge the sealant 701 out of the cannula stylet so as to ensure complete delivery of sealant to the resection cavity 901 as described herein. Alternatively, the stylet 603 may be sized and shaped to fit within the drainage port 802 such that the cannula is optional as described herein.

Figure 13D:
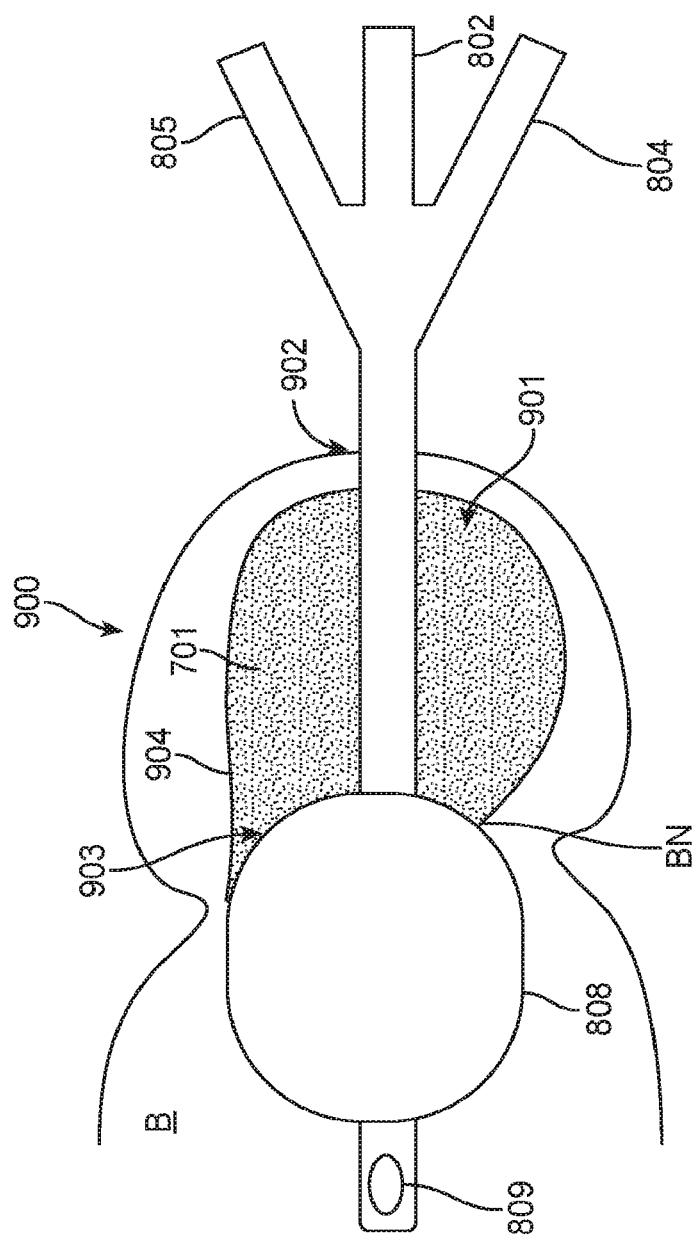

FIG. 13D shows the resection cavity 901 filled with the sealant 701 after delivery through the drainage port or cannula. Following delivery of sealant to the cavity, the sealant delivery device may be advanced into the prostatic capsule 900. The distal balloon 808 may be inflated so as to completely seal off the bladder B from the prostatic capsule 900 at the distal opening 903 of the prostatic capsule 900 comprising the bladder neck BN, such that only the resection cavity 901 receives the sealant 701. Alternatively, the distal balloon 808 may be inflated so as to partially, or nearly completely, seal off the bladder B from the prostatic capsule 900. For example, the distal balloon 808 may be inflated so as to leave a small space between the bladder neck BN and the distal balloon 808 as described herein. The catheter body may seal off the proximal opening 902 while the catheter is positioned within the cavity, such that the sealant does not enter the urethra. The catheter may be left in the patient with the distal balloon 808 inflated for an amount of time to ensure hemostasis has occurred. The amount of time for hemostasis may depend on the sealant used and may range from minutes to hours to overnight. The sealant delivery device may be removed from the patient after the sealant has sealed.

Figure 14:
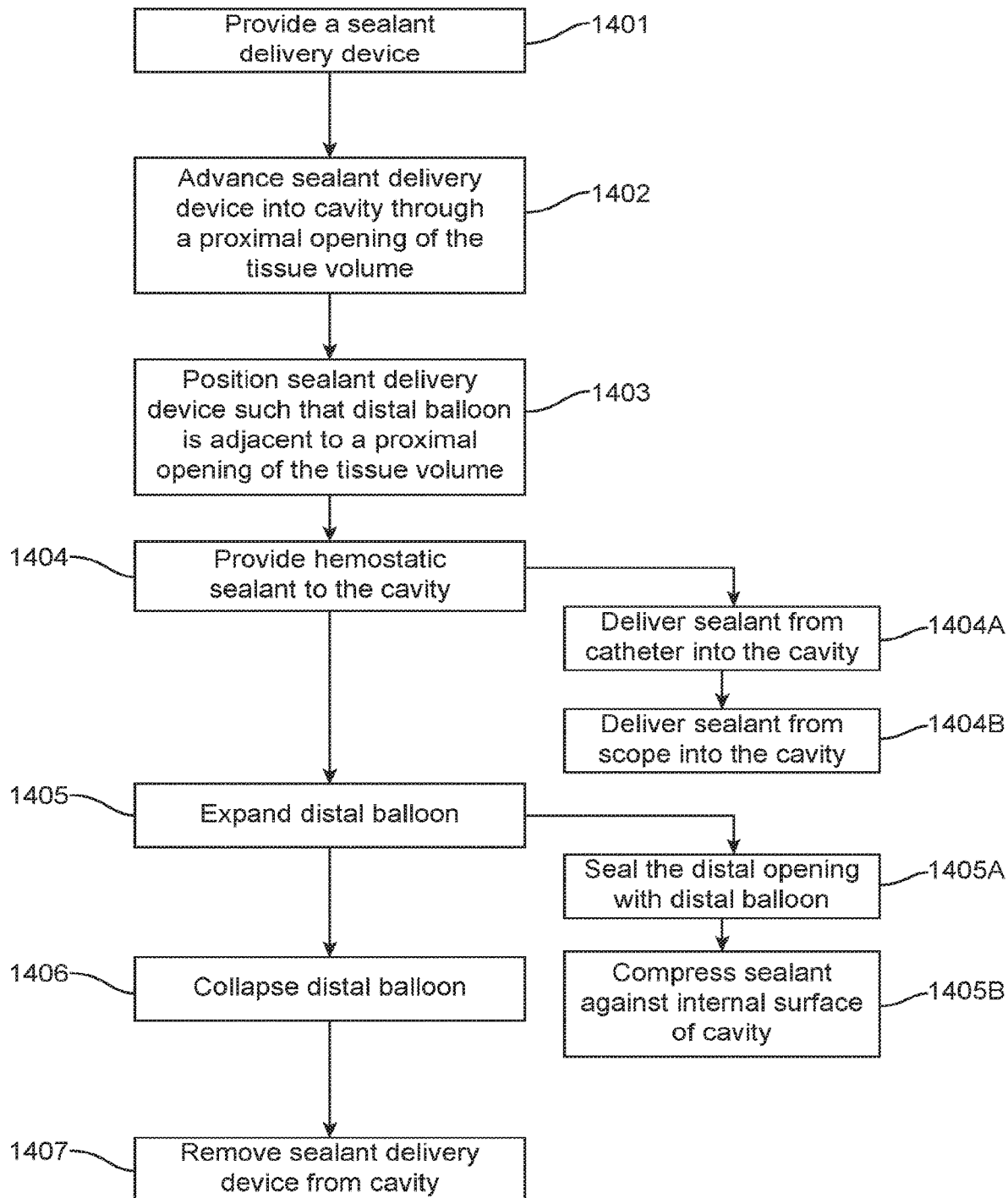
FIG. 14 shows a flowchart of a method of providing hemostasis within a tissue cavity, in accordance with embodiments.

FIG. 14 shows a flowchart of a method 1400 of providing hemostasis within a tissue cavity.

At Step 1401, a sealant delivery device may be provided. The sealant delivery device may, for example, be any of the embodiments described herein.

At Step 1402, the sealant delivery device may be advanced through a proximal opening of the tissue volume into a cavity defined by an internal surface of a bleeding tissue volume.

At Step 1403, the sealant delivery device may be positioned such that a distal balloon is adjacent a distal opening of the tissue volume.

At Step 1404, a hemostatic sealant may be provided to the cavity. Step 1404 may comprise one or more substeps. For example, at Step 1404A, the sealant may be delivered from a catheter of the sealant delivery device into the cavity. At Step 1404B, the sealant may be delivered from a scope into the tissue cavity.

At Step 1405, the distal balloon may be expanded. The distal balloon may be positioned such that inflation causes the balloon to seal the distal opening, for example at the bladder neck (Step 1405A). The distal balloon may be positioned such that inflation causes the balloon to compress sealant against an internal surface or edge of the cavity, for example within the prostatic resection cavity (Step 1405B).

At Step 1406, the distal balloon may be collapsed.

At Step 1407, the sealant delivery device may be removed from the cavity.

Although the steps above show a method of providing hemostasis using sealant delivery device in accordance with embodiments, a person of ordinary skill in the art will recognize many variations based on the teaching described herein. The steps may be completed in a different order. Steps may be added or deleted. Some of the steps may comprise sub-steps. Many of the steps may be repeated to provide hemostasis in a bleeding closed tissue volume. Each of the delivery devices as described herein can be used in accordance with the method 1400.

In an exemplary embodiment of the method described by FIG. 14, the sealant delivery device may comprise the sealant delivery device of FIGS. 13A-13D. The tissue volume may comprise a prostatic capsule of the prostate, wherein the proximal opening comprises an opening to the urethra and the distal opening comprises a bladder neck between the prostate and the bladder. The cavity may comprise a resection cavity left after tissue debulking. The sealant delivery device may be advanced through the urethra into the resection cavity and positioned such that the distal balloon lies in the urethra near the external sphincter during sealant delivery into the resection cavity. The distal balloon may be positioned in the urethra such that the distal end of the catheter is near the proximal opening of the tissue volume. The cannula may be positioned within the catheter such that the distal end of the cannula extends beyond the distal end of the catheter into the cavity for sealant delivery. The sealant may be delivered into the cavity through the cannula. The sealant delivery device may then be advanced into the prostatic capsule such that the distal balloon resides within the bladder adjacent the bladder neck. Expansion of the distal balloon may seal the cavity by sealing the bladder neck. The distal balloon may remain inflated until hemostasis has occurred, at which point the balloon may be collapsed and the sealant delivery device removed from the cavity.

While many of the embodiments described herein comprise one or more balloons, it will be understood that any of the sealant delivery devices described herein may not comprise a balloon. For example, sealant may be delivered by a catheter comprising a sealant delivery port into the resection cavity. Sealing of the tissue may be accomplished without the use of a distal balloon to seal of the bladder or compress the bladder neck. Sealing of the tissue may occur without the use of a distal or proximal balloon to compress or spread the sealant into and along the cavity edge.

Optionally or in combination with one or more of any of the embodiments described herein, the sealant used may be combined with one or more therapeutic agents. The therapeutic agent may comprise one or more of pain relievers, analgesics, anesthetics, chemotherapeutics, drugs to treat cancer, radiopharmaceuticals, antibiotics, hemostatic and sealing agents, or vasoconstrictors. The therapeutic agents can be combined in many ways to improve results, and may comprise a combination of two or more therapeutic agents as disclosed herein.

The therapeutic agent may be delivered to a target region in many ways, and the target region may comprise as a cavity formed in resected tissue as described herein.

Pain relievers may be delivered to a region or optionally combined with a sealant in accordance with one or more of any the embodiments described herein. The pain reliever may comprise one or more of acetaminophen, acetylsalicylic acid, benzocaine, bromfenac, buprenorphine, butorphanol, capsaicin, celecoxib, codeine, dexibuprofen, dibucaine, diclofenac, diflunisal, etodolac, fenoprofen, flufenamic acid, flurbiprofen, hydrocodone dryomorphone, ibuprofen, indomethacin, ketoprofen, ketorolac, levorphanol, lidocaine, lomoxicam, loxoprofen, meclofenamate, mefenamic acid, meloxicam, meperidine, methadone, menthol, morphine, nabumetone, nalbuphine, naproxen, oxaprozin, oxycodone, oxymorphone, pentazocine, phenylbutazone, piroxicam, prilocaine, propoxyphene, salsalate, sulindac, tapentadol, tenoxicam, tolfenamic acid, tolmetin, or tramadol, for example.

Chemotherapeutic agents and other drugs to treat cancer may be delivered to the region and optionally combined with a sealant as described herein. The chemotherapeutic agent may comprise one or more of abiraterone acetate, ABVD, ABVE, ABVE-PC, AC, AC-T, ADE, ado-trastuzumab emtansine, afatinib dimaleate, aldesleukin, alectinib, alemtuzumab, aminolevulinic acid, anastrozole, aprepitant, arsenic trioxide, asparaginase *Erwinia chrysanthemi*, atezolizumab, axitinib, azacitidine, BEACOPP, belinostat, bendamustine hydrochloride, BEP, bevacizumab, bexarotene, bicalutamide, bleomycin, blinatumomab, bortezomib, bosutinib, brentuximab vedotin, BuMel, busulfan, cabazitaxel, cabozantinib-s-malate, CAF, capecitabine, CAPDX, carboplatin, carfilzomib, carmustine, carmustine implant, CEM, ceritinib, cetuximab, chlorambucil, chlorambucil-prednisone, CHOP, cisplatin, clofarabine, CMF, cobimetinib, COPDAC, COPP, COPP-ABV, crizotinib, CVP, cyclophosphamide, cytarabine, cytarabine liposome, dabrafenib, dacarbazine, dactinomycin, daratumumab, dasatinib, daunorubicin hydrochloride, decitabine, defibrotide sodium, degarelix, denileukin diftitox, denosumab, dexamethasone, dexrazoxane hydrochloride, dinutuximab, docetaxel, doxorubicin hydrochloride, doxorubicin hydrochloride liposome, elotuzumab, eltrombopag olamine, enzalutamide, epirubicin hydrochloride, EPOCH, eribulin mesylate, erlotinib hydrochloride, etoposide, etoposide phosphate, everolimus, filgrastim, fludarabine phosphate, fluorouracil injection, fluorouracil—topical, flutamide, FOLFIRI, FOLFIRI-bevacizumab, FOLFIRI-cetuximab, FOLFIRINOX, FOLFOX, FU-LV, fulvestrant, gefitinib, gemcitabine hydrochloride, gemcitabine-cisplatin, gemcitabine-oxaliplatin, gemtuzumab ozogamicin, glucarpidase, goserelin acetate, human papillomarvirus (HPV) bivalent vaccine, recombinant, HPV nonavalent vaccine, recombinant, HPV quadrivalent vaccine, recombinant, hydroxyurea, hyper-CVAD, ibritumomab tiuxetan, ibrutinib, ICE, idarubicin hydrochloride, idelalisib, ifosfamide, imatinib mesylate, imiquimod, interferon alfa-2b, recombinant, interleukin-2, intron A, iodine I 131 tositumomab and tositumomab, ipilimumab, irinotecan hydrochloride, irinotecan hydrochloride liposome, ixabepilone, ixazomib citrate, lanreotide acetate, lapatinib ditosylate, lenalidomide, lenvatinib mesylate, letrozole, leucovorin calcium, leuprolide acetate, lomustine, mechlorethamine hydrochloride, megestrol acetate, melphalan, melphalan hydrochloride, mercaptopurine, mesna, methotrexate, mitomycin C, mitoxantrone hydrochloride, MOPP, nanoparticle paclitaxel, necitumumab, nelarabine, netupitant and palonosetron hydrochloride, nilotinib, obinutuzumab, OEPA, ofatumumab, OFF, olaparib, omacetaxine mepesuccinate, ondansetron hydrochloride, OPPA, osimertinib, oxaliplatin, paclitaxel, paclitaxel albumin-stabilized nanoparticle formulation, PAD, palbociclib, palifermin, palonosetron hydrochloride, palonosetron hydrochloride and netupitant, pamidronate disodium, panitumumab, panobinostat, pazopanib hydrochloride, PCV, PEB, pegaspargase, peginterferon alfa-2b, pembrolizumab, pemetrexed disodium, plerixafor, pomalidomide, ponatinib hydrochloride, pralatrexate, prednisone, procarbazine hydrochloride, radium 223 dichloride, raloxifene hydrochloride, ramucirumab, rasburicase, R-CHOP, R-CVP, recombinant HPV bivalent vaccine, recombinant HPV nonavalent vaccine, recombinant HPV quadrivalent vaccine, recombinant interferon alfa-2b, regorafenib, R-EPOCH, rituximab, rolapitant hydrochloride, romidepsin, romiplostim, ruxolitinib phosphate, siltuximab, sipuleucel-T, sonidegib, sorafenib tosylate, STANFORD V, sunitinib malate, TAC, talc, talimogene laherparepvec, tamoxifen citrate, temozolomide, temsirolimus, thalidomide, thioguanine, thiotepa, topotecan hydrochloride, toremifene, tositumomab and iodine I 131 tositumomab, TPF, trabectedin, trametinib, trastuzumab, trifluridine and tipiracil hydrochloride, uridine triacetate, VAC, vandetanib, VAMP, VeIP, vemurafenib, venetoclax, vinblastine sulfate, vincristine sulfate, vincristine sulfate liposome, vinorelbine tartrate, VIP, vismodegib, vorinostat, XELIRI, XELOX, ziv-aflibercept, or zoledronic acid, for example.

Radiopharmaceuticals that may be delivered to a region or optionally combined with a sealant for any of the embodiments described herein may include but are not limited to calcium-47, carbon-11, carbon-11 choline, carbon-11-L-methyl-methionine, carbon-14, carbon-14 urea, chromium-51, chromium-51 red blood cells, chromium-51 ethylenediaminetetraacetic acid, cobalt-57, cobalt-57 cyanocobalamin, cobalt-58, cobalt-58 cyanocobalamin, erbium-169, erbium-169 colloid, fluorine-18, fluorine-18 desmethoxyfallypride, fluorine-18 florbetapir, fluorine-18 fludeoxyglucose, fluorine-18 fluorocholine, fluorine-18 sodium fluoride, gallium-67, gallium-67 citrate, gallium-68, gallium-68 dotatoc, gallium-68 dotatate, gallium-68 PSMA, indium-111, indium-111 capromab, indium-111 chloride, indium-111 diethylenetriamine pentaacetic acid, indium-111 oxyguinoline, indium-111 pentetreotide, indium-111 satumomab pendetide, iodine-123, iodine-123 iobenguane, iodine-123 iodide, iodine-123 ioflupane, iodine-123 m-iodobenzylguanidine, iodine-123 sodium iodide, iodine-125, iodine-125 human serum albumin, iodine-125 iothalamate, iodine-131, iodine-131 human serum albumin, iodine-131 sodium iodide, iodine-131 tositumomab, iron-59, krypton-81m, molybdenum-99, molybdenum-99 generator, nitrogen-13, nitrogen-13 ammonia, oxygen-15, oxygen-15 water, phosphorus-32, phosphorus-32 phosphate, radium-223, radium-223 dichloride, rubidium-82, rubidium-82 chloride, samarium-153, samarium-153 EDTMP, selenium-75, selenium-75 selenorcholestrerol, selenium-75 23-seleno-25-homo-tauro-cholate, sodium-22, sodium-24, strontium-89, strontium-89 chloride, technetium-99m, technetium-99m bicisate, technetium-99m colloid, technetium-99m diethylenetriaminepenta-acetic acid, technetium-99m dimercaptosuccinic acid, technetium-99m disofenin, technetium-99m ethyl cysteinate dimer, technetium-99m exametazine, etium-99m exametazime labelled leucocytes, technetium-99m hepatic iminodiacetic acid, technetium-99m human albumin, technetium-99m human albumin macroaggregates or microspheres, technetium-99m human immunoglobulin, technetium-99m mebrofenin, technetium-99m medronate, technetium-99m mercaptoacetyltriglycine, technetium-99m mertiatide, technetium-99m oxidronate, technetium-99m pentetate, technetium-99m pertechnetate, technetium-99m phosphonates and phosphates technetium-99m pyrophosphate, technetium-99m red blood cells, technetium-99m red blood cells (denatured), technetium-99m sestamibi, technetium-99m sulesomab, technetium-99m sodium pertechnetate, technetium-99m succimer, technetium-99m sulfur colloid, technetium-99m tetrofosmin, technetium-99m tilmanocept, thallium-201, thallium-201 chloride, xenon-133, xenon-133 gas, xenon-133 in isotonic sodium chloride solution, yttrium-90, yttrium-90 chloride, yttrium-90 ibritumomab tiuxetan, yttrium-90 silicate, or the like. Any material that provides a therapeutic amount of radiation to a region may be used as a radiopharmaceutical for any of the embodiments described herein.

Antibiotics that may be delivered to a region or optionally combined with a sealant for any of the embodiments described herein may include but are not limited to amino- glycosides (amikacin, gentamicin, kanamycin, neomycin, netilmicin, tobramycin, paromomycin, streptomycin, spectinomycin), ansamycins (geldanamycin, herbimycin, rifaximin), carbacephems (loracarbef), carbapenems (ertapenem, doripenem, imipenem/cilastatin, meropenem), cephalosporins (cefaclor, cefadroxil, cefalexin, cefalothin, cefalotin cefamandole, cefazolin, cefdinir, cefditoren, cefepime, cefixime, cefoperazone, cefotaxime, cefoxitin, cefpodoxime, cefprozil, ceftaroline fosamil, ceftazidime, ceftibuten, ceftizoxime, ceftobiprole, ceftriaxone, cefuroxime), glycopeptides (dalbavancin, oritavancin, teicoplanin, telavancin, vancomycin), lincosamides (clindamycin, lincomycin), lipopeptides (daptomycin), macrolides (azithromycin, clarithromycin, dirithromycin, erythromycin, roxithromycin, troleandomycin, telithromycin), monobactams (aztreonam), nitrofurans (furazolidone, nitrofurantoin), oxazolidinones (linezolid, posizolid, radezolid, torezolid), penicillins and penicillin combinations (amoxicillin, amoxicillin/clavulanate, ampicillin, ampicillin/sulbactam, azlocillin, carbenicillin, cloxacillin, dicloxacillin, flucloxacillin, methicillin, mezlocillin, nafcillin, oxacillin, penicillin G, penicillin V, piperacillin, piperacillin/tazobactam, temocillin, ticarcillin, ticarcillin/clavulanate), polypeptides (bacitracin, colistin, polymyxin B), quinolones (ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin), sulfonamides (mafenide, sulfacetamide, sulfadiazine, silver sulfadiazine, sulfadimethoxine, sulfamethizole, sulfamethoxazole, sulfanilamide, sulfasalazine, sulfisoxazole. trimethoprim-sulfamethoxazole(co-trimoxazole), sulfonamidochrysoidine), tetracyclines (demeclocycline, doxycycline, minocycline, oxytetracycline, tetracycline), and others (arsphenamine, capreomycin, chloramphenicol, clofazimine, cycloserine, dapsone, ethambutol, ethionamide, fosfomycin, fusidic acid, isoniazid, metronidazole, mupirocin, platensimycin, pyrazinamide, quinupristin, rifabutin, rifampicin, rifapentine, streptomycin, thiamphenicol, tigecycline, tinidazole, trimethoprim), or the like.

Hemostatic and other sealing agents may be delivered to the target region and optionally combined with a sealant as described herein. The hemostatic agent may comprise one or more of anti-fibrinolytics, Avitene®, BioGlue® Surgical Adhesive (CryoLife), biologic surgical GRF glues, bone wax, chitin, chitosan, COSEAL Surgical Sealant (Baxter Healthcare), cyanoacrylates, Dermabond™, EVISEL®, fibrin sealants, fibrin sealant powders, Floseal® Hemostatic Matrix (Baxter Healthcare), gelatin foams, Gelfoam®, Glubran 2™ (MediVogue), glutaraldehyde cross-linked albumin, Helistat®, Hemaseel APR™ (Haemacure Corporation), Instat®, microfibrillar collagen, matrix hemostats, mineral zeolite, ostene, oxidized cellulose, Oxycel®, Quixil®, PEG polymers or hydrogels, platelet sealants, polymeric hydrogels, rFVIIa, SPONGOSTAN™ Absorbable Haemostatic Gelatin Sponge (Ethicon), Superstat®, Surgicel® (Ethicon), Surgifoam™, Surgiflo™, TachoSil® (Baxter Healthcare), Thrombinar®, thrombins (thrombin-JMI, Evithrom®, thrombin with gelatin), TISSEL® (Baxter Healthcare), topical hemostats, Vitagel®, or Vivostat®.

Vasoconstrictors or vasopressors may be delivered to the target region and optionally combined with a sealant as described herein may comprise one or more of adrenalin, dobutamine, droxidopa, epinephrine, ephedrine, isoproterenol, levophed, neosynephrine, norepinephrine, phenylephrine, or the like.

Any one or more of the therapeutic agents described herein may be combined with any one or more of the sealants described herein, and delivered to the target region.

FIGS. 15A-15C, 16A-16C, 17A-17C, and 18A-18D all show exemplary embodiments of sealant delivery devices configured to deliver a self-expanding gel sealant, such as a sealant made of a mixture of polyethylene glycol (PEG) and chitosan. For the above-mentioned figures, the terms "sealant" and "self-expanding gel" may be used interchangeably. Although reference is made to self-expanding sealants, the sealant may comprise a fully hydrated sealant that does not substantially expand, e.g. expands no more than about 5 percent by volume when released from the delivery device to the target region.

The mixture of PEG and chitosan may have a ratio of PEG weight to chitosan weight within a range defined by any two of the following ratios: 0.01:1, 0.02:1, 0.04:1, 0.05:1, 0.1:1, 0.5:1, 1:1, 1:2, 1:3, 1:4, 1:5, 1:6, 1:7, 1:8, 1:9, 1:10, 1:15, 1:20, 1:25, 1:50, or 1:100. In use, the ratio may have any value between any two aforementioned mixture ratios. The exact mixture may be chosen to improve the degradation time of a sealant (to take on values of about 1, 2, 3, 5, 10, 12, 18, 24, 36, 48 hours, or any value between any two aforementioned degradation times), to optimize the absorbability or solubility of blood, saline, or other fluids for the mixture, to determine the chitosan release rate, to determine the extent of chitosan exposure to blood, saline, other fluids, or surrounding tissues, to facilitate the ability of the mixture to bind tissue, to facilitate the ability of the mixture to not bind to tissue, to take on any preferred size, shape, or configuration as described within this specification, or to be aerosolized.

Figure 15A:
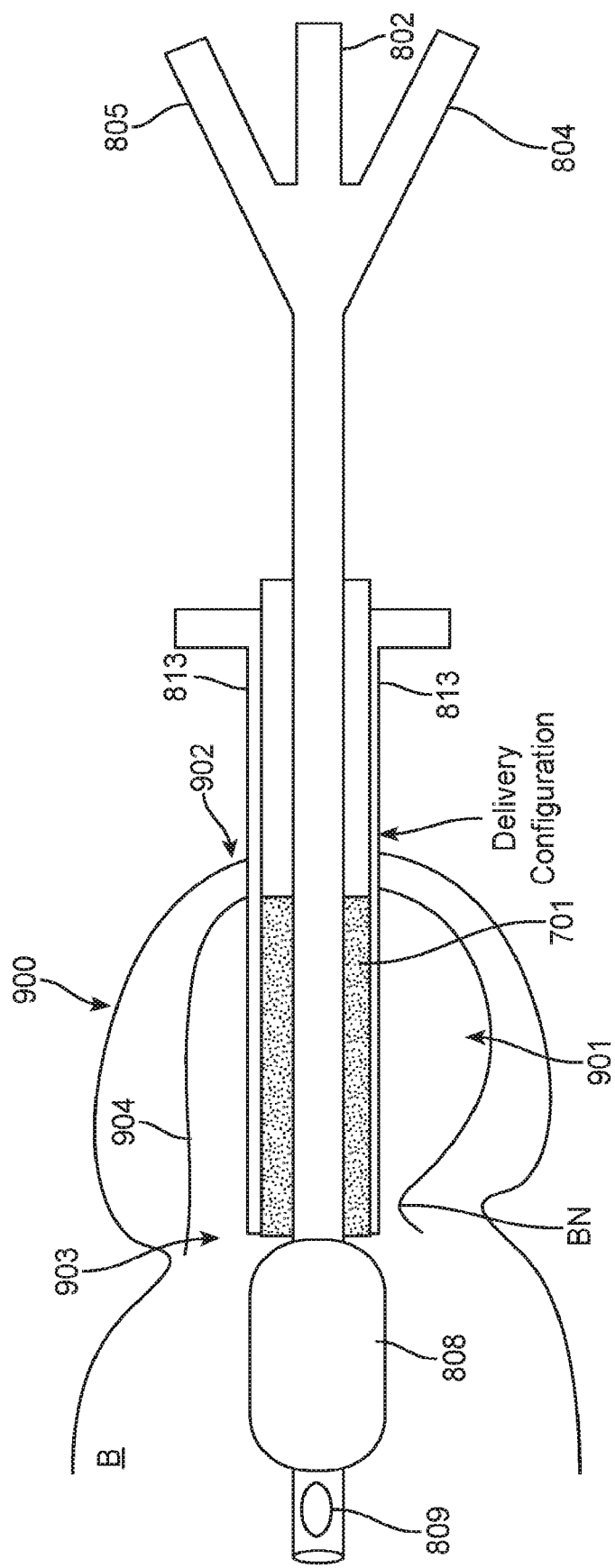
FIGS. 15A-15C show sectional schematic views of an exemplary single-balloon sealant delivery device delivering a self-expanding gel sealant, in accordance with embodiments.
Figure 15B:
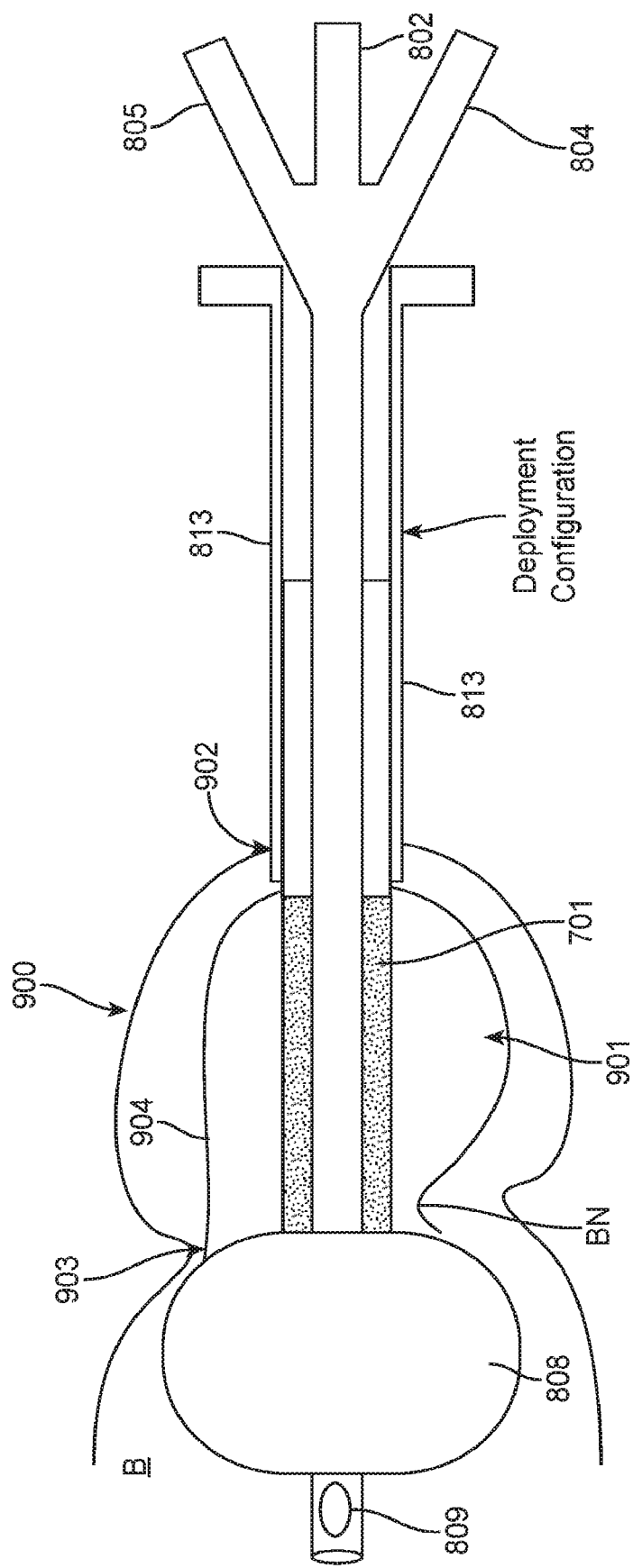
Figure 15C:
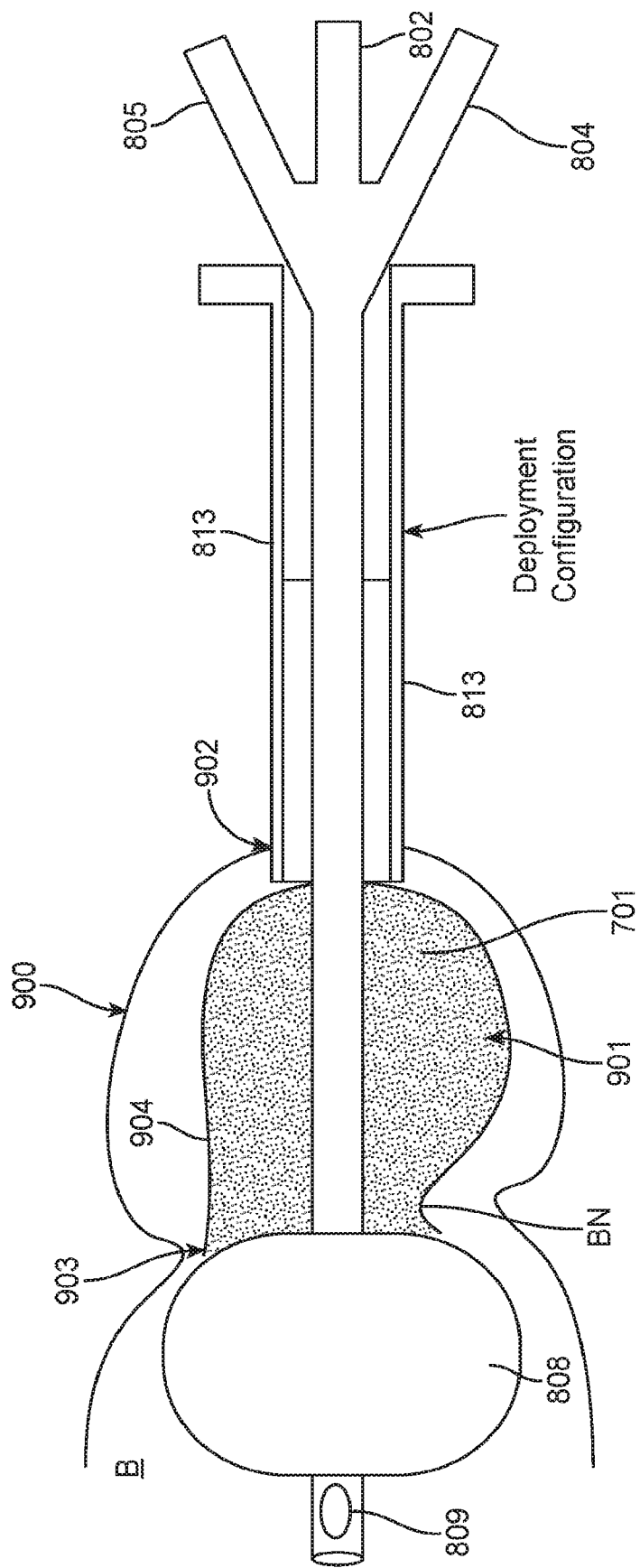

FIGS. 15A-15C show a non-limiting exemplary embodiment of a sealant delivery device having a delivery configuration (as shown in FIG. 15A) and a deployment configuration (as shown in FIGS. 15B-15C). The sealant delivery device may comprise a single distal balloon, a catheter (such as a Foley catheter), and a hemostatic agent or sealant, for example a sealant comprising a self-expanding gel composed of a mixture of PEG and chitosan. The sealant may be disposed along a distal portion of the catheter, and a sheath may be disposed along a distal portion of the catheter, covering the sealant. The sealant can be a self-expanding gel as described herein such as a combination of PEG and chitosan, and one of skill in the art will appreciate that many combinations of other gels and therapeutic agents can be used.

FIG. 15A shows the delivery of a catheter comprising a sealant-containing sheath 813 into a resection cavity 901 of a prostatic capsule 900. The sealant 701 may for example comprise a PEG and chitosan hydrogel as described herein. Prior to delivery, the sealant of this or any embodiment described herein may be pre-loaded into the catheter, the sheath, or both. When in the pre-delivery (also referred to herein as the delivery configuration), the sealant of this or any embodiment described herein may be shaped to conform to the catheter, the sheath, or both. Similarly, the sheath 813 may be sized, shaped, and/or configured to conform to any size, shape, and/or configuration the sealant may have prior to delivery. The sheath 813 may be configured to protect the sealant 701 from contact with liquids that may cause premature expansion, which could make the gel more difficult to place in the cavity.

FIG. 15B shows the deployment of the sealant 701 into the resection cavity 901 of the prostatic capsule 900. In the deployment configuration, the distal balloon 808 may be inflated to partially or completely seal off the bladder B from the prostatic capsule 900 to prevent ingress of the sealant 701 into the bladder B such that only or nearly only the resection cavity 901 receives the sealant 701. In the deployment configuration, the sheath 813 may be retracted so as to expose the sealant 701 to the environment that surrounds it, such as the resection cavity, and may thereby release the self-expanding sealant 701 to the resected or bleeding cavity. When in the post-delivery (also referred to herein as the deployment configuration), the sheath 813 may be retracted such that the sealant of this or any embodiment may be sized, shaped, and/or configured to substantially match or nearly match one or more of the size, shape, profile, or surface profile of the remaining tissue defining the resected cavity. Moreover, the cross-section of the expanded sealant may take on any shape appropriate to engage the surface of the remaining tissue, including a circle, an ellipse, a triangle, a square, a rectangle, a polygon, or any combination thereof.

FIG. 15C shows expansion of the sealant in order to engage the remaining tissue defining the cavity edge 904. As the sealant 701 (e.g. PEG and chitosan) absorbs various materials from the resection cavity 901, such as blood, saline, etc., the sealant may expand to fill the volume of the resection cavity 901, for example by engaging the tissue along the cavity edge 904. The sealant delivery device or the catheter (or both) of this or any embodiment described herein may be removed acutely or may remain indwelling for a period of time (e.g. from about 1 to about 60 minutes, from about 1 to about 24 hours, from about 1 to about 7 days, or any combination of any amount of time within those ranges). Upon removal of the sealant delivery device, any sealant that remains within may erode in one or more of many ways, for example with dissolution, degradation, washing away, or erosion. The eroded sealant may pass through the urethra and out of the body.

Figure 16A:
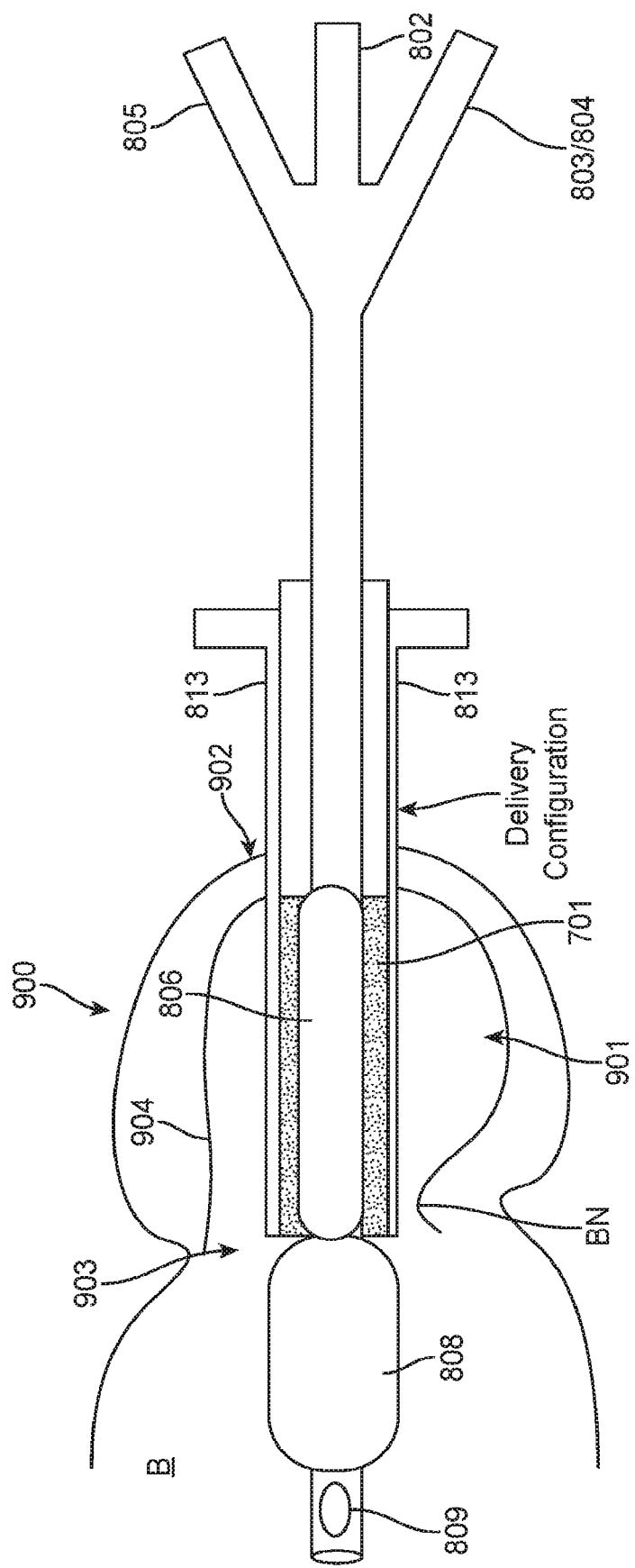
FIGS. 16A-16C show sectional schematic views of an exemplary double-balloon sealant delivery device delivering a self-expanding gel sealant, in accordance with embodiments.
Figure 16B:
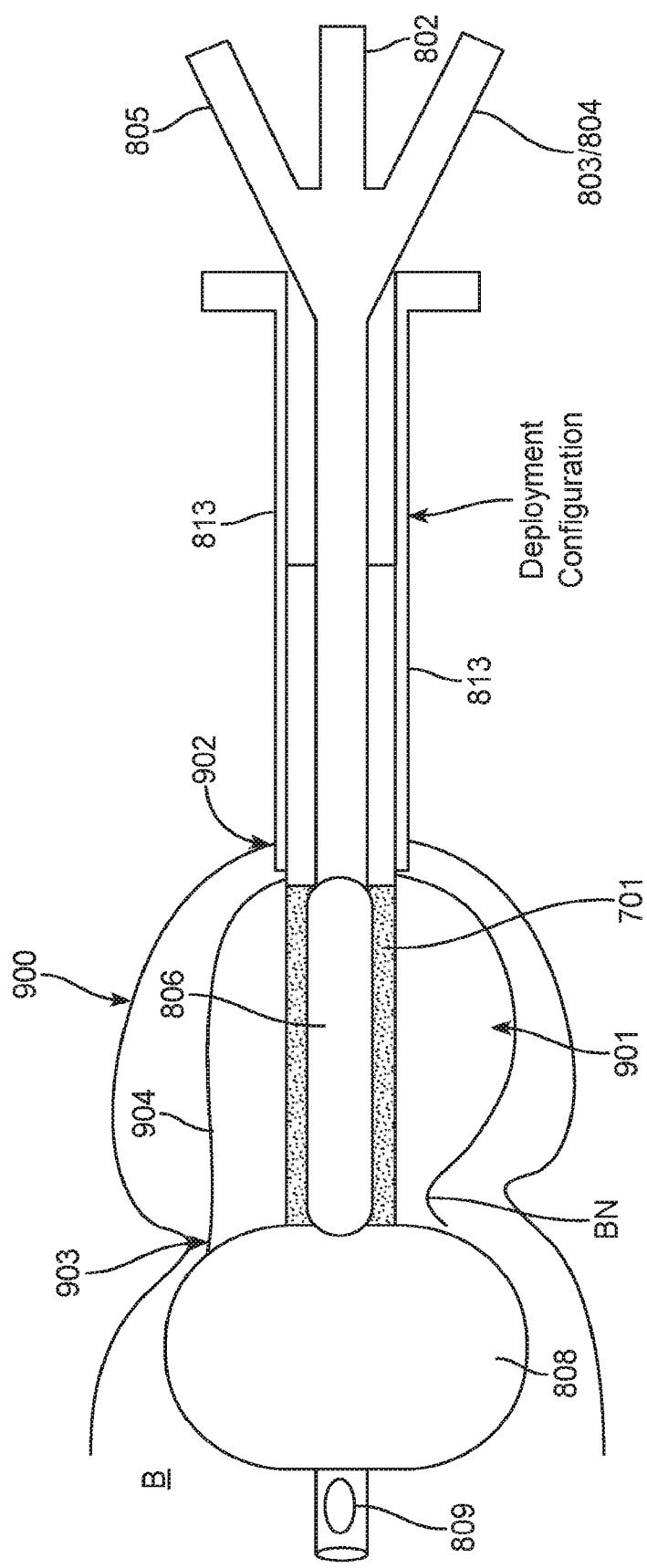
Figure 16C:
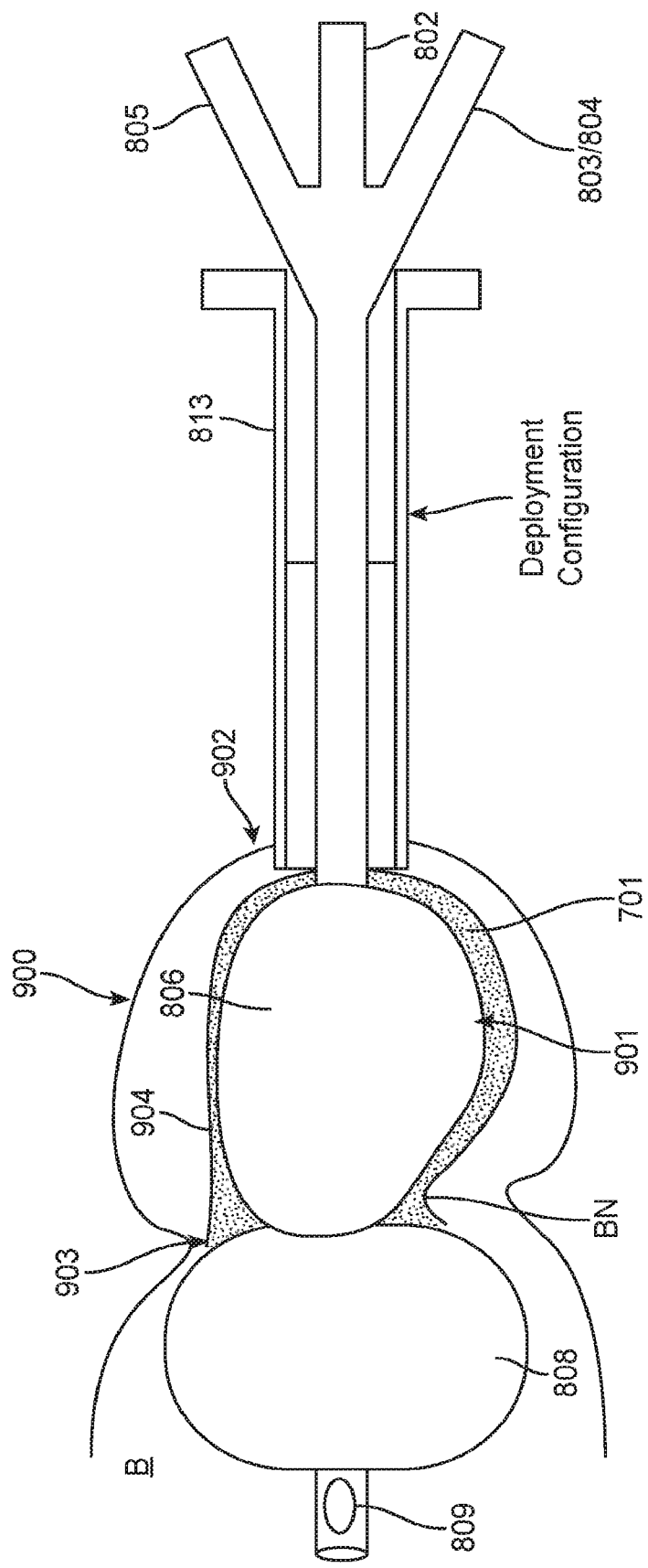

FIGS. 16A-16C show a sealant delivery device and a method of treating tissue. The delivery device may have a delivery configuration and a deployment configuration. The sealant delivery device may comprise a distal balloon, an expandable support (for example a proximal balloon), a catheter, a self-expanding gel sealant, and a sheath disposed along a distal portion of the catheter and covering the sealant. Any of the embodiments described herein may comprise an expandable support, for example one or more inflatable balloons as illustrated in numerous embodiments. The expandable support member of this or any embodiment may comprise one or more of a self-expanding nitinol stent, a polymer-based stent, a dissolvable stent, an inflatable balloon, one or more staples, one or more sutures, one or more barbs, or any combination thereof. The expandable support of this or any embodiment may comprise an inflatable balloon whose shape when expanded in a target region expands to have two bulbs and a slender section in between the two bulbs, similar to a barbell (also referred to herein as a dumbbell) or a guitar body. For example, if a barbell-shaped inflatable balloon expandable support embodiment was disposed within a prostate, one of the two bulbs may be situated in the bladder while the other of the two bulbs may be situated in the prostate with the slender section in between the two bulbs spanning the bladder neck. The expandable support may be substantially surrounded by the sealant so that as the expandable support is expanded it may aid in distributing, dispersing, or dispensing the sealant to a target tissue region. The self-expanding gel matrix may be mechanically bound to the catheter (for instance with sutures, staples, etc.) or chemically bound to the catheter (such as with an adhesive, etc.). In some embodiments, once the balloon is deflated for removal, the self-expanding gel may collapse and be removed with the catheter so that no amount or a negligible amount of the gel sealant may be left in the prostate for natural degradation.

FIG. 16A shows a sealant delivery device in the delivery configuration wherein neither of the two balloons is inflated. The sheath 813 substantially covers the self-expanding gel sealant and the expandable support 806 (e.g. proximal balloon) in the delivery configuration. The sheath 813 may be retracted in the deployment configuration to expose one or more of the self-expanding gel sealant and the proximal balloon 806 as shown in FIGS. 16B-16C.

FIG. 16B shows the sealant delivery device in the deployment configuration. The distal balloon 808 of the sealant delivery device may be expanded so as to partially or completely seal off distal opening 903 and the bladder B from the prostatic capsule 900 to inhibit ingress into the bladder B and so that only or nearly only the resection cavity 901 receives the sealant 701. The sheath 813 may be retracted to expose the self-expanding gel to the surrounding environment.

As the self-expanding gel is exposed to the fluids of the surrounding environment, the gel may self-expand. This self-expansion may be combined with expansion of the proximal balloon 806. As FIG. 16C shows, the proximal balloon 806 or expandable support may aid in this expansion by urging the sealant radially outward to engage the tissue on the wall of the cavity (e.g. the cavity edge 904). This may also allow for engagement of the sealant 701 with the cavity edge 904 with decreased amounts of gel sealant required, and may alternatively or in combination reduce the amount of sealant that may erode away, which may be beneficial. Expanding the expandable support may help compress the sealant into the walls of the resected cavity or cavity edge 904 and may allow the self-expanding gel to reach and compress into surfaces of resected cavities which may have non-uniform geometries. Mechanical compression or the electro-binding effects of chitosan to blood cells may aid in hemostasis.

Figure 17A:
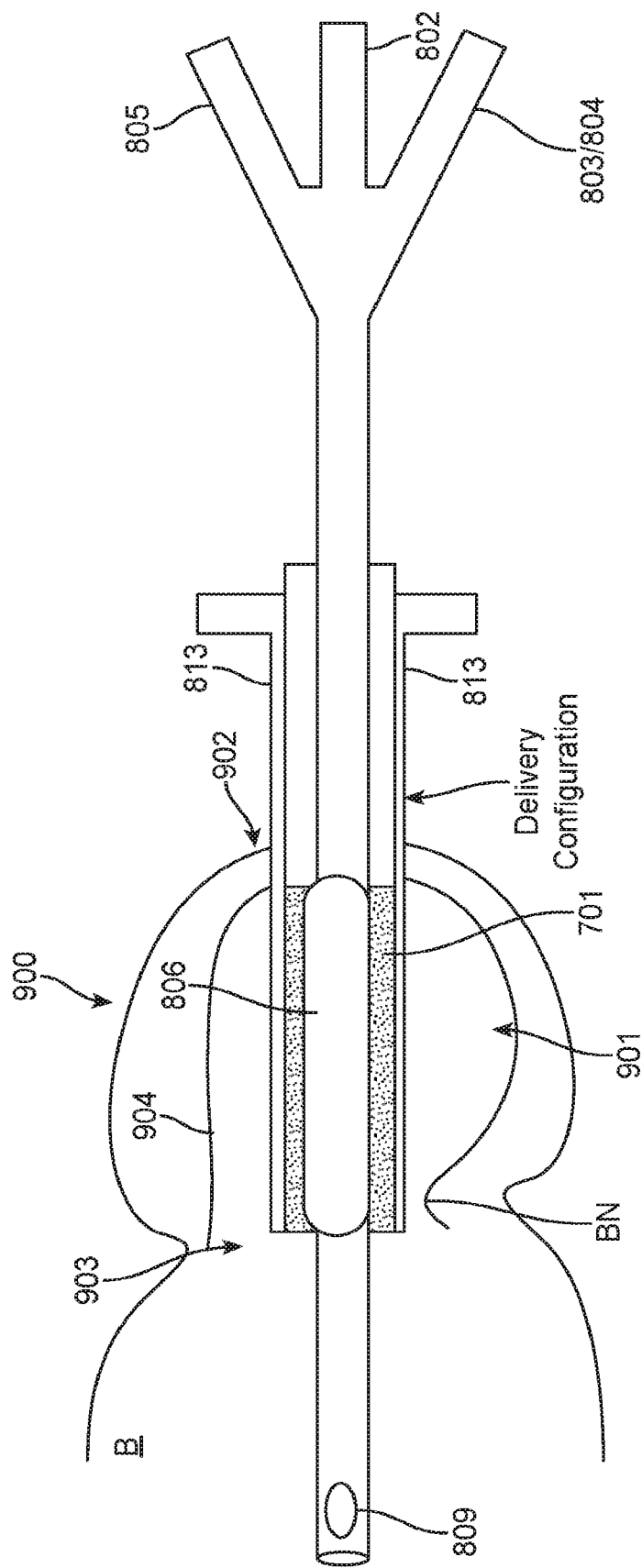
FIGS. 17A-17C show sectional schematic views of an exemplary single-balloon sealant delivery device delivering a self-expanding gel sealant without a balloon to inhibit flow into the bladder, in accordance with embodiments.
Figure 17B:
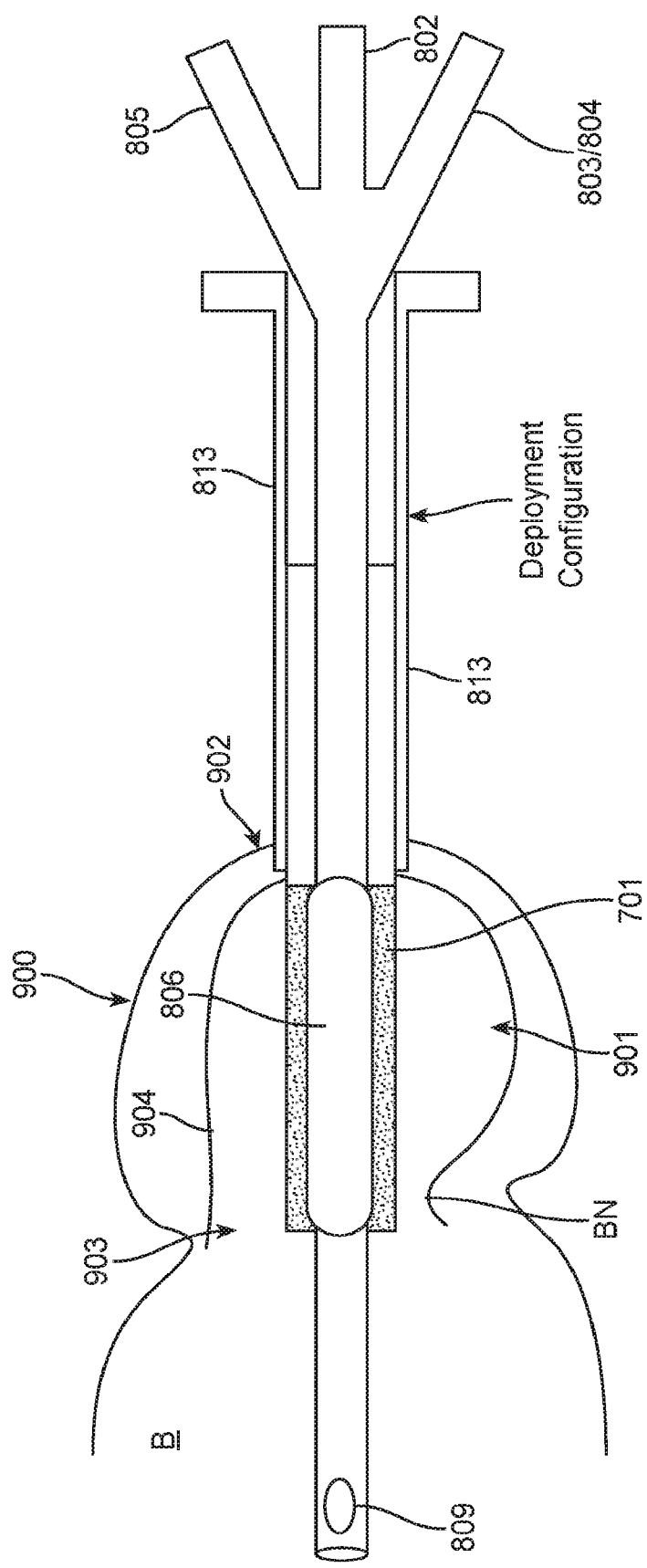
Figure 17C:
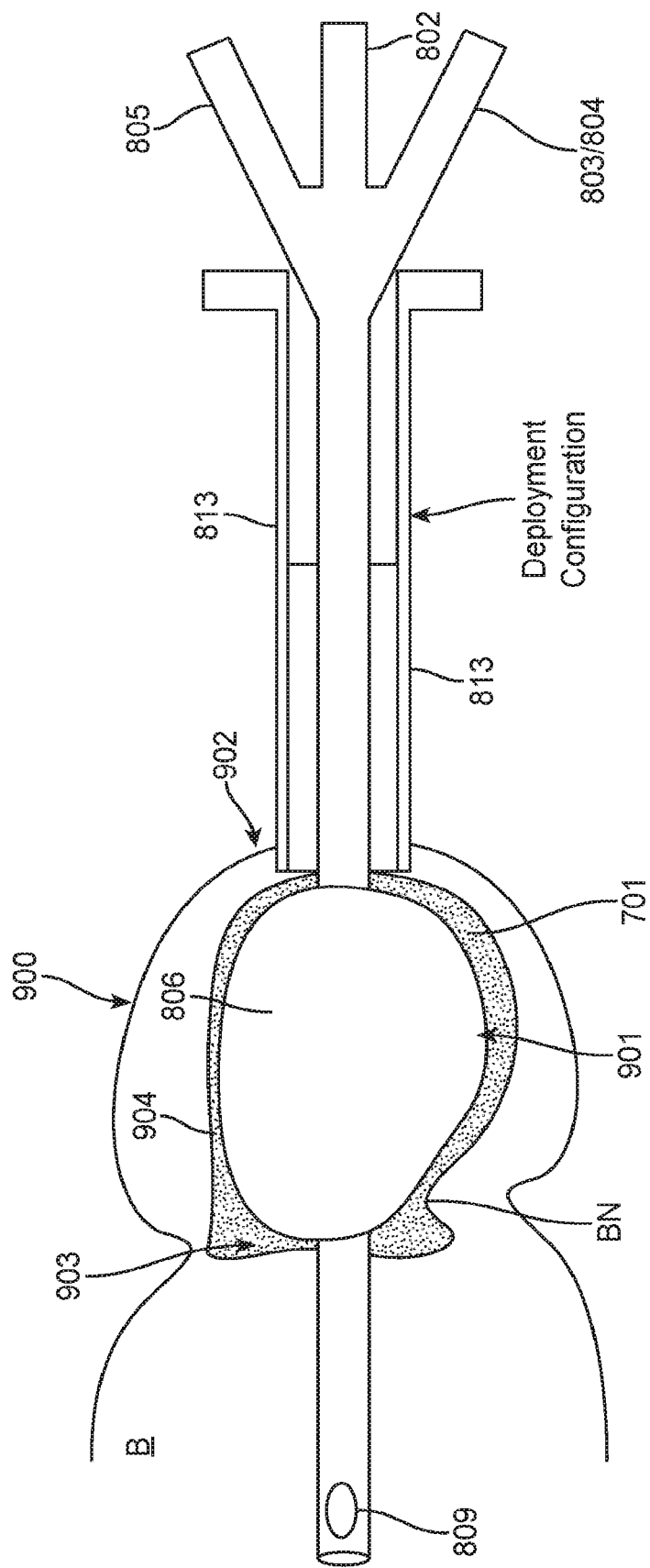

FIGS. 17A-17C show a non-limiting exemplary embodiment of a sealant delivery device having a delivery configuration and a deployment configuration. The sealant delivery device may comprise an expandable support or proximal balloon surrounded by a sealant, for example, a self-expanding gel sealant, a sheath disposed along a distal portion of a catheter, and a catheter. The sheath may cover the sealant, the expandable support, or both. When expanded, the expandable support may aid in distributing, dispersing, or dispensing the sealant to a target as described herein.

FIG. 17A shows the sealant delivery device in the delivery configuration. The non-inflated expandable support or proximal balloon 806 may be surrounded by the self-expanding gel sealant. The expandable support and the self-expanding gel may be disposed within the sheath 813. The sheath 813 may be disposed on the distal end of the catheter. The distal end of the catheter comprising the sheath 813 may be disposed through a proximal opening 902 of the tissue.

FIG. 17B shows the sealant delivery device in the delivery configuration. The sheath 813 may be retracted from the self-expanding gel sealant prior to expansion of the proximal balloon 806, thus exposing the self-expanding gel to the fluids of the surrounding environment. The self-expanding gel may comprise a first amount of hydration prior to retracting the sheath 813, and a second amount of hydration after removal of the sheath 813, in which the second amount of hydration may be greater than the first amount of hydration.

FIG. 17C shows the sealant delivery device after the self-expanding gel has expanded with increased hydration and the expandable support expanded. Expanding the expandable support (or proximal balloon) may help compress the sealant 701 into the walls (e.g., cavity edge 904) of the resected cavity and may allow the self-expanding gel to reach and compress into one or more surfaces of the resected cavity and may be beneficial in cavities having non-uniform geometries. Using a distal balloon 808 to seal the bladder B (as was illustrated, for example, in FIGS. 15A-15C and 16A-16C for certain exemplary embodiments) may not be necessary in many instances. In some instances, it may be beneficial to allow a portion of the self-expanding gel to expand partially into the bladder to address bleeding at or near the bladder neck BN. Also, as the self-expanding gel can readily erode away, having a portion of the gel expand into the bladder neck BN can be acceptable in many instances.

FIGS. 18A-18D show an embodiment of a sealant delivery device and related method. The sealant delivery device may comprise three or more balloons. The sealant delivery device may comprise a distal balloon to seal the bladder, an expandable support or proximal balloon surrounded by a sealant, and a cap balloon proximal to the expandable support. The device may further comprise a self-expanding gel sealant, a flush port, a catheter, and a sheath disposed along a distal portion of a catheter, the sheath covering the sealant, the expandable support, and the cap balloon. The exemplary embodiments illustrated in FIGS. 18A-18D or any of the embodiments described herein can deliver non-hemostatic materials to the resected cavity, such as therapeutic agents as described herein, water, or saline.

Figure 18A:
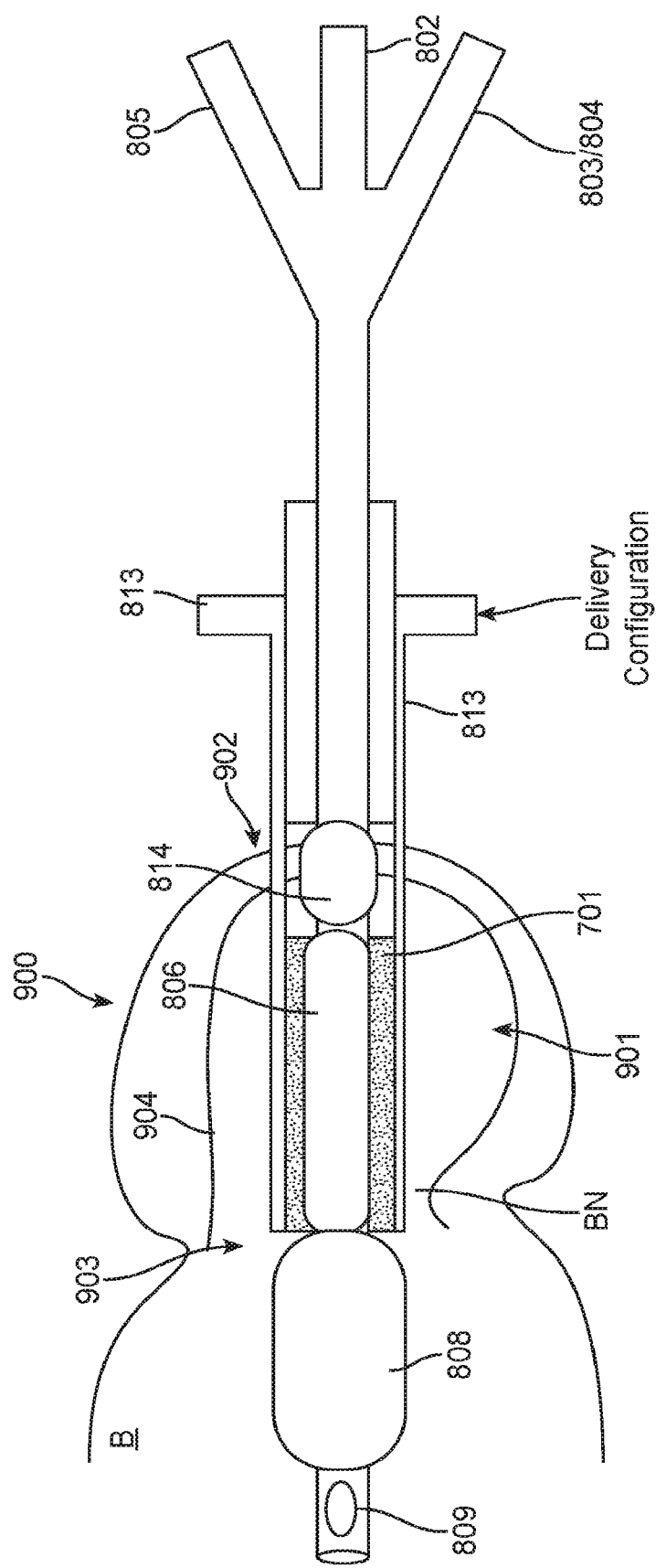
FIGS. 18A-18D show sectional schematic views of an exemplary triple-balloon sealant delivery device delivering a self-expanding gel sealant, in accordance with embodiments.

FIG. 18A shows a sealant delivery device positioned within the resection cavity 901 of the prostatic capsule 900 in the delivery configuration. The three balloons are not inflated, or are substantially uninflated, so as to provide a decreased profile while being delivered to and placed within the cavity. The tissue may comprise a prostatic capsule 900 of a prostate, wherein the proximal opening 902 comprises an opening to a urethra and the distal opening 903 comprises a bladder neck BN between the prostate and a bladder B. The cap balloon 814 may be placed at the proximal opening 902 of the cavity. The distal balloon 808 may be placed at the distal opening 903 of the cavity.

Figure 18B:
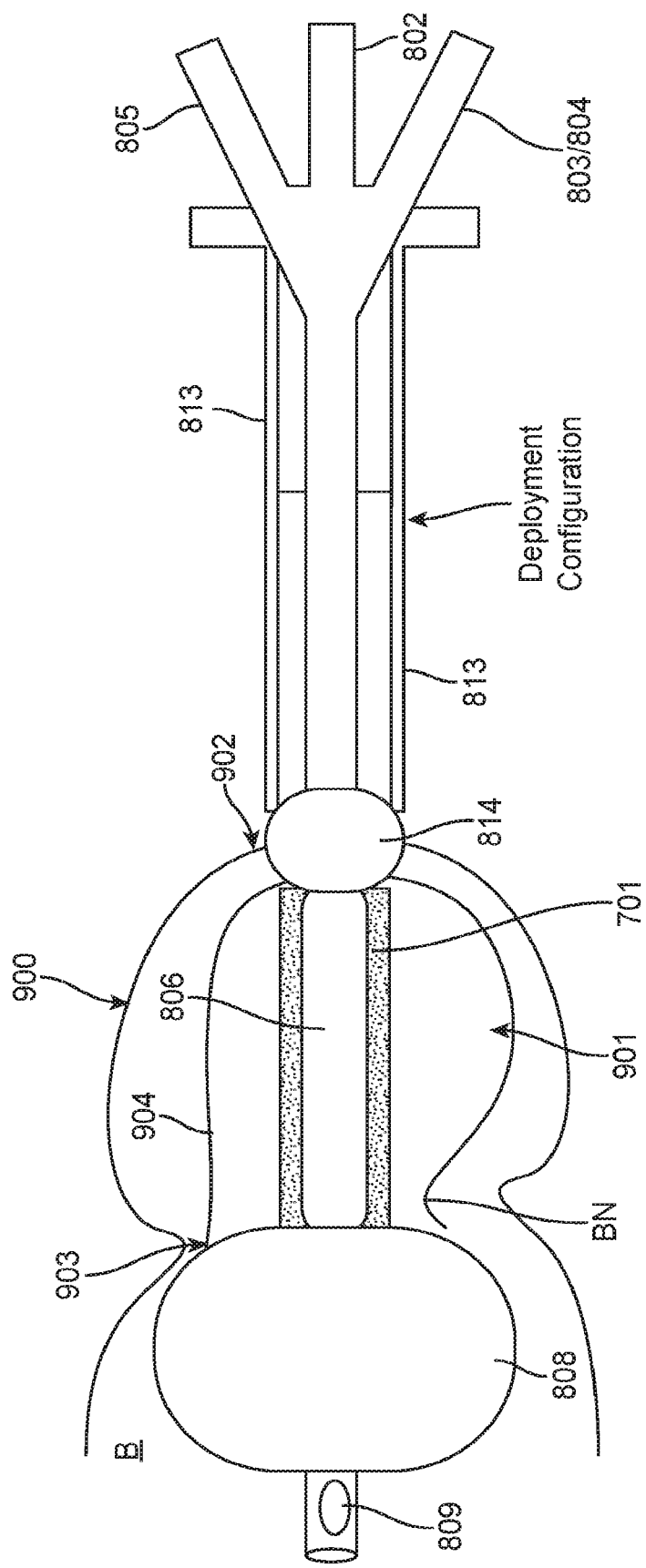

FIG. 18B shows the sealant delivery device in the delivery configuration with the sheath 813 retracted, exposing the self-expanding gel sealant to the fluids of the surrounding environment. Once the sheath 813 has been retracted, the distal balloon 808 and the cap balloon 814 may be inflated simultaneously, sequentially, or independently of one another to isolate the prostatic capsule 900 or resection cavity 901 from the bladder B or any other surrounding tissues. Isolating the prostatic capsule 900 or resection cavity 901 may inhibit therapeutic agents delivered to the region from reaching non-targeted tissue, such as select portions of prostatic tissue. Removal of the sheath 813 may also expose the self-expanding gel sealant to the fluids of the surrounding environment as described herein. Material (for instance, sealant or a therapeutic agent) may optionally be passed into the resection cavity 901 through a flush port (as shown in FIG. 18D) once the distal balloon 808 and cap balloon 814 have been inflated and have sealed off the resection cavity 901. The flush port may be configured to both deliver one or more materials to the resection cavity region and to remove material through such means as previously described. In some embodiments, the flush port may be configured to deliver material to the resection cavity region. In some embodiments, the flush port may be configured to remove material from the resection cavity region.

Figure 18C:
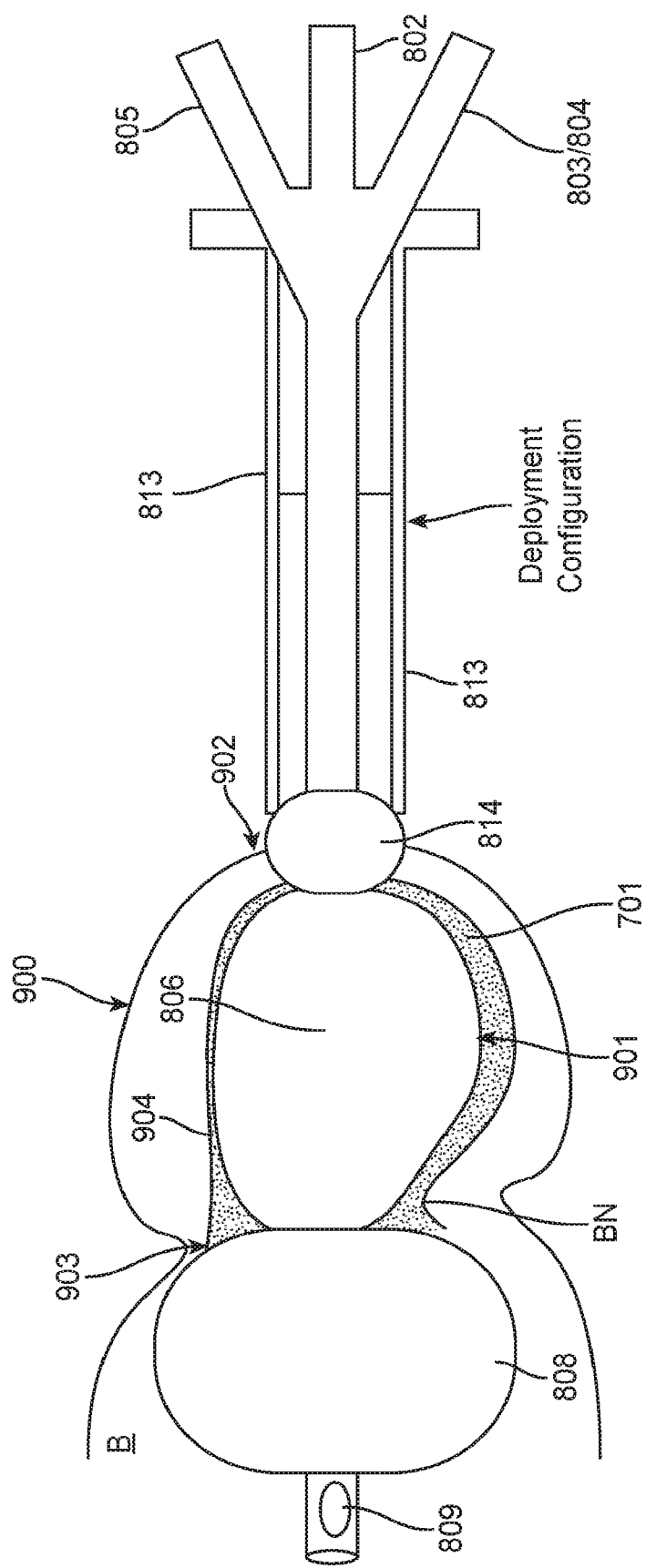
Figure 18D:
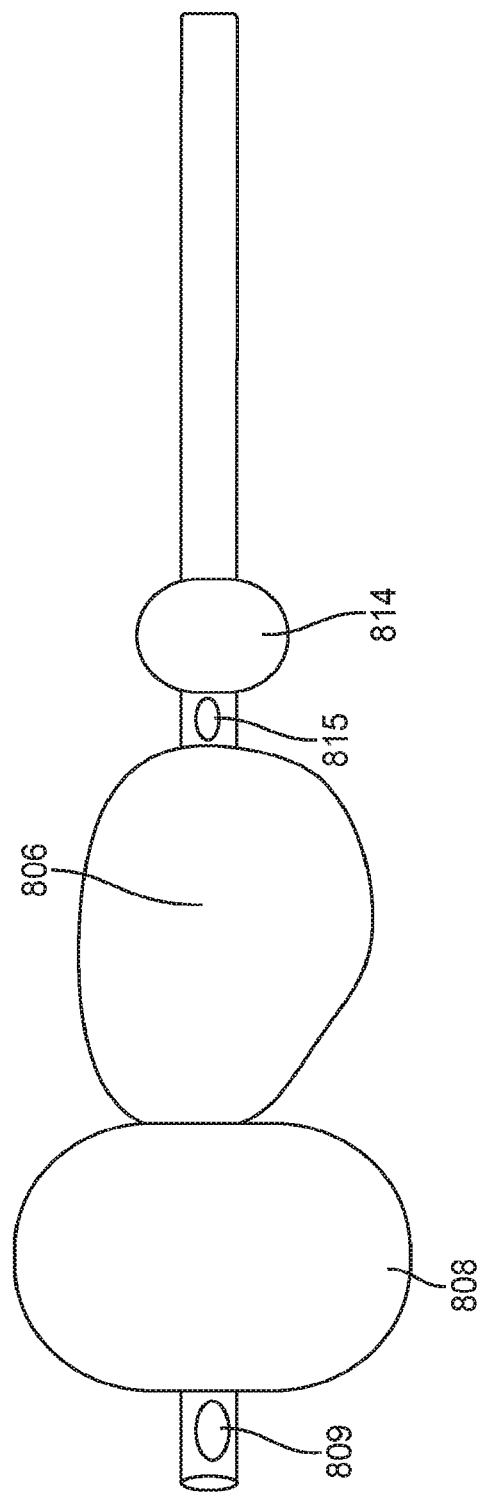

FIG. 18C shows the expandable support expanded to compress the self-expanding gel into the edge of the resection cavity 901 after the cap balloon 814 and distal balloon 808 have been expanded. In this manner, the sealant 701 may contact all or nearly all of the surfaces of resection cavity 901 or other body cavities, for example those having non-uniform geometries. After the expandable support has been expanded to engage the cavity edge 904 with the self-expanding gel sealant, additional material (for instance, a pain reliever or a hemostatic agent) may optionally be passed into the resected cavity through the flush port.

FIG. 18D shows the flush port 815 on a proximal portion of the sealant delivery device. The flush port 815 may comprise a single hole or pore on the catheter shaft situated between the expandable support and the cap balloon 814 as shown. Alternatively or in combination, the flush port may comprise a plurality of holes. The size and shape of the one or more holes or pores may take on any form sufficient to allow any of the aforementioned materials (e.g. hemostatic agents, therapeutic agents, drugs, water, saline) to pass through. Such shapes for one or more holes may include, but are not limited to, a circle, an ellipse, a triangle, a square, a rectangle, a polygon, and the like. The position of the flush port 815 may be near the expandable support so as to deliver material to a target region, for example a region comprising resected tissue or a malignant lesion. This placement of the one or more flush ports between the expanded distal and cap balloons can decrease amounts of material that are released to bladder B and urethra, which can decrease unwanted exposure of untargeted tissue(s) to the material. This can be helpful when the material comprises an anti-cancer material, such as a therapeutic agent to treat cancer like a chemotherapeutic or a radiotherapeutic.

After delivering the sealant to the resected cavity, it may be helpful to remove excess material, such as that left over after delivery of the sealant or other material delivered through the flush port 815. The flush port 815 may remove excess material easily by flushing the area with saline, for example.

Many embodiments may comprise one or more radioactive seeds configured for delivery to the target site, which can be combined with the tissue sealant as described herein. Radioactive seeds and delivery devices and treatments suitable for combination with tissue sealants as disclosed herein are described in PCT/US2015/037521, filed Jun. 24, 2016, entitled "TISSUE SAMPLING AND CANCER TREATMENT METHODS AND APPARATUS", the entire disclosure of which is incorporated herein by reference. The radioactive seeds may comprise any radioactive element as described herein, and may comprise seeds and radioactive dosimetry similar to known brachytherapy, such as interstitial brachytherapy and contact brachytherapy. A plurality of radioactive seeds can be combined with tissue sealant to provide localized delivery of radiation suitable for the treatment of cancer. The seeds can be sized and shaped in many ways and may comprise one or more of many shapes such as cylindrical rods, spheres, prolate ellipsoids, oblate ellipsoids, rice grain shaped, or other shapes. The seeds may comprise a smooth outer surface in order to allow passage through the urethra, for example. Each of the seeds comprises a maximum dimension across within a range from about 0.1 mm to about 5 mm, for example from about 0.2 mm to about 1 mm, such that the seeds can easily pass though the urethra. Alternatively, the seeds may comprise an irregular surface, a rough surface, barbs or other retention structures such that the seed is retained in the target tissue. The seeds may have the benefit of not being absorbed by tissue, and may remain external to the target tissue, for example. The seeds may be provided in a matrix with the gel and eroded away with the gel, for example. Any of the radiotherapeutics (including those in the form of seeds) may be used for brachytherapy, which itself may comprise interstitial brachytherapy or contact brachytherapy. Radiotherapeutics for brachytherapy may comprise a low-dose rate (less than about 2 Gy/h), a medium-dose rate (from about 2 Gy/h to about 12 Gy/h), a high-dose rate (greater than about 12 Gy/h) or a pulsed-dose rate (short pulses of radiation, typically about once per hour), or any combination thereof. The number of seeds that may be used within a single sealant or for a given treatment may be about 1, 5, 10, 20, 30, 40, 50, 75, 100, 125, 150, 200, or 300 seeds, or any value between any two previously listed amounts.

The seeds and sealant may be configured in many ways and are well suited for combination with seeds used in brachherein and may comprise but are not limited to calcium-47, carbon-11, carbon-11 choline, carbon-11-L-methyl-methionine, carbon-14, carbon-14 urea, cesium-131, cesium-137, chromium-51, chromium-51 red blood cells, chromium-51 ethylenediaminetetraacetic acid, cobalt-57, cobalt-57 cyanocobalamin, cobalt-58, cobalt-58 cyanocobalamin, cobalt-60, erbium-169, erbium-169 colloid, fluorine-18, fluorine-18 desmethoxyfallypride, fluorine-18 florbetapir, fluorine-18 fludeoxyglucose, fluorine-18 fluorocholine, fluorine-18 sodium fluoride, gallium-67, gallium-67 citrate, gallium-68, gallium-68 dotatoc, gallium-68 dotatate, gallium-68 PSMA, indium-111, indium-111 capromab, indium-111 chloride, indium-111 diethylenetriamine pentaacetic acid, indium-111 oxyguinoline, indium-111 pentetreotide, indium-111 satumomab pendetide, iodine-123, iodine-123 iobenguane, iodine-123 iodide, iodine-123 ioflupane, iodine-123 m-iodobenzylguanidine, iodine-123 sodium iodide, iodine-125, iodine-125 human serum albumin, iodine-125 iothalamate, iodine-131, iodine-131 human serum albumin, iodine-131 sodium iodide, iodine-131 tositumomab, iridium-192, iron-59, krypton-81m, molybdenum-99, molybdenum-99 generator, nitrogen-13, nitrogen-13 ammonia, oxygen-15, oxygen-15 water, palladium-103, phosphorus-32, phosphorus-32 phosphate, radium-223, radium-223 dichloride, rubidium-82, rubidium-82 chloride, ruthenium-106, samarium-153, samarium-153 EDTMP, selenium-75, selenium-75 selenorcholestrerol, selenium-75 23-seleno-25-homo-tauro-cholate, sodium-22, sodium-24, strontium-89, strontium-89 chloride, technetium-99m, technetium-99m bicisate, technetium-99m colloid, technetium-99m diethylenetriaminepenta-acetic acid, technetium-99m dimercaptosuccinic acid, technetium-99m disofenin, technetium-99m ethyl cysteinate dimer, technetium-99m exametazine, etium-99m exametazime labelled leucocytes, technetium-99m hepatic iminodiacetic acid, technetium-99m human albumin, technetium-99m human albumin macroaggregates or microspheres, technetium-99m human immunoglobulin, technetium-99m mebrofenin, technetium-99m medronate, technetium-99m mercaptoacetyltriglycine, technetium-99m mertiatide, technetium-99m oxidronate, technetium-99m pentetate, technetium-99m pertechnetate, technetium-99m phosphonates and phosphates technetium-99m pyrophosphate, technetium-99m red blood cells, technetium-99m red blood cells (denatured), technetium-99m sestamibi, technetium-99m sulesomab, technetium-99m sodium pertechnetate, technetium-99m succimer, technetium-99m sulfur colloid, technetium-99m tetrofosmin, technetium-99m tilmanocept, thallium-201, thallium-201 chloride, xenon-133, xenon-133 gas, xenon-133 in isotonic sodium chloride solution, yttrium-90, yttrium-90 chloride, yttrium-90 ibritumomab tiuxetan, yttrium-90 silicate, or the like. Any material that provides a therapeutic amount of radiation to a region may be used as a radioactive seed for any of the embodiments described herein. Any of the aforementioned radioactive seeds may be used, alone or in combination with others, as a radiopharmaceutical.

Figure 19A:
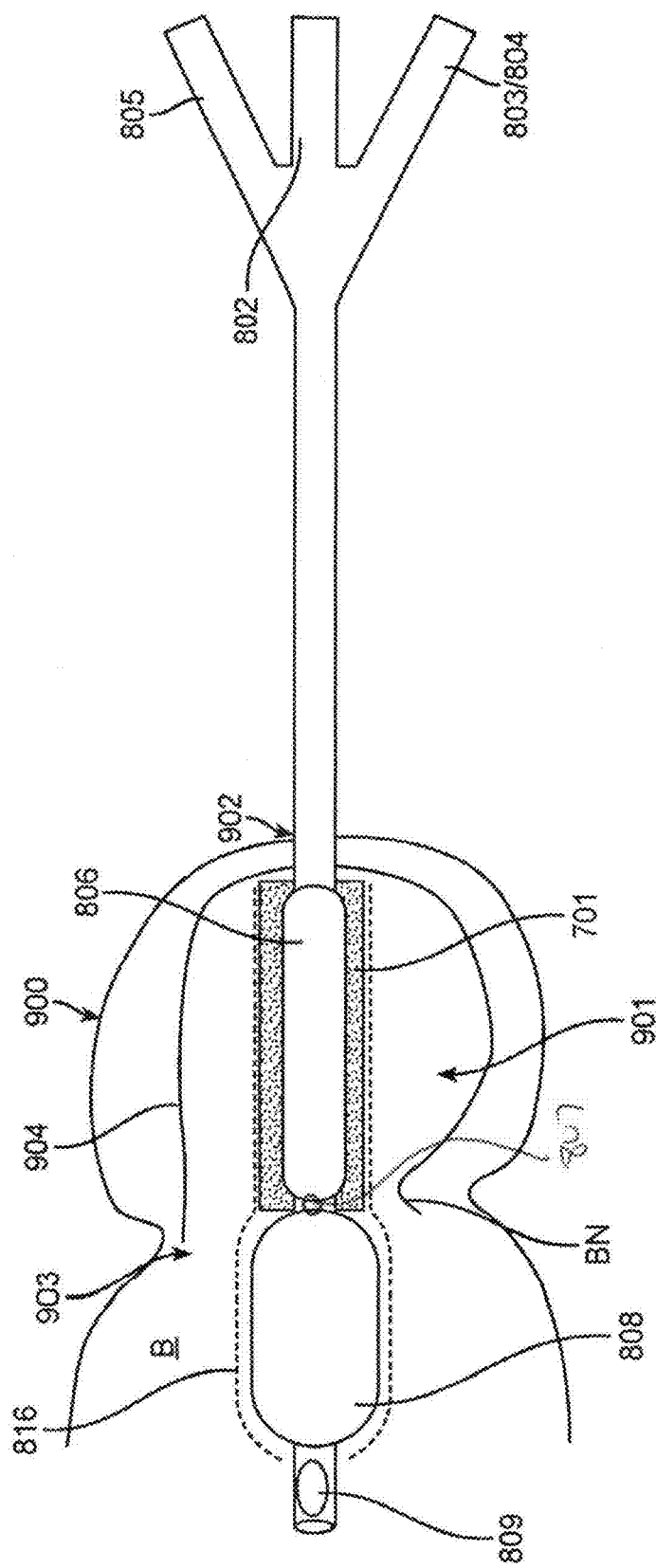
FIGS. 19A-19D show sectional schematic views of a sealant delivery device comprising a catheter and polymer sheath, in accordance with embodiments.

FIGS. 19A-19D show a sealant delivery device comprising a catheter and a polymer sheath. The sealant delivery device may comprise a catheter, distal balloon, and proximal balloon as described herein and may be substantially similar to other dual balloon embodiments described herein. The sealant delivery device may be delivered through the urethra such that distal balloon and proximal balloon are fully inserted into the bladder and prostatic capsule, respectively, as described herein. The sealant delivery device may further comprise a sheath which may cover one or both of the proximal and distal balloons when in a delivery configuration (as shown in FIG. 19A). The sheath may for example comprise a polymer sheath as shown, an elastic sheath (for example as shown in FIGS. 20A-20B), or a substantially rigid sheath (for example as shown in FIGS. 15A-18C). Any of the embodiments described herein may comprise a sheath to aid in device delivery and/or provide for timed delivery of the sealant from the device.

An external surface of the proximal balloon may be coated in a hemostatic agent, for example a sealant. The proximal balloon may be fully coated or partially coated with the hemostatic agent. Alternatively or in combination, the distal balloon may be fully coated or partially coated in a hemostatic agent. The sealant may be any of the sealants described herein. The sealant may for example be a self-expanding gel sealant which expands on exposure to fluids such as blood or saline. The sheath may be disposed about the sealant-coated balloon(s) during delivery so as to allow for dry delivery of the self-expanding sealant and prevent expansion of the sealant until the sheath has been retracted into the deployment configuration (as shown in FIGS. 19B-19C).

FIG. 19A shows the sealant delivery device in the delivery configuration. One or more of the proximal balloon 806 and distal balloon 808 may be coated in a hemostatic agent, for example, a self-expanding gel sealant. The sheath 816, for example a polymer sheath, may be disposed about the sealant-coated balloon(s) so as to allow for dry delivery of the self-expanding sealant and prevent expansion of the sealant during delivery.

Figure 19B:
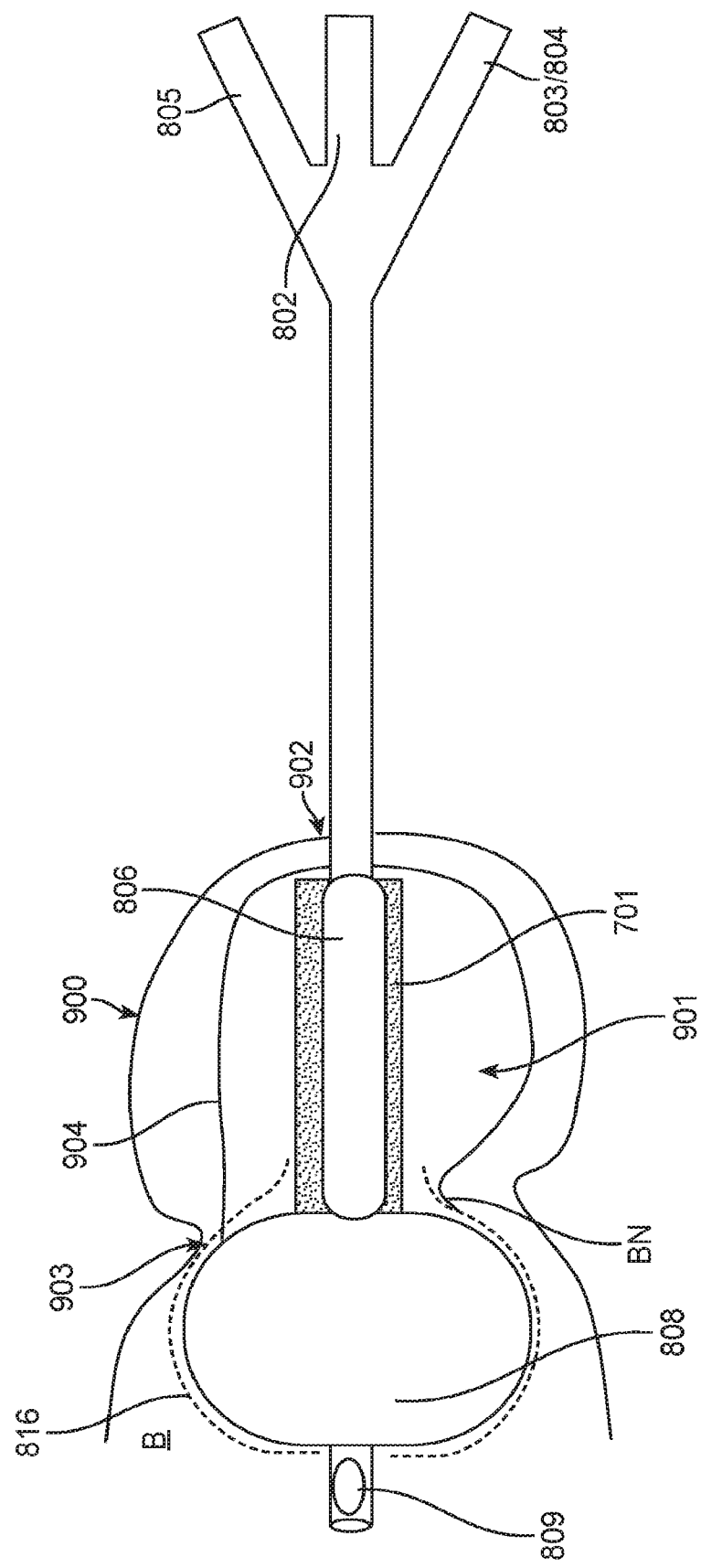
Figure 20A:
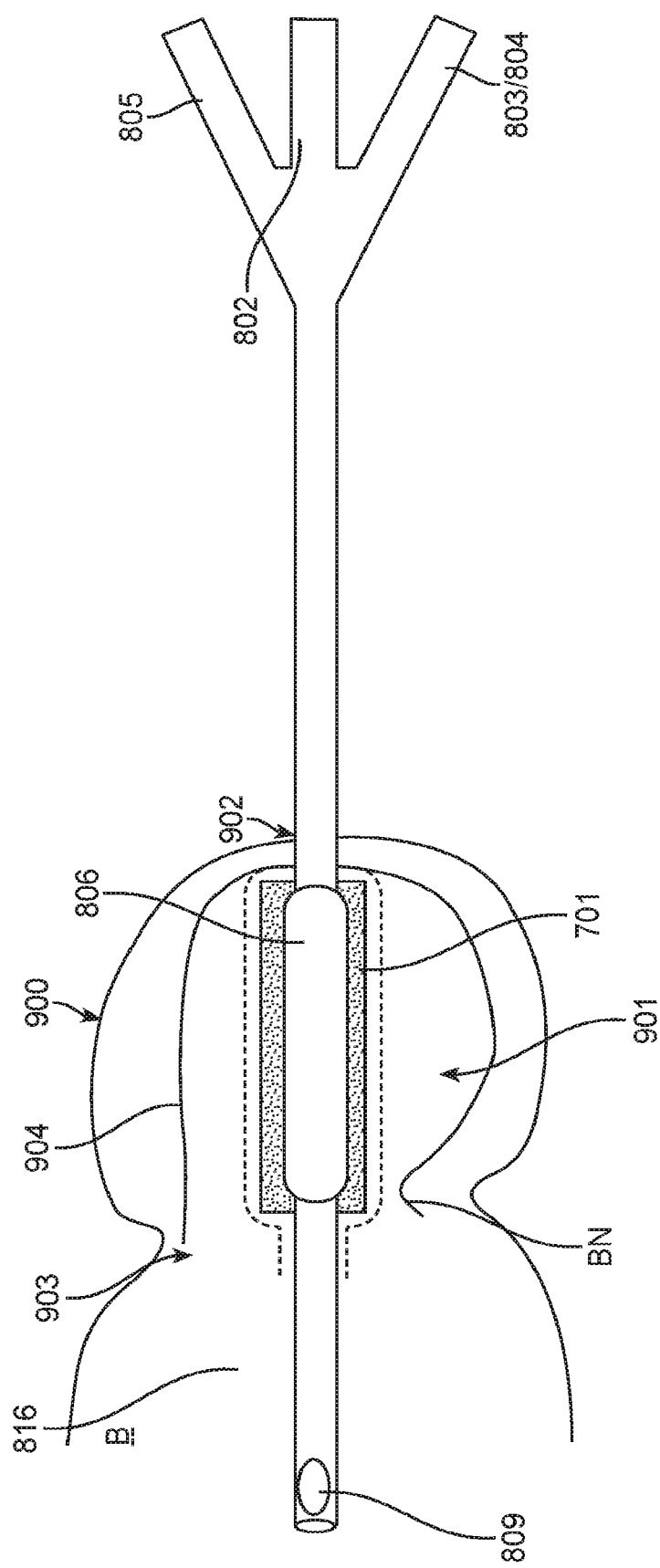
FIGS. 20A-20B show sectional schematic views of a sealant delivery device comprising an elastic sheath, in accordance with embodiments.
Figure 20B:
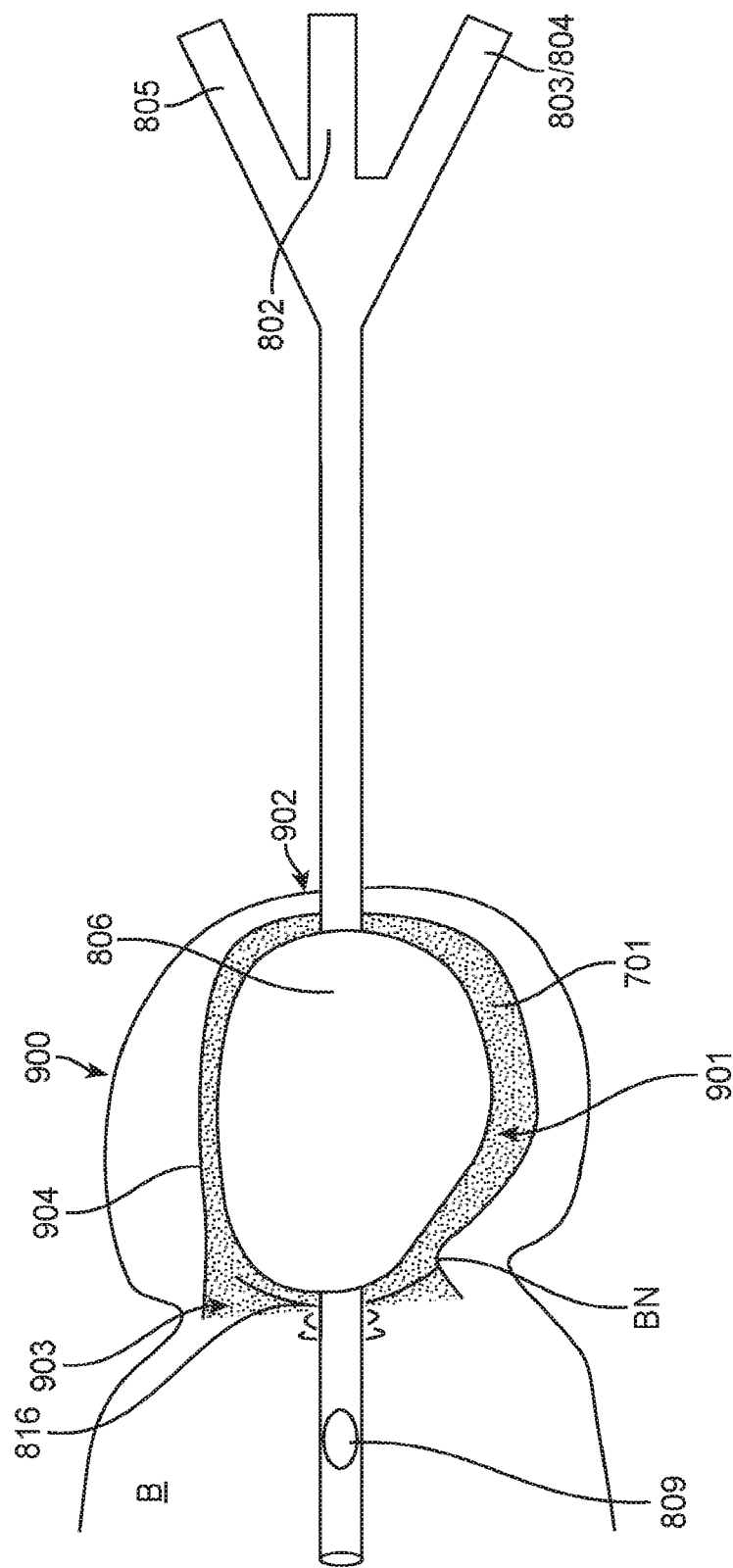

FIG. 19B shows the sealant delivery device in the deployment configuration. The sheath 816 may be coupled to the distal balloon 808 and/or a region of the catheter distal to the distal balloon 808. Expansion of the distal balloon 808 may cause the sheath 816 to retract from the sealant-coated proximal balloon 806 and expose the self-expanding gel sealant to the fluids within the cavity. The self-expanding gel sealant may then expand upon contact with the cavity fluids to fill the cavity and provide hemostasis at the cavity edge 904.

Figure 19C:
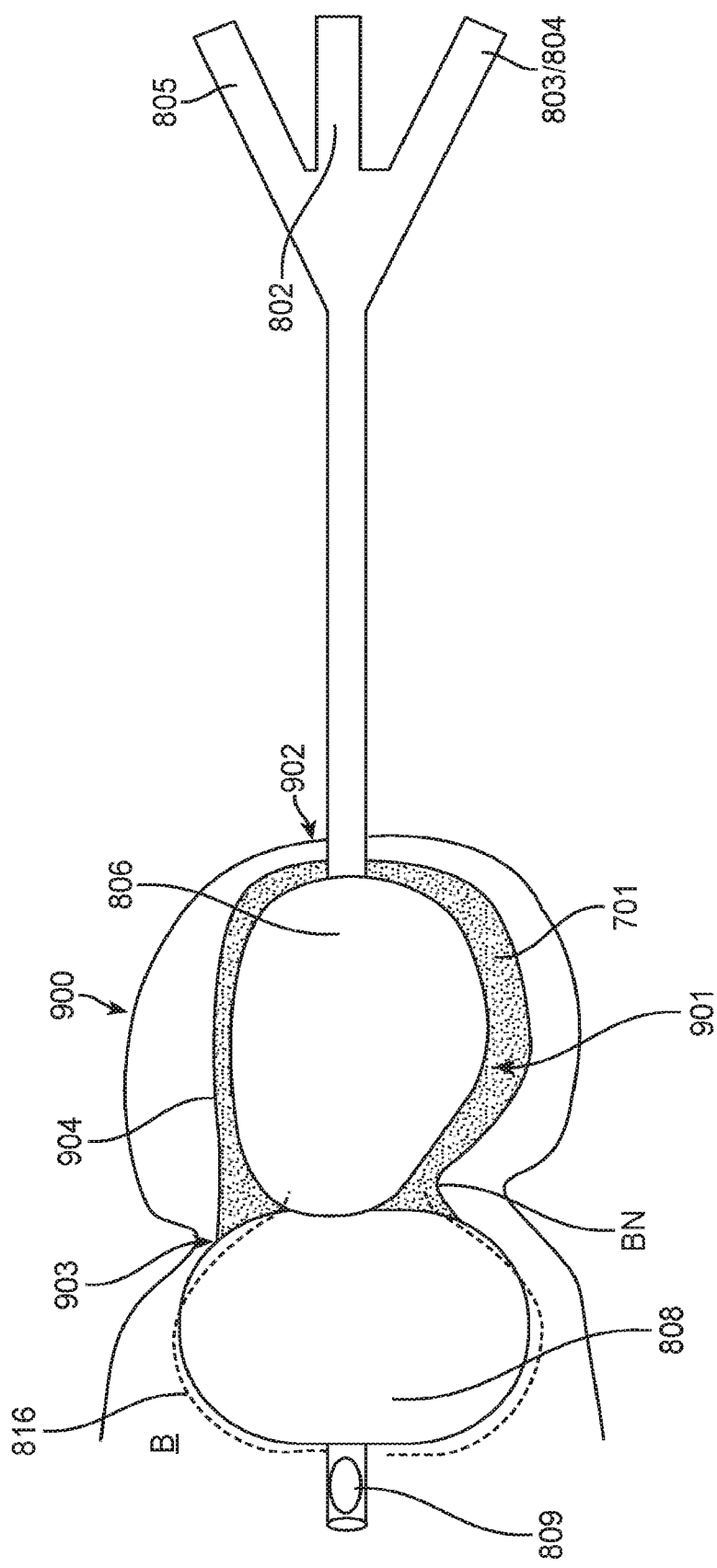

FIG. 19C shows the sealant delivery device in the deployment configuration with the proximal balloon 806 expanded. The proximal balloon 806 may be expanded while the sheath 816 is being retracted (e.g., at or nearly at the same time as the distal balloon 808 is expanded) or after the sheath 816 has been retracted and the sealant has been exposed to the cavity. Expansion of the proximal balloon 806 may facilitate distribution of the sealant to the cavity wall, which may be of particular use when the cavity has a non-uniform geometry or when it may be desired to reduce the amount of sealant delivered to the tissue. Expansion of the proximal balloon 806 may alternatively or in combination provide compression to the cavity wall, which may further enhance hemostasis. The proximal balloon 806 may comprise a compliant material or non-compliant material. The proximal balloon 806 may, for example, comprise a compliant material which may allow the proximal balloon 806 to conform to the volume of the cavity defined by the cavity edge 904 when expanded in order to further enhance sealant distribution, especially in volumes with non-uniform geometries.

Figure 19D:
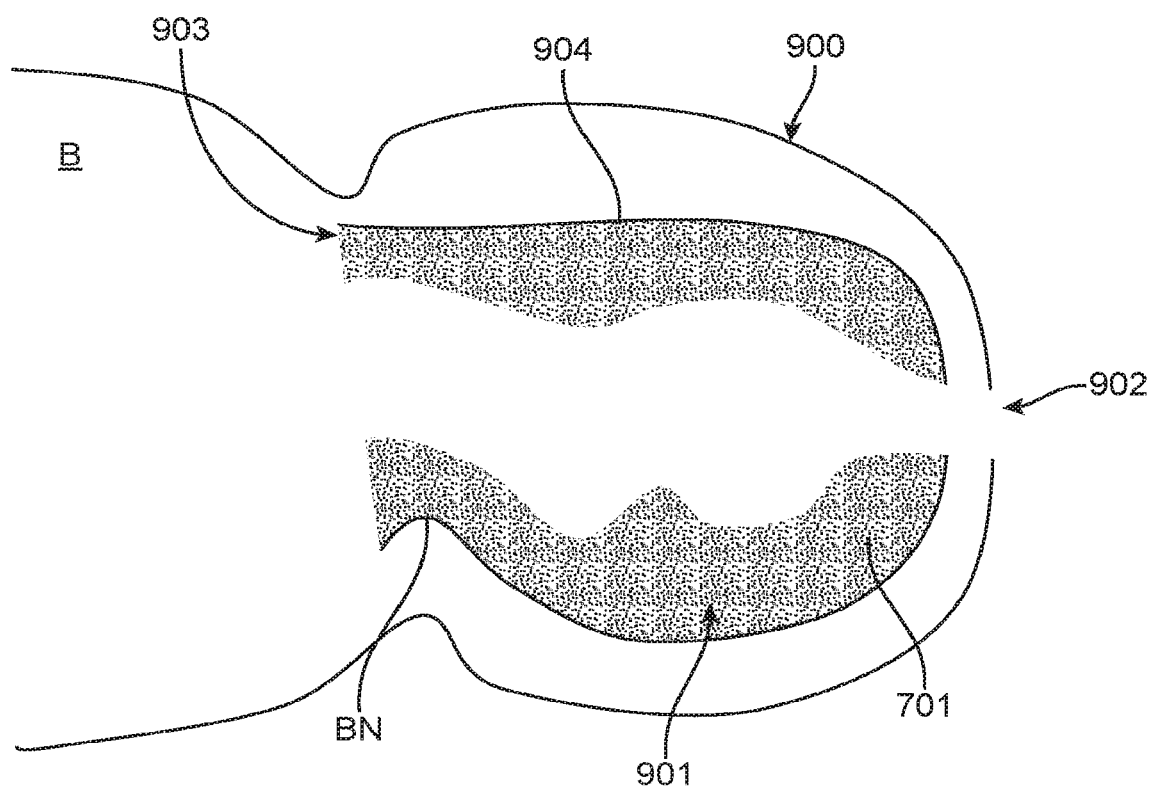

FIG. 19D shows the cavity following removal of the sealant delivery device. The proximal and distal balloons of the sealant delivery device may be deflated after a predetermined amount of time and the catheter may be retracted out of the cavity through the urethra. Some or all of the hemostatic agent may remain within the cavity to continue to prevent bleeding after the device has been removed. As shown here, by expanding the proximal balloon to facilitate sealant delivery, the sealant remaining within the cavity may have a non-uniform distribution, with some areas of the cavity (for example the cavity walls) receiving more sealant than other areas (for example the internal space defined by the cavity walls). Non-uniform distribution of the sealant may be beneficial when trying to conserve the amount of sealant delivered to the tissue and/or when the bleeding tissue has a non-uniform geometry. Any sealant that remains within the cavity following device removal may erode in one or more of many ways, for example with dissolution, degradation, washing away, or erosion. The eroded sealant may pass through the urethra and out of the body.

FIGS. 20A-20B show a sealant delivery device comprising an elastic sheath. The sealant delivery device may comprise a catheter and a proximal balloon as described herein and may be substantially similar to other single proximal balloon embodiments described herein. The sealant delivery device may further comprise a sheath which covers the proximal balloon when in a delivery configuration (as shown in FIG. 20A). The sheath may, for example, comprise any of the sheaths described herein. The sheath may, for example, comprise an elastic sheath. An external surface of the proximal balloon may be fully coated or partially coated in a hemostatic agent, for example a sealant. The sealant may be any of the sealants described herein. The sealant may for example be a self-expanding gel sealant.

FIG. 20A shows the sealant delivery device in the delivery configuration. The proximal balloon 806 may be coated in a hemostatic agent, for example a self-expanding gel sealant. The elastic sheath 816 may be disposed about the sealant-coated balloon during delivery so as to allow for dry delivery of the self-expanding sealant and prevent expansion of the sealant until the sheath 816 has been detached into the deployment configuration (as shown in FIG. 20B). The sheath 816 may be coupled to a region of the catheter distal to the proximal balloon 806. The sheath 816 may further be detachably coupled to the proximal balloon 806 and/or a region of the catheter proximal to the proximal balloon 806.

FIG. 20B shows the sealant delivery device in the deployment configuration. The sheath 816 may be coupled to a region of the catheter distal to the proximal balloon 806. Expansion of the proximal balloon 806 may cause the sheath 816 to detach from the proximal balloon 806 and/or the region of the catheter proximal to the proximal balloon 806. Detachment of the proximal end of the sheath 816 may cause the sheath to migrate towards the attachment to the region distal to the proximal balloon 806 due to the elasticity of the sheath and expose the self-expanding gel sealant to the fluids within the cavity. The self-expanding gel sealant may then expand upon contact with the cavity fluids to fill the cavity and provide hemostasis at the cavity edge 904. Expansion of the proximal balloon 806 may aid in delivery and distribution of the sealant to the cavity wall as described herein.

In any of the embodiments described herein, the sealant may be delivered through a sealant port (also referred to herein as a sealant delivery port) as described herein, either in addition to or as an alternative to delivery of the sealant as a coating on one or more balloons. The sheath may be disposed over a region of the catheter adjacent the sealant port and coupled to one or more of the distal balloon or proximal balloon. When the sheath is flexible—for example when the sheath comprises a polymer sheath or an elastic sheath, expansion of the distal balloon and/or proximal balloon may cause the sheath to retract or detach from the region in order to expose the sealant port and allow the sealant to flow into the resection cavity. When the sheath is rigid or substantially non-compliant, retraction of the sheath as described herein (e.g. FIGS. 15A-18C) from the region may expose the sealant port and allow the sealant to flow into the resection cavity.

Alternatively or in combination, in any of the embodiments described herein the sealant may be delivered through one or more of the balloons (e.g. through pores in the proximal balloon or the distal balloon) as described herein. The sheath may be disposed over a region of the catheter comprising the sealant-delivering balloon(s). Retraction or detachment of the sheath as described herein may expose the sealant-delivering balloon(s) and allow the sealant to flow in to the resection cavity.

In any of the embodiments described herein, the sheath may alternatively or in combination be used to maintain the expandable support in a low profile delivery configuration. The expandable support may for example comprise an expandable stent. The expandable stent may comprise a shape-memory material, for example nitinol. The sheath in the delivery configuration may compress the expandable support and retraction of the sheath may allow the expandable support to expand to an expanded configuration as described herein.

FIG. 21A shows a front view of a prostate, urethra U, and bladder B. FIG. 21B shows a side view of a prostate, urethra U, and bladder B. Embodiments of the sealant delivery device disclosed herein may be used to treat any tissue volume or cavity comprising a proximal opening 902 and a distal opening 903, the proximal and distal openings allowing the tissue volume to fluidly communicate with other organs or parts of the body adjacent the tissue volume. For example, the tissue volume may comprise a prostatic capsule 900 of a prostate, the prostate having a proximal opening 902 to the urethra and a distal opening 903 to the bladder B at the bladder neck BN. The sealant delivery device may be advanced into the urethral os 50, through the urethra into the prostatic capsule 900, and through the bladder neck BN into the bladder B as described herein. As described herein, the sealant delivery device may further be configured to or positioned to make contact with and/or avoid or reduce contact with one or more tissue structures within the prostatic capsule 900. For example, the device may be configured to avoid or reduce contact with sensitive tissue structures of the prostatic capsule 900 like the verumontanum V, which acts as a landmark near the entrance of the seminal vesicles, as described herein. Although shown near a central portion of the prostatic capsule 900, it will be understood by one of ordinary skill in the art that the verumontanum V can be located closer to the proximal opening 902 (e.g. urethra or sphincter) than shown.

FIGS. 22A-22E show a catheter 2200 with an expandable support assembly or inflatable balloon assembly comprising a single compliant distal balloon 808 to provide compression hemostasis. The inflatable balloon assembly may be attached adjacent the distal end of the catheter 2200 at one or more locations. The catheter 2200 may be configured to be advanced into the space enclosed with the prostatic capsule 900 (e.g. the cavity) through a proximal opening 902 into the enclosed space. The catheter 2200 may be delivered into the space such that a distal end of the inflatable balloon assembly is positioned adjacent the bladder neck and/or partially within the bladder. The inflatable balloon assembly may have an expanded configuration configured to anchor along a bladder neck adjacent the distal opening 903 to the prostatic capsule 900 and at least partially fill the space enclosed by the prostatic capsule. The inflatable balloon assembly may be expanded so as to apply compression to the tissue to promote hemostasis in the tissue. The inflatable balloon assembly may, for example, be expanded so as to seal the distal opening 903. The inflatable balloon assembly may be expanded to a target pressure to apply compression to the tissue. The target pressure may be determined in response to a measured blood pressure of a patient. The target pressure may, for example, be slightly higher than the measured blood pressure in order to close bleeding vessels. The target pressure may for example be within a range of about 5% to about 100% (for example, about 50%) above the measured systolic blood pressure in order to close bleeding vessels. Alternatively or in combination, the inflatable balloon assembly may be inflated to a pre-determined target volume and/or shape. The inflatable balloon assembly may, for example, be inflated to a volume and/or shape which corresponds to a resected tissue volume and/or shape.

FIG. 22A shows an inflatable balloon assembly 2210 comprising a uniform compliance. The inflatable balloon assembly 2210 may comprise a unitary compliant material. The inflatable balloon assembly may, for example, comprise a uniform thickness. When inflated in the tissue space, the inflatable balloon assembly 2210 may, for example, comprise an hourglass shape having a distal bladder region 2212, a proximal prostatic region 2214, and a neck region 2213 therebetween. The inflatable balloon assembly 2210 may be long enough to fill the prostate and extrude into the bladder.

FIG. 22B shows an inflatable balloon assembly 2210 comprising a non-uniform compliance. Non-uniform compliance may, for example, be achieved by providing a less compliant region 2201 (for example a region made of a less compliant material or a region with a thicker balloon wall) within the inflatable balloon assembly. Non-uniform compliance may, for example, be achieved by an inflatable balloon assembly with non-uniform thickness. The region (or regions) of non-uniform compliance and/or thickness may be configured to provide the inflatable balloon assembly 2210 with a pre-determined shape. The region (or regions) of non-uniform compliance and/or thickness may be configured to be expanded in a stepwise manner such that one or more regions of the inflatable balloon assembly (for example the distal bladder region 2212, proximal prostatic region 2214, and/or neck region 2213) expands before one or more other regions of the inflatable balloon assembly. The distal bladder region 2212 may for example comprise a rigid balloon.

FIG. 22C shows a front view of an inflated inflatable balloon assembly 2210 comprising a non-uniform compliance, for example having a region of reduced compliance as shown in FIG. 22B. FIG. 22D shows a side-view of the inflated inflatable balloon assembly. The region of non-uniform compliance may, for example, comprise a region of increased thickness corresponding to the neck region 2203 of the inflated balloon compared to the proximal prostatic region 2204 and/or the distal bladder region 2202 of the inflatable balloon assembly 2210. The neck region 2203 may be thicker than the proximal prostatic region 2204 and/or the distal bladder region 2202 so as to reduce compression on and prevent distension of the bladder neck 2203 during expansion of the inflatable balloon assembly 2210. Alternatively or in combination, the distal bladder region 2212 may be thicker than the neck region 2213 and/or the proximal prostatic region 2214 so as to provide traction resistance to dilation of the peripheral sphincter. One or more regions of the inflatable balloon may be inflated to one or more target pressures chosen so as to close bleeding vessels.

FIG. 22E shows an inflatable balloon assembly comprising an adjustable length feature. Any of the embodiments described herein may further comprise an adjustable length feature 2220. The adjustable length feature 2220 may be configured to adjust the length (and volume) of the inflatable balloon assembly prior to or after delivery into the tissue. The adjustable length feature 2220 may, for example, comprise a non-compliant sheath with tear-away sections as shown. Tearing away one or more of the sections may increase the volume of balloon available for expansion, thereby increasing the volume and/or shape of the expanded balloon. Alternatively or in combination, the adjustable length feature 2220 may comprise a retractable cover or an elastomeric sheath disposed over at least a portion of the inflatable balloon assembly. Retraction of the cover or elastomeric sheath may increase the volume of balloon available for expansion. In some instances, the elastomeric sheath may be retracted by increasing the pressure of the balloon assembly. Alternatively or in combination, the cover or sheath may be manually retracted. The adjustable length feature 2220 may comprise a hyperechoic material to allow for the use of ultrasound to visualize the position of the sheath in the tissue. Alternatively or in combination, the adjustable length feature 2220 may comprise a radiopaque material to allow for the use of x-ray imaging to visualize the sheath. Visualizing the adjustable length feature 2220 may allow for better placement of the inflatable balloon assembly and/or adjustment of the length of the balloon prior to, during, or after inflation.

Figure 23C:
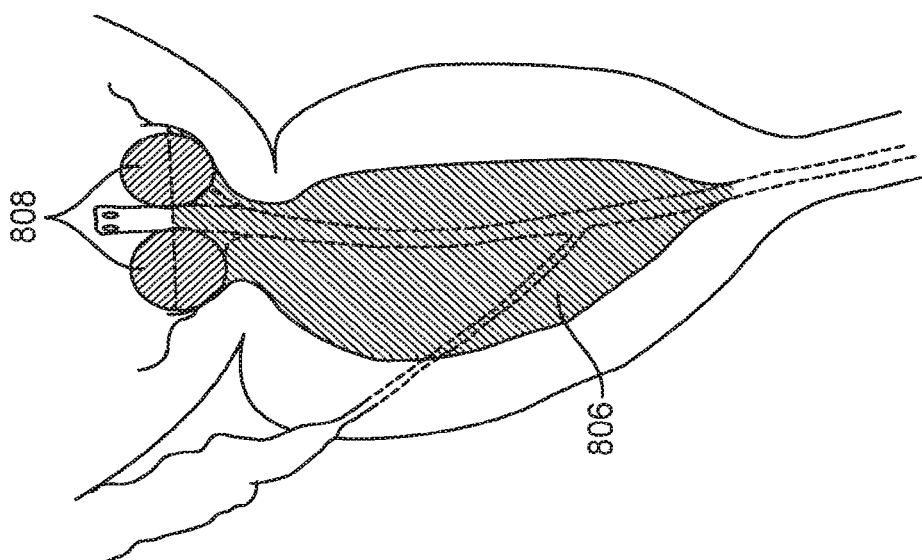
FIGS. 23A-23C show various sectional schematic views of a catheter with inflatable balloon assembly comprising two balloons to provide compression hemostasis, in accordance with embodiments.
Figure 23B:
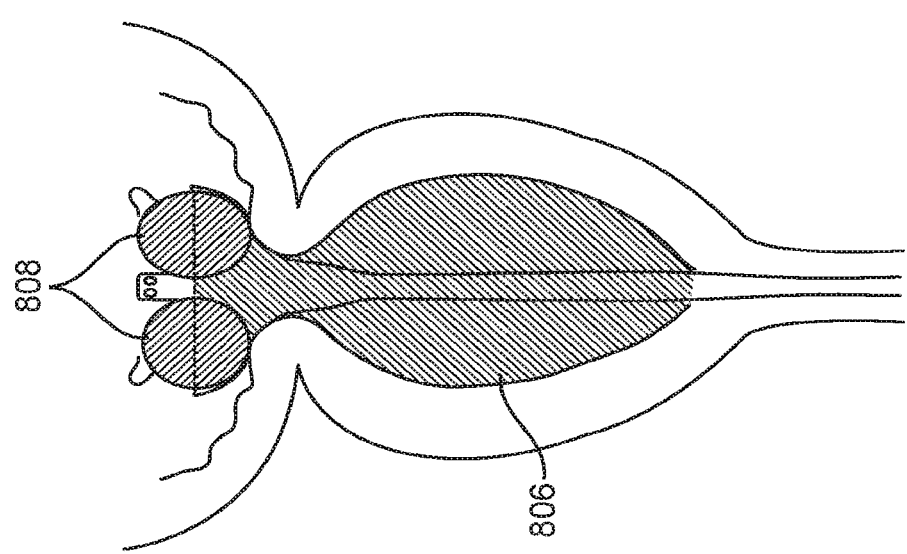
Figure 23A:
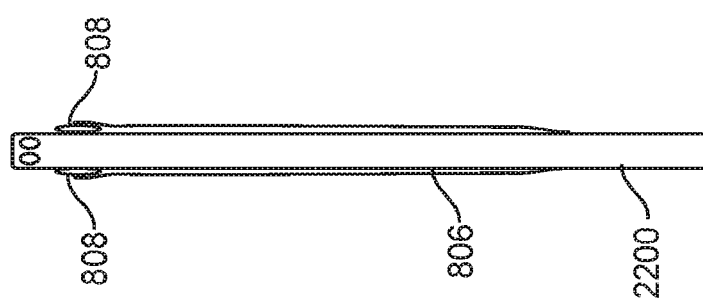

FIGS. 23A-23C show a catheter 2200 with inflatable balloon assembly comprising two balloons to provide compression hemostasis. The inflatable balloon assembly may be shaped substantially similar to that of FIGS. 22A-22E. The inflatable balloon assembly may, for example, comprise a proximal balloon and a distal balloon. The catheter 2200 may be delivered into the tissue space such that the distal balloon is positioned adjacent the bladder neck and/or within the bladder. A portion of the proximal balloon may extend from the distal balloon in the bladder, through the bladder neck, and into the prostatic capsule. The inflatable distal balloon may have an expanded configuration configured to anchor along a bladder neck adjacent the distal opening to the prostatic capsule. The proximal balloon may have an expanded configuration configured to at least partially fill the space enclosed by the prostatic capsule and the bladder neck. The inflatable balloon assembly may be expanded so as to apply compression to the prostatic tissue and/or bladder neck to promote hemostasis in the tissue as described herein. The distal balloon of the inflatable balloon assembly may, for example, be expanded so as to seal the distal opening. The inflatable balloon assembly may be expanded to a target pressure, volume, and or shape to apply compression to the tissue as described herein.

FIG. 23A shows an inflatable balloon assembly comprising a proximal balloon 806 attached to a distal balloon 808 in a low-profile delivery configuration. The proximal balloon 806 and the distal balloon 808 may be continuous with one another or the proximal balloon 806 may be disposed about and attached or adhered to the distal balloon 808 as shown. The inflatable balloon assembly may be attached adjacent the distal end of the catheter 2200 at one or more locations.

FIG. 23B shows a front-view of an inflated inflatable balloon assembly comprising a proximal balloon 806 attached to a distal balloon 808. FIG. 23C shows a side-view of the inflated inflatable balloon assembly. The distal balloon 808 may comprise any of the balloon shapes described herein. The distal balloon 808 may for example comprise a rigid toroidal balloon. The distal balloon 808 may be inflated to seal the bladder neck. Alternatively or in combination, the distal balloon 808 may act as an anchor at the bladder neck in order to prevent unintentional movement and/or removal of the inflatable balloon assembly. The proximal balloon 806 may comprise any of the balloon shapes described herein. The proximal balloon 806 may comprise a very compliant or moderately compliant material. The proximal balloon 806 may be inflated to a pre-determined pressure, shape, or volume as described herein. The proximal balloon 806 may for example be inflated so as to re-approximate tissue to the organ wall and/or provide designed, direct compression on surface vessel within the tissue to establish hemostasis. The region of the proximal balloon 806 within the bladder neck may be inflated in order to seal the bladder neck and provide compression to the bladder neck to prevent or stop bleeding.

FIGS. 24A-24D show a catheter with inflatable balloon assembly comprising adjustable balloons to provide compression hemostasis. The inflatable balloon assembly may comprise a distal balloon 808 and a proximal balloon 806. The catheter may be delivered into the tissue space such that the distal balloon 808 is positioned adjacent the bladder neck and/or within the bladder. The proximal balloon 806 may be positioned in the prostatic capsule. The inflatable distal balloon 808 may have an expanded configuration configured to anchor along a bladder neck adjacent the distal opening to the prostatic capsule. The proximal balloon 806 may have an expanded configuration configured to at least partially fill the space enclosed by the prostatic capsule. The inflatable balloon assembly may be expanded so as to apply compression to the prostatic tissue and/or bladder neck to promote hemostasis in the tissue as described herein. The distal balloon 808 of the inflatable balloon assembly may, for example, be expanded so as to seal the distal opening. The inflatable balloon assembly may be expanded to a target pressure, volume, and or shape to apply compression to the tissue as described herein. One or more of the distal balloon 808 or proximal balloon 806 may be adjustable within the tissue. For example, the proximal balloon 806 may be selectively positionable within the prostatic capsule.

Figure 24A:
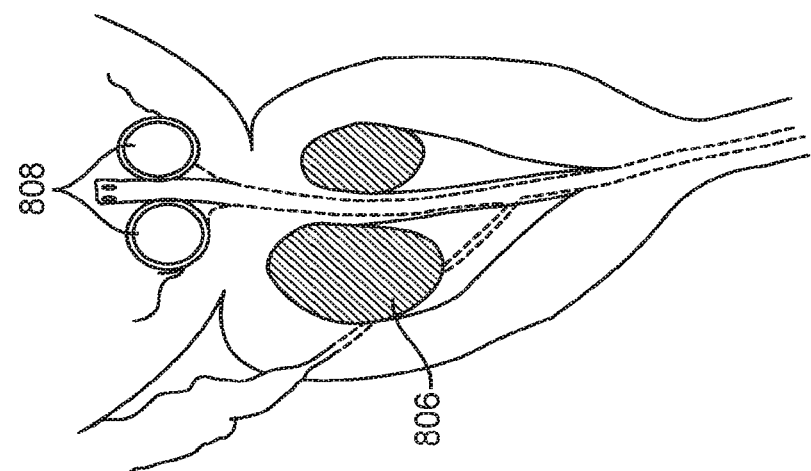
FIGS. 24A-24D show various sectional schematic views a catheter with inflatable balloon assembly comprising adjustable balloons to provide compression hemostasis, in accordance with embodiments.
Figure 24B:
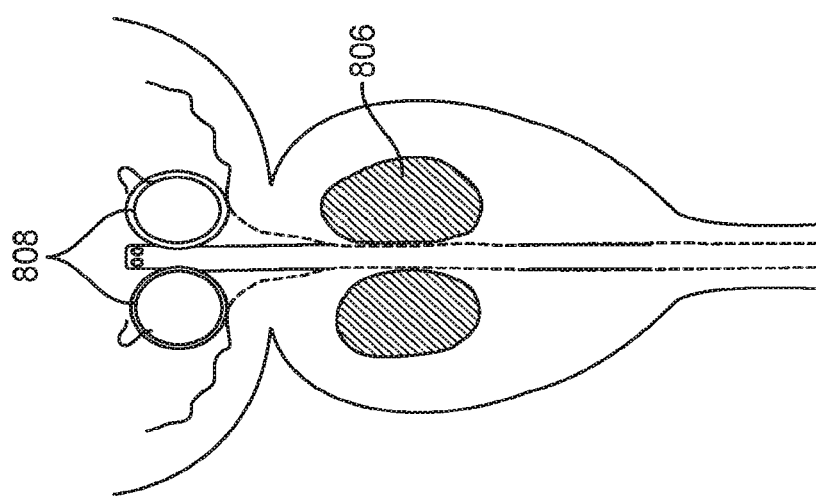

FIGS. 24A-24B shows an inflatable balloon assembly comprising a proximal balloon 806 and a distal balloon 808 in a low-profile delivery configuration. The distal balloon 808 may be attached adjacent the distal end of the catheter at one or more locations. The proximal balloon 806 may be attached to the catheter at one or more locations proximal to the distal balloon 808. The proximal balloon 806 may be attached to an adjustable sheath 2220 configured to re-position the proximal balloon 806 when actuated (for example by a physician). The sheath 2220 may for example be moved distally or proximally along the catheter in order to move the proximal balloon 806 distally or proximally, respectively. The proximal balloon 806 may be re-positioned prior to, during, or after inflation of the proximal balloon 806, distal balloon 808, or both. The location of the proximal balloon 806 relative to the distal balloon 808 may be fixed following re-positioning to a desired location within the prostatic capsule. The proximal balloon 806 may be fixed externally so as to assure movement between the distal balloon 808 and the proximal balloon 806 remains unchanged while the catheter is in place. The distance between the proximal and distal balloons may alternatively or in combination be fixed between the balloons by providing compression or extension between the balloons for targeted compressive therapy. The proximal balloon 806 may comprise any shape described herein or desired. The proximal balloon 806 may, for example, comprise a toroidal shape (as in FIG. 24A) or a cylindrical shape (as in FIG. 24B). The length of the proximal balloon 806 may be adjustable as described herein so as to adjust the shape of the inflated balloon. In some instances, it may be beneficial to provide an inflatable balloon assembly without a distal balloon 808 as shown in FIG. 24B.

Figure 24C:
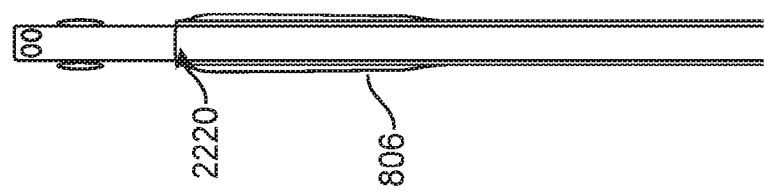
Figure 24D:
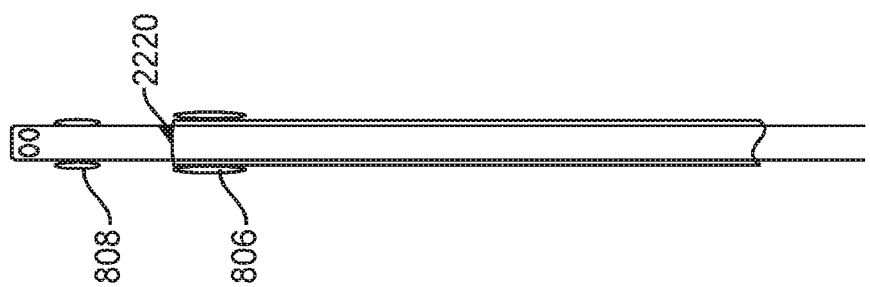

FIG. 24C shows a front-view of an inflated inflatable balloon assembly comprising a proximal balloon 806 and a distal balloon 808. FIG. 24D shows a side-view of the inflated inflatable balloon assembly. The distal balloon 808 may comprise any of the balloon shapes described herein. The distal balloon 808 may for example comprise a rigid toroidal balloon. The distal balloon 808 may be inflated to seal the bladder neck. Alternatively or in combination, the distal balloon 808 may act as an anchor at the bladder neck in order to prevent unintentional movement and/or removal of the inflatable balloon assembly. The proximal balloon 806 may comprise a compliant material or a non-compliant material as described herein. The proximal balloon 806 may be inflated to a pre-determined pressure, shape, or volume as described herein. The proximal balloon 806 may for example be inflated so as to re-approximate tissue to the organ wall and/or provide designed, direct compression on surface vessel within the tissue to establish hemostasis.

FIGS. 25A-25F show a catheter with inflatable balloon assembly shaped to provide compression hemostasis and avoid or reduce compression of select regions or areas of the prostatic capsule or resection cavity, such as the verumontanum. The inflatable balloon assembly may be substantially similar to any of the inflatable balloon assemblies described herein. For example, this or any of the other inflatable balloon assemblies described herein may comprise a proximal balloon and a distal balloon in fluid communication with one another. The inflatable balloon assembly may comprise a single continuous balloon having an expandable distal portion and an expandable proximal portion which may correspond to the distal balloon and proximal balloon of dual balloon assemblies. The inflatable balloon assembly may comprise a proximal balloon, a distal balloon, or both as in any of the embodiments described herein. The inflatable balloon assembly of this or any embodiment described herein may be shaped so as to selectively direct compressive contact with the tissue to specific regions of the tissue. The inflatable balloon assembly may, for example, be shaped to minimize or reduce contact between one or more expanded balloons of the inflatable balloon assembly and the verumontanum of the prostate such as in order to protect the sexual function of the patient. The inflatable balloon assembly may be configured to provide hemostasis and/or re-approximate the remaining prostatic tissue (for example after tissue resection and cavity formation with a known shape profile as described herein). For example, in some instances it may be beneficial to avoid compressing or reduce contact with the region comprising the verumontanum as compression may cause adhesion of and closing of the seminal ducts, thus affecting sexual function of the patient. The inflatable balloon assembly may be shaped to apply outward compression on the internal cavity of the prostatic capsule without displacing or with minimal contact to the verumontanum. The inflatable balloon assembly may be shaped so as to apply non-uniform force circumferentially around the balloon in order to provide reduced or decreased contact or pressure of the balloon with the verumontanum. The inflatable balloon assembly may for example be shaped with a non-uniform cross-sectional circumference. Contact between the inflatable balloon assembly and the verumontanum may thus be decreased when the inflatable balloon assembly is fully expanded.

FIG. 25A shows an inflatable balloon assembly comprising an expandable prostatic balloon 806 in a low-profile delivery configuration. The expandable prostatic balloon 806 may be a compliant balloon configured to inflate to a pre-determined target pressure, shape, or volume and provide direct compression and hemostasis control to a portion of the tissue within the prostatic capsule while avoiding or reducing compression of sensitive tissue near or at the verumontanum. A proximal portion 8061 of the expandable prostatic balloon 806 may for example be adhered to the catheter to cause the balloon to "tent" over a region comprising the verumontanum when expanded and thereby prevent compression of the tissues within the verumontanum region.

FIG. 25B shows a top-view of an inflatable balloon assembly comprise an expandable prostatic balloon 806 in a low-profile delivery configuration. The expandable prostatic balloon 806 may comprise one or more wires 8062, for example, two or three wires. The wires may be deployed against the surface of the balloon near the verumontanum so as to guide the balloon to form a tenting structure or concavity over the verumontanum. The wires may be freely moving against the balloon or may be strategically adhered to the balloon. The wires may be located either inside the balloon or outside the balloon. The wires may comprise a rigid, semi-rigid, or shape-memory material. The wires may, for example, comprise nitinol or spring steel which may readily move from a low profile configuration during delivery to an expanded, shaped configuration when deployed in the prostatic capsule 900.

FIG. 25C shows a front-view of an expanded inflatable balloon assembly comprising a prostatic balloon 806 shaped to avoid compressing or reduce contact with the verumontanum. FIG. 25F shows a side-view of the expanded inflatable balloon assembly shaped to avoid or reduce contact with the verumontanum. The inflatable balloon assembly may optionally further comprise an expandable bladder balloon 806 which may compress the bladder neck and/or act as an anchor for the device as described herein. The inflated prostatic balloon 806 may be shaped by any combination or wires or adherence to the catheter so as to for a concave or tent region over the verumontanum V. Alternatively or in combination, the thickness and/or compliance of the prostatic balloon wall(s) may be varied so as to enable shaped and/or sequential expansion of the balloon as described herein. For example, a distal portion of the balloon (for example at or near line A-A, the cross-section of which is shown in FIG. 25D) may comprise a uniform thickness and/or compliance such that the entire balloon expands at or nearly at the same time. A proximal portion of the balloon (for example, at or near line B-B, the cross-section of which is shown in FIG. 25E) may comprise an non-uniform thickness and/or compliance, with a region of increased thickness or rigidity disposed near the approximate location of the verumontanum V, such that the region of the balloon near the verumontanum V expands after the more compliant portion 2202 of the balloon, or does not expand substantially at all, thereby generating the desired concave tent structure over the verumontanum V. The prostatic balloon material may comprise a variable thickness in order to cause progressive or sequentially inflation of the balloon and create a sweeping motion toward the verumontanum, leaving the balloon pinched and pulled centrally to form the tent-like structure over the verumontanum.

Alternatively or in combination, the prostatic balloon may be molded or shaped to comprise a concavity or wedge/tent-like region so as to avoid contacting or reduce contact with the verumontanum.

In this or any single-balloon embodiment described, it will be understood that the terms "proximal" and "distal" may be used interchangeably as the use of the terms in dual-balloon embodiments denote the relative position of the two balloons to each other. For example, the expandable prostatic balloon shown here may be referred to as a distal balloon. If an expandable bladder balloon were added (as shown in FIG. 25C), the bladder balloon, being located distal to the prostatic balloon, may be referred to as a distal balloon while the prostatic balloon may be referred to as a proximal balloon. It will be understood by one of ordinary skill in the art that any of the embodiments described herein may be modified to add or remove balloons and thus the relative terminology used to describe the final inflatable balloon assembly configuration may be altered as described herein without altering the desired properties of the balloon.

In at least some instances, it may be beneficial to provide a compression in combination with delivery of a hemostatic agent in order to reach hemostasis within the tissue. Any of the embodiments described herein to deliver a hemostatic agent to a tissue space may be configured with a shape, volume, or pressure configured to contact and compress the tissue as described herein. Any of the embodiments described herein to provide compression to the tissue may be configured to deliver a hemostatic agent to the tissue as described herein (for example through a delivery port(s) on the catheter, through pores on one or more balloon, by coating one or more balloon with a hemostatic agent, mesh, or scaffold, etc.). It will be understood by one of ordinary skill in the art that many of the features described herein are optional and/or interchangeable so as to achieve the desired hemostatic results. For example, any of the balloons or inflatable balloon assemblies described herein may be coated with a hemostatic agent such that compressing the balloon into the tissue also compresses the hemostatic agent into the tissue. Combining compression and hemostatic agent delivery may speed up hemostasis and/or provide hemostasis to non-uniform tissue geometries more readily.

In at least some instances, it may be beneficial to modify the hemostatic device so as to prevent migration of the catheter after placement. Any of the embodiments described herein may comprise one or more features configured to minimize or prevent catheter migration.

Figure 26:
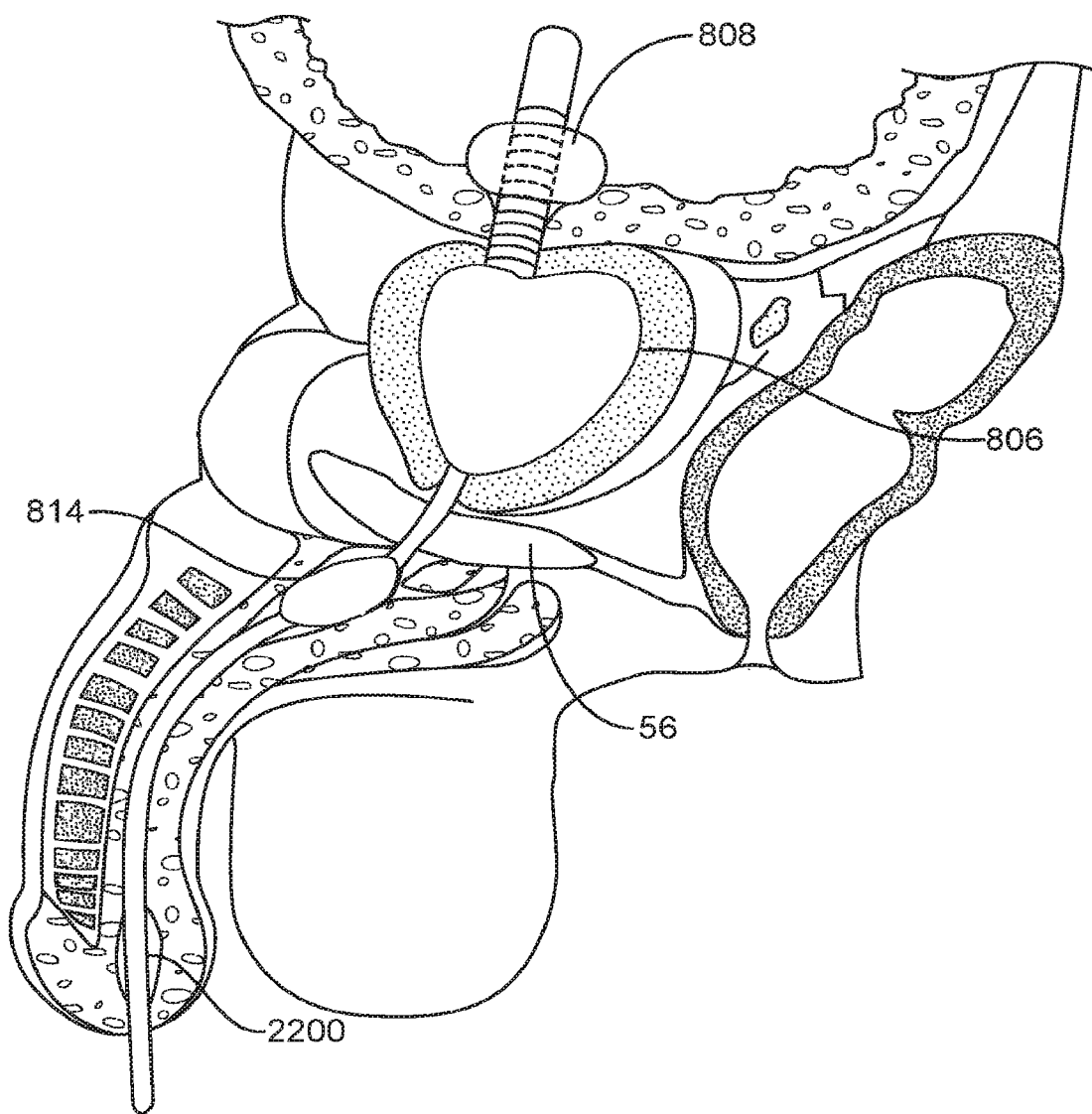
FIG. 26 shows a section view of a catheter with inflatable balloon assembly comprising a urethral bulb to minimize catheter migration, in accordance with embodiments.

FIG. 26 shows an exemplary embodiment of an inflatable balloon assembly comprising a urethral bulb 818 to minimize catheter migration. The inflatable balloon assembly may comprise a proximal balloon, a distal balloon, a single balloon with proximal and distal portions, or any combination thereof. As shown here, the inflatable balloon assembly may for example comprise a distal balloon 808 situated at or near the bladder neck and a proximal balloon 806 at least partially located within the prostatic capsule as described herein. The inflatable balloon assembly may further comprise a bulb 818 positioned on the catheter proximal of the inflatable balloon assembly. The bulb 818 may be configured to be positioned in the ureter when the inflatable balloon assembly is positioned in the prostatic capsule so as to minimize migration of the catheter. The bulb 818 may be expandable or inflatable, for example a balloon. The bulb 818 may alternatively be rigid, for example a tab. The bulb 818 may for example be expanded or inflated after the catheter has been placed in a desired location as described herein. The bulb may alternatively or in combination be configured to maintain tension on the catheter and inflatable balloon assembly in order to promote hemostasis.

The tension on the catheter may be maintained with a range of about 0.1 to about 1.4 kg in order to promote hemostasis as described herein.

Figure 27A:
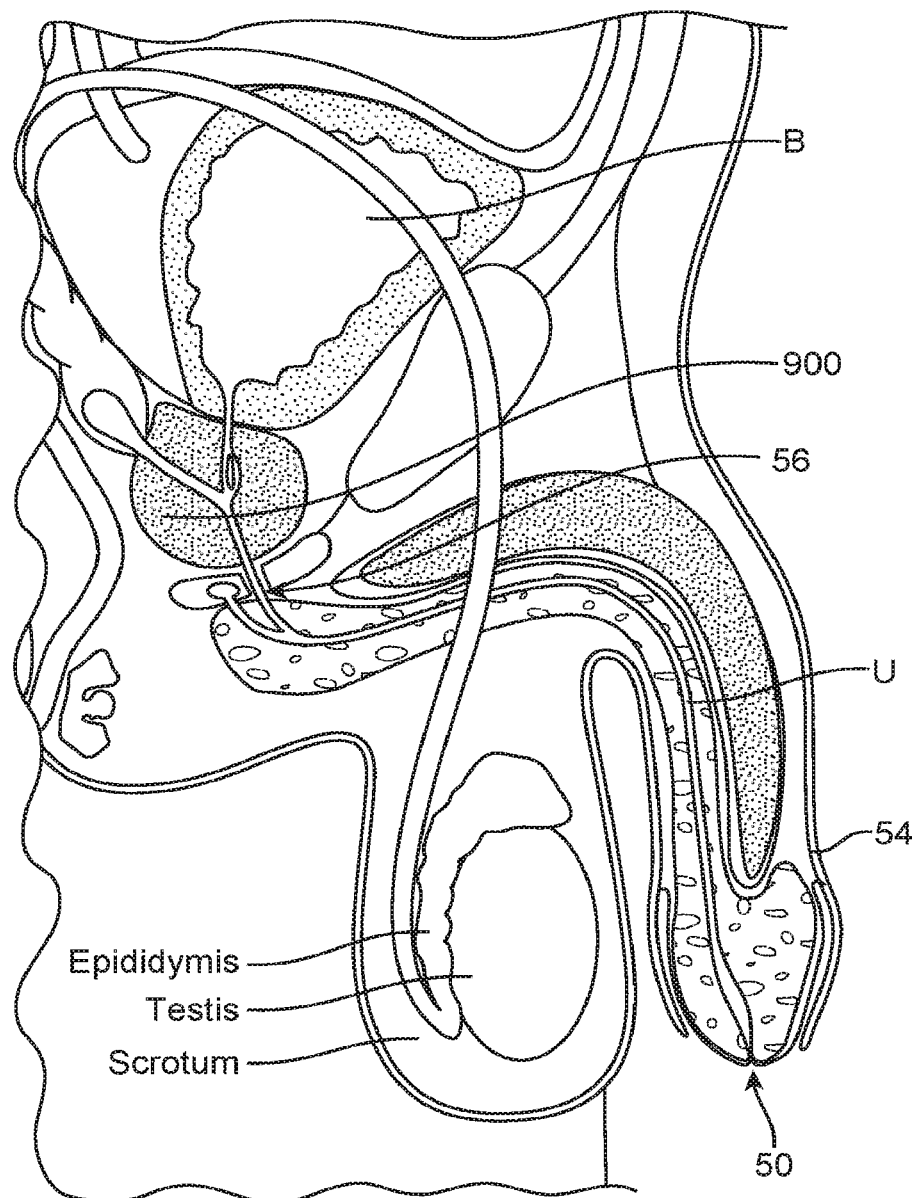
FIG. 27A shows a section view of a bodily member prior to positioning with a flexible enclosure, in accordance with embodiments.
Figure 27B:
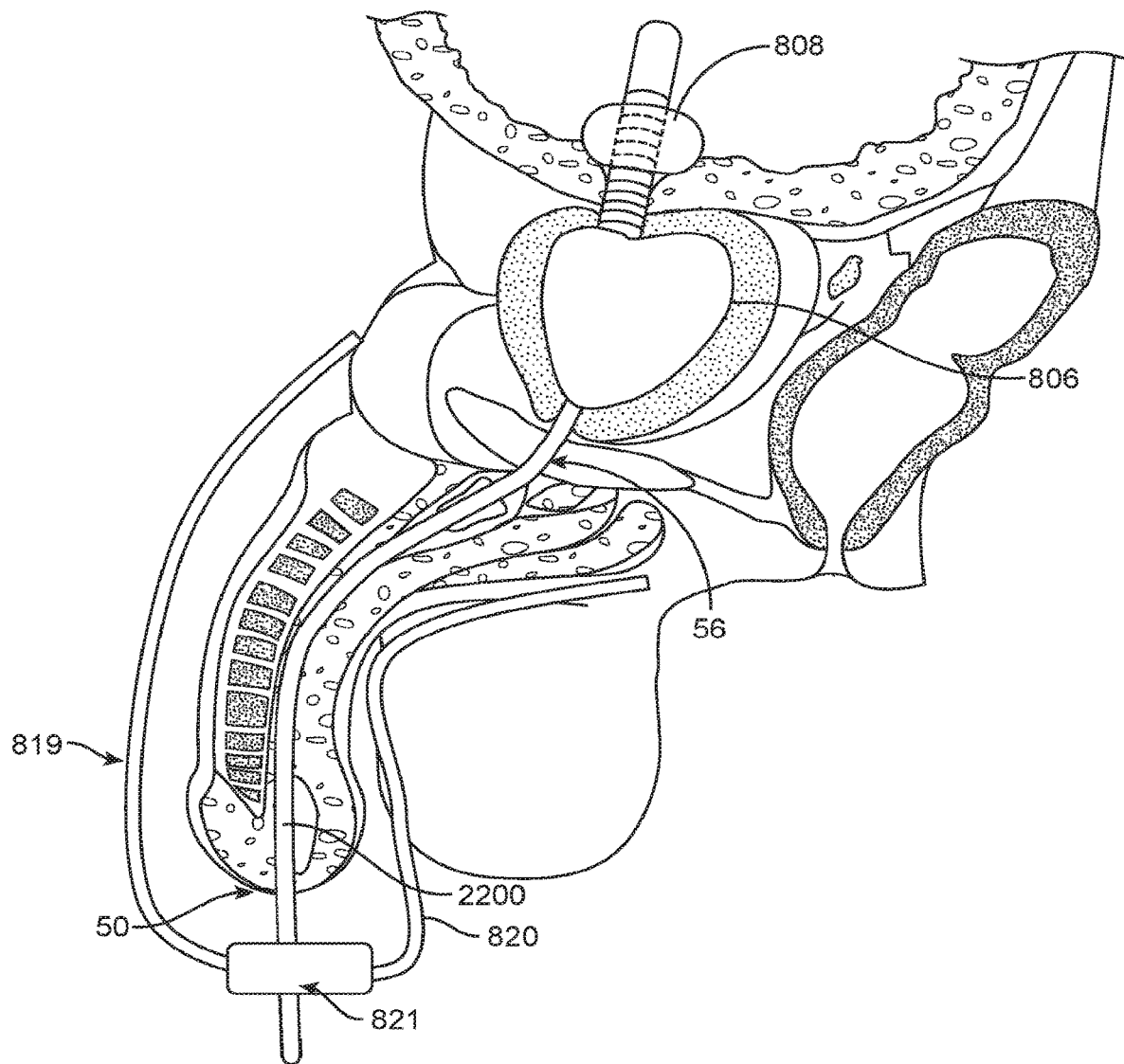
FIG. 27B shows a section view of a catheter coupled to a flexible enclosure adapted to resist repositioning and maintain a position of a bodily member, in accordance with embodiments.
Figure 27C:
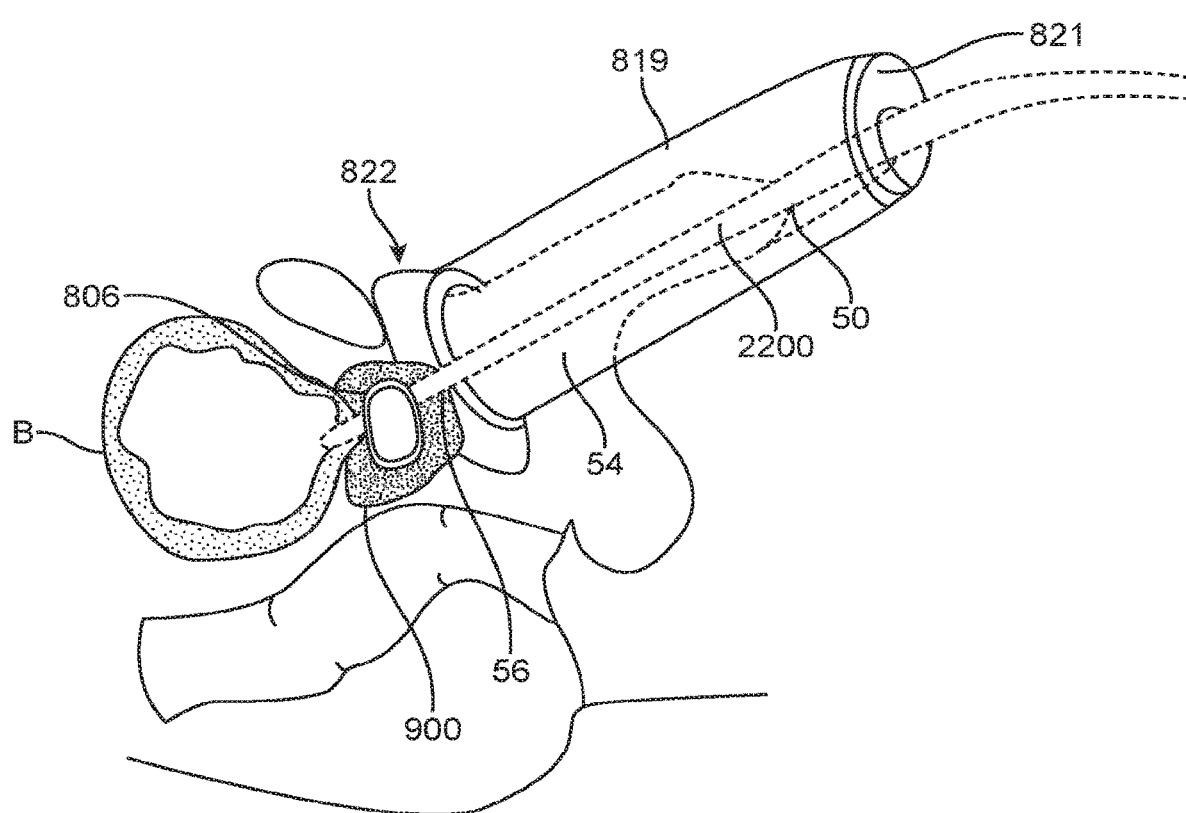
FIG. 27C shows a perspective section view of a saddle traction device in use, in accordance with embodiments.

Alternatively or in combination, the catheter may be coupled to an enclosure adapted to resist repositioning and maintain a position of a bodily member as shown in FIGS. 27B-27C. The enclosure may for example be a flexible enclosure as shown or an inflexible enclosure. The enclosure may be configured to conform to a bodily member. The flexible enclosure may be adapted to enclose the bodily member. The enclosure may comprise a material with a thickness and/or elasticity sized to fit over a bodily member and hold the bodily member in place. The enclosure may comprise a soft, compliant, and/or stretchable material configured to decrease irritation of the bodily member. The catheter may be at least partially positioned with in the bodily member. The flexible enclosure may be shaped to conform to and apply pressure to the bodily member to resist repositioning of the flexible enclosure when enclosing the bodily member. The distal tip of the flexible enclosure may be configured to couple to the catheter. The distal tip of the flexible enclosure may be configured to couple to a retainer element. The retainer element may be coupled to a proximal segment of the catheter extending out of the bodily member. The enclosure may be configured to be coupled to a segment of the catheter extending out of the bodily member through a retainer element coupled to the segment. The bodily member may for example comprise a penis and the catheter may extend out of an urethral os. The flexible enclosure may be configured to be concentric with a urethra of the penis when enclosing the penis.

FIG. 27A shows a section view of a bodily member prior to positioning with a flexible enclosure. The bodily member may for example comprise a penis. The urethra is the tube connecting the bladder B to the urethral os 50 through the prostatic capsule 900, external sphincter 56, and penis 54. When the penis 54 is flaccid as shown, the urethra may comprise may twists and or turns which cause the urethra, prostatic capsule 900, and urethral os 50 are out of alignment. The penis 54 may be positioned described herein to align the urethra with the prostatic capsule 900 so as to prevent movement of the catheter due to movement of the penis 54.

FIG. 27B shows an exemplary embodiment of a catheter 2200 coupled to a flexible enclosure 819 enclosing a penis. The catheter 2200 may comprise any of the catheters and/or any of the balloons, inflatable balloon assemblies, or expandable elements described herein. The catheter 2200 may for example comprise a distal balloon 808 and a proximal balloon 806 as described herein. The flexible enclosure 819 may be at least partially cylindrical in shape. The flexible element may comprise a soft, compliant material to minimize irritation against tissue of the penis. The flexible element may, for example, comprise a penis guard or cover 820. The flexible enclosure 819 may comprise a retainer element 821 coupled to a proximal, external segment of the catheter 2200. The flexible enclosure 819 may be configured to be coupled to a pelvic or groin mount 822 to maintain the position of the flexible enclosure 819 and enclosed penis. For example, the pelvic or groin mount 822 may be configured to pull on the flexible enclosure 819 and the enclosed penis in order to align the urethra with the urethral sphincter such that the hemostatic device (comprising a catheter) is relatively straight within the tissue. The pelvic or groin mount 822 may provide a surface area which presses equally or nearly equally on the pubic region and the perineum. The pelvic or groin mount 822 may provide event comfort when docked on a bony structure, sat upon, or belted on in order to prevent rotation or loss of position of the flexible enclosure 819. The pelvic or groin mount 822 may enclose and grip onto the base of the penis and the scrotum such that the anatomy is pulled down to align the urethra with the prostate (and bladder os). The catheter may be retained in the tissue due to tension between the catheter and the balloons. A distal portion of the catheter may be coupled to one or more balloons and an external proximal portion of the catheter may be secured to the retainer element. The catheter between the one or more balloons and the retainer element may comprise a tension. The pelvic or groin mount 822 may be coupled to the groin or hip bones to counter the tension in the catheter and fixate the catheter (and thus the retainer element and flexible element in tension.

The device may further comprise a tension or traction element configured to couple to one or more of the catheter or the flexible enclosure to align the urethra with the urethral sphincter. The catheter may, for example, be drawn through the retainer element of the flexible enclosure and attached to the tension element. In some instances, it may be beneficial to provide direct therapeutic tension to compress a bleeding tissue in order to achieve hemostasis or to maintain the position of the catheter and/or expandable elements within the tissue. Application of tension may be provided in combination with any of the mechanisms for maintaining catheter position described herein.

FIG. 27C shows a saddle traction device configured to maintain the position of the catheter 2200 as well as provide tension to the catheter and/or balloons. The device may, for example, comprise a flexible enclosure 819 substantially similar to that of FIG. 27B. The device may comprise a flexible enclosure 819 coupled to the catheter 2200, the catheter comprising a proximal balloon 806 within the prostatic capsule. The catheter may alternatively or in combination comprise a distal bladder balloon as described herein (not shown).

The device may further comprise a tension or traction element configured to couple to one or more of the catheter or the flexible enclosure to align the urethra with the urethral sphincter. The catheter may, for example, be drawn through the retainer element of the flexible enclosure and attached to the tension element. In some instances, the retainer element may comprise a tension element and may provide tension as well as position maintenance for the catheter. One or more of the scrotum or penis may be moved to accommodate the tension element. The tension element may apply tension collinearly with the catheter shaft through the sphincter. The tension element may apply tension with the balloon expanded within the tissue space. The expanded balloon(s) may counteract the tension applied to the catheter so as to maintain the position of the catheter within the tissue space. The tension may be applied concentrically in order to avoid or reduce trauma or ischemia to the tissue or surrounds of the sphincter. Movement of the sphincter may be evenly distributed due to the concentric tension.

Figure 27D:
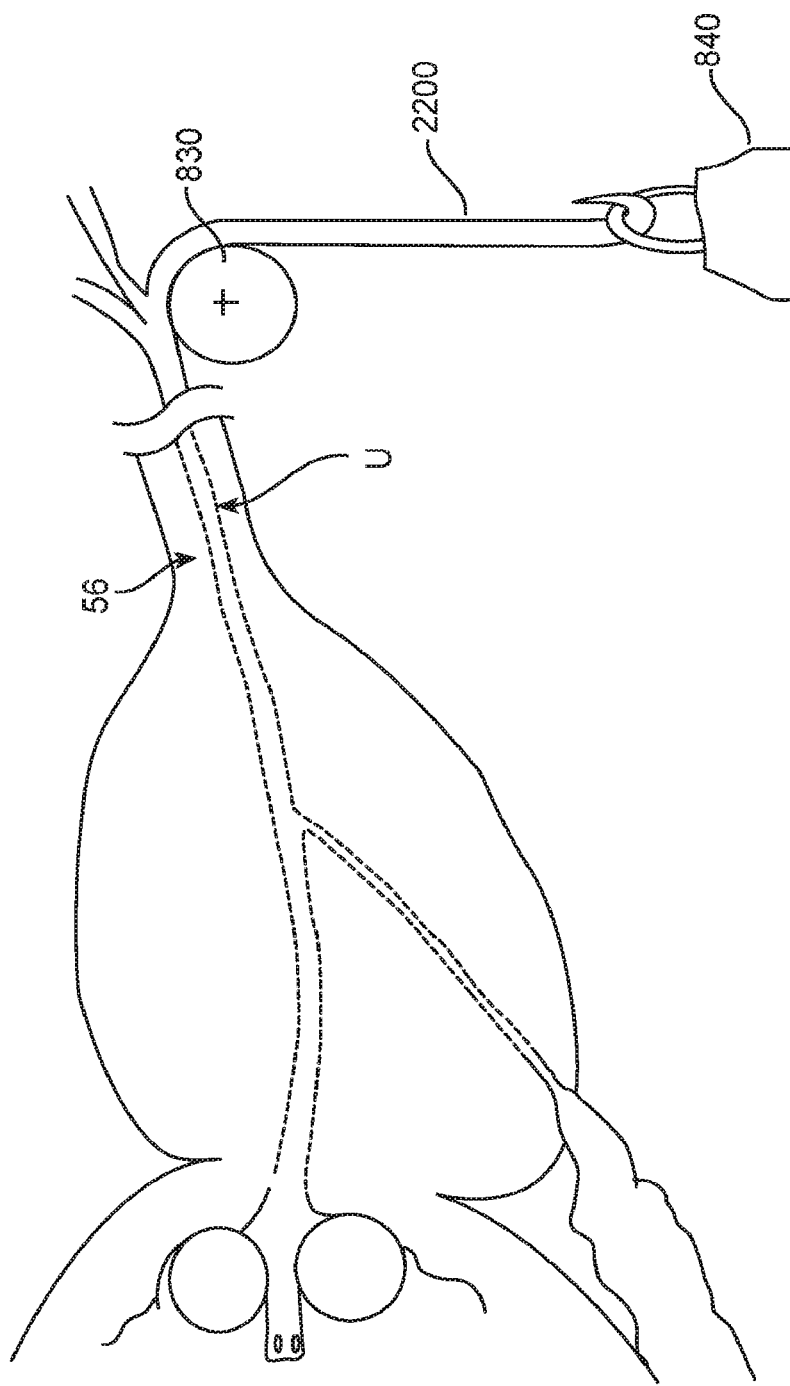
FIG. 27D shows a schematic view of an operating room bed-mounted tension element, in accordance with embodiments.

Alternatively or in combination, the tension element may comprise a pre-selected weight coupled to a proximal portion of the catheter. FIG. 27D shows an exemplary hospital bed-mounted hemostatic device comprising a pre-selected weight tension element 840 coupled to a proximal portion of the catheter 2200. The pre-selected weight 840 may for example comprise a fluid container (e.g. a bag, flask, or the like) configured to hold a pre-selected volume of fluid (e.g. water). The pre-selected weight 840 may for example comprise a pre-selected calibrated weight as known to one of ordinary skill in the art. Alternatively or in combination, the tension element 840 may comprise a calibrated spring device. A calibrated spring device tension element may for example be adjusted by threading or ratcheting to provide a pre-determined amount of tensile force. The catheter 2200 and/or the tension device 840 may be attached to hospital stirrups or a hospital bed frame 830. Attachment to such a low friction device may allow gravity to act directly on the anchor to provide tension to the catheter and/or balloon(s). Alternatively or in combination, attachment to a hospital bed frame, for example, may allow the angle of tension to be adjusted so as to pull the catheter collinearly to the urethra U and avoid or reduce pressure against the sphincter wall 56. The amount of tension and/or the pre-selected weight of the tension element may be selected in response to a measured blood pressure as described herein. For example, the weight of the tension element may be selected to provide a pressure to the balloons which is slightly above the measured blood pressure so as to promote hemostasis and avoid or reduce complications which may arise from applying more or less compression to the tissue as described herein. Optionally, the device may further comprise a tension measurement element or scale configured to couple to the tension element so as to measure the tension applied by the tension element.

Figure 28:
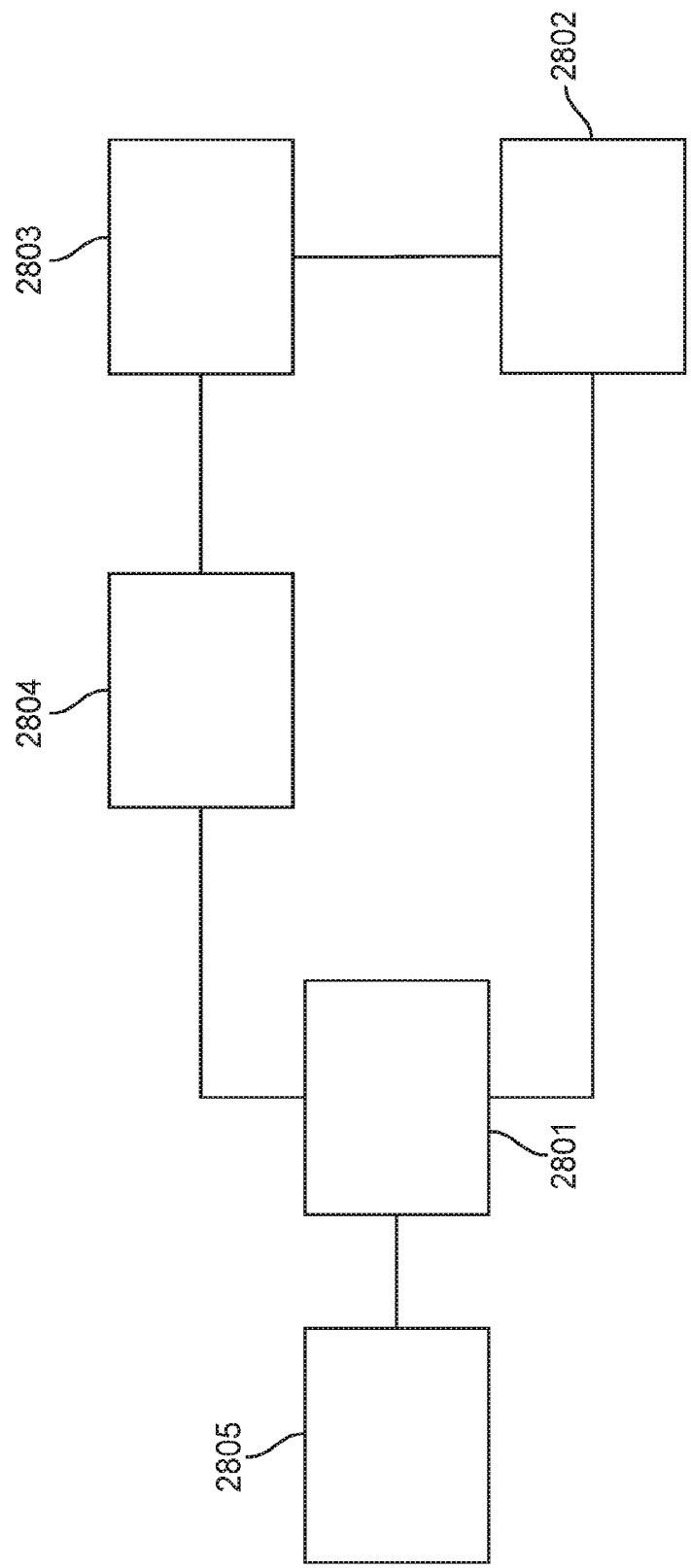
FIG. 28 shows a schematic of a sealant delivery device comprising a processor, in accordance with embodiments.

FIG. 28 shows a schematic of a sealant delivery device comprising a processor. The sealant delivery device may comprise any of the embodiments described herein. The sealant delivery device may for example comprise one or more expandable members 2803 or expandable supports as described herein. The expandable member 2803 may be configured to apply compression to the internal surface of the bleeding tissue space as described herein. The expandable member 2803 may be operably coupled to a processor 2801. The processor 2801 may be configured to receive a blood pressure of the subject and control expansion of the expandable member 2803 in response to the received blood pressure. The blood pressure of the patient may for example be input manually by the operator or may be received from a blood pressure sensor 2802. The processor 2801 may be configured to control expansion of the expandable member 2803 such that the expandable member is expanded o an internal pressure greater than the received blood pressure of the subject in order to apply compression to the tissue. The expandable member 2803 may exert a pressure on the tissue that is above the received blood pressure of the subject. The pressure exerted on the tissue may for example be measured using a pressure sensor. Alternatively or in combination, the internal pressure of the expandable member 2803 may be measured by a pressure sensor fluidly coupled to the expandable member 2803. The pressure sensor may comprise any pressure sensor as known to one of ordinary skill in the art. The processor may be coupled to the pressure sensor and configured to measure a first internal pressure of the expandable member 2803. The processor may then cause the expandable member 2803 to expand to a second internal pressure greater than the blood pressure of the subject in response to the received blood pressure. The processor 2801 may for example be coupled to a controller 2804 which is configured to control inflation of the expandable member 2803. Alternatively or in combination, the processor may comprise a controller to control inflation of the expandable member 2803. The processor 2801 may be coupled to a display 2805 in order to display one or more of the received blood pressure, the first measured internal pressure of the expandable member 2803, or the measured internal pressure of the expandable member 2803 after adjusting inflation in response to the received blood pressure. Any of the sealant delivery device embodiments described herein may comprise a pressure sensor and/or be coupled to a processor.

Figure 29:
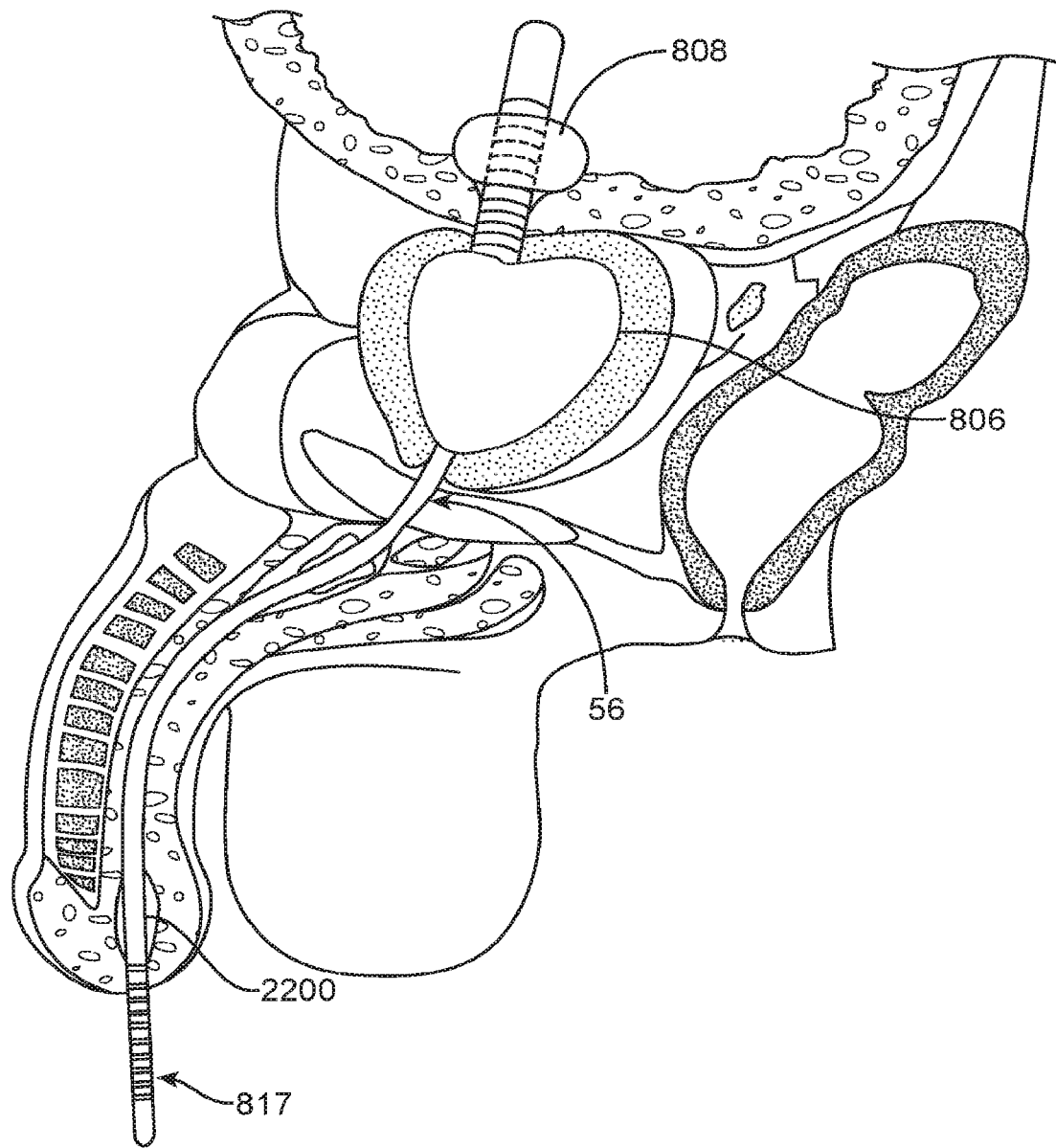
FIG. 29 shows a section view of a catheter comprising distance markers to monitor catheter migration, in accordance with embodiments.
Figure 30B:
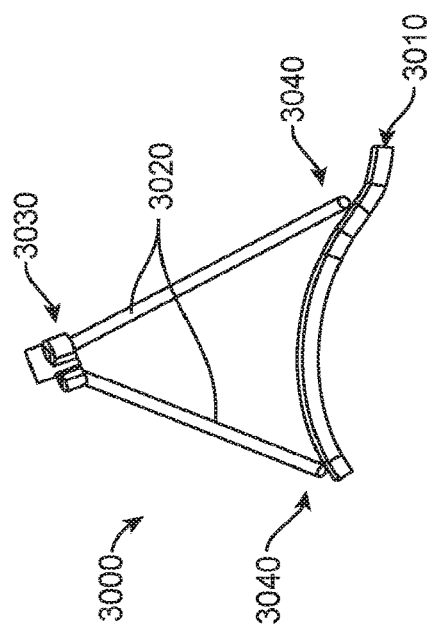
FIGS. 30A, 30B, 30C, and 30D show front, side, top, and perspective views, respectively, of a saddle traction device configured to resist repositioning of an anatomical member and catheter enclosed therewithin, in accordance with embodiments.
Figure 30D:
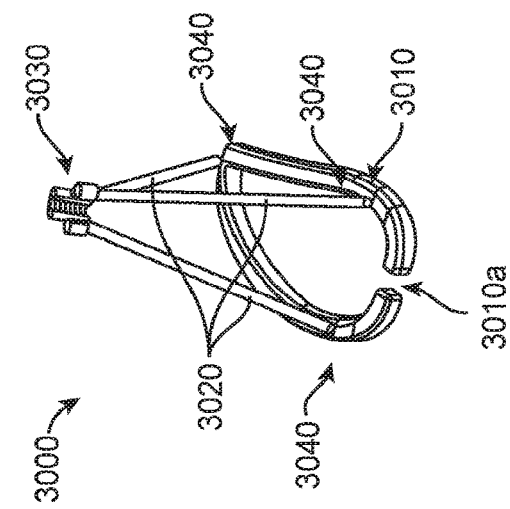
Figure 30A:
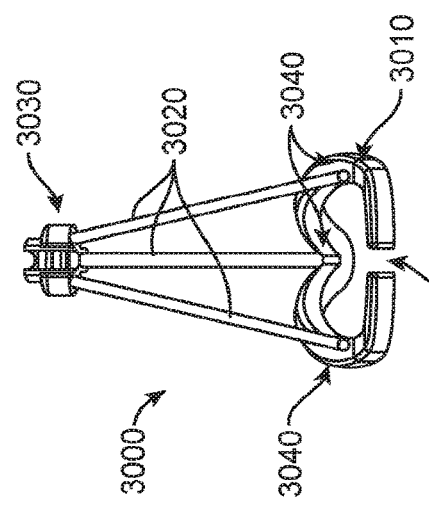
Figure 30C:
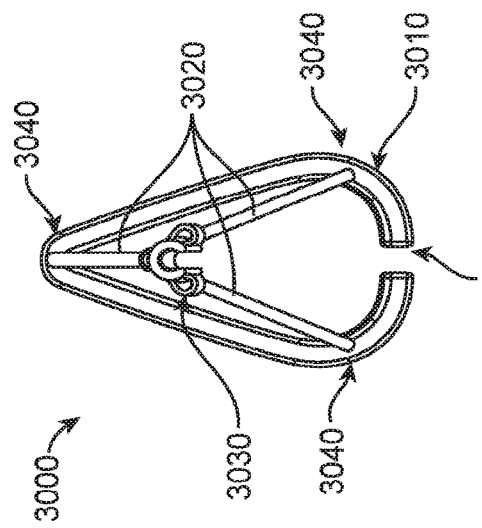
Figure 31B:
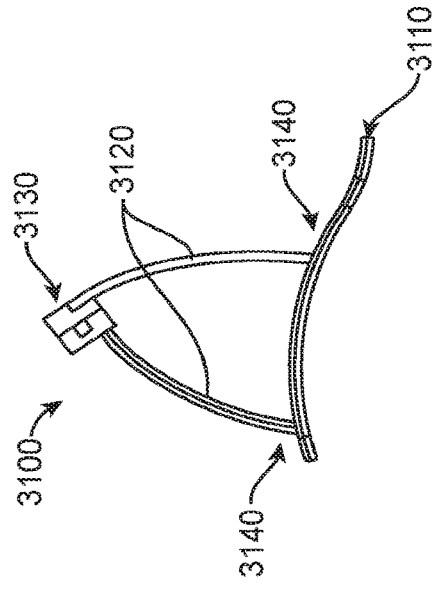
FIGS. 31A, 31B, 31C, and 31D show front, side, top, and perspective views, respectively, of another saddle traction device configured to resist repositioning of an anatomical member and catheter enclosed therewithin, in accordance with embodiments.
Figure 31D:
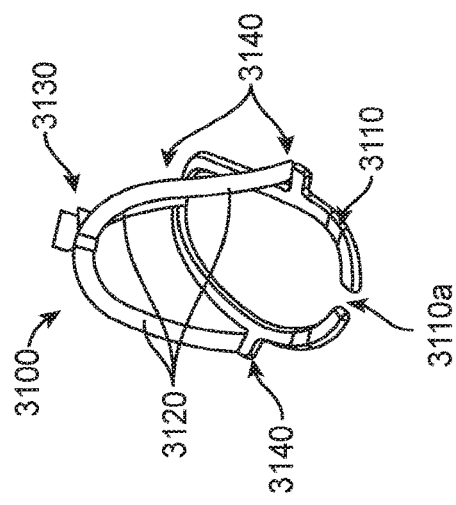
Figure 31A:
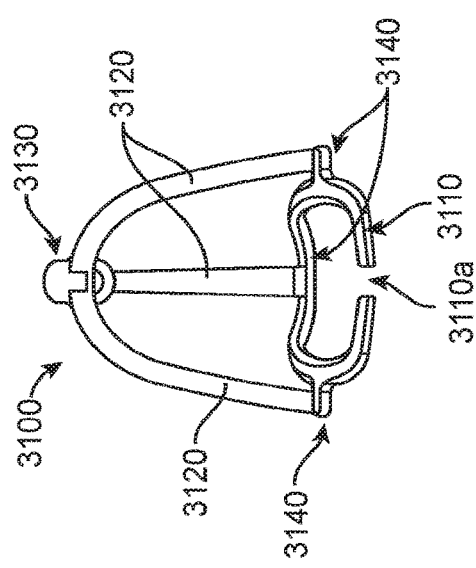
Figure 31C:
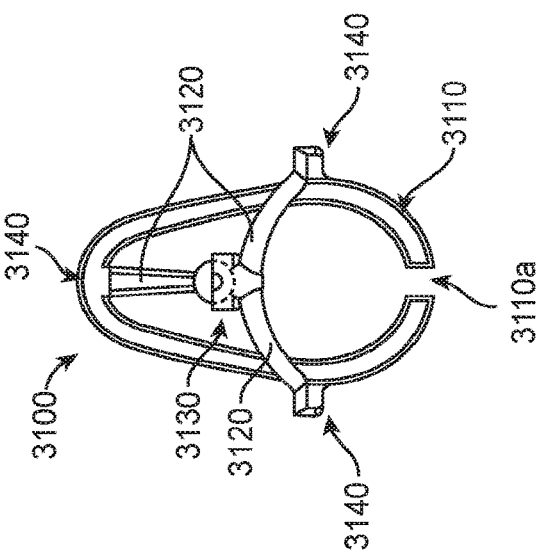
Figure 32A:
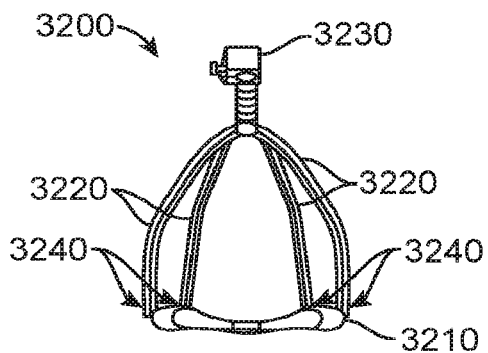
FIGS. 32A, 32B, 32C, and 32D show front, side, top, and perspective views, respectively, of another saddle traction device configured to resist repositioning of an anatomical member and catheter enclosed therewithin, in accordance with embodiments.
Figure 32B:
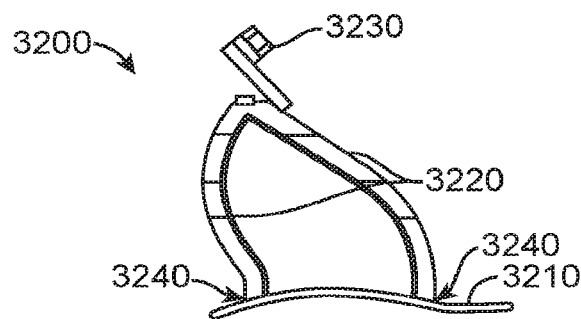
Figure 32C:
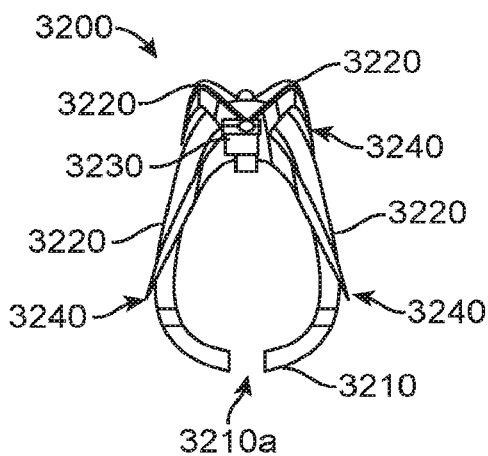
Figure 32D:
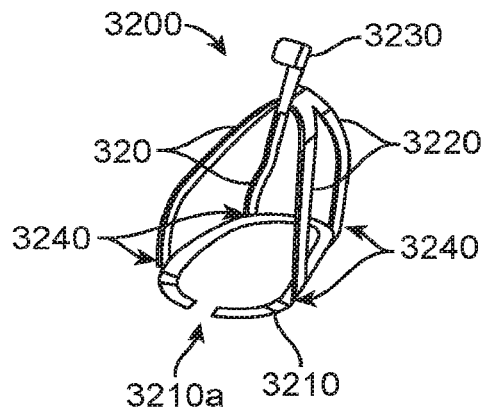

FIG. 29 shows a catheter comprising distance markers to monitor catheter migration. In addition to or as an alternative to providing a feature configured to minimize or prevent migration of the catheter within the tissue, it may be beneficial to directly monitor catheter position or location. In any of the embodiments described herein, the catheter 2200 may further comprise one or more indicia 817 positioned on an outer surface of a proximal portion of the catheter 2200 when the catheter has been advanced into the tissue space of interest, for example the prostatic capsule 900. The indicia 817 may comprise one or more bands positioned on the outer surface of the proximal portion of the catheter for example. The indicia 817 may for example comprise user-perceptible indicia. The location of the catheter may be determined in response to a visual or tactile inspection of the one or more indicia 817. The indicia 817 may be located in a band or region that is adjustable so as to account for the compressibility of the penis. The indicia 817 may be used to monitor catheter migration and/or orientation. For example, the embodiment of FIG. 25A may comprise one or more indicia 817 disposed on a proximal portion of the catheter as shown to indicate the angular orientation of the catheter with reference to the tent structure over the verumontanum in order to ensure correct positioning and reduced contact of the expandable support or inflatable balloon assembly with the verumontanum.

In any of the embodiments described herein, the proximal balloon, distal balloon, both balloons, or any of the inflatable balloon assemblies described herein may comprise one or more pre-determined sizes. In any of the embodiments described herein, the proximal balloon, distal balloon, both the proximal and distal balloons, or any of the inflatable balloon assemblies may comprise a non-uniform thickness or compliance in order to provide stepwise expansion.

In any of the embodiments described herein, the proximal balloon, distal balloon, both balloons, or any of the inflatable balloon assemblies described herein may comprise a compliant material, non-compliant material, or a combination of materials. One or more balloons may have a uniform compliance or a non-uniform compliance. The compliance of the one or more balloons may be chosen by one of ordinary skill in the art to match the hemostasis requirements of the tissue.

One or more balloon may comprise a non-compliant material so as to be substantially rigid. A rigid balloon may be configured so as to comprise a specific volume and/or volume when inflated. It will be understood by one of ordinary skill in the art that the rigid balloon may be configured with any volume or shape desired.

One or more balloon may comprise a compliant material. A compliant balloon may comprise a very compliant material, a moderately compliant material, or any combination thereof.

A very compliant material may for example permit stretching of a balloon during inflation in any direction in the absence of tissue or fluid pressure resistance. Inflation of a very compliant balloon may be controlled by configuring the balloon with a pre-determined internal volume such that the balloon conforms to the tissue cavity and becomes intimate with the cavity wall tissue equally. Alternatively or in combination, inflation of a very compliant balloon may be controlled by inflating the balloon to a pre-determined target pressure in an enclosed tissue space.

In any of the embodiments described herein, the proximal balloon, distal balloon, both the proximal and distal balloons, or any of the inflatable balloon assemblies described herein may be expanded to a target pressure. The target pressure for the proximal balloon may differ from or be the same as the target pressure for the distal balloon. The target pressure may be applied against the prostate, for example uniformly along the cavity wall and openings or at one or more locations within the prostatic capsule. The target pressure may be any pressure desired by one of ordinary skill in the art. The target pressure may for example be determined in response to a blood pressure of a patient in order to apply just enough pressure to inhibit bleeding through direct compression by the balloon. For example, the target pressure at the terminus of a distal balloon at a bleeding bladder neck (or distal opening) or of a proximal balloon at the peripheral/external sphincter (or proximal opening) may be selected to be slightly higher than the blood pressure of the patient so as to inhibit bleeding through compression. The blood pressure of the patient may be measured prior to inflation of the balloon in order that the target pressure may be determined for the measured blood pressure.

A moderately compliant material may for example permit stretching of a balloon during inflation with the dominant distension force (coming from within the balloon via fluid pressure) greater than typical body pressures and tissue flexibility so as to resist conformation to the shape of the cavity. The shape of a moderately compliant balloon may be configured to as to allow for post-procedural guidance of tissue shape during initial tissue approximation healing. The size and shape of the balloon may be selected based on the volume of resected tissue and/or optimized to mimic the anatomic shape of the tissue cavity post-healing.

In any of the embodiments described herein, the proximal balloon, distal balloon, both balloons, or any of the inflatable balloon assemblies described herein may be coupled to an external pressure indicator in order to monitor the pressure of the balloon(s) or assemblies. The external pressure indicator may for example be configured to indicate to a user when the balloon(s) or assemblies have reached a target pressure. The external pressure indicator may for example comprise an external calibrated balloon and/or a gravity pressure device such as a manometer. An external calibrated balloon may for example be coupled to the configured to begin expanding at a target pressure, for example at the target pressure of one or more balloons of the hemostatic device. Alternatively or in combination, the external calibrated balloon may be configured with multiple calibrated elongation thresholds which provide stepped expansion as the pressure increases in order to indicate multiple target pressures being reached. Stepped expansion may for example occur if the calibrated balloon comprises stepped thicknesses and/or compliances such that the thicker or less compliant portions of the balloon are stretched successively following the thinner portions of the balloon reaching their elongation limit(s).

In any of the embodiments described herein, the proximal balloon, distal balloon, both the proximal and distal balloons, or any of the inflatable balloon assemblies described herein may comprise a material to facilitate imaging of the sealant delivery device. In some cases, it may be desirable to image the sealant delivery device to determine the position or location of the device within the tissue during delivery, prior to balloon inflation, during sealant delivery, and/or after balloon deflation. One or more balloon may comprise an ultrasound hyperechoic material to aid visualization with TRUS or other ultrasound technology. Alternatively or in combination, one or more balloon may comprise a radiopaque material such as tantalum or gold to aid visualization with x-ray imaging technologies. Alternatively or in combination, one or more balloon may be coupled to one or more radiopaque markers for visualization.

In any of the embodiments described herein, the proximal balloon, distal balloon, both balloons, or any of the inflatable balloon assemblies described herein may comprise a uniform thickness or a non-uniform thickness. The thickness of the one or more balloons may be controlled in order to allow for timed or sequential inflation of the balloons and/or direction- or shape-controlled inflation of the balloons. The thickness of the one or more balloons may be configured so as to provide the one or more balloons with a pre-determined shape(s).

In any of the embodiments described herein, the proximal balloon, distal balloon, both the proximal and distal balloons, or any of the inflatable balloon assemblies described herein may comprise a pre-determined shape. One or more balloons may have a pre-determined shape that is spherical (e.g., with the balloon attached to the catheter at two points chosen such that the balloon inflates spherically), toroidal (e.g., with the balloon attached to the catheter at a single point such that the balloon inflates toroidally around the catheter shaft), cylindrical (e.g., with the balloon attached to the catheter at two distant points such that the balloon inflates in an elongated cylinder), or any shape desired (e.g., a non-compliant balloon may be molded with a distended shape or a balloon may have varying regions of compliance to reach the desired shape upon inflation), or any combination thereof. The pre-determined shape may be a dumbbell shape as described herein.

In any of the embodiments described herein, both the proximal and distal balloons, or any of the inflatable balloon assemblies described herein may comprise a textured outer surface. The outer surface of one or more balloons may for example comprise ribbing, dimpling, chevrons, concentric rings, and/or elements of progressive changing dimension in order to control positioning, migration, expansion order, and/or progression of the balloons. The one or more balloons may, for example, be substantially smooth when deflated and textured when inflated to help hold the sealant delivery device in place within the tissue cavity. The entire outer surface or a portion of the outer surface of the one or more balloons may be textured.

One or more balloons may comprise a variety of materials, a variety of thicknesses, a variety of textures, a variety of shapes, or any combination thereof in order to reach the desired hemostatic control.

Any of the embodiments disclosed herein may further comprise an external pressure indicator. The external pressure indicator may, for example, comprise an external calibrated balloon. The balloon may be calibrated with elongation thresholds in order to provide stepped expansion and pressure indications. For example, the balloon may comprise one or more thicker portions and one or more thinner portions. Stepped expansion may be achieved by first expanding the thinner portions to an elongation threshold or limit then successively stretching the thicker portions which may be configured to resist expansion while the thinner portions are below their elongation threshold. Alternatively or in combination, the external pressure indicator may comprise a gravity pressure indicator device, for example a monometer.

Any of the embodiments described herein may comprise a mesh disposed over one or more balloons, inflatable balloon assemblies, or expandable members. Expansion of the mesh-covered member(s) may comprise pressing the mesh against the tissue as described herein. The mesh may remain in the tissue space for a time after the member(s) have been removed or may be removed with the member(s). For example, expanding a distal balloon may comprise pressing a mesh disposed over the distal balloon against the tissue. The distal balloon may be collapsed and retracted from the tissue space along with the catheter while the mesh is left in the tissue space. The mesh may then be later removed or may comprise a material that is at least partially bioabsorbable or resorbable such that it is degraded or absorbed by the tissue over time. The mesh may alternatively be permanently implantable. The mesh may be coated with a hemostatic agent, for example a clot promoting agent like fibrin or thrombin.

Any of the embodiments described herein may comprise a scaffold disposed over one or more balloons, inflatable balloon assemblies, or expandable members. Expansion of the scaffold-covered member(s) may comprise pressing the scaffold against the tissue as described herein. The scaffold may remain in the tissue space for a time after the member(s) have been removed or may be removed with the member(s). For example, expanding a distal balloon may comprise pressing a scaffold disposed over the distal balloon against the tissue. The distal balloon may be collapsed and retracted from the tissue space along with the catheter while the scaffold is left in the tissue space. The scaffold may then be later removed from the tissue space after a time delay, for example between about 1 to about 3 days. The scaffold may for example comprise a silicone shaped stent configured to maintain shape and protect the verumontanum.

Any of the embodiments described herein may comprise one or more balloons, inflatable balloon assemblies, or expandable members comprising one or more pores. Any of the embodiments described herein may comprise a plurality of pores. The one or more pores may be configured to deliver a hemostatic agent to the tissue. Alternatively or in combination, the one or more pores may configured to deliver a therapeutic agent to the tissue, for example, a chemotherapeutic agent or any therapeutic agent known to one of ordinary skill in the art. For example, a distal balloon may comprise a plurality of pores through which a therapeutic agent may be delivered into the space between the expanded distal balloon and an internal surface of the tissue. Delivery of the hemostatic agent and/or therapeutic agent may occur with a variety of shape profiles, time constants, and/or penetrations following tissue resection for example. It will be apparent to one of ordinary skill in the art that delivery of the hemostatic and/or therapeutic agents may be altered depending on the material being delivered and the desired delivery pattern, timing, and/or other delivery characteristics.

Referring to FIGS. 30A-41D, various saddle traction devices for enclosing an anatomical member, such as a penis, and a catheter, such as a Foley catheter or the hemostatic catheter 2200 described herein, extending therefrom are described. The saddle traction devices may be configured to couple to the catheter and rest against the pelvic area of a patient to align the urethra with the urethral sphincter. The saddle traction devices may further apply tension to the coupled catheter. In some instances, it may be beneficial to provide direct therapeutic tension to compress a bleeding tissue in order to achieve hemostasis or to maintain the position of the catheter and/or expandable elements within the tissue. The application of tension may be provided in combination with any of the mechanisms for maintaining catheter position described herein.

FIGS. 30A, 30B, 30C, and 30D show a saddle traction device 3000. The saddle traction device 3000 may comprise a pelvic or groin mount or base 3010, which may provide a surface area which presses equally or nearly equally on the pubic region and the perineum. The pelvic or groin mount 3010 may provide event comfort when docked on a bony structure, sat upon, or belted on in order to prevent rotation or loss of position of the flexible enclosure 3010. The pelvic or groin mount 3010 may enclose and grip onto the base of the penis and the scrotum such that the anatomy is pulled down to align the urethra with the prostate (and bladder os).

The saddle traction device 3000 may further comprise a retainer element 3020 through which a catheter, such as a Foley catheter or the catheter 2200 may be fixedly attached, and a plurality of extension struts 3030 extending from the base 3020 to couple to the retainer element 3030. The extension struts 3030 may be coupled to the base 3020 through hinges 3040, for example, living hinges, such that the saddle traction device 3000 may be collapsed for easier storage and transportation. In a non-collapsed configuration, the base 3010 and the extension struts 3030 together define an opening or a concavity through with one or more anatomical members, such as the penis and the scrotum, can extend into. As shown in FIGS. 30A-30D, the extension struts 3040 may be relatively straight and may be arranged to form a tripod. The extension struts 3040 may instead be rounded so that the saddle traction device 3000 may provide greater internal clearance to accommodate larger anatomies. Also, greater numbers of extension struts 3040 may be provided, for example, four or more to form a pyramid. The retainer element 3020 may comprise a series of internal threads, teeth, or other friction elements to facilitate attachment with the catheter through frictional interference. The base 3010 may have an opening 3010a through which the catheter can pass as the saddle traction device 3000 is mounted over the one or more anatomical members.

As described herein, a tension or traction element may be provided to couple to the catheter or the flexible enclosure to align the urethra with the urethral sphincter. The catheter may, for example, be drawn through the retainer element 3040 and attached to the tension element. In some embodiments, the tension may be applied simply be tensioning the catheter to apply a predetermined and/or user-desired amount of force before fixing the catheter on the retainer element 3030. A user-desired amount of force can be provided by lengthening the catheter by a stroke length, such as between about 1 cm to about 8 cm, or about 2 cm to about 5 cm, to apply tension. The force or tension applied may be constant over a significant range of the stroke length, such as 50% over the stroke length range, so that the force or tension applied to the anatomy can be known and maintained at safe and optimal levels. Alternatively or in combination, the catheter may be coupled to a constant force spring to apply tension as described herein. In some instances, it may be beneficial to provide direct therapeutic tension with the saddle traction device 3000 to compress a bleeding tissue in order to achieve hemostasis or to maintain the position of the catheter and/or expandable elements within the tissue. For example, the saddle traction device 3000 may be applied for 2-4 hours after a procedure to achieve hemostasis. Application of tension may be provided in combination with any of the mechanisms for maintaining catheter position described herein.

FIGS. 31A, 31B, 31C, and 31D show a saddle traction device 3100 which may be similar to the saddle traction device 3000 and other described herein. The saddle traction device 3100 may comprise a pelvic or groin mount or base 3110 having an opening 3110a to allow a catheter to pass through, a retainer element 3120, and a plurality of extension struts 3130 extending from the base 3110 and coupled thereto with hinges 3140 to couple to the retainer element 3120. The extension struts 3130 may be rounded. The retainer element 3120 may be similar to the retainer element 3020 and may be configured to fix to a catheter with frictional interference. The retainer element 3120 may comprise first and second sides which may be snapped or closed together to capture the catheter 2200. The hinges 3140 may comprise living hinges or pinned hinges. The saddle traction device 3100 may be manufactured as a single piece, integral device (such as in cases where the hinges 3140 are living hinges), and may be collapsed to a flat configuration. In some cases, the penis may be positioned adjacent the opening 3110a and the scrotum may be positioned diametrically opposed to the opening 3110a. In other cases, the scrotum may be positioned adjacent the opening 3110a and the penis may be positioned diametrically opposed to the opening 3110a.

FIGS. 32A, 32B, 32C, and 32D show a saddle traction device 3200 which may be similar to any of the saddle traction devices 3100, 3000 and other described herein. The saddle traction device 3200 may comprise a pelvic or groin mount or base 3210 having an opening 3210a to allow a catheter 2200 to pass through, a retainer element 3220, and a plurality of extension struts 3230 extending from the base 3210 and coupled thereto with hinges 3240 to couple to the retainer element 3220.

Figure 33:
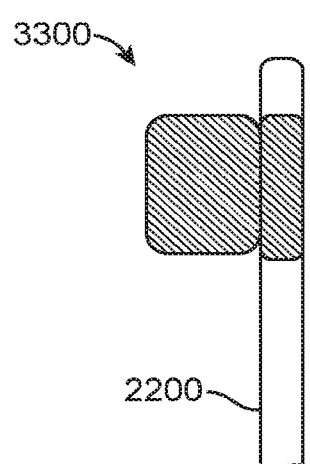
FIG. 33 shows a catheter provided with a "flag" to assist with maintaining a fixed position of the catheter with various saddle traction devices, in accordance with embodiments.
Figure 34A:
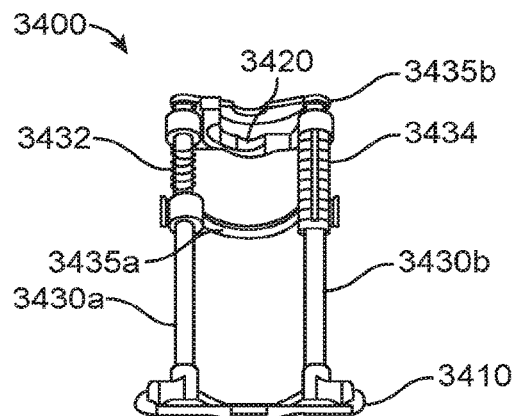
FIGS. 34A, 34B, 34C, and 34D show front, side, top, and perspective views, respectively, of another saddle traction device configured to resist repositioning of an anatomical member and catheter enclosed therewithin, in accordance with embodiments.
Figure 34B:
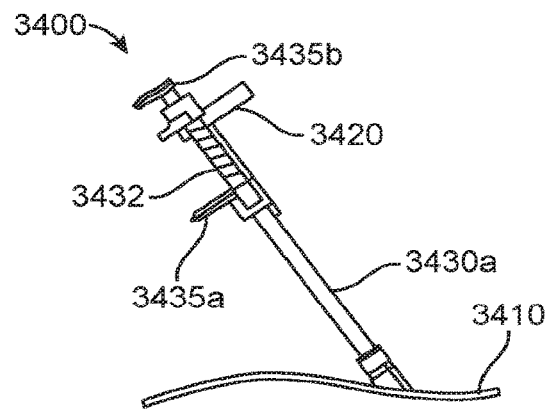
Figure 34C:
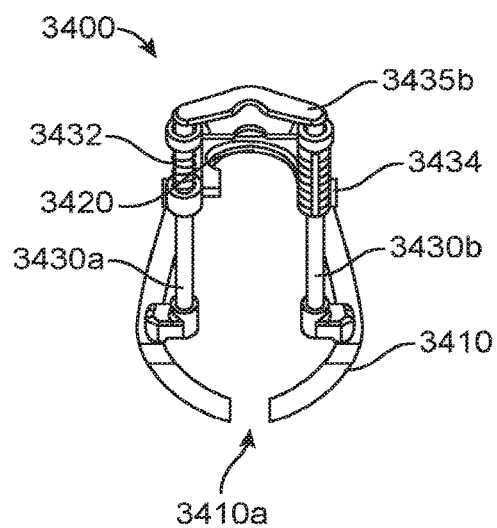
Figure 34D:
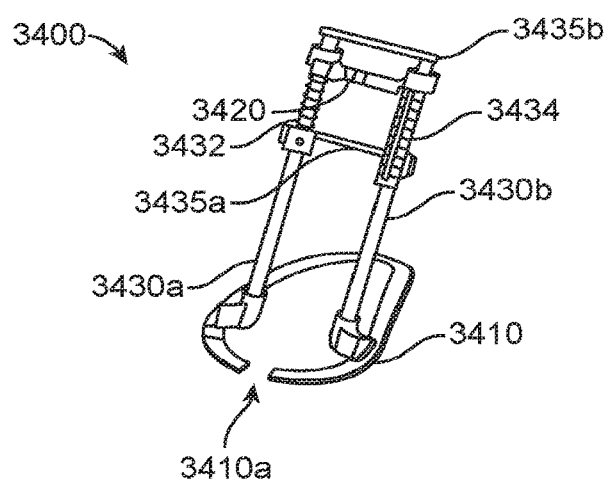
Figure 35A:
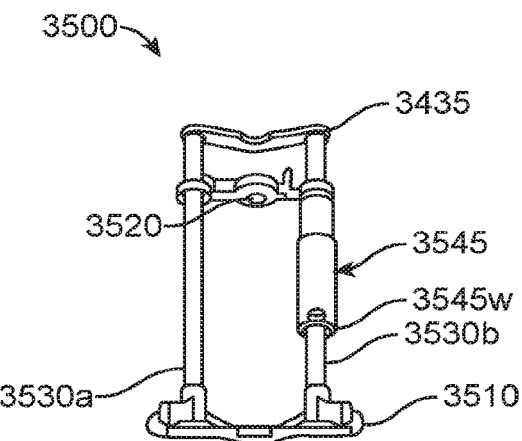
FIGS. 35A, 35B, 35C, and 35D show front, side, top, and perspective views, respectively, of another saddle traction device configured to resist repositioning of an anatomical member and catheter enclosed therewithin, in accordance with embodiments.
Figure 35B:
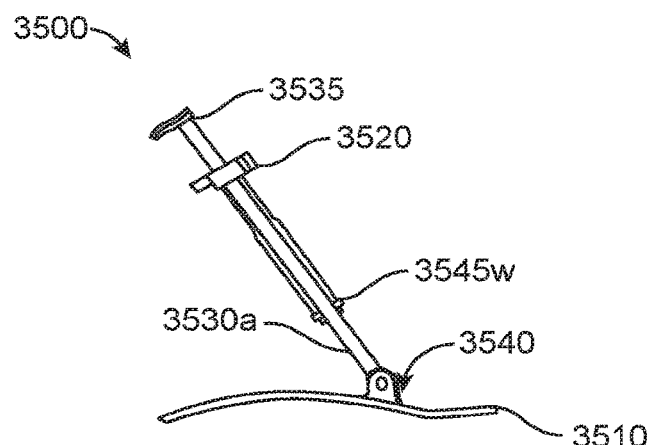
Figure 35C:
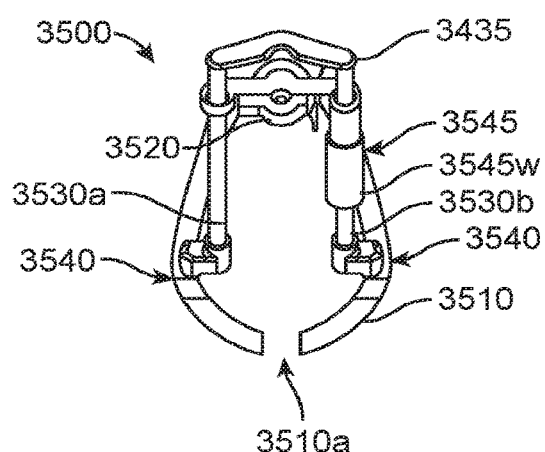
Figure 35D:
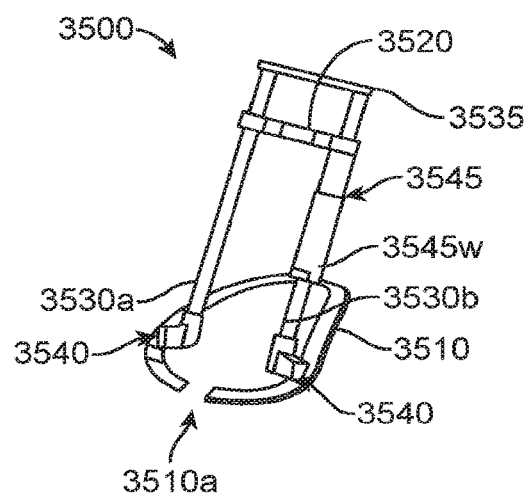
Figure 36A:
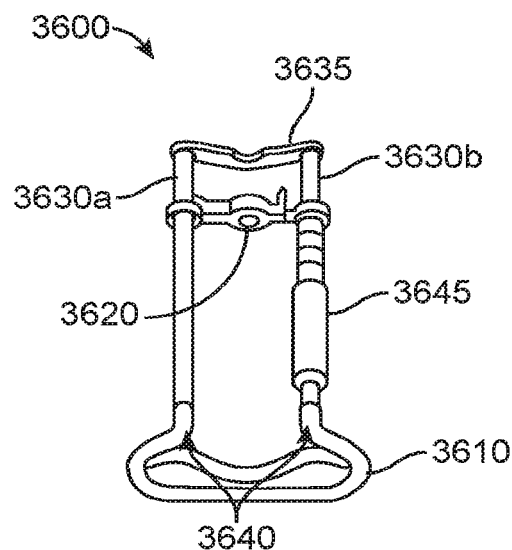
FIGS. 36A, 36B, 36C, and 36D show front, side, top, and perspective views, respectively, of another saddle traction device configured to resist repositioning of an anatomical member and catheter enclosed therewithin, in accordance with embodiments.
Figure 36B:
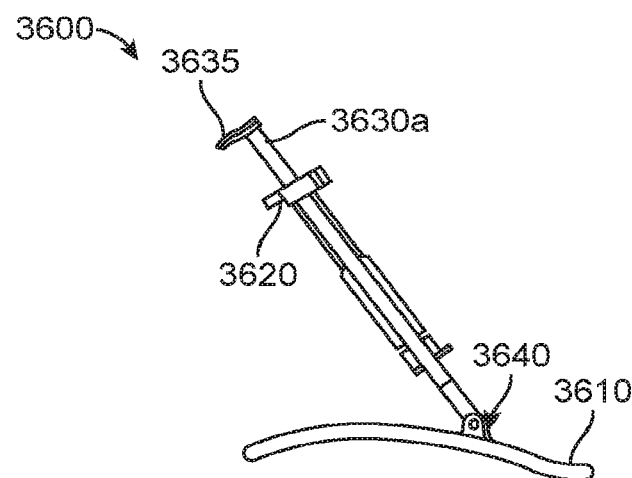
Figure 36C:
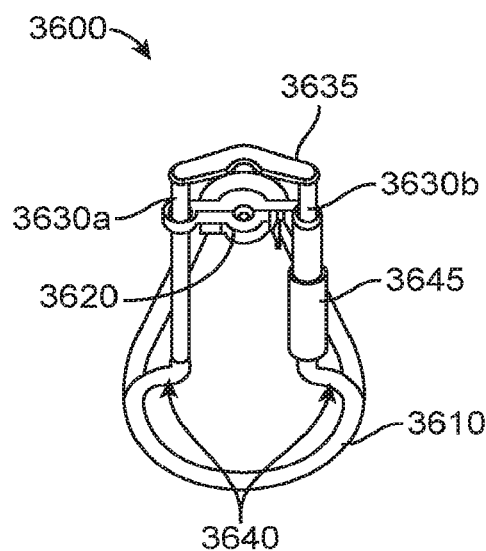
Figure 36D:
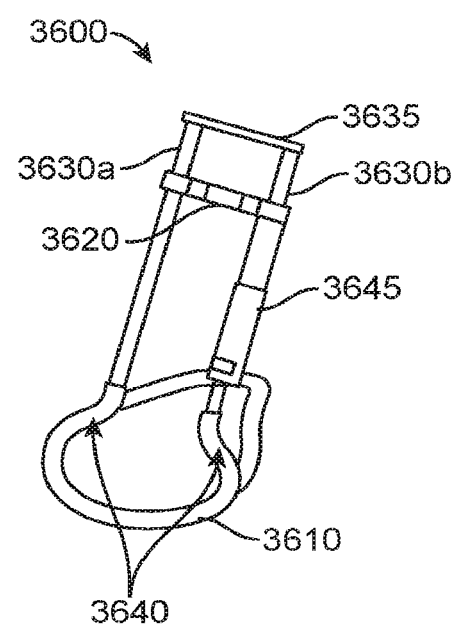
Figure 37A:
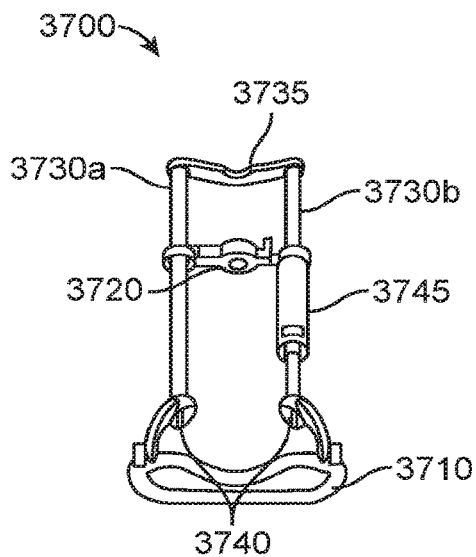
FIGS. 37A, 37B, 37C, and 37D show front, side, top, and perspective views, respectively, of another saddle traction device configured to resist repositioning of an anatomical member and catheter enclosed therewithin, in accordance with embodiments.
Figure 37B:
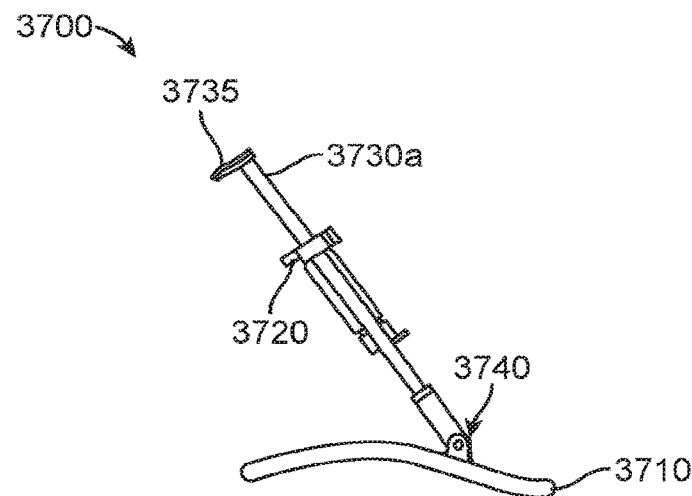
Figure 37C:
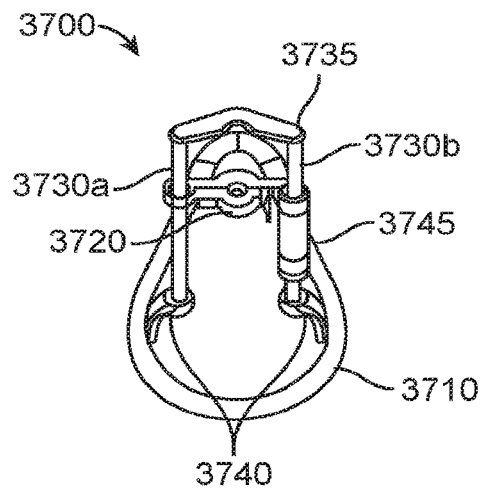
Figure 37D:
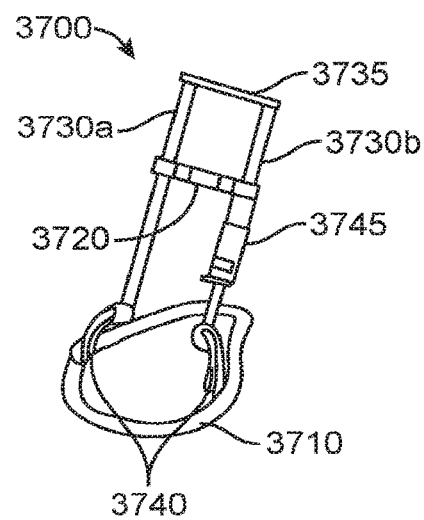
Figure 39A:
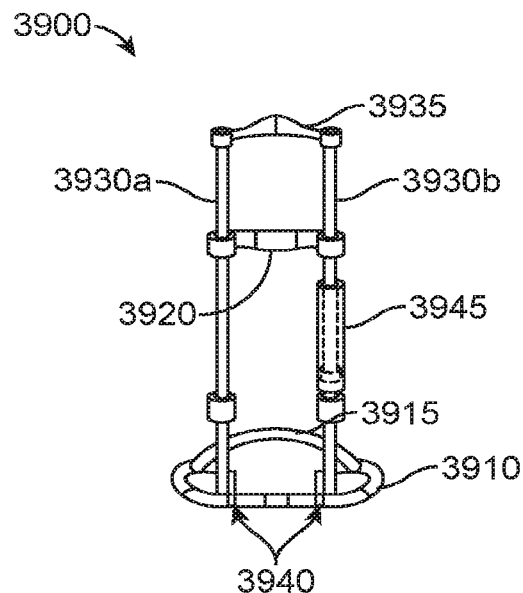
FIGS. 39A, 39B, 39C, and 39D show front, side, top, and perspective views, respectively, of another saddle traction device configured to resist repositioning of an anatomical member and catheter enclosed therewithin, in accordance with embodiments.
Figure 39B:
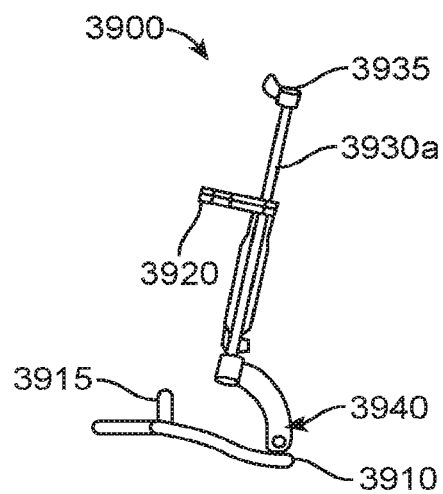
Figure 39C:
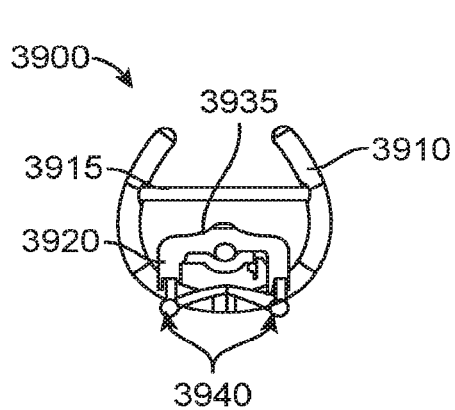
Figure 39D:
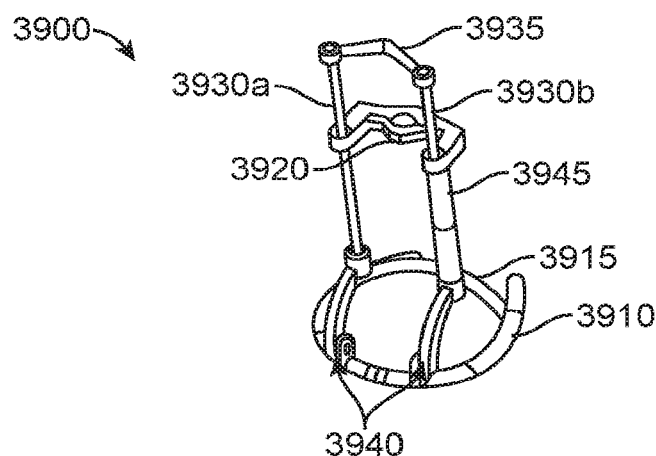
Figure 40A:
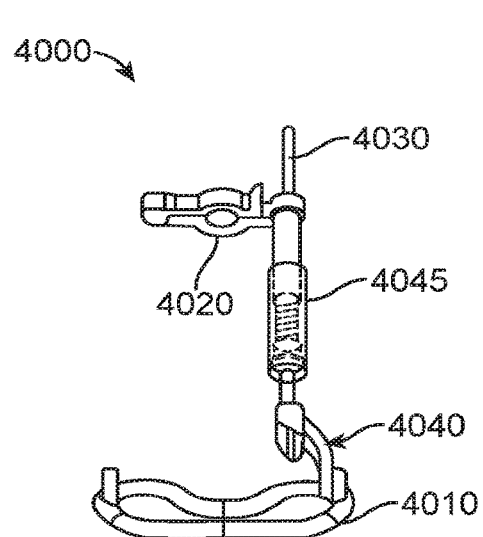
FIGS. 40A, 40B, 40C, and 40D show front, side, top, and perspective views, respectively, of another saddle traction device configured to resist repositioning of an anatomical member and catheter enclosed therewithin, in accordance with embodiments.
Figure 40B:
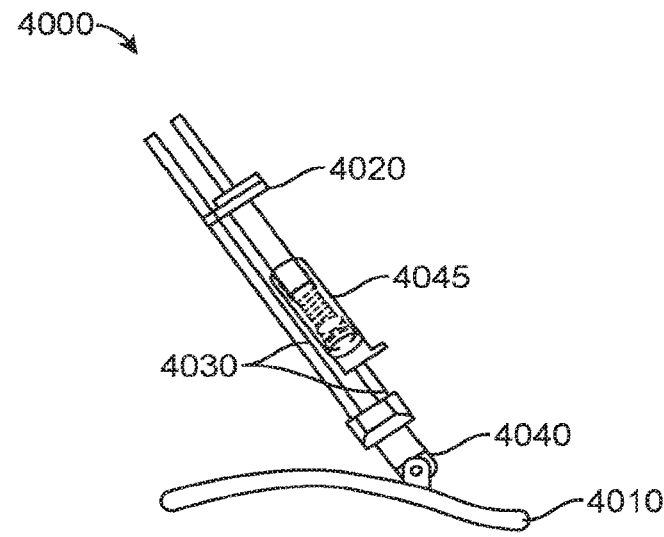
Figure 40C:
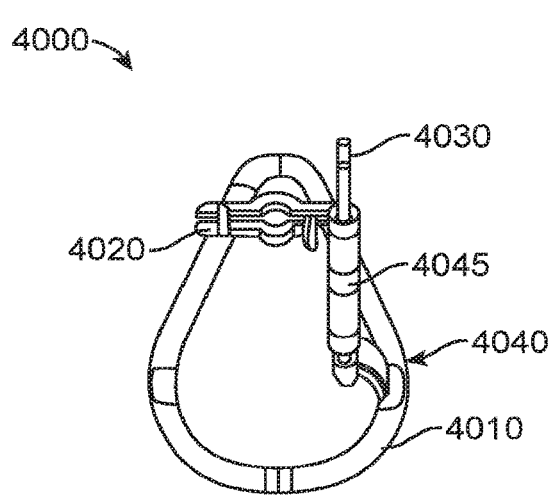
Figure 40D:
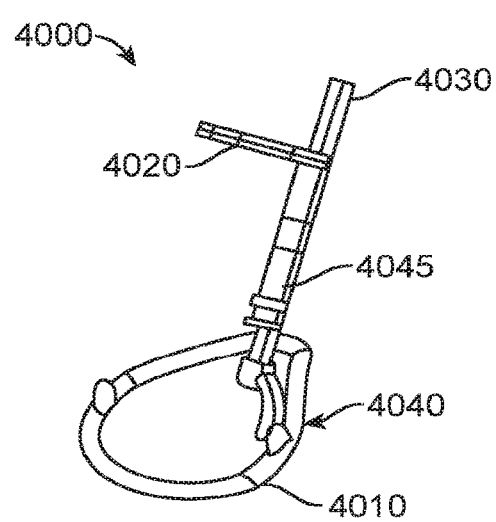

FIG. 33 shows the catheter 2200 with medical tape adhered thereon to provide a flag 3300 which may be used to assist with coupling the catheter 2200 with the retainer element 3220. Alternatively or in addition to providing frictional interference, the retainer element 3220 may comprise a clamp configured to be closed onto the flag 3300 provided on the catheter 2200. In some cases, it may be desirable for the retainer element to couple to the flag 3300 rather than the catheter 2200 itself to reduce a risk of interrupting or obstructing fluid flow through the catheter 2200, for example, if the fit between the retainer element and catheter 2200 is too tight. A latch may be provided to the retainer element 3220 to allow the retainer element 3220 to open and close.

FIGS. 34A, 34B, 34C, and 34D show a saddle traction device 3400 which may be similar to any of the saddle traction devices 3200, 3100, 3000, and other described herein. The saddle traction device 3400 may comprise a pelvic or groin mount or base 3410 having an opening 3410a to allow a catheter 2200 to pass through, a retainer element 3420, a first extension strut 3430a extending from the base 3210 and coupled thereto with a hinge 3440 to couple to the retainer element 3420, a second extension strut 3430b extending from the base 3210 and coupled thereto with a hinge 3440 to couple to the retainer element 3220, a first cross-member 3435a connecting the first and second extension struts 3430a, 3430b to one another, and a second cross-member 3435b connecting the first and second extension struts 3430a, 3430b to one another. The saddle traction device 3400 may further comprise an external spring 3432 coupled to the first extension strut 3430a and the retainer element 3440. The retainer element 3440 can be moved along the first and second extension struts 3430a, 3430b to apply or release tension to the catheter 2200 when it is coupled thereto. For instance, the ends of the cross-member of the retainer element 3440 may be releasably clamped to the first and second extension struts 3430a, 3430b. The spring 3432, in many cases, may apply the tension. The saddle traction device 3400 may further comprise a scale 3434 coupled to the second extension strut 3430b such that the amount of tension applied can be indicated.

FIGS. 35A, 35B, 35C, and 35D show a saddle traction device 3500 which may be similar to any of the saddle traction devices 3400, 3200, 3100, 3000 and other described herein. The saddle traction device 3500 may comprise a pelvic or groin mount or base 3510 having an opening 3510a to allow a catheter 2200 to pass through, a retainer element 3520, a first extension strut 3530a extending from the base 3510 and coupled thereto with a hinge 3540 to couple to the retainer element 3520, a second extension strut 3530b extending from the base 3510 and coupled thereto with a hinge 3540 to couple to the retainer element 3520, and a cross-member 3535 connecting the first and second extension struts 3530a, 3530b to one another. The saddle traction device 3500 may further comprise a telescoping, infinitely adjustable tensioning mechanism 3545 coupled to the second extension strut 3530b and the retainer element 3540 to adjustably apply tension to the retainer element 3540 and the catheter 2200 to be coupled thereto. For example, the amount of tension applied may be adjusted by adjusting a washer 3545w on the tensioning mechanism 3545. The tensioning mechanism 3545 may include an indicator for the amount of tension applied. For example, the indicator may indicate amounts of tension in gradations between 0 to 1.4 kg.

FIGS. 36A, 36B, 36C, and 36D show a saddle traction device 3600 which may be similar to any of the saddle traction devices 3500, 3400, 3200, 3100, 3000 and other described herein. The saddle traction device 3600 may comprise a pelvic or groin mount or base 3610 with an increased cross-section compared to the base 3510, a retainer element 3620, a first extension strut 3630a extending from the base 3610 and coupled thereto with a rigid coupling 3640 to couple to the retainer element 3620, a second extension strut 3630b extending from the base 3610 and coupled thereto with a rigid coupling 3640 to couple to the retainer element 3620, and a cross-member 3635 connecting the first and second extension struts 3630a, 3630b to one another. The first and second extension struts 3630a, 3630b may be coupled to curved extension portions of the base 3610 such that the couplings 3640 are positioned away from the main body of the base 3610, allowing additional clearance for the patient's anatomy. The rigid couplings 3640 may provide structural support for the extension struts 3630a, 3630b so that tension applied does not inadvertently deform the saddle traction device 3600. The saddle traction device 3600 may further comprise a telescoping, infinitely adjustable tensioning mechanism 3645 coupled to the second extension strut 3630b and the retainer element 3640.

FIGS. 37A, 37B, 37C, and 37D show a saddle traction device 3700 which may be similar to any of the saddle traction devices 3600, 3500, 3400, 3200, 3100, 3000 and other described herein. The saddle traction device 3700 may comprise a pelvic or groin mount or base 3710, a retainer element 3720, a first extension strut 3730a extending from the base 3710 and coupled thereto with an adjustable hinge 3740 to couple to the retainer element 3720, a second extension strut 3730b extending from the base 3710 and coupled thereto with an adjustable hinge 3740 to couple to the retainer element 3720, and a cross-member 3735 connecting the first and second extension struts 3730a, 3730b to one another. The portions of the first and second extension struts 3730a, 3730b coupled to the base 3710 may be curved away from the longitudinal axes of their respective extension strut to allow additional clearance for the patient's anatomy. The adjustable hinges 3740 may allow the angle of the extension struts 3730a, 3730b to be varied so that the angle at which the catheter 2200 is tensioned relative to the patient can be varied. The saddle traction device 3700 may further comprise a telescoping, infinitely adjustable tensioning mechanism 3745 coupled to the second extension strut 3730b and the retainer element 3740.

FIGS. 38A, 38B, 38C, 38D, and 38E show a saddle traction device 3800 which may be similar to any of the saddle traction devices 3700, 3600, 3500, 3400, 3200, 3100, 3000 and other described herein. The saddle traction device 3800 may comprise a pelvic or groin mount or base 3810, a retainer element 3820, a first extension strut 3830a extending from the base 3810 and coupled thereto with an adjustable hinge 3840 to couple to the retainer element 3820, a second extension strut 3830b extending from the base 3810 and coupled thereto with an adjustable hinge 3840 to couple to the retainer element 3820, and a cross-member 3835 connecting the first and second extension struts 3830a, 3830b to one another. The adjustable hinges 3840 may allow the angle of the extension struts 3830a, 3830b to be varied so that the angle at which the catheter is tensioned relative to the patient can be varied. FIG. 38E shows a magnified view of the adjustment mechanism of the adjustable hinge 3840. The adjustment mechanism may comprise a spring 3840a and a releasable coupling interface 3840b. The second extension strut 3830b may be urged inward to be released from the releasable coupling interface 3840b so that the angle of the second extensions strut 3830b can be adjusted. Once the angle is adjusted as desired, the second extension strut 3830b may be released from the inward force such that the spring 3840a can urge the second extension strut 3830b back toward the releasable coupling interface 3840b to couple thereto. The saddle traction device 3800 may further comprise a telescoping, infinitely adjustable tensioning mechanism 3845 coupled to the second extension strut 3830b and the retainer element 3840.

FIGS. 39A, 39B, 39C, and 39D show a saddle traction device 3900 which may be similar to any of the saddle traction devices 3800, 3700, 3600, 3500, 3400, 3200, 3100, 3000 and other described herein. The saddle traction device 3900 may comprise a pelvic or groin mount or base 3910 having a base cross-member 3915, a retainer element 3920, a first extension strut 3930a extending from the base 3910 and coupled thereto with an adjustable hinge 3940 to couple to the retainer element 3920, a second extension strut 3930b extending from the base 3910 and coupled thereto with an adjustable hinge 3940 to couple to the retainer element 3920, and a cross-member 3935 connecting the first and second extension struts 3930a, 3930b to one another. The portions of the first and second extension struts 3930a, 3930b coupled to the base 3910 may be curved away from the longitudinal axes of their respective extension strut to allow additional clearance for the patient's anatomy. The base 3910 may be U-shaped with a large open side to improve access to the rectum and provide scrotal comfort. The base cross-member 3915 may protrude away from the plane of the base 3910 to provide greater clearance. The saddle traction device 3900 may further comprise a telescoping, infinitely adjustable tensioning mechanism 3945 coupled to the second extension strut 3930b and the retainer element 3940. The retainer element 3940 may comprise a bracket-shaped cross-member to couple to the first and second extension struts 3930a, 3930b such that the coupled catheter 2200 is offset from the plane of the first and second extension struts 3930a, 3930b, which may improve clearance and comfort as the penis would be offset from the first and second extension struts 3930a, 3930b as well.

FIGS. 40A, 40B, 40C, and 40D show a saddle traction device 4000 which may be similar to any of the saddle traction devices 3900, 3800, 3700, 3600, 3500, 3400, 3200, 3100, 3000 and other described herein. The saddle traction device 4000 may comprise a pelvic or groin mount or base 4010, a retainer element 4020, and a single extension strut pair 4030 extending from one side of the base 4010 and coupled thereto with an adjustable hinge 4040 to couple to the retainer element 4020. Providing only an extension struts on one side of the base 4010 may provide improved clearance and catheter access. Having a pair of extension struts 4030 may reduce inadvertent rotation of the retainer element 4020. The saddle traction device 4000 may further comprise a telescoping, infinitely adjustable tensioning mechanism 4045 coupled to the extension strut pair 4030 and the retainer element 4040.

FIGS. 41A, 41B, 41C, 41D, and 41E show a saddle traction device 4100 which may be similar to any of the saddle traction devices 4000, 3900, 3800, 3700, 3600, 3500, 3400, 3200, 3100, 3000 and other described herein. The saddle traction device 3900 may comprise an open, U-shaped pelvic or groin mount or base 4110, a retainer element 4120, a first extension strut 4130a extending from the base 4110 and coupled thereto with a coupling 4140 to couple to the retainer element 4120, a second extension strut 4130b extending from the base 4110 and coupled thereto with a coupling 4140 to couple to the retainer element 4120, and a cross-member 4135 connecting the first and second extension struts 4130a, 4130b to one another. The base 4110 may comprise a malleable wire with a soft covering for improved patient comfort, customization, and device positioning. The first and second extension struts 4130a, 4130b may be coupled to curved extension portions of the base 4110 such that the couplings 4140 are positioned away from the main body of the base 4110, allowing additional clearance for the patient's anatomy. The couplings 4140 may be rigid to provide structural support for the extension struts 4130a, 4130b so that tension applied does not inadvertently deform the saddle traction device 4100. The saddle traction device 4100 may further comprise a telescoping, infinitely adjustable tensioning mechanism 4145 coupled to the second extension strut 4130b and the retainer element 4140. As shown on FIG. 41E, the saddle traction device 4100 may further comprise a securement strap or belt which may be secured to the body of the patient so as to maintain patient contact when the catheter 2200 is not tensioned and to prevent potential slippage, for example.

Figure 42:
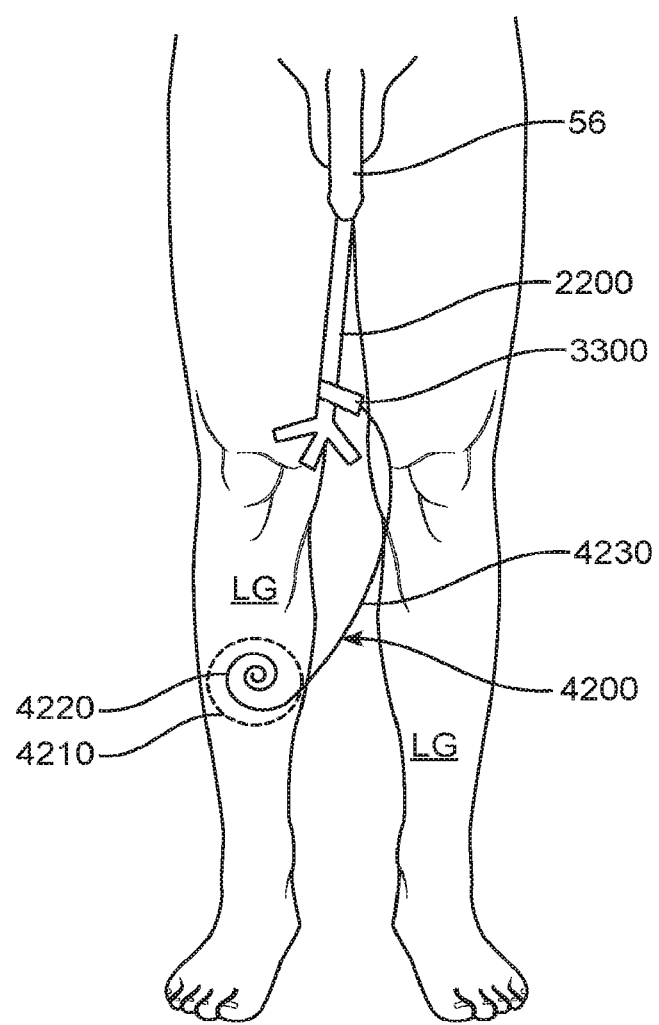
FIG. 42 shows a schematic illustration of a catheter extending from an anatomical member and coupled to a constant force spring, in accordance with embodiments.

FIG. 42 shows an exemplary use of a constant force spring mechanism 4200 to apply tension to the catheter 2200 extending from the penis 56. The constant force spring 4200 may be attached to a leg LG of the patient, such as with medical tape or a strap, to apply tension toward the feet. The constant force spring mechanism 4200 may be attached near the inner knee of the leg LG, for example. Alternatively, tension may be applied toward the head and the constant force spring mechanism 4200 may be coupled with the patient at the neck, chest, or abdomen such as with a neck worn lanyard, torso strap, or adhesive. The constant force spring mechanism 4200 may maintain constant tension to the catheter 2200 in spite of any patient movement. The constant force spring mechanism 4200 may comprise an enclosure 4210, a spring or constant force spring 4220, and a cord 4230 to couple to the catheter. The spring 4210 may apply tension to the cord 4220 to pull the cord back within the enclosure 4210 much like a retractable tape measure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for providing treatment to a tissue enclosing a space, the apparatus comprising:
    a catheter having a distal end and a proximal end, the catheter comprising a treatment agent infusion port near the proximal end;
    a treatment agent delivery port of the catheter coupled to the treatment agent infusion port, the treatment agent delivery port disposed proximally of the distal end of the catheter;
    a distal expandable support near the distal end of the catheter, the distal expandable support distal to the treatment agent delivery port;
    a distal port of the catheter coupled to a drainage port and forming a drainage channel extending between the distal port and the drainage port, the drainage channel configured to allow fluid drainage through the catheter, the distal port positioned distal of the distal expandable support; and
    a proximal expandable support positioned proximally with respect to the distal expandable support along a longitudinal axis of the catheter and configured to be inflated and moved relative to the distal expandable support along the longitudinal axis of the catheter;
    wherein the catheter is configured to be advanced into the space enclosed with the tissue through an opening into the enclosed space, and
    wherein the treatment agent delivery port is configured to deliver a treatment agent introduced into the catheter through the treatment agent infusion port to the space; and
    wherein the proximal expandable support is configured to be inflated and then moved relative to the distal expandable support along the longitudinal axis of the catheter to spread the treatment agent along the tissue.

2. An apparatus as in claim 1, wherein the proximal expandable support is configured to be expanded within the space to compress the treatment agent delivered to the space against an internal surface of the tissue.

3. An apparatus as in claim 1, wherein the proximal expandable support is fluidly coupled to a proximal inflation port and comprises a plurality of pores, wherein the treatment agent infusion port and the proximal inflation port are the same port, and wherein the treatment agent introduced into the catheter is delivered to the proximal expandable support to expand the proximal expandable support and to subsequently enter the space through the plurality of pores of the proximal expandable support.

4. An apparatus as in claim 1, wherein the proximal expandable support is configured to be expanded near a proximal opening of the tissue to seal the proximal opening, and wherein the treatment agent delivery port is positioned distally with respect to the proximal expandable support to deliver the treatment agent in the space between a sealed distal opening and the sealed proximal opening.

5. An apparatus as in claim 4, further comprising an actuation mechanism coupled to the proximal expandable support, the actuation mechanism configured to move the proximal expandable support, in an expanded configuration, along the longitudinal axis of the catheter between the proximal opening and the distal opening to spread the treatment agent over an internal surface of the tissue.

6. An apparatus as in claim 1, wherein at least one of the proximal expandable support or the distal expandable support is configured to have one or more of a spherical, toroidal, cylindrical, conical, dual cone, irregular, or dumbbell shape when expanded.

7. An apparatus as in claim 1, wherein the proximal expandable support comprises a proximal inflatable balloon.

8. An apparatus as in claim 7, wherein at least one of the proximal expandable support or the distal expandable support has a non-uniform thickness.

9. An apparatus as in claim 8, wherein the non-uniform thickness of the proximal expandable support is configured to provide the proximal inflatable balloon with a predetermined shape, and wherein the non-uniform thickness of the distal expandable support is configured to provide the distal expandable support with a predetermined shape.

10. An apparatus as in claim 1, wherein the tissue comprises a prostatic capsule of a prostate, and wherein the proximal expandable support has a fully expanded shape configured to reduce contact with a verumontanum of the prostate.

11. An apparatus as in claim 10, wherein the proximal expandable support in the fully expanded shape comprises tissue concavity configured for placement near the verumontanum of the prostate to reduce contact between the proximal expandable support and the verumontanum.

12. An apparatus as in claim 11, wherein the proximal expandable support further comprises a user-perceptible indicia for the concavity.

13. An apparatus as in claim 1, wherein at least a portion of an outer surface of the proximal expandable support or the distal expandable support is textured.

14. An apparatus as in claim 1, wherein at least one of the proximal expandable support or the distal expandable support comprises one or more of an ultrasound hyperechoic material or a radiopaque marker to aid visualization.

15. An apparatus as in claim 1, wherein at least one of the proximal expandable support or the distal expandable support comprises one or more of a compliant material or a non-compliant material.

16. An apparatus as in claim 1, wherein at least a portion of the proximal expandable support is coated with a hemostatic agent.

17. An apparatus as in claim 1, wherein at least a portion of the distal expandable support is coated with a hemostatic agent.

18. An apparatus as in claim 1, wherein the catheter further comprises a treatment agent overflow port distally adjacent the treatment agent delivery port, the treatment agent overflow port configured to remove excess treatment agent from the space.

19. An apparatus as in claim 1, wherein the tissue comprises a prostatic capsule of a prostate, the proximal opening comprises an opening to a urethra, and a distal opening comprises a bladder neck between the prostate and a bladder, and wherein the distal expandable support comprises a distal balloon sized and shaped to be advanced into the bladder and engage the bladder neck when expanded.

20. An apparatus as in claim 1, further comprising a sheath positioned over a region of the catheter adjacent the treatment agent delivery port and coupled to the distal expandable support, wherein expansion of the distal expandable support causes the sheath to retract or detach from the region to expose the treatment agent delivery port.

21. An apparatus as in claim 1, wherein the catheter comprises one or more indicia disposed on an outer surface of a proximal portion thereof, the one or more indicia being configured to be visually or tactilely inspected to determine a location of the catheter relative to the tissue.

22. An apparatus as in claim 21, wherein the one or more indicia comprise a plurality of bands positioned on the outer surface of the proximal portion of the catheter.

23. An apparatus as in claim 21, wherein the treatment agent comprises a hemostatic agent, and wherein the treatment agent delivery port is configured to deliver the hemostatic agent from the treatment agent infusion port to the space to decrease bleeding of the tissue.

24. An apparatus as in claim 21, wherein the treatment agent comprises a sealant, and wherein the treatment agent delivery port is configured to deliver the sealant from the treatment agent infusion port to the space to decrease bleeding of the tissue.

25. An apparatus as in claim 1, wherein the distal expandable support is fluidly coupled to a distal inflation port and comprises a plurality of pores, wherein the treatment agent infusion port and the distal inflation port are the same port, and wherein the treatment agent introduced into the catheter is delivered to the distal expandable support to expand the distal expandable support and to subsequently enter the space through the plurality of pores of the distal expandable support.

26. An apparatus as in claim 1, wherein the apparatus is configured to prevent the treatment agent from occluding the opening into the space.

\* \* \* \* \*